(12) United States Patent
Iwata et al.

(10) Patent No.: US 8,124,617 B2
(45) Date of Patent: Feb. 28, 2012

(54) IMIDAZOPYRIDINE COMPOUNDS

(75) Inventors: Hidehisa Iwata, Osaka (JP); Yasuhisa Kohara, Osaka (JP); Sheldon X. Cao, San Diego, CA (US); Prasuna Guntupalli, San Diego, CA (US); Stephen L. Gwaltney, Escondido, CA (US); David J. Hosfield, Solana Beach, CA (US); Yan Liu, San Diego, CA (US); Jeffrey A Stafford, San Diego, CA (US); Beverly Wolgast, San Diego, CA (US)

(73) Assignees: Takeda San Diego, Inc., San Diego, CA (US); Takeda Pharmaceutical Company Limited, Osaka (JP)

( * ) Notice: Subject to any disclaimer, the term of this patent is extended or adjusted under 35 U.S.C. 154(b) by 628 days.

(21) Appl. No.: 12/065,607

(22) PCT Filed: Sep. 1, 2006

(86) PCT No.: PCT/US2006/034441
§ 371 (c)(1),
(2), (4) Date: Sep. 15, 2008

(87) PCT Pub. No.: WO2007/028135
PCT Pub. Date: Mar. 8, 2007

(65) Prior Publication Data
US 2010/0069431 A1    Mar. 18, 2010

(30) Foreign Application Priority Data
Sep. 1, 2005 (JP) .............................. 2005-254194 U

(51) Int. Cl.
 *A61K 31/44* (2006.01)
 *C07D 513/02* (2006.01)
 *C07D 515/02* (2006.01)
(52) U.S. Cl. ....................... 514/303; 546/118
(58) Field of Classification Search .................. 514/303; 546/118
See application file for complete search history.

(56) References Cited

U.S. PATENT DOCUMENTS

| | | | |
|---|---|---|---|
| 3,287,463 A | 11/1966 | Rufenacht et al. | |
| 3,985,891 A | 10/1976 | Kutter | |
| 4,900,423 A | 2/1990 | Iida et al. | |
| 4,959,212 A | 9/1990 | Stancesco et al. | |
| 5,104,881 A * | 4/1992 | Jonas et al. | 514/303 |
| 5,239,080 A | 8/1993 | Sohda et al. | |
| 5,424,204 A | 6/1995 | Aoyama et al. | |
| 5,501,965 A | 3/1996 | Iwata et al. | |
| 5,541,060 A | 7/1996 | Bell et al. | |
| 5,854,067 A | 12/1998 | Newgard et al. | |
| 6,320,050 B1 | 11/2001 | Bizzarro et al. | |
| 6,353,111 B1 | 3/2002 | Corbett et al. | |
| 6,369,232 B1 | 4/2002 | Sidduri et al. | |
| 6,384,220 B2 | 5/2002 | Corbett et al. | |
| 6,388,071 B2 | 5/2002 | Mahaney | |
| 6,388,088 B1 | 5/2002 | Sidduri | |
| 6,433,188 B1 | 8/2002 | Corbett et al. | |
| 6,441,180 B1 | 8/2002 | Sidduri | |
| 6,441,184 B1 | 8/2002 | Corbett et al. | |
| 6,448,399 B1 | 9/2002 | Corbett et al. | |
| 6,482,951 B2 | 11/2002 | Guertin | |
| 6,486,184 B2 | 11/2002 | Kester et al. | |
| 6,486,380 B1 | 11/2002 | Epstein | |
| 6,489,485 B2 | 12/2002 | Bizzarro et al. | |
| 6,503,887 B1 | 1/2003 | During et al. | |
| 6,528,543 B1 | 3/2003 | Haynes et al. | |
| 6,545,155 B2 | 4/2003 | Corbett et al. | |
| 6,566,109 B2 | 5/2003 | Kawase et al. | |
| 6,583,288 B2 | 6/2003 | Goodnow, Jr. et al. | |
| 6,608,218 B2 | 8/2003 | Kester et al. | |
| 6,610,846 B1 | 8/2003 | Bizzarro et al. | |
| 6,784,298 B2 | 8/2004 | Goodnow, Jr. et al. | |
| 6,881,844 B2 | 4/2005 | Corbett et al. | |
| 7,118,811 B2 | 10/2006 | Ise et al. | |
| 2001/0039344 A1 | 11/2001 | Bizzarro et al. | |
| 2001/0051731 A1 | 12/2001 | Bizzarro et al. | |

(Continued)

FOREIGN PATENT DOCUMENTS

| | | |
|---|---|---|
| DE | 1445824 | 11/1969 |
| DE | 2305339 | 8/1974 |
| GB | 1026361 | 4/1966 |
| JP | 2001192653 | 7/2001 |
| WO | WO 00/53756 A2 | 9/2000 |
| WO | WO 00/53756 A3 | 9/2000 |
| WO | WO 00/58293 A2 | 10/2000 |
| WO | WO 00/58293 A3 | 10/2000 |
| WO | WO 01/44216 A1 | 6/2001 |
| WO | WO 01/83465 A2 | 11/2001 |
| WO | WO 01/83465 A3 | 11/2001 |
| WO | WO 01/83478 A2 | 11/2001 |

(Continued)

OTHER PUBLICATIONS

Yutilov Y M et al. "Preparation of 2-aryl-substitued imidazo[4,5-b] pyridines and imidazo[4,5-c] pyridines" Chemistry of Heterocyclic Compounds, Plenum Press Co. New York, No. 5, 1987, pp. 639-645, XP002231885.

*Primary Examiner* — Janet Andres
*Assistant Examiner* — Niloofar Rahmani
(74) *Attorney, Agent, or Firm* — Mitchell R. Brustein; Matthew J. Russo

(57) ABSTRACT

Compounds, pharmaceutical compositions, kits and methods are provided for use with glucokinase that comprise a compound selected from the group consisting of formula (I) wherein the variables are as defined herein.

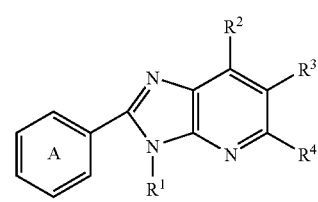

(I)

3 Claims, 1 Drawing Sheet

U.S. PATENT DOCUMENTS

| | | |
|---|---|---|
| 2001/0053851 A1 | 12/2001 | Mahaney |
| 2001/0056191 A1 | 12/2001 | Goodnow, Jr. et al. |
| 2002/0002190 A1 | 1/2002 | Corbett et al. |
| 2002/0032330 A1 | 3/2002 | Nomura et al. |
| 2002/0035266 A1 | 3/2002 | Sidduri |
| 2002/0035267 A1 | 3/2002 | Sidduri |
| 2002/0042512 A1 | 4/2002 | Kester et al. |
| 2002/0065239 A1 | 5/2002 | Caplan et al. |
| 2002/0065275 A1 | 5/2002 | Sidduri |
| 2002/0082260 A1 | 6/2002 | Guertin |
| 2002/0103199 A1 | 8/2002 | Corbett et al. |
| 2002/0103241 A1 | 8/2002 | Corbett et al. |
| 2002/0107396 A1 | 8/2002 | Corbett et al. |
| 2002/0110863 A1 | 8/2002 | Kawase et al. |
| 2002/0198200 A1 | 12/2002 | Kester et al. |
| 2003/0060625 A1 | 3/2003 | Bizzarro et al. |
| 2003/0082700 A1 | 5/2003 | Baker et al. |
| 2003/0082706 A1 | 5/2003 | Baker et al. |
| 2003/0082728 A1 | 5/2003 | Baker et al. |
| 2003/0092106 A1 | 5/2003 | Baker et al. |
| 2003/0096964 A1 | 5/2003 | Baker et al. |
| 2003/0096967 A1 | 5/2003 | Baker et al. |
| 2003/0100725 A1 | 5/2003 | Baker et al. |
| 2003/0100730 A1 | 5/2003 | Baker et al. |
| 2003/0129691 A1 | 7/2003 | Baker et al. |
| 2003/0129694 A1 | 7/2003 | Baker et al. |
| 2003/0138416 A1 | 7/2003 | Lau |
| 2003/0171411 A1 | 9/2003 | Kodra et al. |
| 2003/0181653 A1 | 9/2003 | Eaton et al. |
| 2003/0181657 A1 | 9/2003 | Eaton et al. |
| 2003/0181684 A1 | 9/2003 | Eaton et al. |
| 2003/0181686 A1 | 9/2003 | Eaton et al. |
| 2003/0181707 A1 | 9/2003 | Eaton et al. |
| 2003/0190716 A1 | 10/2003 | Eaton et al. |
| 2003/0194779 A1 | 10/2003 | Baker et al. |
| 2003/0194793 A1 | 10/2003 | Baker et al. |
| 2003/0199025 A1 | 10/2003 | Baker et al. |
| 2003/0199027 A1 | 10/2003 | Baker et al. |
| 2003/0207385 A1 | 11/2003 | Baker et al. |
| 2003/0219887 A1 | 11/2003 | Corbett et al. |
| 2003/0225283 A1 | 12/2003 | Corbett et al. |
| 2003/0225286 A1 | 12/2003 | Goodnow, Jr. et al. |
| 2003/0232370 A1 | 12/2003 | Trifiro |
| 2004/0009492 A1 | 1/2004 | Kim et al. |
| 2004/0014968 A1 | 1/2004 | Bizzarro et al. |
| 2004/0039164 A1 | 2/2004 | Baker et al. |
| 2004/0043457 A1 | 3/2004 | Schumacher et al. |
| 2004/0044179 A1 | 3/2004 | Baker et al. |
| 2004/0044180 A1 | 3/2004 | Baker et al. |
| 2004/0048332 A1 | 3/2004 | Ashkenazi et al. |
| 2004/0048333 A1 | 3/2004 | Baker et al. |
| 2004/0048334 A1 | 3/2004 | Baker et al. |
| 2004/0048335 A1 | 3/2004 | Baker et al. |
| 2004/0053245 A1 | 3/2004 | Tang et al. |
| 2004/0053397 A1 | 3/2004 | Iwamoto et al. |
| 2004/0058398 A1 | 3/2004 | Sarvetnick et al. |
| 2004/0063156 A1 | 4/2004 | Rademacher et al. |
| 2004/0067222 A1 | 4/2004 | Walker et al. |
| 2004/0067939 A1 | 4/2004 | Corbett et al. |
| 2004/0081981 A1 | 4/2004 | Egashira et al. |
| 2004/0086875 A1 | 5/2004 | Agee et al. |
| 2004/0086954 A1 | 5/2004 | Goueli et al. |
| 2004/0091959 A1 | 5/2004 | Baker et al. |
| 2004/0091972 A1 | 5/2004 | Baker et al. |
| 2004/0106555 A1 | 6/2004 | German |
| 2004/0108226 A1 | 6/2004 | Polychronakos et al. |
| 2004/0110246 A1 | 6/2004 | Ebinuma et al. |
| 2004/0116423 A1 | 6/2004 | Nivorozhkin et al. |
| 2004/0122235 A1 | 6/2004 | Polisetti et al. |
| 2004/0126839 A1 | 7/2004 | Baker et al. |
| 2004/0127400 A1 | 7/2004 | Smith et al. |
| 2004/0128707 A1 | 7/2004 | Ishino et al. |
| 2004/0132679 A1 | 7/2004 | Chan et al. |
| 2004/0137517 A1 | 7/2004 | Andrews et al. |
| 2004/0142373 A1 | 7/2004 | Gonye et al. |
| 2004/0142901 A1 | 7/2004 | German |
| 2004/0143110 A1 | 7/2004 | Krolewski et al. |
| 2004/0143854 A1 | 7/2004 | Klebl et al. |
| 2004/0146922 A1 | 7/2004 | Gonye et al. |
| 2004/0147017 A1 | 7/2004 | Ashkenazi et al. |
| 2004/0147725 A1 | 7/2004 | Chuntharapai et al. |
| 2004/0147748 A1 | 7/2004 | Chen et al. |
| 2004/0175740 A1 | 9/2004 | Brennan et al. |
| 2004/0180808 A1 | 9/2004 | Nye et al. |
| 2004/0180845 A1 | 9/2004 | Newgard et al. |
| 2004/0181067 A1 | 9/2004 | Fyfe et al. |
| 2004/0185531 A1 | 9/2004 | Ashkenazi et al. |
| 2004/0185548 A1 | 9/2004 | Ji |
| 2004/0186290 A1 | 9/2004 | Fyfe et al. |
| 2004/0191901 A1 | 9/2004 | Assady et al. |
| 2004/0197792 A1 | 10/2004 | Whyte et al. |
| 2004/0198969 A1 | 10/2004 | Baldwin et al. |
| 2004/0209797 A1 | 10/2004 | Karas |
| 2004/0213769 A1 | 10/2004 | Ferber |
| 2004/0214187 A1 | 10/2004 | Van Der Vuurst De Vries et al. |
| 2004/0214265 A1 | 10/2004 | Baker et al. |
| 2004/0214266 A1 | 10/2004 | Baker et al. |
| 2004/0214267 A1 | 10/2004 | Baker et al. |
| 2004/0214269 A1 | 10/2004 | Baker et al. |
| 2004/0214868 A1 | 10/2004 | Hayter et al. |
| 2004/0223964 A1 | 11/2004 | Ashkenazi et al. |
| 2005/0009129 A1 | 1/2005 | Rizzo et al. |
| 2005/0031605 A1 | 2/2005 | Bunn et al. |
| 2005/0032711 A1 | 2/2005 | Patel et al. |
| 2005/0032712 A1 | 2/2005 | Urbanski |
| 2005/0043391 A1 | 2/2005 | Fong et al. |
| 2005/0049310 A1 | 3/2005 | Mjalli et al. |
| 2005/0054715 A1 | 3/2005 | Hayter et al. |

FOREIGN PATENT DOCUMENTS

| | | |
|---|---|---|
| WO | WO 01/83478 A3 | 11/2001 |
| WO | WO 01/85706 A1 | 11/2001 |
| WO | WO 01/85707 A1 | 11/2001 |
| WO | WO 01/88088 A2 | 11/2001 |
| WO | WO 01/88088 A3 | 11/2001 |
| WO | WO 01/90325 A2 | 11/2001 |
| WO | WO 01/90325 A3 | 11/2001 |
| WO | WO 01/92523 A2 | 12/2001 |
| WO | WO 01/92523 A3 | 12/2001 |
| WO | WO 01/98454 A2 | 12/2001 |
| WO | WO 02/00691 A2 | 1/2002 |
| WO | WO 02/00691 A3 | 1/2002 |
| WO | WO 02/06339 A2 | 1/2002 |
| WO | WO 02/06339 A3 | 1/2002 |
| WO | WO 02/08209 A1 | 1/2002 |
| WO | WO 02/08277 A2 | 1/2002 |
| WO | WO 02/08277 A3 | 1/2002 |
| WO | WO 02/08288 A2 | 1/2002 |
| WO | WO 02/08288 A3 | 1/2002 |
| WO | WO 02/08289 A2 | 1/2002 |
| WO | WO 02/08289 A3 | 1/2002 |
| WO | WO 02/14312 A1 | 2/2002 |
| WO | WO 02/14358 A2 | 2/2002 |
| WO | WO 02/14358 A3 | 2/2002 |
| WO | WO 02/14500 A2 | 2/2002 |
| WO | WO 02/14500 A3 | 2/2002 |
| WO | WO 02/16578 A2 | 2/2002 |
| WO | WO 02/16578 A3 | 2/2002 |
| WO | WO 02/16599 A2 | 2/2002 |
| WO | WO 02/16599 A3 | 2/2002 |
| WO | WO 02/18409 A1 | 3/2002 |
| WO | WO 02/18621 A2 | 3/2002 |
| WO | WO 02/26801 A2 | 4/2002 |
| WO | WO 02/26801 A3 | 4/2002 |
| WO | WO 02/32939 A2 | 4/2002 |
| WO | WO 02/32939 A3 | 4/2002 |
| WO | WO 02/46173 A1 | 6/2002 |
| WO | WO 02/46409 A2 | 6/2002 |
| WO | WO 02/46409 A3 | 6/2002 |
| WO | WO 02/48106 A2 | 6/2002 |
| WO | WO 02/48106 A3 | 6/2002 |
| WO | WO 02/48361 A2 | 6/2002 |
| WO | WO 02/48361 A3 | 6/2002 |
| WO | WO 02/49423 A1 | 6/2002 |
| WO | WO 02/50277 A2 | 6/2002 |
| WO | WO 02/50277 A3 | 6/2002 |
| WO | WO 02/055704 A2 | 7/2002 |

| | | | | | | |
|---|---|---|---|---|---|---|
| WO | WO 02/055704 A3 | 7/2002 | | WO | WO 03/055482 A1 | 7/2003 |
| WO | WO 02/055705 A2 | 7/2002 | | WO | WO 03/080585 A1 | 10/2003 |
| WO | WO 02/055705 A3 | 7/2002 | | WO | WO 03/095438 A1 | 11/2003 |
| WO | WO 02/057450 A2 | 7/2002 | | WO | WO 03/097824 A1 | 11/2003 |
| WO | WO 02/057450 A3 | 7/2002 | | WO | WO 03/101284 A2 | 12/2003 |
| WO | WO 02/057453 A2 | 7/2002 | | WO | WO 03/101284 A3 | 12/2003 |
| WO | WO 02/057453 A3 | 7/2002 | | WO | WO 03/102161 A2 | 12/2003 |
| WO | WO 02/059315 A2 | 8/2002 | | WO | WO 03/102161 A3 | 12/2003 |
| WO | WO 02/059315 A3 | 8/2002 | | WO | WO 03/102163 A2 | 12/2003 |
| WO | WO 02/064791 A2 | 8/2002 | | WO | WO 03/103597 A2 | 12/2003 |
| WO | WO 02/064791 A3 | 8/2002 | | WO | WO 03/103597 A3 | 12/2003 |
| WO | WO 02/065985 A2 | 8/2002 | | WO | WO 03/103601 A2 | 12/2003 |
| WO | WO 02/065985 A3 | 8/2002 | | WO | WO 03/103601 A3 | 12/2003 |
| WO | WO 02/068649 A3 | 9/2002 | | WO | WO 03/105879 A1 | 12/2003 |
| WO | WO 02/068680 A2 | 9/2002 | | WO | WO 2004/002481 A1 | 1/2004 |
| WO | WO 02/068680 A3 | 9/2002 | | WO | WO 2004/031179 A1 | 4/2004 |
| WO | WO 02/070539 A2 | 9/2002 | | WO | WO 2004/039954 A2 | 5/2004 |
| WO | WO 02/070539 A3 | 9/2002 | | WO | WO 2004/039954 A3 | 5/2004 |
| WO | WO 02/072757 A2 | 9/2002 | | WO | WO 2004/045614 A1 | 6/2004 |
| WO | WO 02/072757 A3 | 9/2002 | | WO | WO 2004/046139 A1 | 6/2004 |
| WO | WO 02/072875 A1 | 9/2002 | | WO | WO 2004/050645 A1 | 6/2004 |
| WO | WO 02/081498 A2 | 10/2002 | | WO | WO 2004/052869 A1 | 6/2004 |
| WO | WO 02/081498 A3 | 10/2002 | | WO | WO 2004/063179 A1 | 7/2004 |
| WO | WO 02/081517 A2 | 10/2002 | | WO | WO 2004/063194 A1 | 7/2004 |
| WO | WO 02/081517 A3 | 10/2002 | | WO | WO 2004/072031 A2 | 8/2004 |
| WO | WO 02/093127 A2 | 11/2002 | | WO | WO 2004/072031 A3 | 8/2004 |
| WO | WO 02/093127 A3 | 11/2002 | | WO | WO 2004/072066 A1 | 8/2004 |
| WO | WO 02/097434 A1 | 12/2002 | | WO | WO 2004/076420 A1 | 9/2004 |
| WO | WO 02/098355 A2 | 12/2002 | | WO | WO 2004/081001 A1 | 9/2004 |
| WO | WO 02/098355 A3 | 12/2002 | | WO | WO 2004/099246 A2 | 11/2004 |
| WO | WO 02/101074 A2 | 12/2002 | | WO | WO 2004/100944 A1 | 11/2004 |
| WO | WO 02/101074 A3 | 12/2002 | | WO | WO 2004/101505 A1 | 11/2004 |
| WO | WO 03/000262 A1 | 1/2003 | | WO | WO 2005/030032 A2 | 4/2005 |
| WO | WO 03/000267 A1 | 1/2003 | | WO | WO 2005/030032 A3 | 4/2005 |
| WO | WO 03/015774 A1 | 2/2003 | | WO | WO 2005/054200 A1 | 6/2005 |
| WO | WO 03/026587 | 4/2003 | | WO | WO 2005/054233 A1 | 6/2005 |
| WO | WO 03/047626 A1 | 6/2003 | | WO | 2006125958 * | 11/2006 |
| WO | WO 03/054198 A1 | 7/2003 | | | | |

* cited by examiner

FIGURE 1

[SEQ. ID No. 1]

cagctctcca tccaagcagc cgttgct

[SEQ. ID No. 2]

ggcggcctgg gtcctgacaa g

[SEQ. ID No. 3]

ggatccatgc ccagaccaag atcccaactc ccacaaccca actcccaggt
agagcagatc ctggcagag

[SEQ. ID No. 4]

gaattcctgg cccagcatac aggc

[SEQ. ID No. 5]

MKLMALTLVEQILAEFQLQEEDLKKVMRRMQKEMDRGLRLETHEEASVKMLPTYVRSTPE
GSEVGDFLSLDLGGTNFRVMLVKVGEGEEGQWSVKTKHQMYSIPEDAMTGTAEMLFDYIS
ECISDFLDKHQMKHKKLPLGFTFSFPVRHEDIDKGILLNWTKGFKASGAEGNNVVGLLRD
AIKRRGDFEMDVVAMVNDTVATMISCYYEDHQCEVGMIVGTGCNACYMEEMQNVELVEGD
EGRMCVNTEWGAFGDSGELDEFLLEYDRLVDESSANPGQQLYEKLIGGKYMGELVRLVLL
RLVDENLLFHGEASEQLRTRGAFETRFVSQVESDTGDRKQIYNILSTLGLRPSTTDCDIV
RRACESVSTRAAHMCSAGLAGVINRMRESRSEDVMRITVGVDGSVYKLHPSFKERFHASV
RRLTPSCEITFIESEEGSGRGAALVSAVACKKACMLGQ

IMIDAZOPYRIDINE COMPOUNDS

FIELD OF THE INVENTION

The present invention relates to imidazopyridine compounds having a glucokinase activation action, which are useful as therapeutic agents for diabetes and the like.

BACKGROUND OF THE INVENTION

Glucokinase (sometimes to be abbreviated as GK in the present specification) (EC2.7.1.1) is one of the four kinds of hexokinases found in mammals, and is also called hexokinase IV. GK is an enzyme that catalyzes conversion of glucose to glucose-6-phosphoric acid, which is the first step of the glycolytic pathway. GK is mainly present in pancreatic β cells and the liver, and acts as a sensor of extracellular glucose concentration that defines glucose-stimulated insulin secretion in pancreatic β cells. In the liver, the enzyme reaction of GK is a rate-limiting factor to regulate glycogen synthesis and glycolysis. Three hexokinases (I, II, III) other than GK show the maximum enzyme activity at a glucose concentration of not more than 1 mM. In contrast, GK shows low affinity for glucose, and the Km value thereof is 8-15 mM, which is close to the physiological blood glucose level. Accordingly, promotion of intracellular glucose metabolism via GK occurs in response to the changes in the blood glucose level from the normal blood glucose (5 mM) to the postprandial hyper-blood glucose (10-15 mM).

The hypothesis proposed by Matschinsky et al. in 1984 that GK functions as a glucose sensor in pancreatic β cells and hepatocytes has been demonstrated through analysis of glucokinase gene engineered mouse in recent years (see The Journal of Biological Chemistry, 1995, vol. 270, pages 30253-30256; The Journal of Biological Chemistry, 1997, vol. 272, pages 22564-22569; The Journal of Biological Chemistry, 1997, vol. 272, pages 22570-22575; Japan clinical, 2002, vol. 60, pages 523-534; and Cell, 1995, vol. 83, pages 69-78.)

To be specific, GK heterozygous deleted mouse showed hyperglycemia and impaired glucose-stimulated insulin secretion. GK homozygous deleted mice die of marked hyperglycemia and sugar urine some time soon after birth. On the other hand, in GK overexpressing mice (hetero type), lower blood glucose level, higher blood glucose clearance rate, increased liver glycogen content and the like were observed. From these findings, it has been clarified that GK plays an important role in systemic glucose homeostasis. In other words, lower GK activity causes insulin hyposecretion and lower liver glucose metabolism, and the onset of impaired glucose tolerance and diabetes. Conversely, enhanced GK activity due to the activation or overexpression of GK causes enhanced insulin secretion and promoted liver glucose metabolism, which in turn increases systemic glucose utilization and improves glucose tolerance.

In human, too, it has been clarified from the analysis of GK gene abnormality reported mainly in the families of juvenile-onset adult diabetes called MODY2 (Maturity Onset Diabetes of the Young) that GK acts as a glucose sensor and plays an important role in glucose homostasis (see Nature, 1992, vol. 356, pages 721-722).

In GK gene abnormality, blood glucose threshold value of insulin secretion increases and insulin secretion ability decreases due to the decreased affinity of GK for glucose (increased Km value) and decreased Vmax. In the liver, decreased glucose uptake, promotion of gluconeogenesis, lower glycogen synthesis and liver insulin resistance are observed due to the decreased GK activity. On the other hand, some families having a mutation that increases the GK activity have been found, and in such families, fasting hypoglycemia accompanying increased plasma insulin concentration is observed (see New England Journal Medicine, 1998, vol. 338, pages 226-230).

As mentioned above, GK functions as a glucose sensor in mammals including human, and plays an important role in blood glucose control. Incidentally, blood glucose control utilizing the glucose sensor system of GK in many type 2 diabetic patients is considered to open a new way to a diabetes treatment. Particularly, a GK activating substance is considered to be useful as a drug for the prophylaxis or treatment of type 2 diabetes, since an insulin secretagogue action in pancreatic β cells, and glucose uptake promotion and glucose release inhibitory action in the liver can be expected.

Recently, pancreatic β cell type glucokinase has been clarified to be regionally expressed in the feeding center (Ventromedial Hypothalamus: VMH) of the rat brain. A subset of nerve cells present in VMH is called glucose responsive neuron and plays a key role in the body weight control. According to electrophysiological experiments, this neuron is activated in response to physiological changes in the glucose concentration (5-20 mM). Since the VHM glucose concentration sensor system assumes a mechanism mediated by glucokinase, as in the case of insulin secretion by pancreatic β cells, a pharmaceutical agent capable of glucokinase activation in the VHM besides the pancreatic β cells and liver is potentially capable of achieving not only a blood glucose correction effect but also improvement of obesity.

As mentioned above, a pharmaceutical agent capable of GK activation is useful as a drug for the prophylaxis or treatment of diabetes and chronic diabetic complications such as retinopathy, nephropathy, neurosis, ischemic cardiac diseases, arteriosclerosis and the like, and further as a drug for the prophylaxis or treatment of obesity.

As imidazopyridine compounds, it has been reported that a compound represented by formula:

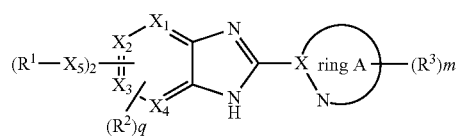

wherein

X, $X^1$-$X^4$ are each C or N;

ring A is a 5- or 6-membered nitrogen-containing aromatic heterocycle which is optionally condensed with phenyl or pyridyl;

$R^1$ is an optionally substituted aryl or an optionally substituted 4-10-membered heterocycle;

$X^5$ is —O—, —S—, —SO—, —SO$_2$—, a single bond or —O—C$_{1-6}$ alkylene-;

q and m are each 0-2;

$R^2$ is a hydroxy group, a formyl group and the like; and $R^3$ is a C$_{1-6}$ alkyl group and the like is a glucokinase activator, which is useful for the treatment of diabetes, complications, obesity and the like (see WO2005/063738).

However, the above-mentioned literatures do not disclose that compounds represented by the following formula (I) have a glucokinase activating action, nor do they disclose a compound represented by the following formula (II).

SUMMARY OF THE INVENTION

The present invention aims at providing a glucokinase activator useful as a pharmaceutical agent such as an agent for the prophylaxis or treatment of diabetes, obesity and the like.

The present inventors have conducted various studies and found that the compounds represented by the following formulas (I) and (II) unexpectedly have a superior glucokinase activating action and superior properties as a pharmaceutical product such as stability and the like, and can be a safe and useful pharmaceutical agent, and completed the present invention based on these findings.

Accordingly, the present invention relates to

[1] a glucokinase activator comprising a compound represented by the formula (I):

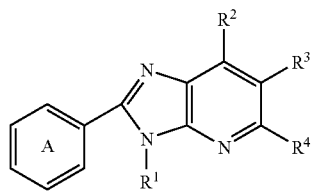

wherein ring A is an optionally substituted phenyl group; and $R^1$, $R^2$, $R^3$ and $R^4$ are the same or different and each is a hydrogen atom or a substituent, or a salt thereof (hereinafter sometimes to be abbreviated as compound (I)), or a prodrug thereof;

[2] an agent for activating glucokinase, which comprises a compound represented by the formula (Ip)

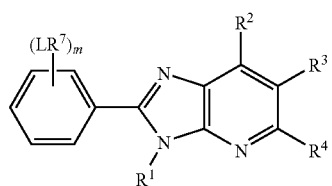

wherein m is 1, 2 or 3, and, in particular, m is 2;

each L is independently absent or a linker providing 1, 2, 3, 4, 5 or 6 atom separation between $R^7$ and the ring to which L is attached, wherein the atoms of the linker providing the separation are selected from the group consisting of carbon, oxygen, nitrogen, and sulfur, and, in particular, said linker is selected from the group consisting of —($C_{1-3}$)alkyl-, —($C_{2-3}$)alkenyl-, —NH—, —NH—$SO_2$—, —NH—CO—, —CO—NH—, —O—, —O—$CH_2$— and —S—;

$R^1$ is a hydrogen atom or a substituent convertible in vivo to hydrogen;

$R^2$, $R^3$ and $R^4$ are independently a hydrogen atom or a substituent; and each $R^7$ is independently selected from the group consisting of hydrogen, ($C_{1-3}$)alkyl, aryl($C_{1-3}$)alkyl, ($C_{3-12}$)cycloalkyl, hetero($C_{3-12}$)cycloalkyl, heteroaryl($C_{1-3}$)alkyl, aryl and heteroaryl, each substituted or unsubstituted, and, in particular, $R_7$ is selected from the group consisting of methyl, ethyl, propyl, phenyl, benzyl, pyridinyl, pyrimidinyl, thiophenyl, imidazolyl and furanyl, each substituted or unsubstituted, or a salt thereof (hereinafter sometimes to be abbreviated as compound (Ip)), or a prodrug thereof;

[3] a compound represented by the formula (II):

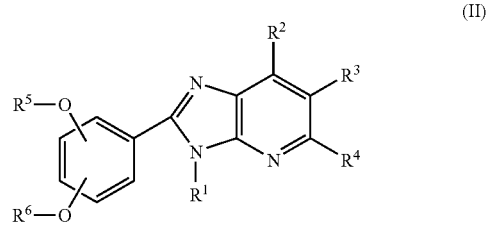

wherein $R^1$, $R^2$, $R^3$ and $R^4$ are the same or different and each is a hydrogen atom or a substituent; and $R^5$ and $R^6$ are the same or different and each is an optionally substituted $C_{1-6}$ alkyl group, provided that when the alkyl group is a $C_{1-2}$ alkyl group, then the $C_{1-2}$ alkyl group should be substituted by optionally substituted cyclic group(s), or a salt thereof (hereinafter sometimes to be abbreviated as compound (II));

[4] compound (II) wherein $R^1$ is a hydrogen atom;

[5] compound (II) wherein $R^2$ is a hydrogen atom;

[6] compound (II) wherein $R^3$ is
  (1) a hydrogen atom;
  (2) a $C_{6-14}$ aryl group optionally substituted by 1 to 3 substituents selected from
    (a) a halogen atom,
    (b) a $C_{1-6}$ alkyl group optionally substituted by 1 to 3 halogen atoms,
    (c) a $C_{1-6}$ alkoxy group, and
    (d) a hydroxy group;
  (3) a $C_{1-6}$ alkyl group optionally substituted by 1 to 3 substituents selected from
    (a) an amino group optionally substituted by 1 or 2 substituents selected from
      (i) a $C_{1-6}$ alkyl group optionally substituted by 1 to 3 substituents selected from a $C_{1-6}$ alkoxy group, a $C_{6-14}$ aryloxy group, a carboxyl group and a $C_{1-6}$ alkoxy-carbonyl group, and
      (ii) a $C_{7-13}$ aralkyl group, and
    (b) a hydroxy group;
  (4) an optionally substituted aromatic heterocyclic group;
  (5) a formyl group;
  (6) a carboxyl group;
  (7) a $C_{1-6}$ alkoxy-carbonyl group; or
  (8) a halogen atom;

[7] compound (II) wherein $R^4$ is
  (1) a hydrogen atom;
  (2) a $C_{1-6}$ alkyl group optionally substituted by 1 to 3 substituents selected from
    (a) a hydroxy group,
    (b) a carboxyl group,
    (c) a $C_{1-6}$ alkoxy-carbonyl group,
    (d) a halogen atom, and
    (e) a cyano group;
  (3) a cyano group;
  (4) a carboxyl group; or
  (5) a $C_{1-6}$ alkoxy-carbonyl group;

[8] compound (II) wherein $R^5$ and $R^6$ are the same or different and each is
  (1) a $C_{1-6}$ alkyl group substituted by 1 to 3 substituents selected from
    (a) a $C_{6-14}$ aryl group,
    (b) a $C_{3-10}$ cycloalkyl group,
    (c) a 5- or 6-membered aromatic heterocyclic group, and
    (d) a 5- or 6-membered non-aromatic heterocyclic group (each of the above-mentioned (a) to (d) is optionally substituted by 1 to 3 substituents selected from a halogen atom, a $C_{1-6}$ alkyl group, a $C_{1-6}$ alkoxy group, a thiol group, a $C_{1-6}$ alkyl-carbonyl group, a $C_{1-6}$ alkylsulfonyl group, a $C_{6-14}$ aryloxy group, a mono- or di-$C_{1-6}$ alkyl-amino group); or (2) a $C_{3-6}$ alkyl group optionally substituted by 1 to 3 substituents selected from a $C_{1-6}$ alkoxy group and a $C_{6-14}$ aryloxy group optionally substituted by 1 to 3 substituents selected from a cyano group and a halogen atom;

[9] a compound represented by the formula (Iq):

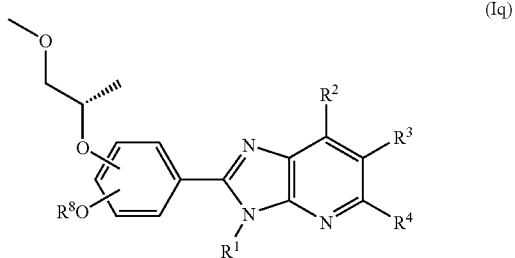

wherein $R^1$ is a hydrogen atom or a substituent convertible in vivo to hydrogen; $R^2$, $R^3$ and $R^4$ are independently a hydrogen or a substituent; and $R^8$ is selected from the group consisting of ($C_{1-3}$)alkyl, aryl($C_{1-3}$)alkyl, ($C_{3-12}$)cycloalkyl, hetero($C_{3-12}$)cycloalkyl, heteroaryl($C_{1-3}$)alkyl, aryl and heteroaryl, each substituted or unsubstituted, or a salt thereof (hereinafter sometimes to be abbreviated as compound (Iq));

[10] a compound represented by the formula (Ir):

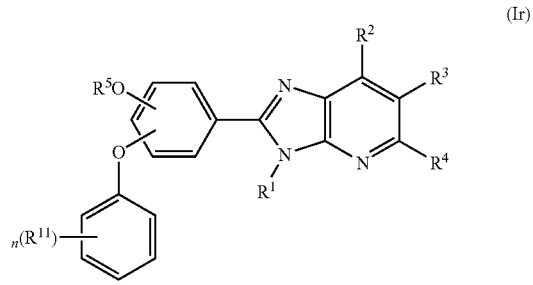

wherein $R^1$ is a hydrogen atom or a substituent convertible in vivo to hydrogen; $R^2$, $R^3$, $R^4$ and each $R^{11}$ are independently a hydrogen or a substituent; $R^5$ is an optionally substituted $C_{1-6}$ alkyl group; and n is 0, 1, 2, 3, 4 or 5, or a salt thereof (hereinafter sometimes to be abbreviated as compound (Ir));

[11] a compound represented by the formula (Is):

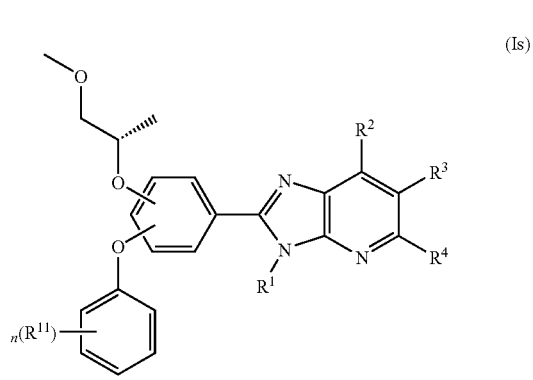

wherein $R^1$ is a hydrogen atom or a substituent convertible in vivo to hydrogen; $R^2$, $R^3$ and $R^4$ are independently a hydrogen or a substituent; each $R^{11}$ is independently selected from the group consisting of ($C_{1-3}$)alkyl, aryl($C_{1-3}$)alkyl, ($C_{3-12}$)cycloalkyl, hetero($C_{3-12}$)cycloalkyl, heteroaryl($C_{1-3}$)alkyl, aryl and heteroaryl, each substituted or unsubstituted; and n is 0, 1, 2, 3, 4 or 5, or a salt thereof (hereinafter sometimes to be abbreviated as compound (Is));

[12] a compound represented by the formula (It):

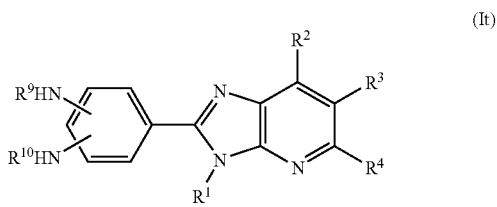

wherein $R^1$ is a hydrogen atom or a substituent convertible in vivo to hydrogen; $R^2$, $R^3$ and $R^4$ are independently a hydrogen or a substituent; and $R^9$ and $R^{10}$ are independently an optionally substituted $C_{1-6}$ alkyl, acyl or sulfonyl group, or a salt thereof (hereinafter sometimes to be abbreviated as compound (It));

[13] a compound selected from the group consisting of:
2-[5-(benzyloxy)-2-isopropoxyphenyl]-6-(3-fluorophenyl)-3H-imidazo[4,5-b]pyridine;
2-(3-(benzyloxy)-5-isopropoxyphenyl)-3H-imidazo[4,5-b]pyridine;
2-(3-isopropoxy-5-(3-phenylpropoxy)phenyl)-3H-imidazo[4,5-b]pyridine;
2-(3-isopropoxy-5-phenethoxyphenyl)-3H-imidazo[4,5-b]pyridine;
2-(3-(benzyloxy)-5-((1-methyl-1H-imidazol-2-yl)methoxy)phenyl)-3H-imidazo[4,5-b]pyridine;
2-(3-(benzyloxy)-5-((1-methyl-1H-imidazol-2-yl)methoxy)phenyl)-6-bromo-3H-imidazo[4,5-b]pyridine;
6-bromo-2-(3-((1-methyl-1H-imidazol-2-yl)methoxy)-5-(2-(thiophen-3-yl)ethoxy)phenyl)-3H-imidazo[4,5-b]pyridine;
2-(3-(2-fluorobenzyloxy)-5-((1-methyl-1H-imidazol-2yl)methoxy)phenyl)-3H-imidazo[4,5-b]pyridine;
6-chloro-2-(3-(2-fluorobenzyloxy)-5-((1-methyl-1H-imidazol-2-yl)methoxy)phenyl)-3H-imidazo[4,5-b]pyridine;
6-bromo-2-(3-(2-fluorobenzyloxy)-5-((1-methyl-1H-imidazol-2-yl)methoxy)phenyl)-3H-imidazo[4,5-b]pyridine;
3-(2-(3-(2-fluorobenzyloxy)-5-((1-methyl-1H-imidazol-2-yl)methoxy)phenyl)-3H-imidazo[4,5-b]pyridin-6-yl)propan-1-ol;
(R)-2-(3-(2-fluorobenzyloxy)-5-(1-methoxypropan-2-yloxy)phenyl)-3H-imidazo[4,5-b]pyridine;
(R)-6-chloro-2-(3-(2-fluorobenzyloxy)-5-(1-methoxypropan-2-yloxy)phenyl)-3H-imidazo[4,5-b]pyridine;
(R)-6-bromo-2-(3-(2-fluorobenzyloxy)-5-(1-methoxypropan-2-yloxy)phenyl)-3H-imidazo[4,5-b]pyridine;
(S)-3-(2-(3-(2-fluorobenzyloxy)-5-(1-methoxypropan-2-yloxy)phenyl)-3H-imidazo[4,5-b]pyridin-6-yl)propan-1-ol;
(S)-methyl 2-(3-(2-fluorobenzyloxy)-5-(1-methoxypropan-2-yloxy)phenyl)-3H-imidazo[4,5-b]pyridine-6-carboxylate;
(S)-2-(3-(2-fluorobenzyloxy)-5-(1-methoxypropan-2-yloxy)phenyl)-3H-imidazo[4,5-b]pyridine-6-carboxylic acid (S)-2-(3-(1-methoxypropan-2-yloxy)-5-(4-(methylsulfonyl)phenoxy)phenyl)-3H-imidazo[4,5-b]pyridine;
6-bromo-2-(2-phenoxyphenyl)-3H-imidazo[4,5-b]pyridine;
(E)-2-(2-isopropoxy-5-styrylphenyl)-3H-imidazo[4,5-b]pyridine;
N-(3-(6-bromo-3H-imidazo[4,5-b]pyridin-2-yl)-5-((1-methyl-1H-imidazol-2-yl)methylamino)phenyl)benzenesulfonamide;
N-(3-(6-bromo-3H-imidazo[4,5-b]pyridin-2-yl)-5-((1-methyl-1H-imidazol-2-yl)methylamino)phenyl)methanesulfonamide;
2-(5-(benzyloxy)-2-methoxyphenyl)-6-bromo-3H-imidazo[4,5-b]pyridine;
6-bromo-2-(2-(pyridin-3-yloxy)phenyl)-3H-imidazo[4,5-b]pyridine;
6-bromo-2-(3-(2-fluorobenzyloxy)-5-(pyrimidin-2-yloxy)phenyl)-3H-imidazo[4,5-b]pyridine; and
(E)-2-(2-methoxy-5-(2-(pyridin-4-yl)vinyl)phenyl)-3H-imidazo[4,5-b]pyridine.

[14] a prodrug of a compound according to any one of the above [3] to [13];

[15] a pharmaceutical agent comprising a compound according to any one of the above [3] to [13] or a prodrug thereof;

[16] a method for activating glucokinase in a mammal in need thereof, which comprises administering to the mammal a compound according to any one of the above [1] to [13], or a salt or prodrug thereof; and

[17] use of compound according to any one of the above [1] to [13], or a salt or prodrug thereof, for the production of a glucokinase activator; and the like.

BRIEF DESCRIPTION OF THE FIGURES

FIG. 1 illustrates SEQ. ID Nos. 1-5 referred to in this application.

DETAILED DESCRIPTION OF THE INVENTION

The glucokinase activator of the present invention has a superior activity and is useful as a pharmaceutical agent such as an agent for the prophylaxis or treatment of diabetes, obesity and the like.

In the present specification, unless otherwise specified, the "halogen atom" means fluorine atom, chlorine atom, bromine atom or iodine atom.

In the present specification, unless otherwise specified, the "$C_{1-3}$ alkylenedioxy group" means methylenedioxy, ethylenedioxy, trimethylenedioxy or the like.

In the present specification, unless otherwise specified, the "$C_{1-6}$ alkyl group" means methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

In the present specification, unless otherwise specified, the "$C_{1-6}$ alkoxy group" means methoxy, ethoxy, propoxy, isopropoxy, butoxy, isobutoxy, sec-butoxy, tert-butoxy or the like.

In the present specification, unless otherwise specified, the "$C_{1-6}$ alkoxy-carbonyl group" means methoxycarbonyl, ethoxycarbonyl, propoxycarbonyl, tert-butoxycarbonyl or the like.

In the present specification, unless otherwise specified, the "$C_{1-6}$ alkyl-carbonyl group" means acetyl, propanoyl, butanoyl, isobutanoyl, pentanoyl, isopentanoyl, hexanoyl or the like.

Each symbol in the formulas (I) and (II) is described in detail in the following.

$R^1$, $R^2$, $R^3$ and $R^4$ are the same or different and each is a hydrogen atom or a substituent.

As the "substituent" for $R^1$, $R^2$, $R^3$ or $R^4$, an "optionally substituted hydrocarbon group", an "optionally substituted heterocyclic group", an "optionally substituted hydroxy group", an "optionally substituted thiol group", an "optionally substituted amino group", a "cyano group", a "nitro group", an "acyl group", a "halogen atom" and the like can be mentioned.

As the "hydrocarbon group" of the aforementioned "optionally substituted hydrocarbon group", for example, a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-13}$ aralkyl group, a $C_{8-13}$ arylalkenyl group, a $C_{3-10}$ cycloalkyl-$C_{1-6}$ alkyl group and the like can be mentioned.

Here, as the $C_{1-10}$ alkyl group, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like can be mentioned.

As the $C_{2-10}$ alkenyl group, for example, ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like can be mentioned.

As the $C_{2-10}$ alkynyl group, for example, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-hepynyl, 1-octynyl and the like can be mentioned.

As the $C_{3-10}$ cycloalkyl group, for example, cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like can be mentioned.

As the $C_{3-10}$ cycloalkenyl group, for example, 2-cyclopenten-1-yl, 3-cyclopenten-1-yl, 2-cyclohexen-1-yl, 3-cyclohexen-1-yl and the like can be mentioned.

As the $C_{4-10}$ cycloalkadienyl group, for example, 2,4-cyclopentadien-1-yl, 2,4-cyclohexadien-1-yl, 2,5-cyclohexadien-1-yl and the like can be mentioned.

The above-mentioned $C_{3-10}$ cycloalkyl group, $C_{3-10}$ cycloalkenyl group and $C_{4-10}$ cycloalkadienyl group are each optionally condensed with a benzene ring, and as such a fused ring group, for example, indanyl, dihydronaphthyl, tetrahydronaphthyl, fluorenyl and the like can be mentioned.

As the $C_{6-14}$ aryl group, for example, phenyl, naphthyl, anthryl, phenanthryl, acenaphthylenyl biphenylyl and the like can be mentioned. Of these, phenyl, 1-naphthyl, 2-naphthyl and the like are preferable.

As the $C_{7-13}$ aralkyl group, for example, benzyl, phenethyl, naphthylmethyl, biphenylylmethyl and the like can be mentioned.

As the $C_{8-13}$ arylalkenyl group, for example, styryl and the like can be mentioned.

As the $C_{3-10}$ cycloalkyl-$C_{1-6}$ alkyl group, for example, cyclohexylmethyl and the like can be mentioned.

The $C_{1-10}$ alkyl group, $C_{2-10}$ alkenyl group and $C_{2-10}$ alkynyl group, which are exemplarily recited as the aforementioned "hydrocarbon group", each optionally have 1 to 3 substituents at substitutable position(s).

As such substituents, for example, (1) a $C_{3-10}$ cycloalkyl group (e.g., cyclopropyl, cyclohexyl) optionally substituted by 1 to 3 substituents selected from a $C_{1-6}$ alkyl group optionally substituted by 1 to 3 halogen atoms, a hydroxy group, a $C_{1-6}$ alkoxy group, a halogen atom, a thiol group, a $C_{1-6}$ alkyl-carbonyl group, a $C_{1-6}$ alkylsulfonyl group (preferably methylsulfonyl), a $C_{6-14}$ aryloxy group (preferably phenyloxy, naphthyloxy) and a mono- or di-$C_{1-6}$ alkyl-amino group;

(2) a $C_{6-14}$ aryl group (e.g., phenyl, naphthyl) optionally substituted by 1 to 3 substituents selected from a $C_{1-6}$ alkyl group optionally substituted by 1 to 3 halogen atoms, a hydroxy group, a $C_{1-6}$ alkoxy group, a halogen atom, a thiol group, a $C_{1-6}$ alkyl-carbonyl group, a $C_{1-6}$ alkylsulfonyl group (preferably methylsulfonyl), a $C_{6-14}$ aryloxy group (preferably phenyloxy, naphthyloxy) and a mono- or di-$C_{1-6}$ alkyl-amino group;

(3) an aromatic heterocyclic group (e.g., thienyl, furyl, pyridyl, oxazolyl, thiazolyl, tetrazolyl, oxadiazolyl, pyrazinyl, imidazolyl, pyrazolyl, quinolyl, indolyl) optionally substituted by 1 to 3 substituents selected from a $C_{1-6}$ alkyl group optionally substituted by 1 to 3 halogen atoms, a hydroxy group, a $C_{1-6}$ alkoxy group, a halogen atom, a thiol group, a $C_{1-6}$ alkyl-carbonyl group, a $C_{1-6}$ alkylsulfonyl group (preferably methylsulfonyl), a $C_{6-14}$ aryloxy group (preferably phenyloxy, naphthyloxy) and a mono- or di-$C_{1-6}$ alkyl-amino group;

(4) a non-aromatic heterocyclic group (e.g., tetrahydrofuryl, morpholinyl, thiomorpholinyl, piperidinyl, pyrrolidinyl, piperazinyl, dioxolyl, dioxolanyl, 1,3-dihydro-2-benzofuranyl, thiazolidinyl) optionally substituted by 1 to 3 substituents selected from a $C_{1-6}$ alkyl group optionally substituted by 1 to 3 halogen atoms, a hydroxy group, a $C_{1-6}$ alkoxy group, a halogen atom, a thiol group, a $C_{1-6}$ alkyl-carbonyl group, a $C_{1-6}$ alkylsulfonyl group (preferably methylsulfonyl), a $C_{6-14}$ aryloxy group (preferably phenyloxy, naphthyloxy) and a mono- or di-$C_{1-6}$ alkyl-amino group;

(5) an amino group optionally substituted by 1 or 2 substituents selected from
- a $C_{1-6}$ alkyl group optionally substituted by 1 to 3 substituents selected from a $C_{1-6}$ alkoxy group, a $C_{6-14}$ aryloxy group (e.g., phenoxy), a carboxyl group and a $C_{1-6}$ alkoxy-carbonyl group;
- a $C_{7-13}$ aralkyl group (e.g., benzyl);
- a $C_{1-6}$ alkyl-carbonyl group;
- a $C_{1-6}$ alkoxy-carbonyl group;
- a $C_{6-14}$ aryl-carbonyl group (e.g., benzoyl);
- a $C_{7-13}$ aralkyl-carbonyl group (e.g., benzylcarbonyl, phenethylcarbonyl);
- a $C_{1-6}$ alkyl-carbamoyl group (e.g., methylcarbamoyl, ethylcarbamoyl);
- a $C_{6-14}$ aryl-carbamoyl group (e.g., phenylcarbamoyl, 1-naphthylcarbamoyl, 2-naphthylcarbamoyl);
- a $C_{7-13}$ aralkyl-carbamoyl group (e.g., benzylcarbamoyl);
- a $C_{1-6}$ alkylsulfonyl group (e.g., methylsulfonyl, ethylsulfonyl, isopropylsulfonyl);
- a $C_{6-14}$ arylsulfonyl group (e.g., benzenesulfonyl, toluenesulfonyl, 1-naphthalenesulfonyl, 2-naphthalenesulfonyl); and
- a $C_{7-13}$ aralkylsulfonyl group (e.g., benzylsulfonyl);

(6) an amidino group;

(7) a $C_{1-6}$ alkyl-carbonyl group optionally substituted by 1 to 3 halogen atoms;

(8) a $C_{1-6}$ alkoxy-carbonyl group optionally substituted by 1 to 3 halogen atoms;

(9) a $C_{1-6}$ alkylsulfonyl group (e.g., methylsulfonyl)optionally substituted by 1 to 3 halogen atoms;

(10) a carbamoyl group optionally mono- or di-substituted by substituent(s) selected from a $C_{1-6}$ alkyl group optionally substituted by 1 to 3 halogen atoms, a $C_{6-14}$ aryl group (e.g., phenyl), a $C_{7-13}$ aralkyl group (e.g., benzyl) and an aromatic heterocyclyl-$C_{1-6}$ alkyl group (e.g., furfuryl);

(11) a thiocarbamoyl group optionally mono- or di-substituted by $C_{1-6}$ alkyl group(s) optionally substituted by 1 to 3 halogen atoms;

(12) a sulfamoyl group optionally mono- or di-substituted by $C_{1-6}$ alkyl group(s) optionally substituted by 1 to 3 halogen atoms;

(13) a carboxyl group;

(14) a hydroxy group;

(15) a $C_{1-6}$ alkoxy group optionally substituted by 1 to 3 substituents selected from a halogen atom, a carboxyl group, a $C_{1-6}$ alkoxy group and a $C_{1-6}$ alkoxy-carbonyl group;

(16) a $C_{2-6}$ alkenyloxy group (e.g., ethenyloxy) optionally substituted by 1 to 3 halogen atoms;

(17) a $C_{3-10}$ cycloalkyloxy group (e.g., cyclohexyloxy);

(18) a $C_{7-13}$ aralkyloxy group (e.g., benzyloxy);

(19) a $C_{6-14}$ aryloxy group (e.g., phenyloxy, naphthyloxy) optionally substituted by 1 to 3 substituents selected from a cyano group and a halogen atom;

(20) a $C_{1-6}$ alkyl-carbonyloxy group (e.g., acetyloxy, tert-butylcarbonyloxy);

(21) a thiol group;

(22) a $C_{1-6}$ alkylthio group (e.g., methylthio, ethylthio) optionally substituted by 1 to 3 halogen atoms;

(23) a $C_{7-13}$ aralkylthio group (e.g., benzylthio);

(24) a $C_{6-14}$ arylthio group (e.g., phenylthio, naphthylthio);

(25) a sulfo group;

(26) a cyano group;

(27) an azido group;

(28) a nitro group;

(29) a nitroso group;

(30) a halogen atom;

(31) a $C_{1-6}$ alkylsulfinyl group (e.g., methylsulfinyl);

(32) an oxo group;

(33) a $C_{3-10}$ cycloalkyl-$C_{1-6}$ alkyloxy group (e.g., cyclopropylmethyloxy);

(34) a $C_{1-3}$ alkylenedioxy group;

and the like can be mentioned. When the number of the substituents is not less than 2, respective substituents may be the same or different.

The $C_{3-10}$ cycloalkyl group, $C_{3-10}$ cycloalkenyl group, $C_{4-10}$ cycloalkadienyl group, $C_{6-14}$ aryl group, $C_{7-13}$ aralkyl group, $C_{8-13}$ arylalkenyl group and $C_{3-10}$ cycloalkyl-$C_{1-6}$ alkyl group, which are exemplarily recited as the aforementioned "hydrocarbon group", each optionally have 1 to 3 substituents at substitutable position(s).

As such substituents, for example, (1) those exemplarily recited as the substituents of the aforementioned $C_{1-10}$ alkyl group and the like;

(2) a $C_{1-6}$ alkyl group optionally substituted by 1 to 3 substituents selected from a halogen atom, a carboxyl group, a hydroxy group, a $C_{1-6}$ alkoxy-carbonyl group, a $C_{1-6}$ alkyl-carbonyloxy group (e.g., acetyloxy, tert-butylcarbonyloxy), a carbamoyl group and a non-aromatic heterocyclic group (e.g., piperidino);

(3) a $C_{2-6}$ alkenyl group (e.g., ethenyl, 1-propenyl) optionally substituted by 1 to 3 substituents selected from a halogen atom, a carboxyl group, a $C_{1-6}$ alkoxy-carbonyl group and a carbamoyl group; and (4) a $C_{7-13}$ aralkyl group (e.g., benzyl) optionally substituted by 1 to 3 substituents selected from a $C_{1-6}$ alkyl group optionally substituted by 1 to 3 halogen atoms, a hydroxy group, a $C_{1-6}$ alkoxy group and a halogen atom; and the like can be mentioned. When the number of the substituents is not less than 2, respective substituents may be the same or different.

As the "heterocyclic group" of the aforementioned "optionally substituted heterocyclic group", an aromatic heterocyclic group and a non-aromatic heterocyclic group can be mentioned.

Here, as the aromatic heterocyclic group, for example, a 4- to 7-membered (preferably 5- or 6-membered) monocyclic aromatic heterocyclic group containing, as a ring-constituting atom besides carbon atoms, 1 to 4 heteroatoms selected from an oxygen atom, a sulfur atom and a nitrogen atom, and a fused aromatic heterocyclic group can be mentioned. The fused aromatic heterocyclic group, for example, a group wherein the 4- to 7-membered monocyclic aromatic heterocyclic group, and 1 or 2 rings selected from a 5- or 6-membered ring containing 1 or 2 nitrogen atoms, a 5-membered ring containing one sulfur atom, a benzene ring and the like are condensed, and the like can be mentioned.

As preferable examples of the aromatic heterocyclic group, monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-5-yl, 1,2,4-triazin-3-yl, 1,2,4-triazin-6-yl) and the like; fused aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like can be mentioned.

As the non-aromatic heterocyclic group, for example, a 4- to 7-membered (preferably 5- or 6-membered) monocyclic non-aromatic heterocyclic group containing, as a ring-constituting atom besides carbon atoms, 1 to 4 heteroatoms selected from an oxygen atom, a sulfur atom and a nitrogen atom, and a fused non-aromatic heterocyclic group can be mentioned. As the fused non-aromatic heterocyclic group, for example, a group wherein the 4- to 7-membered monocyclic non-aromatic heterocyclic group, and 1 or 2 rings selected from a 5- or 6-membered ring containing 1 or 2 nitrogen atoms, a 5-membered ring containing one sulfur atom, a benzene ring and the like are condensed, and the like can be mentioned.

As preferable examples of the non-aromatic heterocyclic group, monocyclic non-aromatic heterocyclic groups such as pyrrolidinyl (e.g., 1-pyrrolidinyl, 2-pyrrolidinyl), piperidinyl (e.g., piperidino, 2-piperidinyl, 3-piperidinyl, 4-piperidinyl), morpholinyl (e.g., morpholino), thiomorpholinyl (e.g., thiomorpholino), piperazinyl (e.g., 1-piperazinyl, 2-piperazinyl, 3-piperazinyl), hexamethyleneiminyl (e.g., hexamethyleneimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), 2-thioxo-1,3-oxazolidin-5-yl, pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxidotetrahydrothiopyranyl (e.g., 1-oxidotetrahydrothiopyran-4-yl), 1,1-dioxidetetrahydrothiopyranyl (e.g., 1,1-dioxidetetrahydrothiopyran-4-yl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl) and the like; fused non-aromatic heterocyclic groups such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl) and the like can be mentioned.

The "heterocyclic group" of the aforementioned "optionally substituted heterocyclic group" optionally has 1 to 3 substituents at substitutable position(s). As such substituents, for example, those exemplarily recited as the substituents of the $C_{3-10}$ cycloalkyl group and the like exemplarily recited as the "hydrocarbon group" of the aforementioned "optionally substituted hydrocarbon group" can be mentioned. When the number of the substituents is not less than 2, respective substituents may be the same or different.

As the aforementioned "optionally substituted hydroxy group", for example, a hydroxy group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a 5- or 6-membered aromatic heterocyclic group and the like, each of which is optionally substituted, can be mentioned.

Here, as the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group, those exemplarily recited as the "hydrocarbon group" of the aforementioned "optionally substituted hydrocarbon group" can be mentioned.

As the 5- or 6-membered aromatic heterocyclic group, 5- or 6-membered ring groups from among the "aromatic heterocyclic group" exemplarily recited as the "heterocyclic group" of the aforementioned "optionally substituted heterocyclic group" can be mentioned.

The aforementioned $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group, $C_{1-6}$ alkyl-carbonyl group and 5- or 6-membered aromatic heterocyclic group each optionally have 1 to 3 substituents at substitutable position(s). When the number of the substituents is not less than 2, respective substituents may be the same or different.

As the substituents of the $C_{1-10}$ alkyl group, $C_{2-10}$ alkenyl group and $C_{1-6}$ alkyl-carbonyl group, those exemplarily recited as the substituents of the $C_{1-10}$ alkyl group and the like exemplarily recited as the "hydrocarbon group" of the aforementioned "optionally substituted hydrocarbon group" can be mentioned.

As the substituents of the $C_{3-10}$ cycloalkyl group, $C_{3-10}$ cycloalkenyl group, $C_{6-14}$ aryl group, $C_{7-13}$ aralkyl group, $C_{8-13}$ arylalkenyl group and 5- or 6-membered aromatic heterocyclic group, those exemplarily recited as the substituents of the $C_{3-10}$ cycloalkyl group and the like exemplarily recited as the "hydrocarbon group" of the aforementioned "optionally substituted hydrocarbon group" can be mentioned.

As the aforementioned "optionally substituted thiol group", for example, a thiol group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a 5- or 6-membered aromatic heterocyclic group and the like, each of which is optionally substituted, can be mentioned.

As the substituents, those exemplarily recited as the substituents of the aforementioned "optionally substituted hydroxy group" can be mentioned.

As the aforementioned "optionally substituted amino group", for example, an amino group optionally mono- or di-substituted by substituent(s) selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group and a $C_{8-13}$ arylalkenyl group, each of which is optionally substituted; an acyl group and the like, can be mentioned.

Here, as the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group, those exemplarily recited as the "hydrocarbon group" of the aforementioned "optionally substituted hydrocarbon group" can be mentioned.

The aforementioned $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group each optionally have 1 to 3 substituents at substitutable position(s). When the number of the substituents is not less than 2, respective substituents may be the same or different.

Here, as the substituents of the $C_{1-10}$ alkyl group and $C_{2-10}$ alkenyl group, those exemplarily recited as the substituents of the $C_{1-10}$ alkyl group and the like exemplarily recited as the "hydrocarbon group" of the aforementioned "optionally substituted hydrocarbon group" can be mentioned.

As the substituents of the $C_{3-10}$ cycloalkyl group, $C_{3-10}$ cycloalkenyl group, $C_{6-14}$ aryl group, $C_{7-13}$ aralkyl group and $C_{8-13}$ arylalkenyl group, those exemplarily recited as the substituents of the $C_{3-10}$ cycloalkyl group and the like exemplarily recited as the "hydrocarbon group" of the aforementioned "optionally substituted hydrocarbon group" can be mentioned.

As the "acyl group" exemplarily recited as the substituent of the "optionally substituted amino group" and as the "substituent" for $R^1$, $R^2$, $R^3$ or $R^4$, for example, a group represented by the formula: $-COR^a$, $-CO-OR^a$, $-SO_2R^a$, $-SOR^a$, $-CO-NR^{a'}R^{b'}$ or $-CS-NR^{a'}R^{b'}$ wherein $R^a$ is a hydrogen atom, an optionally substituted hydrocarbon group or an optionally substituted heterocyclic group, and $R^{a'}$ and $R^{b'}$ are the same or different and each is a hydrogen atom, an optionally substituted hydrocarbon group or an optionally substituted heterocyclic group, or $R^{a'}$ and $R^{b'}$ optionally form, together with the adjacent nitrogen atom, an optionally substituted nitrogen-containing heterocycle, and the like can be mentioned.

As the "optionally substituted hydrocarbon group" and "optionally substituted heterocyclic group" for $R^a$, $R^{a'}$ or $R^{b'}$, those exemplarily recited as the "optionally substituted hydrocarbon group" and "optionally substituted heterocyclic group", which are those exemplarily recited as the "substituent" for $R^1$, $R^2$, $R^3$ or $R^4$ can be mentioned.

As the "nitrogen-containing heterocycle" of the "optionally substituted nitrogen-containing heterocycle" formed by $R^{a'}$ and $R^{b'}$ together with the adjacent nitrogen atom, for example, a 5- to 7-membered nitrogen-containing heterocycle containing, as a ring-constituting atom besides carbon atoms, at least one nitrogen atom and optionally further containing one or two heteroatoms selected from an oxygen atom, a sulfur atom and a nitrogen atom can be mentioned. As preferable examples of the nitrogen-containing heterocycle, pyrrolidine, imidazolidine, pyrazolidine, piperidine, piperazine, morpholine, thiomorpholine, oxopiperazine and the like can be mentioned.

The nitrogen-containing heterocycle optionally has 1 to 3 (preferably 1 or 2) substituents at substitutable position(s). As such substituents, those exemplarily recited as the substituents of the $C_{3-10}$ cycloalkyl group and the like exemplarily recited as the "hydrocarbon group" of the aforementioned "optionally substituted hydrocarbon group" can be mentioned. When the number of the substituents is not less than 2, respective substituents may be the same or different.

As preferable examples of the "acyl group", (1) a formyl group;
(2) a carboxyl group;
(3) a $C_{1-6}$ alkyl-carbonyl group;
(4) a $C_{1-6}$ alkoxy-carbonyl group optionally substituted by 1 to 3 substituents selected from a carboxyl group, a carbamoyl group, a thiocarbamoyl group, a $C_{1-6}$ alkoxy-carbonyl group and a $C_{1-6}$ alkyl-carbonyloxy group;
(5) a $C_{3-10}$ cycloalkyl-carbonyl group (e.g., cyclopentylcarbonyl, cyclohexylcarbonyl);
(6) a $C_{6-14}$ aryl-carbonyl group (e.g., benzoyl, 1-naphthoyl, 2-naphthoyl) optionally substituted by 1 to 3 substituents selected from a halogen atom, a cyano group, an optionally halogenated $C_{1-6}$ alkyl group (i.e., a $C_{1-6}$ alkyl group optionally substituted by 1 to 3 halogen atoms), a $C_{1-6}$ alkoxy group, a carboxyl group, a $C_{1-6}$ alkoxy-carbonyl group and a carbamoyl group;
(7) a $C_{6-14}$ aryloxy-carbonyl group (e.g., phenyloxycarbonyl, naphthyloxycarbonyl) optionally substituted by 1 to 3 substituents selected from a carboxyl group, a $C_{1-6}$ alkoxy-carbonyl group and a carbamoyl group;
(8) a $C_{7-13}$ aralkyloxy-carbonyl group optionally substituted by 1 to 3 substituents selected from a carboxyl group, a carbamoyl group, a thiocarbamoyl group, a $C_{1-6}$ alkoxy-carbonyl group, a halogen atom, a cyano group, a nitro group, a $C_{1-6}$ alkoxy group, a $C_{1-6}$ alkylsulfonyl group and a $C_{1-6}$ alkyl group (e.g., benzyloxycarbonyl, phenethyloxycarbonyl; carboxybenzyloxycarbonyl; methoxycarbonylbenzyloxycarbonyl; biphenylylmethoxycarbonyl);

(9) a carbamoyl group optionally mono- or di-substituted by $C_{1-6}$ alkyl group(s) optionally substituted by 1 to 3 substituents selected from a halogen atom and a $C_{1-6}$ alkoxy group (e.g., methylcarbamoyl, ethylcarbamoyl, dimethylcarbamoyl, diethylcarbamoyl, ethylmethylcarbamoyl, propylcarbamoyl, isopropylcarbamoyl, butylcarbamoyl, isobutylcarbamoyl, trifluoroethylcarbamoyl, N-methoxyethyl-N-methylcarbamoyl);

(10) a $C_{1-6}$ alkylsulfonyl group optionally substituted by 1 to 3 substituents selected from a carboxyl group, a carbamoyl group and a $C_{1-6}$ alkoxy-carbonyl group (e.g., methylsulfonyl, carboxymethylsulfonyl);

(11) a $C_{1-6}$ alkylsulfinyl group (e.g., methylsulfinyl);

(12) a thiocarbamoyl group;

(13) a $C_{7-13}$ aralkyl-carbonyl group (e.g., benzylcarbonyl, phenethylcarbonyl);

(14) an aromatic heterocyclyl (e.g., furyl, thienyl, oxazolyl, thiazolyl, isoxazolyl, isothiazolyl, pyrazolyl, pyridyl, pyrazinyl, benzofuranyl, benzothienyl, quinoxalinyl)-carbonyl group (e.g., furylcarbonyl, thienylcarbonyl, thiazolylcarbonyl, pyrazolylcarbonyl, pyridylcarbonyl, pyrazinylcarbonyl, benzofuranylcarbonyl, benzothienylcarbonyl, quinoxalinylcarbonyl) optionally substituted by 1 to 3 substituents selected from a $C_{1-6}$ alkyl group, a $C_{6-14}$ aryl group, a $C_{7-13}$ aralkyl group, a $C_{1-6}$ alkoxy group, a carboxyl group, a $C_{1-6}$ alkoxy-carbonyl group and a carbamoyl group;

(15) a $C_{6-14}$ arylsulfonyl group (e.g., phenylsulfonyl);

(16) a $C_{7-13}$ aralkylsulfonyl group (e.g., benzylsulfonyl);

(17) an aromatic heterocyclylsulfonyl group (e.g., thienylsulfonyl); and the like can be mentioned.

$R^1$, $R^2$, $R^3$ and $R^4$ are each preferably a hydrogen atom, an optionally substituted hydrocarbon group, an optionally substituted heterocyclic group, a cyano group, an acyl group, a halogen atom or the like. More preferably, both $R^1$ and $R^2$ are hydrogen atoms or the like, $R^3$ is a hydrogen atom, an optionally substituted hydrocarbon group, an optionally substituted heterocyclic group, an acyl group, a halogen atom or the like, particularly preferably (1) a hydrogen atom;

(2) a $C_{6-14}$ aryl group (preferably phenyl) optionally substituted by 1 to 3 substituents selected from
  (a) a halogen atom (preferably fluorine atom, bromine atom),
  (b) a $C_{1-6}$ alkyl group (preferably methyl) optionally substituted by 1 to 3 halogen atoms (preferably fluorine atom),
  (c) a $C_{1-6}$ alkoxy group (preferably methoxy),
  (d) a hydroxy group, and the like;

(3) a $C_{1-6}$ alkyl group (preferably methyl) optionally substituted by 1 to 3 substituents selected from
  (a) an amino group optionally substituted by 1 or 2 substituents selected from
    (i) a $C_{1-6}$ alkyl group (preferably methyl, ethyl, isobutyl) optionally substituted by 1 to 3 substituents selected from a $C_{1-6}$ alkoxy group (preferably methoxy), a $C_{6-14}$ aryloxy group (preferably phenoxy), a carboxyl group, a $C_{1-6}$ alkoxy-carbonyl group (preferably methoxycarbonyl, ethoxycarbonyl) and the like,
    (ii) a $C_{7-13}$ aralkyl group (preferably benzyl), and the like,
  (b) a hydroxy group, and the like;

(4) an optionally substituted aromatic heterocyclic group (preferably pyridyl);

(5) a formyl group;

(6) a carboxyl group;

(7) a $C_{1-6}$ alkoxy-carbonyl group (preferably methoxycarbonyl, ethoxycarbonyl);

(8) a halogen atom (preferably chlorine atom, bromine atom); or the like, and $R^4$ is a hydrogen atom, an optionally substituted hydrocarbon group, a cyano group, an acyl group or the like, particularly preferably (1) a hydrogen atom;

(2) a $C_{1-6}$ alkyl group (preferably methyl) optionally substituted by 1 to 3 substituents selected from
  (a) a hydroxy group,
  (b) a carboxyl group,
  (c) a $C_{1-6}$ alkoxy-carbonyl group (preferably methoxycarbonyl, ethoxycarbonyl),
  (d) a halogen atom (preferably chlorine atom),
  (e) a cyano group, and the like;

(3) a cyano group;

(4) a carboxyl group;

(5) a $C_{1-6}$ alkoxy-carbonyl group (preferably methoxycarbonyl, ethoxycarbonyl); or the like.

Ring A is an optionally substituted phenyl group.

The "phenyl group" of the "optionally substituted phenyl group" for ring A optionally has 1 to 3 substituents at substitutable position(s). As such substituents, those exemplarily recited as the aforementioned "substituent" for $R^1$, $R^2$, $R^3$ or $R^4$ can be mentioned. Of these, an "optionally substituted hydrocarbon group", an "optionally substituted heterocyclic group", an "optionally substituted hydroxy group", an "optionally substituted amino group", a "halogen atom", an "optionally substituted thiol group", a "nitro group", an "acyl group" and the like are preferable. When the number of the substituents is not less than 2, respective substituents may be the same or different.

As preferable substituents, (1) a group represented by —$OR^5$ or —$OR^6$ wherein $R^5$ and $R^6$ are the same or different and each is an optionally substituted $C_{1-6}$ alkyl group, provided that when the alkyl group is a $C_{1-2}$ alkyl group, then the $C_{1-2}$ alkyl group should be substituted by optionally substituted cyclic group(s);

(2) a halogen atom;

(3) a $C_{1-6}$ alkyl group (preferably methyl) optionally substituted by 1 to 3 $C_{6-14}$ aryloxy groups (preferably phenoxy) optionally substituted by 1 to 3 substituents selected from a cyano group and a halogen atom;

(4) an aromatic heterocyclic group (preferably pyrazolyl, pyridyl) optionally substituted by 1 to 3 substituents selected from a $C_{1-6}$ alkyl group (preferably methyl) and a halogen atom;

(5) an amino group optionally mono- or di-substituted by substituent(s) selected from
  (a) a $C_{6-14}$ aryl group (preferably phenyl) optionally substituted by 1 to 3 substituents selected from a $C_{1-6}$ alkoxy group (preferably methoxy) and a $C_{1-6}$ alkyl group (preferably methyl);
  (b) a $C_{1-6}$ alkyl group optionally substituted by 1 to 3 $C_{1-6}$ alkoxy groups;
  (c) a $C_{7-13}$ aralkyl group (preferably benzyl) optionally substituted by 1 to 3 substituents selected from a $C_{1-6}$ alkyl group (preferably methyl), a $C_{1-6}$ alkoxy group (preferably methoxy) and a halogen atom;
  (d) an aromatic heterocyclyl(preferably imidazolyl, pyrazolyl, pyridyl)-$C_{1-6}$ alkyl group optionally substituted by 1 to 3 substituents selected from a $C_{1-6}$ alkyl group (preferably methyl), a $C_{1-6}$ alkoxy group (preferably methoxy) and a halogen atom;

(e) a $C_{1-6}$ alkyl-carbonyl group;

(f) a $C_{6-14}$ aryl-carbonyl group (preferably benzoyl) optionally substituted by 1 to 3 halogen atoms;

(g) a $C_{7-13}$ aralkyl-carbonyl group (preferably benzylcarbonyl);

(h) an aromatic heterocyclylcarbonyl group (preferably furylcarbonyl) optionally substituted by 1 to 3 $C_{1-6}$ alkyl groups;

(i) a $C_{1-6}$ alkylsulfonyl group (preferably methylsulfonyl);

(j) a $C_{6-14}$ arylsulfonyl group (preferably phenylsulfonyl);

(k) a $C_{7-13}$ aralkylsulfonyl group (preferably benzylsulfonyl); and (l) an aromatic heterocyclylsulfonyl group (preferably thienylsulfonyl);

(6) a $C_{1-2}$ alkoxy group (e.g., methoxy, ethoxy);

(7) a $C_{6-14}$ aryloxy group (preferably phenoxy) optionally substituted by 1 to 3 $C_{1-6}$ alkylsulfonyl groups (preferably methylsulfonyl);

(8) a 5- or 6-membered aromatic heterocyclyloxy group (preferably pyrimidinyloxy);

(9) a 5- or 6-membered aromatic heterocyclylthio group (preferably imidazolylthio) optionally substituted by 1 to 3 $C_{1-6}$ alkyl groups;

(10) a nitro group;

(11) a carbamoyl group optionally mono- or di-substituted by a $C_{6-14}$ aryl group (e.g., phenyl) and a $C_{7-13}$ aralkyl group (e.g., benzyl); and the like can be mentioned, and a group represented by —$OR^5$ or —$OR^6$ wherein $R^5$ and $R^6$ are as defined above, and the like are more preferable.

The "$C_{1-6}$ alkyl group" of the "optionally substituted $C_{1-6}$ alkyl group, provided that when the alkyl group is a $C_{1-2}$ alkyl group, then the $C_{1-2}$ alkyl group should be substituted by optionally substituted cyclic group(s)" for $R^5$ or $R^6$, optionally has 1 to 3 substituents at substitutable position(s). As such substituents, those exemplarily recited as the substituents of the $C_{1-10}$ alkyl group and the like exemplarily recited as the aforementioned "substituent" for $R^1$, $R^2$, $R^3$ or $R^4$ can be mentioned. When the number of the substituents is not less than 2, respective substituents may be the same or different.

As preferable substituents, a $C_{1-6}$ alkoxy group, an optionally substituted cyclic group and the like can be mentioned. As the cyclic group, for example, a $C_{3-10}$ cycloalkyl group (e.g., cyclopropyl, cyclohexyl), a $C_{6-14}$ aryl group (e.g., phenyl, naphthyl), an aromatic heterocyclic group (e.g., thienyl, furyl, pyridyl, oxazolyl, thiazolyl, tetrazolyl, oxadiazolyl, imidazolyl, isoxazolyl, triazolyl, thiadiazolyl, pyrazinyl, quinolyl, indolyl), a non-aromatic heterocyclic group (e.g., tetrahydrofuryl, morpholinyl, thiomorpholinyl, piperidinyl, pyrrolidinyl, piperazinyl, dioxolyl, dioxolanyl, 1,3-dihydro-2-benzofuranyl, thiazolidinyl, tetrahydropyranyl) and the like can be mentioned.

The above-mentioned cyclic group is preferably a $C_{6-14}$ aryl group (preferably phenyl, naphthyl), a $C_{3-10}$ cycloalkyl group (preferably cyclopropyl, cyclohexyl), a 5- or 6-membered aromatic heterocyclic group (preferably thienyl, pyridyl, imidazolyl, oxazolyl, isoxazolyl, thiazolyl, triazolyl, thiadiazolyl, pyrazinyl), a 5- or 6-membered non-aromatic heterocyclic group (e.g., tetrahydrofuryl, morpholinyl, piperidinyl, piperazinyl, tetrahydropyranyl) or the like.

The above-mentioned cyclic group optionally has 1 to 3 substituents at substitutable position(s). As such substituents, for example a $C_{1-6}$ alkyl group optionally substituted by 1 to 3 halogen atoms, a hydroxy group, a $C_{1-6}$ alkoxy group, a halogen atom, a thiol group, a $C_{1-6}$ alkyl-carbonyl group, a $C_{1-6}$ alkylsulfonyl group (preferably methylsulfonyl), a $C_{6-14}$ aryloxy group (preferably phenyloxy, naphthyloxy), a mono- or di-$C_{1-6}$ alkyl-amino group and the like can be mentioned. Of these, a halogen atom is preferable. When the number of the substituents is not less than 2, respective substituents may be the same or different.

The "optionally substituted $C_{1-6}$ alkyl group, provided that when the alkyl group is a $C_{1-2}$ alkyl group, then the $C_{1-2}$ alkyl group should be substituted by optionally substituted cyclic group(s)" for $R^5$ or $R^6$ is preferably (1) a $C_{1-6}$ alkyl group substituted by optionally substituted cyclic group(s), (2) a $C_{3-6}$ alkyl group optionally substituted by 1 to 3 substituents selected from a $C_{1-6}$ alkoxy group and a $C_{6-14}$ aryloxy group (e.g., phenyloxy, naphthyloxy) optionally substituted by 1 to 3 substituents selected from a cyano group and a halogen atom, or the like, more preferably (1) a $C_{1-6}$ alkyl group (preferably methyl, ethyl, propyl) substituted by 1 to 3 substituents selected from (a) a $C_{6-14}$ aryl group (preferably phenyl, naphtyl), (b) a $C_{3-10}$ cycloalkyl group (preferably cyclopropyl, cyclohexyl), (c) a 5- or 6-membered aromatic heterocyclic group (preferably thienyl, pyridyl, imidazolyl, oxazolyl, isoxazolyl, thiazolyl, triazolyl, thiadiazolyl, pyrazinyl), and (d) a 5- or 6-membered non-aromatic heterocyclic group (e.g., tetrahydrofuryl, morpholinyl, piperidinyl, piperazinyl, tetrahydropyranyl)

(each of the above-mentioned (a) to (d) is optionally substituted by 1 to 3 substituents selected from a halogen atom, a $C_{1-6}$ alkyl group, a $C_{1-6}$ alkoxy group, a thiol group, a $C_{1-6}$ alkyl-carbonyl group, a $C_{1-6}$ alkylsulfonyl group (preferably methylsulfonyl), a $C_{6-14}$ aryloxy group (preferably phenyloxy, naphthyloxy), a mono- or di-$C_{1-6}$ alkyl-amino group), and the like;

(2) a $C_{3-6}$ alkyl group (preferably isopropyl) optionally substituted by 1 to 3 substituents selected from a $C_{1-6}$ alkoxy group and a $C_{6-14}$ aryloxy group (e.g., phenyloxy, naphthyloxy) optionally substituted by 1 to 3 substituents selected from a cyano group and a halogen atom; or the like.

The substituents for ring A is more preferably a group represented by —$OR^5$ or —$OR^6$ wherein $R^5$ and $R^6$ are the same or different and each is (1) a $C_{1-6}$ alkyl group substituted by an optionally substituted cyclic group and the like, (2) a $C_{3-6}$ alkyl group optionally substituted by 1 to 3 substituents selected from a $C_{1-6}$ alkoxy group and a $C_{6-14}$ aryloxy group (e.g., phenyloxy, naphthyloxy) optionally substituted by 1 to 3 substituents selected from a cyano group and a halogen atom, or the like, particularly preferably a group represented by —$OR^5$ or —$OR^6$ wherein $R^5$ and $R^6$ are the same or different and each is (1) a $C_{1-6}$ alkyl group (preferably methyl, ethyl, propyl) substituted by 1 to 3 substituents selected from (a) a $C_{6-14}$ aryl group (preferably phenyl, naphtyl), (b) a $C_{3-10}$ cycloalkyl group (preferably cyclopropyl, cyclohexyl), (c) a 5- or 6-membered aromatic heterocyclic group (preferably thienyl, pyridyl, imidazolyl, oxazolyl, isoxazolyl, thiazolyl, triazolyl, thiadiazolyl, pyrazinyl), and (d) a 5- or 6-membered non-aromatic heterocyclic group (e.g., tetrahydrofuryl, morpholinyl, piperidinyl, piperazinyl, tetrahydropyranyl)

(each of the above-mentioned (a) to (d) is optionally substituted by 1 to 3 substituents selected from a halogen atom, a $C_{1-6}$ alkyl group, a $C_{1-6}$ alkoxy group, a thiol group, a $C_{1-6}$ alkyl-carbonyl group, a $C_{1-6}$ alkylsulfonyl group (preferably methylsulfonyl), a $C_{6-14}$ aryloxy group (preferably phenyloxy, naphthyloxy), a mono- or di-$C_{1-6}$ alkyl-amino group), and the like;

(2) a $C_{3-6}$ alkyl group (preferably isopropyl) optionally substituted by 1 to 3 substituents selected from a $C_{1-6}$ alkoxy group and a $C_{6-14}$ aryloxy group (e.g., phenyloxy, naphthyloxy) optionally substituted by 1 to 3 substituents selected from a cyano group and a halogen atom; or the like.

Ring A is preferably substituted by the above-mentioned substituent(s).

Preferable examples of Compound (I) include a compound wherein ring A is a phenyl group optionally substituted by 1 to 3 substituents selected from (1) a group represented by —$OR^5$ or —$OR^6$ wherein $R^5$ and $R^6$ are as defined above;

(2) a halogen atom;

(3) a $C_{1-6}$ alkyl group (preferably methyl) optionally substituted by 1 to 3 $C_{6-14}$ aryloxy groups (preferably phenoxy) optionally substituted by 1 to 3 substituents selected from a cyano group and a halogen atom;

(4) an aromatic heterocyclic group (preferably pyrazolyl, pyridyl) optionally substituted by 1 to 3 substituents selected from a $C_{1-6}$ alkyl group (preferably methyl) and a halogen atom;

(5) an amino group optionally mono- or di-substituted by substituent(s) selected from
- (a) a $C_{6-14}$ aryl group (preferably phenyl) optionally substituted by 1 to 3 substituents selected from a $C_{1-6}$ alkoxy group (preferably methoxy) and a $C_{1-6}$ alkyl group (preferably methyl);
- (b) a $C_{1-6}$ alkyl group optionally substituted by 1 to 3 $C_{1-6}$ alkoxy groups;
- (c) a $C_{7-13}$ aralkyl group (preferably benzyl) optionally substituted by 1 to 3 substituents selected from a $C_{1-6}$ alkyl group (preferably methyl), a $C_{1-6}$ alkoxy group (preferably methoxy) and a halogen atom;
- (d) an aromatic heterocyclyl(preferably imidazolyl, pyrazolyl, pyridyl)-$C_{1-6}$ alkyl group optionally substituted by 1 to 3 substituents selected from a $C_{1-6}$ alkyl group (preferably methyl), a $C_{1-6}$ alkoxy group (preferably methoxy) and a halogen atom;
- (e) a $C_{1-6}$ alkyl-carbonyl group;
- (f) a $C_{6-14}$ aryl-carbonyl group (preferably benzoyl) optionally substituted by 1 to 3 halogen atoms;
- (g) a $C_{7-13}$ aralkyl-carbonyl group (preferably benzylcarbonyl);
- (h) an aromatic heterocyclylcarbonyl group (preferably furylcarbonyl) optionally substituted by 1 to 3 $C_{1-6}$ alkyl groups;
- (i) a $C_{1-6}$ alkylsulfonyl group (preferably methylsulfonyl);
- (j) a $C_{6-14}$ arylsulfonyl group (preferably phenylsulfonyl);
- (k) a $C_{7-13}$ aralkylsulfonyl group (preferably benzylsulfonyl); and
- (l) an aromatic heterocyclylsulfonyl group (preferably thienylsulfonyl);

(6) a $C_{1-2}$ alkoxy group (e.g., methoxy, ethoxy);

(7) a $C_{6-14}$ aryloxy group (preferably phenoxy) optionally substituted by 1 to 3 $C_{1-6}$ alkylsulfonyl groups (preferably methylsulfonyl);

(8) a 5- or 6-membered aromatic heterocyclyloxy group (preferably pyrimidinyloxy);

(9) a 5- or 6-membered aromatic heterocyclylthio group (preferably imidazolylthio) optionally substituted by 1 to 3 $C_{1-6}$ alkyl groups;

(10) a nitro group;

(11) a carbamoyl group optionally mono- or di-substituted by a $C_{6-14}$ aryl group (e.g., phenyl) and a $C_{7-13}$ aralkyl group (e.g., benzyl); or the like.

Preferable examples of Compound (I) further include a compound wherein ring A is a phenyl group optionally substituted by 1 to 3 substituents selected from (1) a group represented by —$OR^5$ or —$OR^6$ wherein $R^5$ and $R^6$ are as defined above;

(2) a halogen atom;

(3) a $C_{1-6}$ alkyl group (preferably methyl) optionally substituted by 1 to 3 $C_{6-14}$ aryloxy groups (preferably phenoxy);

(4) an aromatic heterocyclic group (preferably pyrazolyl) optionally substituted by 1 to 3 $C_{1-6}$ alkyl groups (preferably methyl);

(5) an amino group optionally mono- or di-substituted by $C_{6-14}$ aryl group(s) (preferably phenyl) optionally substituted by 1 to 3 $C_{1-6}$ alkoxy groups (preferably methoxy); and (6) a $C_{1-2}$ alkoxy group (e.g., methoxy, ethoxy); or the like.

Compound (I) is more preferably compound (II), (Ip), (Iq), (Ir), (Is), (It) or the like.

Compound (II) is preferably a compound wherein $R^1$, $R^2$, $R^3$ and $R^4$ are the same or different and each is a hydrogen atom, an optionally substituted hydrocarbon group, an optionally substituted heterocyclic group, a cyano group, an acyl group or a halogen atom; and $R^5$ and $R^6$ are the same or different and each is (1) a $C_{1-6}$ alkyl group substituted by optionally substituted cyclic group(s), or (2) a $C_{3-6}$ alkyl group optionally substituted by 1 to 3 substituents selected from a $C_{1-6}$ alkoxy group and a $C_{6-14}$ aryloxy group (e.g., phenyloxy, naphthyloxy) optionally substituted by 1 to 3 substituents selected from a cyano group and a halogen atom, or the like.

Preferable examples of Compound (II) include a compound wherein both $R^1$ and $R^2$ are hydrogen atoms;

$R^3$ is a hydrogen atom, an optionally substituted hydrocarbon group, an optionally substituted heterocyclic group, an acyl group or a halogen atom, [preferably (1) a hydrogen atom;

(2) a $C_{6-14}$ aryl group (preferably phenyl) optionally substituted by 1 to 3 substituents selected from
- (a) a halogen atom (preferably fluorine atom, bromine atom),
- (b) a $C_{1-6}$ alkyl group (preferably methyl) optionally substituted by 1 to 3 halogen atoms (preferably fluorine atom),
- (c) a $C_{1-6}$ alkoxy group (preferably methoxy), and
- (d) a hydroxy group;

(3) a $C_{1-6}$ alkyl group (preferably methyl) optionally substituted by 1 to 3 substituents selected from
- (a) an amino group optionally substituted by 1 or 2 substituents selected from
  - (i) a $C_{1-6}$ alkyl group (preferably methyl, ethyl, isobutyl) optionally substituted by 1 to 3 substituents selected from a $C_{1-6}$ alkoxy group (preferably methoxy), a $C_{6-14}$ aryloxy group (preferably phenoxy), a carboxyl group and a $C_{1-6}$ alkoxy-carbonyl group (preferably methoxycarbonyl, ethoxycarbonyl), and
  - (ii) a $C_{7-13}$ aralkyl group (preferably benzyl), and
- (b) a hydroxy group;

(4) an optionally substituted aromatic heterocyclic group (preferably pyridyl);

(5) a formyl group;

(6) a carboxyl group;

(7) a $C_{1-6}$ alkoxy-carbonyl group (preferably methoxycarbonyl, ethoxycarbonyl); or (8) a halogen atom (preferably chlorine atom, bromine atom)];

$R^4$ is a hydrogen atom, an optionally substituted hydrocarbon group, a cyano group or an acyl group, preferably
(1) a hydrogen atom;
(2) a $C_{1-6}$ alkyl group (preferably methyl) optionally substituted by 1 to 3 substituents selected from
  (a) a hydroxy group,
  (b) a carboxyl group,
  (c) a $C_{1-6}$ alkoxy-carbonyl group (preferably methoxycarbonyl, ethoxycarbonyl),
  (d) a halogen atom (preferably chlorine atom), and
  (e) a cyano group;
(3) a cyano group;
(4) a carboxyl group; or
(5) a $C_{1-6}$ alkoxy-carbonyl group (preferably methoxycarbonyl, ethoxycarbonyl); and
$R^5$ and $R^6$ are the same or different and each is
(1) a $C_{1-6}$ alkyl group (preferably methyl, ethyl, propyl) substituted by 1 to 3 substituents selected from
  (a) a $C_{6-14}$ aryl group (preferably phenyl, naphtyl),
  (b) a $C_{3-10}$ cycloalkyl group (preferably cyclopropyl, cyclohexyl),
  (c) a 5- or 6-membered aromatic heterocyclic group (preferably thienyl, pyridyl, imidazolyl, oxazolyl, isoxazolyl, thiazolyl, triazolyl, thiadiazolyl, pyrazinyl), and
  (d) a 5- or 6-membered non-aromatic heterocyclic group (e.g., tetrahydrofuryl, morpholinyl, piperidinyl, piperazinyl, tetrahydropyranyl)
(each of the above-mentioned (a) to (d) is optionally substituted by 1 to 3 substituents selected from a halogen atom, a $C_{1-6}$ alkyl group, a $C_{1-6}$ alkoxy group, a thiol group, a $C_{1-6}$ alkyl-carbonyl group, a $C_{1-6}$ alkylsulfonyl group (preferably methylsulfonyl), a $C_{6-14}$ aryloxy group (preferably phenyloxy, naphthyloxy), a mono- or di-$C_{1-6}$ alkyl-amino group); or
(2) a $C_{3-6}$ alkyl group (preferably isopropyl) optionally substituted by 1 to 3 substituents selected from a $C_{1-6}$ alkoxy group and a $C_{6-14}$ aryloxy group (e.g., phenyloxy, naphthyloxy) optionally substituted by 1 to 3 substituents selected from a cyano group and a halogen atom; or the like.

Preferable examples of Compound (II) further include a compound wherein
both $R^1$ and $R^2$ are hydrogen atoms;
$R^3$ is a hydrogen atom, an optionally substituted hydrocarbon group, an optionally substituted heterocyclic group, an acyl group or a halogen atom, preferably
(1) a hydrogen atom;
(2) a $C_{6-14}$ aryl group (preferably phenyl) optionally substituted by 1 to 3 substituents selected from
  (a) a halogen atom (preferably fluorine atom, bromine atom),
  (b) a $C_{1-6}$ alkyl group (preferably methyl) optionally substituted by 1 to 3 halogen atoms (preferably fluorine atom),
  (c) a $C_{1-6}$ alkoxy group (preferably methoxy), and
  (d) a hydroxy group;
(3) a $C_{1-6}$ alkyl group (preferably methyl) optionally substituted by 1 to 3 substituents selected from
  (a) an amino group optionally substituted by 1 or 2 substituents selected from
    (i) a $C_{1-6}$ alkyl group (preferably methyl, ethyl, isobutyl) optionally substituted by 1 to 3 substituents selected from a $C_{1-6}$ alkoxy group (preferably methoxy), a $C_{6-14}$ aryloxy group (preferably phenoxy), a carboxyl group and a $C_{1-6}$ alkoxy-carbonyl group (preferably methoxycarbonyl, ethoxycarbonyl), and
    (ii) a $C_{7-13}$ aralkyl group (preferably benzyl), and
  (b) a hydroxy group;
(4) an optionally substituted aromatic heterocyclic group (preferably pyridyl);
(5) a formyl group;
(6) a carboxyl group;
(7) a $C_{1-6}$ alkoxy-carbonyl group (preferably methoxycarbonyl, ethoxycarbonyl); or
(8) a halogen atom (preferably chlorine atom, bromine atom);
$R^4$ is a hydrogen atom, an optionally substituted hydrocarbon group, a cyano group or an acyl group, preferably
(1) a hydrogen atom;
(2) a $C_{1-6}$ alkyl group (preferably methyl) optionally substituted by 1 to 3 substituents selected from
  (a) a hydroxy group,
  (b) a carboxyl group,
  (c) a $C_{1-6}$ alkoxy-carbonyl group (preferably methoxycarbonyl, ethoxycarbonyl),
  (d) a halogen atom (preferably chlorine atom), and
  (e) a cyano group;
(3) a cyano group;
(4) a carboxyl group; or
(5) a $C_{1-6}$ alkoxy-carbonyl group (preferably methoxycarbonyl, ethoxycarbonyl); and
$R^5$ and $R^6$ are the same or different and each is
(1) a $C_{1-6}$ alkyl group (preferably methyl) substituted by 1 to 3 substituents selected from
  (a) a $C_{6-14}$ aryl group (preferably phenyl),
  (b) a $C_{3-10}$ cycloalkyl group (preferably cyclopropyl, cyclohexyl), and
  (c) a 5- or 6-membered aromatic heterocyclic group (preferably thienyl, pyridyl)
(each of the above-mentioned (a) to (c) is optionally substituted by 1 to 3 halogen atoms); or
(2) a $C_{3-6}$ alkyl group (preferably isopropyl); or the like.

Of compounds (I), compound (II) is a novel compound.

As a salt of compound (I) [hereinafter including compounds (II), (Ip), (Iq), (Ir), (Is) and (It)], a pharmacologically acceptable salt is preferable. Examples of such a salt include a salt with inorganic base, a salt with organic base, a salt with inorganic acid, a salt with organic acid, a salt with basic or acidic amino acid, and the like.

Preferable examples of the salt with inorganic base include alkali metal salts such as sodium salt, potassium salt and the like; alkaline earth metal salts such as calcium salt, magnesium salt and the like; aluminum salt; ammonium salt and the like.

Preferable examples of the salt with organic base include a salt with trimethylamine, triethylamine, pyridine, picoline, ethanolamine, diethanolamine, triethanolamine, dicyclohexylamine, N,N-dibenzylethylenediamine or the like.

Preferable examples of the salt with inorganic acid include a salt with hydrochloric acid, hydrobromic acid, nitric acid, sulfuric acid, phosphoric acid or the like.

Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid or the like.

Preferable examples of the salt with basic amino acid include a salt with arginine, lysine, ornithine or the like.

Preferable examples of the salt with acidic amino acid include a salt with aspartic acid, glutamic acid or the like.

A prodrug of compound (I) is a compound that converts to compound (I) due to the reaction by enzyme, gastric acid and the like under the physiological conditions in the body; that is, a compound that converts to compound (I) by enzymatic oxidation, reduction, hydrolysis and the like, and a compound that converts to compound (I) by hydrolysis and the like by gastric acid and the like. Examples of a prodrug of compound (I) include a compound wherein an amino group of compound (I) is acylated, alkylated or phosphorylated (e.g., a compound where an amino group of compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated); a compound wherein a hydroxy group of compound (I) is acylated, alkylated, phosphorylated or borated (e.g., a compound where a hydroxy group of compound (I) is acetylated, palmitoylated, propanoylated, pivaloylated, succinylated, fumarylated, alanylated or dimethylaminomethylcarbonylated); a compound wherein a carboxyl group of compound (I) is esterified or amidated (e.g., a compound where a carboxyl group of compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified or methylamidated) and the like. These compounds can be produced from compound (I) according to a method known per se.

A prodrug of compound (I) may be a compound that converts to compound (I) under physiological conditions as described in Development of Pharmaceutical Products, vol. 7, Molecule Design, pp. 163-198, Hirokawa Shoten (1990).

Compound (I) may be labeled with an isotope (e.g., $^3$H, $^{14}$C, $^{35}$S, $^{125}$I and the like) and the like.

Compound (I) may be an anhydride or a hydrate.

The compound (I) or a prodrug thereof (hereinafter sometimes to be simply abbreviated as the compound of the present invention) shows low toxicity, and can be used as it is or as a pharmaceutical composition in admixture with a commonly known pharmaceutically acceptable carrier etc., as an agent for the prophylaxis or treatment of the below-mentioned various disease in mammals (e.g., humans, mice, rats, rabbits, dogs, cats, bovines, horses, pigs, monkeys).

Here, as the pharmacologically acceptable carrier, various organic or inorganic carrier substances conventionally used as a preparation material can be used. They are incorporated as excipient, lubricant, binder and disintegrant for solid preparations; solvent, dissolution aids, suspending agent, isotonicity agent, buffer and soothing agent for liquid preparations and the like. Where necessary, preparation additives such as preservatives, antioxidants, coloring agents, sweetening agents and the like can be used.

As preferable examples of the excipient, lactose, sucrose, D-mannitol, D-sorbitol, starch, α-starch, dextrin, crystalline cellulose, low-substituted hydroxypropylcellulose, sodium carboxymethylcellulose, gum arabic, pullulan, light anhydrous silicic acid, synthetic aluminum silicate, magnesium alumino metasilicate and the like can be mentioned.

As preferable examples of the lubricant, magnesium stearate, calcium stearate, talc, colloidal silica and the like can be mentioned.

As preferable examples of the binder, α-starch, saccharose, gelatin, gum arabic, methylcellulose, carboxymethylcellulose, carboxymethylcellulose sodium, crystalline cellulose, sucrose, D-mannitol, trehalose, dextrin, pullulan, hydroxypropylcellulose, hydroxypropylmethylcellulose, polyvinylpyrrolidone and the like can be mentioned.

As preferable examples of the disintegrant, lactose, sucrose, starch, carboxymethylcellulose, carboxymethylcellulose calcium, croscarmellose sodium, carboxymethylstarch sodium, light anhydrous silicic acid, low-substituted hydroxypropylcellulose and the like can be mentioned.

As preferable examples of the solvent, water for injection, physiological brine, Ringer solution, alcohol, propylene glycol, polyethylene glycol, sesame oil, corn oil, olive oil, cottonseed oil and the like can be mentioned.

As preferable examples of the dissolution aids, polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like can be mentioned.

As preferable examples of the suspending agent, surfactants such as stearyltriethanolamine, sodium lauryl sulfate, laurylaminopropionic acid, lecithin, benzalkonium chloride, benzethonium chloride, glycerol monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; polysorbates, polyoxyethylene hydrogenated castor oil, and the like can be mentioned.

As preferable examples of the isotonicity agent, sodium chloride, glycerin, D-mannitol, D-sorbitol, glucose and the like can be mentioned.

As preferable examples of the buffer, buffers such as phosphate, acetate, carbonate, citrate and the like, and the like can be mentioned.

As preferable examples of the soothing agent, benzyl alcohol and the like can be mentioned.

As preferable examples of the preservative, p-oxybenzoates, chlorobutanol, benzyl alcohol, phenethyl alcohol, dehydroacetic acid, sorbic acid and the like can be mentioned.

As preferable examples of the antioxidant, sulfite, ascorbate and the like can be mentioned.

As preferable examples of the coloring agent, water-soluble food tar colors (e.g., food colors such as Food Red Nos. 2 and 3, Food Yellow Nos. 4 and 5, Food Blue Nos. 1 and 2 and the like), water insoluble lake dye (e.g., aluminum salts of the aforementioned water-soluble food tar colors), natural dyes (e.g., β-carotene, chlorophyll, red iron oxide) and the like can be mentioned.

As preferable examples of the sweetening agent, saccharin sodium, dipotassium glycyrrhizinate, aspartame, stevia and the like can be mentioned.

As the dosage form of the aforementioned pharmaceutical composition, for example, oral preparation such as tablets (including sublingual tablet, orally disintegrating tablet), capsules (including soft capsule, microcapsule), granule, powder, troche, syrup, emulsion, suspension and the like; and parenteral preparation such as injections (e.g., subcutaneous injection, intravenous injection, intramuscular injection, intraperitoneal injection, drip infusion), external preparations (e.g., dermal preparation, ointment), suppositories (e.g., rectal suppository, vaginal suppository), pellets, transnasal preparations, pulmonary preparations (inhalant), eye drops and the like can be mentioned. They can be safely administered orally or parenterally.

These preparations may be controlled-release preparations (e.g., sustained-release microcapsule) such as immediate-release preparation, sustained-release preparation and the like.

The pharmaceutical composition can be produced by a method conventionally used in the preparation technical field, such as a method described in the Japanese Pharmacopoeia and the like.

While the content of the compound of the present invention in the pharmaceutical composition varies depending on the dosage form, the dose of the compound of the present invention and the like, it is, for example, about 0.1 to 100 wt %.

The compound of the present invention has a superior GK activating action, and can be used as an agent for the prophylaxis or treatment of various diseases in mammals (e.g., human, bovine, horse, dog, cat, monkey, mouse, rat). In addition, since the compound of the present invention has a selective GK activating action, it shows low toxicity (e.g., acute toxicity, chronic toxicity, cardiotoxicity, carcinogenicity, genetic toxicity) and a fewer side effects.

The compound of the present invention can be used, for example, as an agent for the prophylaxis or treatment of diabetes (e.g., type-1 diabetes, type-2 diabetes, gestational diabetes, obesity diabetes etc.); an agent for the prophylaxis or treatment of hyperlipidemia (e.g., hypertriglyceridemia, hypercholesterolemia, hypo-HDL-emia, postprandial hyperlipidemia); an agent for the prophylaxis or treatment of arteriosclerosis; an agent for the prophylaxis or treatment of impaired glucose tolerance (IGT); and an agent for preventing progress of impaired glucose tolerance into diabetes.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) and WHO reported new diagnostic criteria of diabetes.

According to these reports, diabetes is a condition showing a fasting blood glucose level (glucose concentration of intravenous plasma) of not less than 126 mg/dl and a 75 g oral glucose tolerance test 2 h level (glucose concentration of intravenous plasma) of not less than 200 mg/dl.

According to the above-mentioned reports of ADA and WHO, impaired glucose tolerance is a condition showing a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 100 mg/dl and less than 126 mg/dl is called IFG (Impaired Fasting Glucose). On the other hand, WHO defines the IFG (Impaired Fasting Glucose) to be a condition showing a fasting blood glucose level (glucose concentration of intravenous plasma) of not less than 110 mg/dl and less than 126 mg/dl, and calls it IFG (Impaired Fasting Glycaemia).

The compound of the present invention can be also used as an agent for the prophylaxis or treatment of diabetes, borderline type, impaired glucose tolerance, IFG (Impaired Fasting Glucose) and IFG (Impaired Fasting Glycaemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycaemia) into diabetes.

The compound of the present invention can also be used as an agent for the prophylaxis or treatment of, for example, diabetic complications [e.g., neuropathy, nephropathy, retinopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], obesity, osteoporosis, cachexia (e.g., cancerous cachexia, tuberculosis cachexia, diabetic cachexia, blood disease cachexia, endocrine disease cachexia, infectious disease cachexia or cachexia due to acquired immunodeficiency syndrome), fatty liver, hypertension, polycystic ovary syndrome, kidney disease (e.g., diabetic nephropathy, glomerular nephritis, glomerulosclerosis, nephrotic syndrome, hypertensive nephrosclerosis, end stage kidney disease), muscular dystrophy, myocardial infarction, angina pectoris, cerebrovascular accident (e.g., cerebral infarction, cerebral apoplexy), glucose metabolism abnormality, lipid metabolism abnormality, insulin resistance syndrome, Syndrome X, metabolic syndrome (pathology having at least one of type 2 diabetes, impaired glucose tolerance and insulin resistance in combination with at least two or more of obesity, lipid metabolism abnormality, hypertension and trace albumin urine), Cushing's syndrome, hyperinsulinemia, hyperinsulinemia-induced sensory disorder; tumor (e.g., leukemia, breast cancer, prostate cancer, skin cancer), irritable bowel syndrome, acute or chronic diarrhea, inflammatory diseases (e.g., chronic rheumatoid arthritis, spondylitis deformans, osteoarthritis, lumbago, gout, postoperative or traumatic inflammation, swelling, neuralgia, pharyngolaryngitis, cystitis, hepatitis (inclusive of nonalcoholic steatohepatitis), pneumonia, pancreatitis, inflammatory bowel disease, ulcerative colitis, stomach mucous membrane injury (including stomach mucous membrane caused by aspirin)), visceral obesity syndrome and the like.

The compound of the present invention can also be used for improvement of insulin resistance, promotion or increase of insulin secretion, reduction of visceral fat, inhibition of visceral fat accumulation, glycometabolism improvement, lipometabolism improvement, oxidized LDL production inhibition, lipoprotein metabolism improvement, coronary metabolism improvement, prophylaxis or treatment of cardiovascular complications, prophylaxis or treatment of heart failure complications, decrease of blood remnant, prophylaxis or treatment of anovulation, prophylaxis or treatment of hirsutism, prophylaxis or treatment of hyperandrogenemia, pancreas (β cell) function improvement, pancreas (β cell) regeneration, promotion of pancreas (β cell) regeneration and the like.

The compound of the present invention can also be used as secondary prevention and suppression of progression of the above-mentioned various diseases (e.g., cardiovascular events such as cardiac infarction and the like).

The compound of the present invention is particularly useful as an agent for the prophylaxis or treatment of type 2 diabetes, obesity diabetes and the like.

While the dose of the compound of the present invention varies depending on the administration subject, administration route, target disease, condition and the like, for example, it is generally about 0.01 to 100 mg/kg body weight, preferably 0.05 to 30 mg/kg body weight, more preferably 0.1 to 10 mg/kg body weight, for oral administration to adult diabetic patients, which is desirably administered in one to three portions a day.

The compound of the present invention can be used in combination with pharmaceutical agents (hereinafter to be abbreviated as combination drug) such as therapeutic agents for diabetes, therapeutic agents for diabetic complications, therapeutic agents for hyperlipidemia, antihypertensive agents, antiobesity agents, diuretics, chemotherapeutic agents, immunotherapeutic agents, antithrombotic agents, therapeutic agents for osteoporosis, antidementia agents, erectile dysfunction ameliorating agents, therapeutic agents for urinary incontinence or pollakiuria, therapeutic agents for dysuria and the like. The administration time of the compound of the present invention and the combination drug is not restricted, and these can be administered to an administration subject simultaneously, or may be administered at staggered times. Moreover, the compound of the present invention and a combination drug may be administered as two kinds of preparations containing respective active ingredients or may be administered as a single preparation containing both active ingredients.

The dose of the combination drug can be appropriately determined based on the dose employed clinically. The mixing ratio of the compound of the present invention and a combination drug can be appropriately determined depending on the administration subject, administration route, target disease, symptom, combination and the like. When the administration subject is human, for example, a combination drug can be used in 0.01 to 100 parts by weight relative to 1 part by weight of the compound of the present invention.

As the therapeutic agents for diabetes, for example, insulin preparations (e.g., animal insulin preparations extracted from pancreas of bovine and swine; human insulin preparations genetically synthesized using *Escherichia coli*, yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Netoglitazone, Edaglitazone (BM-13.1258), Rivoglitazone (CS-011), FK-614, the compound described in WO01/38325, Tesaglitazar (AZ-242), Ragaglitazar (NN-622), Muraglitazar (BMS-298585), Metaglidasen (MBX-102), Naveglitazar (LY-519818), MX-6054, LY-510929, Balaglitazone (NN-2344), T-131 or a salt thereof, THR-0921), PPARγ agonist, PPARγ antagonist, PPARγ/α dual agonist, α-glucosidase inhibitors (e.g., voglibose, acarbose, miglitol, emiglitate etc.), biguanides (e.g., phenformin, metformin, buformin or a salt thereof (e.g., hydrochloride, fumarate, succinate)), insulin secretagogues [sulfonylurea (e.g., tolbutamide, glibenclamide, gliclazide, chlorpropamide, tolazamide, acetohexamide, glyclopyramide, glimepiride, glipizide, glybuzole), repaglinide, senaglinide, nateglinide, mitiglinide or calcium salt hydrate thereof], GPR40 agonists, GLP-1 receptor agonists [e.g., GLP-1, GLP-1MR agent, NN-2211, AC-2993 (exendin-4), BIM-51077, Aib(8,35)hGLP-1(7,37)NH$_2$, CJC-1131], amylin agonists (e.g., pramlintide), phosphotyrosine phosphatase inhibitors (e.g., sodium vanadate), dipeptidyl peptidase IV inhibitors (e.g., NVP-DPP-278, PT-100, P32/98, Vildagliptin (LAF-237), P93/01, TS-021, Sitagliptin phosphate (MK-431), Saxagliptin (BMS-477118), E-3024, T-6666 (TA-6666), 823093, 825964, 815541), β3 agonists (e.g., AJ-9677), gluconeogenesis inhibitors (e.g., glycogen phosphorylase inhibitors, glucose-6-phosphatase inhibitors, glucagon antagonists), SGLT (sodium-glucose cotransporter) inhibitors (e.g., T-1095), 11β-HSD1 inhibitors (e.g., BVT-3498), adiponectin or agonists thereof, IKK inhibitors (e.g., AS-2868), leptin resistance improving drugs, somatostatin receptor agonists (compounds described in WO01/25228, WO03/42204, WO98/44921, WO98/45285, WO99/22735) and the like can be mentioned.

Examples of the therapeutic agents for diabetic complications include aldose reductase inhibitors (e.g., Tolrestat, Epalrestat, Zenarestat, Zopolrestat, Minalrestat, Fidarestat, CT-112), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy)propyl]oxazole), neuranagenesis stimulator (e.g., Y-128), PKC inhibitors (e.g., ruboxistaurin mesylate)), AGE inhibitors (e.g., ALT946, pimagedine, N-phenacylthiazolium bromide (ALT-766), ALT-711, EXO-226, Pyridorin, Pyridoxamine), active oxygen scavengers (e.g., thioctic acid), cerebral vasodilators (e.g., tiapuride, mexiletine), somatostatin receptor agonist (e.g., BIM23190), apoptosis signal regulating kinase-1 (ASK-1) inhibitors and the like.

Examples of the therapeutic agents for hyperlipidemia include HMG-CoA reductase inhibitors (e.g., pravastatin, simvastatin, lovastatin, atorvastatin, fluvastatin, pitavastatin, rosuvastatin or a salt thereof (e.g., sodium salt, calcium salt)), squalene synthase inhibitors (e.g., compounds described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), ACAT inhibitors (e.g., Avasimibe), Eflucimibe)), anion exchange resins (e.g., colestyramine), probucol, nicotinic acid drugs (e.g., nicomol, niceritrol)), ethyl icosapentate, plant sterol (e.g., soysterol), γ-oryzanol) and the like.

Examples of the antihypertensive agents include angiotensin converting enzyme inhibitors (e.g., captopril, enalapril, delapril), angiotensin II receptor antagonists (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium antagonists (e.g., manidipine, nifedipine, amlodipine, efonidipine, nicardipine), potassium channel openers (e.g., levcromakalim, L-27152, AL0671, NIP-121), clonidine and the like.

Examples of the antiobesity agents include antiobesity agents acting on the central nervous system (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonists (e.g., CP-422935); cannabinoid receptor antagonists (e.g., SR-141716, SR-147778); ghrelin antagonists; pancreatic lipase inhibitors (e.g., orlistat, ATL-962), β3 agonists (e.g., AJ-9677), peptidic anorexiants (e.g., leptin, CNTF (Ciliary Neurotropic Factor)), cholecystokinin agonists (e.g., lintitript, FPL-15849), feeding deterrents (e.g., P-57) and the like.

Examples of the diuretics include xanthine derivatives (e.g., sodium salicylate and theobromine, calcium salicylate and theobromine), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonate dehydratase inhibitors (e.g., acetazolamide), chlorobenzenesulfonamide preparations (e.g., chlortalidone, mefruside, indapamide), azosemide, isosorbide, etacrynic acid, piretanide, bumetanide, furosemide and the like.

Examples of the chemotherapeutic agents include alkylating agents (e.g., cyclophosphamide, ifosfamide), metabolic antagonists (e.g., methotrexate, 5-fluorouracil and a derivative thereof), antitumor antibiotics (e.g., mitomycin, adriamycin), plant-derived antitumor agent (e.g., vincristine, vindesine, Taxol), cisplatin, carboplatin, etoposide and the like.

Of these, Furtulon or NeoFurtulon, which are 5-fluorouracil derivatives, and the like are preferable.

Examples of the immunotherapeutic agents include microorganism or bacterial components (e.g., muramyl dipeptide derivative, Picibanil), polysaccharides having immunity potentiating activity (e.g., lentinan, schizophyllan, krestin), cytokines obtained by genetic engineering techniques (e.g., interferon, interleukin (IL)), colony stimulating factors (e.g., granulocyte colony stimulating factor, erythropoietin) and the like, with preference given to interleukins such as IL-1, IL-2, IL-12 and the like.

Examples of the antithrombotic agents include heparin (e.g., heparin sodium, heparin calcium, dalteparin sodium), warfarin (e.g., warfarin potassium), anti-thrombin drugs (e.g., aragatroban), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride) and the like.

Examples of the therapeutic agents for osteoporosis include alfacalcidol, calcitriol, elcatonin, calcitonin salmon, estriol, ipriflavone, risedronate disodium, pamidronate disodium, alendronate sodium hydrate, incadronate disodium and the like.

Examples of the antidementia agents include tacrine, donepezil, rivastigmine, galanthamine and the like.

Examples of the erectile dysfunction ameliorating agents include apomorphine, sildenafil citrate and the like.

Examples of the therapeutic agents for urinary incontinence or pollakiuria include flavoxate hydrochloride, oxybutynin hydrochloride, propiverine hydrochloride and the like.

Examples of the therapeutic agents for dysuria include acetylcholine esterase inhibitors (e.g., distigmine) and the like.

Furthermore, drugs having a cachexia-ameliorating action established in animal models and clinical situations, such as cyclooxygenase inhibitors (e.g., indomethacin), progesterone derivatives (e.g., megestrol acetate), glucosteroids (e.g., dexamethasone), metoclopramide agents, tetrahydrocannabinol agents, fat metabolism improving agents (e.g., eicosapentanoic acid), growth hormones, IGF-1, or antibodies to a cachexia-inducing factor such as TNF-α, LIF, IL-6, oncostatin M and the like can be used in combination with the compound of the present invention.

The combination drug is preferably an insulin preparation, an insulin sensitizer, an α-glucosidase inhibitor, biguanide, insulin secretagogue (preferably sulfonylurea) and the like.

The above-mentioned combination drugs may be used in a mixture of two or more kinds thereof at an appropriate ratio.

When the compound of the present invention is used in combination with a combination drug, the dose of each agent can be reduced within a safe range in consideration of the side effects thereof. Particularly, the doses of insulin sensitizers, insulin secretagogues (preferably sulfonylurea) and biguanides can be reduced from generally dose levels. Therefore, the side effects possibly caused by these agents can be safely prevented. In addition, the doses of the therapeutic agents for diabetic complications, the therapeutic agents for hyperlipidemia and the antihypertensive agents can be reduced, and as a result, the side effects possibly caused by these agents can be effectively prevented.

The production methods of compound (I) are explained in the following.

Compound (I) can be produced according to a method known per se, for example, the method described in Comprehensive Heterocyclic Chemistry II, vol. 7, pages 313-316 (1996), and the like.

To be specific, compound (I) can be produced, for example, according to the following Production method 1-a, 1-b, 2, 3, 4-a, 4-b, 5, 6 or 7.

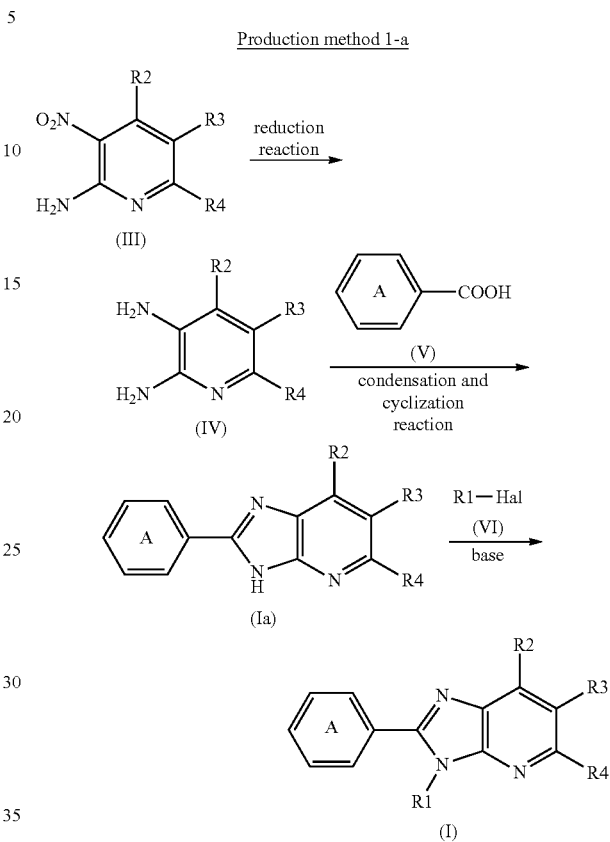

Production method 1-a wherein Hal is a halogen atom, and other symbols are as defined above.

In this method, compound (IV) is first produced by subjecting the nitro group of compound (III) to a reduction reaction. For the reduction reaction, conventional methods such as reduction using a combination of iron powder and a suitable acid (e.g., hydrochloric acid), catalytic reduction by hydrogenation in the presence of a palladium catalyst, and the like can be employed.

The amount of the iron powder to be used is generally about 1 mol to 100 mol, preferably about 10 mol to 30 mol, per 1 mol of compound (III). The amount of the acid to be used is generally about 1 mol to 100 mol, preferably about 10 mol to 30 mol, per 1 mol of compound (III).

The reduction reaction is generally carried out in a solvent (e.g., ethanol) that does not adversely influence the reaction.

The reaction temperature is generally 0° C. to about 100° C. The reaction time is generally 30 min. to 8 hr. For the reduction reaction using iron, the reaction is preferably carried out in ethanol at 80° C. for several hours.

Then, compound (I) wherein $R^1$ is a hydrogen atom, i.e., compound (Ia), can be produced by subjecting compound (IV) and compound (V) to a condensation and cyclization reaction.

The condensation and cyclization reaction is carried out, for example, by 1) a method comprising heating with stirring in polyphoric ester (PPE), 2) a method comprising heating with stirring in methanesulfonic acid in the presence of a suitable amount of diphosphorus pentaoxide, 3) a method comprising heating with stirring in phosphorus oxychloride, and the like.

The amount of compound (V) to be used is generally about 1 mol to 2 mol, preferably about 1 mol to 1.1 mol, per 1 mol of compound (VI).

The reaction temperature is room temperature to 180° C., preferably 100° C. to 140° C. The reaction time is generally 1 hr to 12 hr.

Then, compound (I) can be produced by reacting compound (Ia) with compound (VI) in a solvent that does not adversely influence the reaction, in the presence of a base.

As the "solvent that does not adversely influence the reaction", for example, ethers (e.g., ethyl ether, dioxane, dimethoxyethane, tetrahydrofuran), aromatic hydrocarbons (e.g., benzene, toluene), amides (e.g., dimethylformamide, dimethylacetamide), halogenated hydrocarbons (e.g., chloroform, dichloromethane) and the like can be mentioned. Two or more kinds of these solvents can be mixed in an appropriate ratio and used.

As the "base", for example, inorganic bases such as sodium carbonate, sodium hydrogencarbonate, potassium carbonate, potassium hydrogencarbonate, sodium hydroxide, potassium hydroxide, thallium hydroxide, sodium hydride and the like; organic bases such as triethylamine, pyridine, 2-tert-butyl-imino-2-diethylamino-1,3-dimethylperhydro-1,3,2-diazaphosphorin (BEMP), BEMP resin and the like; and the like can be mentioned. The amount of the base to be used is generally about 1 mol to 10 mol, preferably about 1 mol to 3 mol, per 1 mol of compound (Ia).

The amount of compound (VI) to be used is generally about 1 mol to 10 mol, preferably about 1 mol to 2 mol, per 1 mol of compound (Ia).

The reaction temperature is 0° C. to 100° C., preferably room temperature to 50° C. The reaction time is generally 1 hr to 24 hr.

Compound (III), compound (V) and compound (VI), which are used as starting material compounds in Production method 1-a, can be produced according to a method known per se.

Compound (Ia) can also be produced according to the following Production method 1-b.

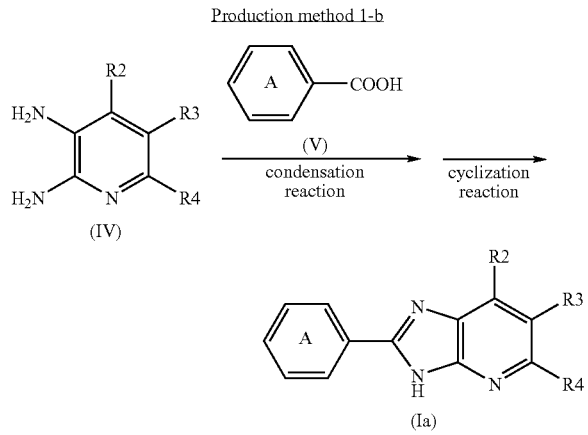

Production method 1-b wherein each symbol is as defined above.

In this method, compound (Ia) can be produced by subjecting compound (IV) and compound (V) to a conventional condensation reaction in a solvent that does not adversely influence the reaction, in the presence of, where desired, a base and subjecting the obtained compound to a cyclization reaction.

In the condensation reaction, compound (IV) may be used as a reactive derivative at an amino group thereof, and as the "reactive derivative at the amino group of compound (IV)", for example, a Schiff base type imino or enamine type tautomer thereof produced by the reaction of compound (IV) and a carbonyl compound (e.g., aldehyde, ketone); a silyl derivative produced by the reaction of compound (IV) and a silyl compound (e.g., bis(trimethylsilyl)acetamide, mono(trimethylsilyl)acetamide, bis(trimethylsilyl)urea); a derivative produced by the reaction of compound (IV) and phosphorus trichloride or phosgene, and the like can be mentioned. These reactive derivatives can be freely selected according to the kind of compound (IV).

Compound (V) may be used as a reactive derivative at the carboxyl group thereof, and as the "reactive derivative at the carboxyl group of compound (V)", for example, acid chlorides, acid anhydrides, activated amides, activated esters and the like can be mentioned. To be specific, acid chlorides; acid azides; mixed acid anhydrides with acid selected from substituted phosphoric acids (e.g., dialkylphosphoric acids, phenylphosphoric acid, diphenylphosphoric acid, dibenzylphosphoric acid, halogenated phosphoric acids), dialkylphosphorous acids, sulfurous acid, thiosulfuric acid, sulfuric acid, sulfonic acids (e.g., methanesulfonic acid), aliphatic carboxylic acids (e.g., acetic acid, propionic acid, butyric acid, isobutyric acid, pivalic acid, pentanoic acid, isopentanoic acid, trichloroacetic acid), aromatic carboxylic acids (e.g., benzoic acid) and the like, or mixed acid anhydrides with chlorocarbonates (e.g., methyl chlorocarbonate, ethyl chlorocarbonate, isobutyl chlorocarbonate); symmetric acid anhydrides; activated amides with imidazole, 4-substituted imidazoles, dimethylpyrazole, triazole or tetrazole; activated esters (e.g., cyanomethyl ester, methoxymethyl ester, dimethyliminomethyl ester, vinyl ester, propargyl ester, p-nitrophenyl ester, trichlorophenyl ester, pentachlorophenyl ester, mesylphenyl ester, phenylazophenyl ester, phenyl thioester, p-nitrophenyl ester, p-cresyl thioester, carboxymethyl thioester, pyranyl ester, pyridyl ester, piperidyl ester, 8-quinolyl thioester), or esters with N-hydroxy compounds (e.g., N,N-dimethylhydroxyamine, 1-hydroxy-2-(1H)-pyridone, N-hydroxysuccinimide, N-hydroxyphthalimide, 1-hydroxy-1H-benzotriazol), and the like can be mentioned. These reactive derivatives can be freely selected according to the kind of compound (V).

When compound (V) is converted to a mixed acid anhydride with chlorocarbonate (e.g., methyl chlorocarbonate, ethyl chlorocarbonate, isobutyl chlorocarbonate), the reaction is carried out in the presence of a base (e.g., triethylamine, N-methylmorpholine, N,N-dimethylaniline, sodium hydrogencarbonate, sodium carbonate, potassium carbonate).

The reactive derivative of compound (V) may be used as a salt and, as preferable salts, for example, alkali metal salts such as sodium salt, potassium salt and the like; alkaline earth metal salts such as calcium salt, magnesium salt and the like; ammonium salt; organic base salts such as trimethylamine salt, triethylamine salt, pyridine salt, picoline salt, dicyclohexylamine salt, N,N-dibenzylethylenediamine salt and the like; and the like can be mentioned.

As the "solvent that does not adversely influence the reaction", for example, water, alcohols (e.g., methanol, ethanol), acetone, dioxane, acetonitrile, chloroform, methylene chloride, ethylene chloride, tetrahydrofuran, ethyl acetate, N,N-dimethylformamide, pyridine and the like can be mentioned. Two or more kinds of these solvents can be mixed in an appropriate ratio and used.

As the "base", for example, organic bases such as triethylamine, pyridine, 4-dimethylaminopyridine, diisopropylethylamine and the like; inorganic bases such as sodium carbonate, potassium carbonate and the like, and the like can be mentioned. The amount of the base to be used is generally about 1 mol to 10 mol, preferably about 1 mol to 3 mol, per 1 mol of compound (V).

The amount of compound (IV) to be used is generally 1 to 10 mol, preferably 1 to 3 mol, per 1 mol of compound (V).

The reaction temperature is generally −30° C. to 100° C. The reaction time is generally 0.5 to 20 hr.

In this reaction, when compound (V) is used in the form of a free acid or a salt thereof, the reaction is desirably carried out in the presence of a condensing agent and, as the condensing agent, for example, carbodiimides such as N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide and the like; N,N'-carbonylbis(2-methylimidazole); pentamethyleneketene-N-cyclohexylimine; diphenylketene-N-cyclohexylimine; ethoxyacetylene; 1-alkoxy-1-chloroethylene; trialkyl phosphites; alkyl polyphosphates such as ethyl polyphosphate, isopropyl polyphosphates and the like; phosphorus oxychloride; diphenylphosphoryl azide; thionyl chloride; oxalyl chloride; lower alkyl haloformates such as ethyl chloroformate, isopropyl chloroformate and the like; triphenylphosphine; 2-ethyl-7-hydroxybenzisoxazolium salt, 2-ethyl-5-(m-sulfophenyl)isoxazolium hydroxide inner salt; N-hydroxybenzotriazol; 1-(p-chlorobenzenesulfonyloxy)-6-chloro-1H-benzotriazol; what is called the Vilsmeier reagent prepared by reacting N,N'-dimethylformamide and thionyl chloride, phosgene, trichloromethyl chloroformate, phosphorus oxychloride and the like; and the like can be mentioned. The amount of the condensing agent to be used is generally about 1 mol to 5 mol, preferably about 1 mol to 2 mol, per 1 mol of compound (V).

The cyclization reaction is carried out, for example, by a method comprising stirring with heating in formic acid, acetic acid or trifluoroacetic acid, or a mixed solvent of these acids and alcohol, a method comprising irradiation of microwave and the like. The amount of the acid to be used is 3 ml per 1 mmol of the reaction substrate.

The reaction temperature is generally about 50° C. to about 200° C. The reaction time is generally 5 min to 24 hr.

According to the following Production method 2, compound (Ic) (compound (I) wherein $R^1$ is a hydrogen atom, one of $R^2$, $R^3$ and $R^4$ is Q (Q is an optionally substituted $C_{6-14}$ aryl group or an optionally substituted aromatic heterocyclic group), and the others are hydrogen atoms) can be produced from compound (Ib) (compound (I) wherein $R^1$ is a hydrogen atom, one of $R^2$, $R^3$ and $R^4$ is a halogen atom, and the others are hydrogen atoms).

Here, as the "optionally substituted $C_{6-14}$ aryl group" and "optionally substituted aromatic heterocyclic group" for Q, the "optionally substituted hydrocarbon group" and "optionally substituted heterocyclic group" exemplarily recited as the aforementioned "substituent" for $R^1$, $R^2$, $R^3$ or $R^4$, wherein the hydrocarbon group and heterocyclic group are each a $C_{6-14}$ aryl group and an aromatic heterocyclic group can be mentioned.

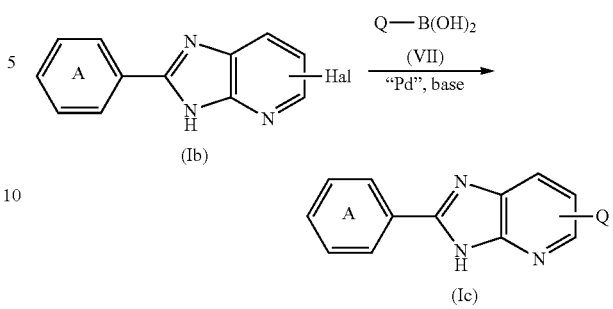

wherein each symbol is as defined above.

In this method, compound (Ic) can be produced by reacting compound (Ib) with compound (VII) in a solvent (e.g., toluene, tetrahydrofuran, dimethoxyethane) that does not adversely influence the reaction, in the presence of a palladium catalyst (e.g., tetrakistriphenylphosphine palladium) and a base, under an inert gas atmosphere.

As the "base", for example, inorganic bases such as sodium carbonate, sodium hydrogencarbonate, potassium carbonate, potassium hydrogencarbonate, sodium hydroxide, potassium hydroxide, thallium hydroxide and the like; organic bases such as triethylamine, pyridine and the like, and the like can be mentioned. The amount of the base to be used is generally about 2 mol to 20 mol, preferably about 5 mol to 12 mol, per 1 mol of compound (Ib).

The amount of the palladium catalyst to be used is a catalytic amount.

The amount of the compound (VII) to be used is 1 mol to a slightly excess amount per 1 mol of compound (Ib).

The reaction temperature is generally room temperature to about 100° C. The reaction time is generally 1 hr to 12 hr.

Compound (VII), which is used as a starting material compound in Production method 2, can be produced according to a method known per se. In addition, compound (Ib) can be produced, for example, according to Production method 1-a or 1-b mentioned above.

Compound (Ic) can also be produced according to in the following Production method 3.

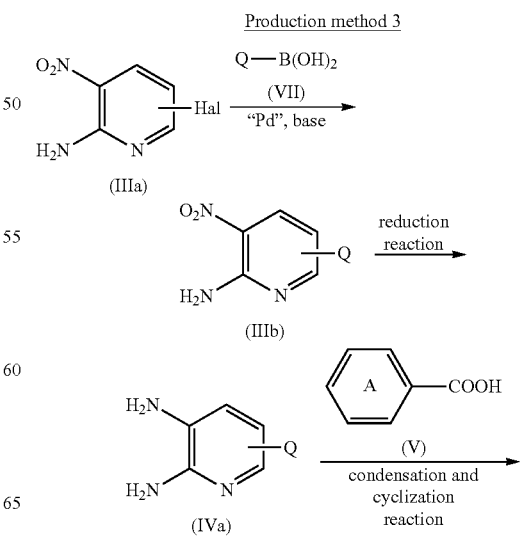

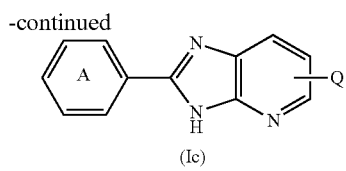

wherein each symbol is as defined above.

In this method, compound (IIIb) can be produced by reacting compound (IIIa) with compound (VII) in a solvent that does not adversely influence the reaction, in the presence of a palladium catalyst and a base, under an inert gas atmosphere. This reaction is carried out in the same manner as in Production method 2 mentioned above.

Then, compound (IVa) can be produced by subjecting the nitro group of compound (IIIb) to a reduction reaction. This reaction is carried out in the same manner as in the reduction reaction of compound (III) in Production method 1-a mentioned above.

Compound (Ic) can be produced by subjecting compound (IVa) and compound (V) to a condensation and cyclization reaction. This reaction is carried out in the same manner as in the condensation and cyclization reaction of compound (IV) and compound (V) in Production method 1-a mentioned above.

Compound (IIIa), which is used as a starting material compound in Production method 3, can be produced according to a method known per se.

Compound (Ig) (compound (I) wherein $R^1$, $R^2$ and $R^3$ are hydrogen atoms and $R^4$ is a carboxyl group) can be produced according to a method described in J. Am. Chem. Soc. (Journal of American Chemical Society) vol. 125, pages 5707-5716 (2003); or the following Production method 4.

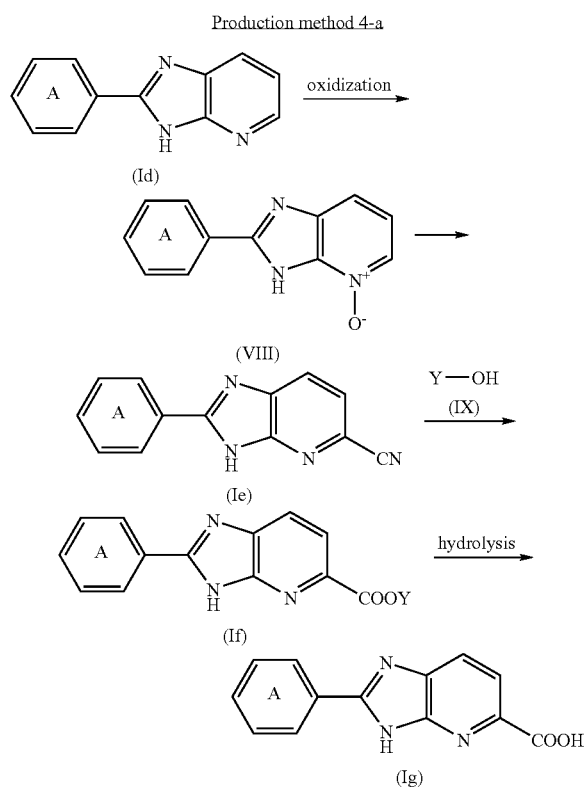

wherein Y is an optionally substituted hydrocarbon group and other symbols are as defined above.

Here, as the "optionally substituted hydrocarbon group" for Y, those exemplarily recited as the aforementioned "substituent" for $R^1$, $R^2$, $R^3$ or $R^4$ can be mentioned. Of these, a $C_{1-6}$ alkyl group is preferable.

In this method, compound (VIII) can be first produced by subjecting compound (Id) (compound (I) wherein $R^1$, $R^2$, $R^3$ and $R^4$ are hydrogen atoms) to an oxidization reaction.

The oxidization reaction is carried out, for example, using an oxidant such as peroxide (e.g., aqueous hydrogen peroxide, peracetic acid), organic peracid (e.g., m-chloroperbenzoic acid) and the like. The amount of the oxidant to be used is generally about 1 mol to 5 mol, preferably about 1.5 mol to 2 mol, per 1 mol of compound (Id).

The reaction temperature is generally −20° C. to 50° C., preferably 0° C. to room temperature. The reaction time is generally 1 hr to 24 hr.

Then, compound (Ie) can be produced by reacting compound (VIII) with a cyanating agent in the presence of a base.

As the "cyanating agent", for example, trimethylsilyl cyanide, diethyl cyanophosphate and the like can be mentioned. The amount of the cyanating agent to be used is generally about 1 mol to 10 mol, preferably about 1 mol to 2 mol, per 1 mol of compound (VIII).

As the "base", for example, organic bases such as triethylamine, pyridine and the like, and the like can be mentioned. The amount of the base to be used is generally about 1 mol to 5 mol, preferably about 2 mol to 3 mol, per 1 mol of compound (VIII).

The reaction temperature is generally 0° C. to 180° C., preferably room temperature to 100° C. The reaction time is generally 1 hr to 24 hr.

Then, compound (If) can be produced by reacting compound (Ie) with compound (IX) in the presence of an acid.

As the "acid", for example, mineral acids such as hydrochloric acid, sulfuric acid and the like, and the like can be mentioned. The amount of the acid to be used is generally about 2 mol to 200 mol, preferably about 5 mol to 100 mol, per 1 mol of compound (Ie).

The amount of compound (IX) to be used is generally about 1 mol to 1000 mol, preferably about 10 mol to 1000 mol, per 1 mol of compound (Ie).

The reaction temperature is generally 0° C. to 180° C., preferably room temperature to 100° C. The reaction time is generally 1 hr to 24 hr.

Then, compound (Ig) can be produced by subjecting compound (If) to hydrolysis reaction. This reaction is generally carried out in the presence of a base or an acid.

As the "base", for example, inorganic bases such as alkali metal hydroxides (e.g., sodium hydroxide, calcium hydroxide), alkaline earth metal hydroxides (e.g., magnesium hydroxide, calcium hydroxide), alkali metal carbonates (e.g., sodium carbonate, potassium carbonate), alkaline earth metal carbonates (e.g., magnesium carbonate, calcium carbonate), alkali metal bicarbonates (e.g., sodium bicarbonate, potassium bicarbonate), alkali metal acetates (e.g., sodium acetate, potassium acetate), alkaline earth metal phosphates (e.g., magnesium phosphate, calcium phosphate), alkali metal hydrogenphosphate (e.g., disodium hydrogenphosphate, dipotassium hydrogenphosphate) and the like; organic bases such as trialkylamines (e.g., trimethylamine, triethylamine), picoline, N-methylpyrrolidine, N-methylmorpholine, 1,5-diazabicyclo[4.3.2]non-5-ene, 1,4-diazabicyclo[2.2.2]non-5-ene, 1,8-diazabicyclo[4.3.0]-7-undecene and the like, and the like can be mentioned.

As the acid, for example, hydrochloric acid, formic acid, hydrogen bromide acid, sulfuric acid and the like can be mentioned.

The amount of the base or acid to be used is preferably an excess amount, to be specific, about 2 mol to 50 mol per 1 mol of compound (If).

When the above-mentioned base is used, this reaction can be generally carried out in water, hydrophilic organic solvent or a mixed solvent thereof. As the hydrophilic organic solvent, alcohols (e.g., methanol, ethanol), dioxane, tetrahydrofuran and the like can be mentioned.

The reaction temperature is generally 0° C. to 180° C., preferably room temperature to 100° C. The reaction time is generally 1 hr to 24 hr.

Compound (IX), which is used as a starting material compound in Production method 4-a, can be produced according to a method known per se. In addition, compound (Id) can be produced according to Production method 1-a or 1-b mentioned above.

The aforementioned compound (Ie) can also be produced according to the following Production method 4-b.

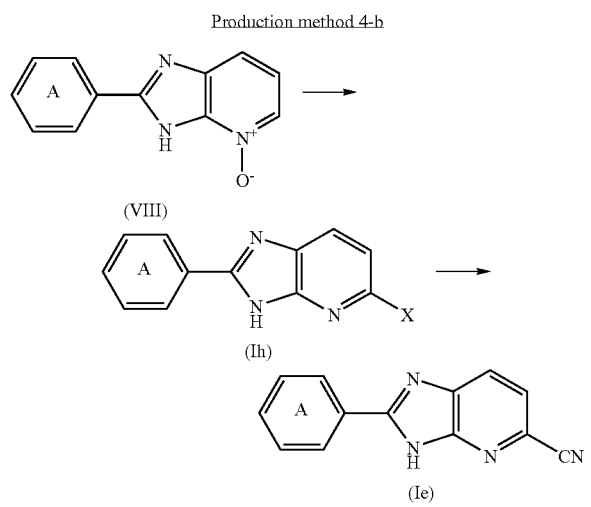

wherein X is a halogen atom, a $C_{6-14}$ aryloxy group, a $C_{1-6}$ alkoxy group or a $C_{1-6}$ alkylthio group, and other symbols are as defined above.

In this method, compound (Ih) can be first produced by reacting compound (VIII) with a nucleophilic reagent in a solvent that does not adversely influence the reaction.

As the "nucleophilic reagent", a thiol, an alcohol and halogenating agent each corresponding to the aforementioned X can be mentioned. The amount of the nucleophilic reagent to be used is generally about 0.5 mol to 5 mol per 1 mol of compound (VIII).

As the "solvent that does not adversely influence the reaction", for example, ethers such as diethyl ether, tetrahydrofuran and the like, and the like can be mentioned.

The reaction temperature is generally −20° C. to 150° C., preferably 0° C. to 100° C. The reaction time is generally 1 hr to 12 hr.

Now, compound (If) can be produced by reacting compound (Ih) with a cyanating agent in the presence of a base. This reaction is carried out in the same manner as in the reaction of compound (VIII) with a cyanating agent in Production method 4-a mentioned above.

Compound (Ii) (compound (I) wherein $R^1$ is a hydrogen atom, one of $R^2$, $R^3$ or $R^4$ is a hydroxymethyl group, and the others are hydrogen atoms) can be produced from compound (If') (compound (I) wherein $R^1$ is a hydrogen atom, one of $R^2$, $R^3$ or $R^4$ is —COOY (Y is as defined above), and the others are hydrogen atoms), according to the following Production method 5.

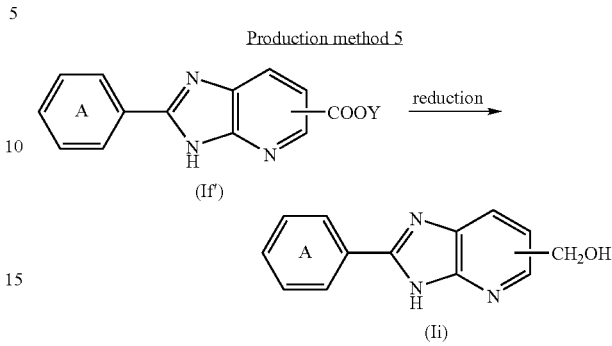

wherein each symbol is as defined above.

In this method, compound (Ii) can be produced by subjecting compound (If') to a reduction reaction. The reduction reaction is carried out using a reducing agent in a solvent that does not adversely influence the reaction.

As the "solvent that does not adversely influence the reaction", for example, ethers such as diethyl ether, tetrahydrofuran and the like, and the like can be mentioned.

As the "reducing agent", for example, lithium aluminum hydride, sodium borohydride, sodium triacetoxyborohydride, sodium cyanoborohydride, lithium borohydride and the like can be mentioned. The amount of the reducing agent to be used is generally about 1 mol to 5 mol per 1 mol of compound (If').

The reaction temperature is generally −20° C. to 150° C., preferably 0° C. to 100° C. The reaction time is generally 1 hr to 12 hr.

Compound (If'), which is used as a starting material compound in Production method 5, for example, can be produced according to Production method 1-a, 1-b or 4-a mentioned above.

Compound (Ik) (compound (I) wherein $R^1$ is a hydrogen atom, one of $R^2$, $R^3$ or $R^4$ is —CH$_2$W (W is an optionally substituted amino group), and the others are hydrogen atoms) can be produced from compound (Ii), according to the following Production method 6.

Here, as the "optionally substituted amino group" for W, an "amino group optionally substituted by 1 or 2 substituents selected from a $C_{1-6}$ alkyl group optionally substituted by 1 to 3 substituents selected from a $C_{1-6}$ alkoxy group, a $C_{6-14}$ aryloxy group, a carboxyl group and a $C_{1-6}$ alkoxy-carbonyl group;

a $C_{7-13}$ aralkyl group;

a $C_{1-6}$ alkyl-carbonyl group;

a $C_{1-6}$ alkoxy-carbonyl group;

a $C_{6-14}$ aryl-carbonyl group;

a $C_{7-13}$ aralkyl-carbonyl group;

a $C_{1-6}$ alkyl-carbamoyl group;

a $C_{6-14}$ aryl-carbamoyl group;

a $C_{7-13}$ aralkyl-carbamoyl group;

a $C_{1-6}$ alkylsulfonyl group;

a $C_{6-14}$ arylsulfonyl group; and a $C_{7-13}$ aralkylsulfonyl group", which are exemplarily recited as the substituents of the $C_{1-10}$ alkyl group and the like exemplarily recited as "hydrocarbon group" of the "optionally substituted hydrocarbon group" for $R^1$, $R^2$, $R^3$ or $R^4$, can be mentioned.

Production method 6

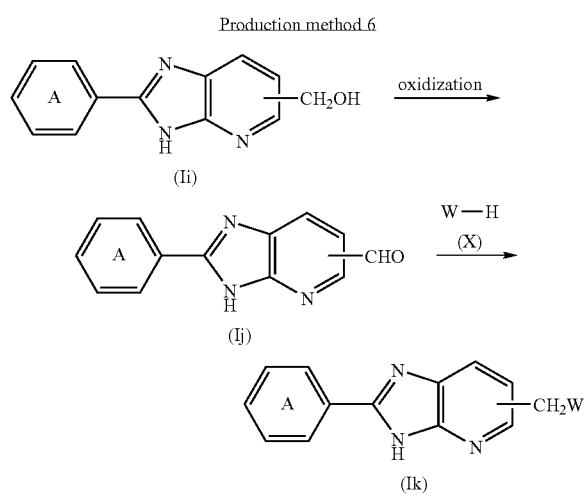

wherein each symbol is as defined above.

The amount of the compound (X) to be used is generally about 1 mol to 10 mol, preferably about 1 mol to 2 mol, per 1 mol of compound (Ij).

The reaction temperature is generally 0° C. to about 100° C. The reaction time is generally 30 min to 12 hr.

Compound (X), which is used as a starting material compound in Production method 6, can be produced according to a method known per se.

Production Method 7

A general synthetic route for producing compounds represented by formula I of the present invention is shown in Scheme 1. Compound II is treated with compound III (HBTU, $Et_3N$, DMF), followed by cyclization using microwave (1:1 EtOH-AcOH, 180° C., 30 min to 60 min). Compound IV is treated with base (i.e., 1N NaOH or 1N LiOH) to give Compound II. Mitsunobu reaction (i.e., diisopropylazodicarboxylate (DIAD) and $PPh_3$) between Compound V and alcohol $R^6$—OH or alkylation (i.e., $K_2CO_3$, $Na_2CO_3$, or NaH) between Compound V and halide $R^6$—X provides Compound IV. Alkylation (i.e., $K_2CO_3$, $Na_2CO_3$) between Compound VI and halide $R^5$—X provides Compound V.

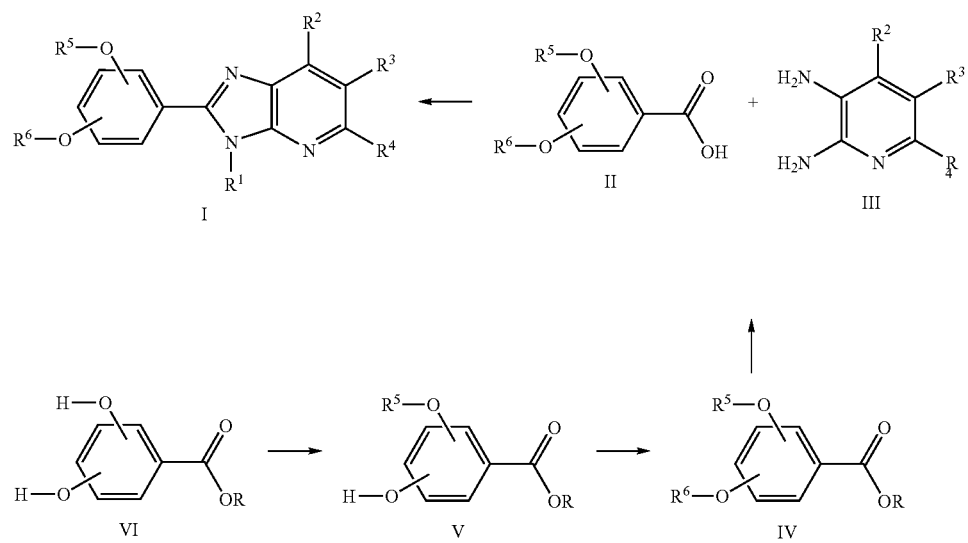

In this method, compound (Ij) (compound (I) wherein $R^1$ is a hydrogen atom, one of $R^2$, $R^3$ or $R^4$ is —CHO, and the others are hydrogen atoms) can be produced by subjecting compound (Ii) to an oxidization reaction.

This reaction is generally carried out according to a conventional oxidization reaction of primary alcohol. For example, a method using chromium oxide and sulfuric acid in combination, a method using dioxide manganese and the like can be mentioned.

The reaction temperature is generally 0° C. to about 100° C. The reaction time is generally 30 min to 12 hr.

Then, compound (Ik) can be produced by reacting compound (Ij) with compound (X) in the presence of a reducing agent.

As the "reducing agent", for example, sodium triacetoxyborohydride, sodium cyanoborohydride and the like can be mentioned. The amount of the reducing agent to be used is generally about 1 mol to 5 mol per 1 mol of compound (Ij).

In each of the aforementioned production methods, when the starting material compound or compound (I) has an amino group, a carboxyl group, a hydroxy group or a thiol group, a protecting group generally used in peptide chemistry and the like may be introduced into these groups. In addition, the protecting group can be removed according to a conventional method in any step of each reaction scheme.

The compound of the present invention obtained by the above-mentioned production methods can be isolated and purified according to a known means, such as concentration, concentration under reduced pressure, solvent extraction, crystallization, recrystallization, phase transfer, chromatography and the like. Each starting material compound used in each Production method mentioned above can be isolated and purified according to known methods as mentioned above. In addition, these starting material compounds may be used in the form of a reaction mixture without isolation, as a starting material for the next step.

When the starting material compound can form a salt in the production of compound (I), the compound can be used in the form of a salt. As such salt, for example, those exemplarily recited as the salt of compound (I) can be mentioned.

When compound (I) contains an optical isomer, a stereoisomer, a positional isomer or a rotational isomer, these are also encompassed in compound (I), and can be obtained as a single product according to a synthetic method and separation method known per se. For example, when compound (I) has an optical isomer, an optical isomer resolved from this compound is also encompassed in compound (I).

The compound (I) may be in the form of a crystal.

The crystal of compound (I) (hereinafter sometimes to be referred to as crystal of the present invention) can be produced by crystallization of compound (I) according to a crystallization method known per se.

The crystal of the present invention is superior in the physicochemical properties (e.g., melting point, solubility, stability) and biological properties (e.g., in vivo kinetics (absorbability, distribution, metabolism, excretion), efficacy expression) and is extremely useful as a pharmaceutical agent.

EXAMPLES

The present invention is explained in detail by referring to the following Reference Examples, Examples, Experimental Examples and Formulation Examples, which are mere working examples not to be construed as limitative and may be changed without departing from the scope of the present invention.

LC-MS Measurement Condition

In the following Reference Examples and Examples, HPLC-mass spectrum (LC-MS) was measured under the following conditions.
 measurement device: ZMD manufactured by Micromass, and HP1100 manufactured by Agilent Technologies
 column: CAPCELL PAK C18UG120, S-3 μm, 1.5×35 mm
 solvents:
 Solution A; 0.05% trifluoroacetic acid-containing water,
 Solution B; 0.04% trifluoroacetic acid-containing acetonitrile
 gradient cycle: 0.00 min (Solution A/Solution B=90/10), 2.00 min (Solution A/Solution B=5/95), 2.75 min (Solution A/Solution B=5/95), 2.76 min (Solution A/Solution B=90/10), 3.45 min (Solution A/Solution B=90/10)
 injection volume: 2 μl,
 flow rate: 0.5 ml/min,
 detection method: UV 220 nm
 ionizing method: Electron Spray Ionization (ESI)

Preparative HPLC Conditions

In the following Reference Examples and Examples, purification by preparative HPLC was performed under the following conditions.
 apparatus: high throughput purification system manufactured by Gilson
 column: YMC CombiPrep ODS-A, S-5 μm, 50×20 mm
 solvents:
 Solution A; 0.1% trifluoroacetic acid (or 0.1% formic acid)-containing water,
 Solution B; 0.1% trifluoroacetic acid (or 0.1% formic acid)-containing acetonitrile
 gradient cycle: 0.00 min (Solution A/Solution B=90/10), 1.00 min (Solution A/Solution B=90/10), 4.00 min (Solution A/Solution B=10/95), 8.50 min (Solution A/Solution B=10/95), 8.60 min (Solution A/Solution B=90/10), 8.70 min (Solution A/Solution B=90/10).
 flow rate: 20 ml/min,
 detection method: UV 220 nm Other Conditions $^1$H-NMR spectra were measured with a BRUKER AVANCE DPX-300 spectrometer (300 MHz) or AV-400M (400 MHz) using tetramethylsilane as an internal standard. All of the δ values are represented in ppm. The numerical value indicated for the mixed solvent shows a mixed volume ratio of each solvent unless otherwise specified, and % means weight % unless otherwise specified. The room temperature (ambient temperature) in the present specification means a temperature between about 10° C. and about 35° C. The microwave reactor used was Emrys optimizer manufactured by Biotage.

The symbols used in Reference Examples and Examples mean the following.
 s: singlet
 br: broad
 d: doublet
 t: triplet
 q: quartet
 dd: double doublet
 dt: double triplet
 ddd: double double doublet
 m: multiplet
 J: coupling constant
 Hz: hertz
 DMF: N,N-dimethylformamide
 THF: tetrahydrofuran Reference Example 1

5-benzyloxy-2-methoxybenzoic acid (Step 1)

To a mixed solution of methyl 2,5-dihydroxybenzoate (10.0 g), potassium carbonate (12.3 g) and acetone (100 ml) was added benzyl bromide (7.43 ml), and the mixture was stirred overnight at room temperature. After the insoluble material was removed by filtration, the mother solution was concentrated. The obtained residue was purified by column chromatography (LL, Biotage cartridge, ethyl acetate:n-hexane=1:9→1:5) to give methyl 5-benzyloxy-2-hydroxybenzoate (9.63 g, 63%) as colorless crystals.

(Step 2)

To a suspended solution of methyl 5-benzyloxy-2-hydroxybenzoate (3.91 g) and cesium carbonate (6.41 g) in acetone (100 ml) was added methyl iodide (1.41 ml), and the mixture was stirred at 50° C. for 6 hr. The reaction mixture was concentrated, dissolved again in ethyl acetate and washed with saturated brine. The organic layer was dried (over MgSO$_4$), and the solvent was evaporated under reduced pressure. The residue was purified by column chromatography (Biotage cartridge 40+M, ethyl acetate:n-hexane=15:85→1:4) to give methyl 5-benzyloxy-2-methoxybenzoate (3.72 g, 90%) as colorless crystals.

(Step 3)

Methyl 5-benzyloxy-2-methoxybenzoate (3.72 g) was dissolved in a mixed solvent of THF (30 ml) and methanol (30 ml), and 1N aqueous sodium hydroxide solution (27.3 ml) was added to the mixed solution. The mixture was stirred at room temperature for 2 days, and 1N aqueous hydrochloric acid solution (40 ml) was added. The precipitate was collected by filtration and washed with water to give 5-benzyloxy-2-methoxybenzoic acid (3.10 g, 88%) as colorless crystals.

$^1$H NMR (DMSO-d$_6$) δ ppm 3.75 (3 H, s), 5.08 (2 H, s), 7.05 (1 H, d, J=9.05 Hz), 7.15 (1 H, dd, J=9.05, 3.18 Hz), 7.24

(1 H, d, J=3.18 Hz), 7.28-7.36 (1 H, m), 7.36-7.42 (2 H, m), 7.42-7.47 (2 H, m), 12.71 (1 H, s).

The following compounds of Reference Examples 2 to 8 were obtained according to the method of Reference Example 1 and using commercially available dihydroxybenzoate and various halides appropriately selected as stating materials.

Reference Example 2

5-benzyloxy-2-isopropoxybenzoic acid

M+H: 287

Reference Example 3

2,5-dibenzyloxybenzoic acid $^1$H NMR (DMSO-$d_6$) δ ppm 5.03 (2 H, s), 5.05 (2 H, s), 6.83-6.89 (1 H, m), 6.89-6.95 (1 H, m, J=8.80 Hz), 6.98-7.06 (1 H, m, J=2.93 Hz), 7.23-7.53 (10 H, m).

Reference Example 4

5-(cyclopropylmethoxy)-2-isopropoxybenzoic acid $^1$H NMR (CDCl$_3$) δ ppm 0.30-0.38 (2 H, m), 0.60-0.68 (2 H, m), 1.18-1.34 (1 H, m), 1.45 (5 H, d, J=6.11 Hz), 3.82 (2 H, d, J=7.09 Hz), 4.77 (1 H, ddd, J=18.10, 12.10, 5.99 Hz), 6.99 (1 H, d, J=9.05 Hz), 7.13 (1 H, dd, J=9.05, 3.18 Hz), 7.64 (1 H, d, J=3.18 Hz), 11.49 (1 H, s).

Reference Example 5

3-benzyloxy-5-isopropoxybenzoic acid

1H NMR (DMSO-d6) δ ppm 1.25 (6 H, d, J=6.11 Hz), 4.64 (1 H, ddd, J=17.97, 11.98, 5.99 Hz), 5.14 (2 H, s), 6.79 (1 H, t, J=2.20 Hz), 7.00-7.05 (1 H, m, J=1.71 Hz), 7.07-7.14 (1 H, m), 7.30-7.37 (1 H, m), 7.37-7.43 (2 H, m), 7.43-7.48 (2 H, m), 13.02 (1 H, s).

Reference Example 6

3-cyclohexylmethoxy-5-isopropoxybenzoic acid

1H NMR (DMSO-d6) δ ppm 0.94-1.12 (2 H, m), 1.12-1.33 (3 H, m), 1.26 (6 H, d, J=5.87 Hz), 1.57-1.86 (6 H, m), 3.79 (2 H, d, J=6.11 Hz), 4.55-4.70 (1 H, m), 6.61-6.70 (1 H, m), 6.97-7.04 (2 H, m).

Reference Example 7

3,5-diisopropoxybenzoic acid

1H NMR (DMSO-d6) δ ppm 1.26 (12 H, d, J=6.11 Hz), 4.64 (1 H, ddd, J=17.97, 11.98, 5.99 Hz), 6.67 (1 H, t, J=2.20 Hz), 6.99 (2 H, d, J=2.20 Hz), 12.98 (1 H, s).

Reference Example 8

4-benzyloxy-2-isopropoxybenzoic acid

1H NMR (DMSO-d6) δ ppm 1.25 (6H, d, J=5.87 Hz), 4.66 (1H, ddd, J=18.03, 11.92, 5.99), 5.17 (2H, s), 6.64 (1H, dd, J=8.80, 2.20 Hz), 6.70 (1H, d, J=2.20 Hz), 7.30-7.37 (1H, m), 7.37-7.44 (2H, m), 7.44-7.50 (2H, m), 7.67 (1H, d, J=8.56 Hz), 12.06 (1H, s).

Reference Example 9

3-isopropoxy-5-(3-pyridin-3-ylpropoxy)benzoic acid (Step 1)
To a solution (60 ml) of methyl 5-hydroxy-3-isopropoxybenzoate (2.0 g) and 3-(pyridin-3-yl)propanol (1.6 g) in THF were added successively 1,1'-(azodicarbonyl)dipiperidine (2.9 g) and tributylphosphine (2.8 ml) under ice-cooling, and the mixture was stirred overnight at room temperature. n-Hexane (100 ml) was added to the reaction mixture, and the precipitated crystals were removed by filtration. The filtrate was concentrated under reduced pressure, and the residue was purified by column chromatography (LL, Biotage cartridge, ethyl acetate:n-hexane=15:85→1:4) to give methyl 3-isopropoxy-5-(3-pyridin-3-ylpropoxy)benzoate (2.70 g, 86%) as a colorless oil.
(Step 2)
Methyl 3-isopropoxy-5-(3-pyridin-3-ylpropoxy)benzoate (2.70 g) was dissolved in a mixed solvent of THF (30 ml) and methanol (30 ml), and 1N aqueous sodium hydroxide solution (25 ml) was added to the mixed solution. The mixture was stirred overnight at room temperature and concentrated under reduced pressure to dryness. 1N Aqueous hydrochloric acid solution (25 ml) was added thereto, and the precipitated crystals were collected by filtration and washed with water to give 3-isopropoxy-5-(3-pyridin-3-ylpropoxy)benzoic acid (1.55 g, 60%) as colorless crystals.

$^1$H NMR (DMSO-$d_6$) δ ppm 1.26 (6 H, d, J=6.11 Hz), 1.97-2.12 (2 H, m), 2.76 (2 H, t, J=7.58 Hz), 4.00 (2 H, t, J=6.24 Hz), 4.51-4.74 (1 H, m), 6.60-6.76 (1 H, m), 7.01 (2 H, s), 7.31 (1 H, dd, J=7.70, 4.77 Hz), 7.67 (1 H, d, J=7.83 Hz), 8.40 (1 H, d, J=4.65 Hz), 8.46 (1 H, s), 12.95 (1 H, s).

Reference Example 10

3-isopropoxy-5-[2-(3-thienyl)ethoxy]benzoic acid

The title compound was obtained according to the method of Reference Example 9. $^1$H NMR (DMSO-$d_6$) δ ppm 1.23 (6 H, d, J=5.62 Hz), 3.02 (2 H, t, J=6.60 Hz), 4.15 (2 H, t, J=6.60 Hz), 4.47-4.65 (1 H, m), 6.39-6.59 (1 H, m), 6.97-7.20 (3 H, m), 7.28 (1 H, s), 7.39-7.51 (1 H, m).

Reference Example 11

6-amino-5-nitronicotinic acid

A mixture of concentrated sulfuric acid (7.5 ml) and concentrated nitric acid (7.5 ml) was added dropwise to a solution of 6-aminonicotinic acid (15 g) in concentrated sulfuric acid (30 ml) under ice-cooling. The reaction mixture was stirred at room temperature for 3 hrs and poured into ice water, and the mixture was stirred for 30 min. The precipitated crystals were collected by filtration and washed with water. The obtained crystals were suspended in concentrated sulfuric acid (60 ml), and the mixture was stirred at 100° C. for 2 hr. The reaction mixture was adjusted with sodium hydroxide to pH 4, and the precipitated crystals were collected by filtration to give the title compound (7.26 g, yield 36%) as pale-as yellow crystals. purity 94%. M+H: 184.

Reference Example 12 ethyl 6-amino-5-nitronicotinate

A solution of 6-amino-5-nitronicotinic acid (10 g) and concentrated sulfuric acid (20 ml) in ethanol (250 ml) was heated under reflux for 18 hr. The reaction mixture was concentrated, diluted with water and adjusted with sodium hydrogencarbonate to pH 8. The precipitated crystals were collected by filtration and washed with water to give the title compound (8.5 g, yield 73%) as yellow crystals. purity 84%. M+H: 212.

Reference Example 13 ethyl 5,6-diaminonicotinate

To a solution (150 ml) of ethyl 6-amino-5-nitronicotinate (5.0 g) and 6N aqueous calcium chloride solution (50 ml) in ethanol was added zinc powder (77 g) with heating under reflux. The reaction mixture was heated under reflux for 2 hr, and the zinc powder was removed by filtration. The filtrate was concentrated, diluted with water and extracted with ethyl acetate. The extract was washed with water, dried over magnesium sulfate and concentrated to give the title compound (3.85 g, yield 89%) as pale-brown crystals. $^1$H NMR (DMSO-$d_6$) δ: 1.37 (3H, t, J=7.0 Hz), 4.38 (2H, q, J=7.1 Hz), 4.95 (2H, s), 6.28 (2H, s), 7.15 (1H, d, J=2.1 Hz), 7.94 (1H, d, J=2.1 Hz).

Reference Example 14

3-nitro-5-phenylpyridine-2-amine

A mixture of 5-bromo-3-nitropyridine-2-amine (10 g), phenylboronic acid (8.39 g), tetrakis(triphenylphosphine) palladium(0) (5.3 g), 2N aqueous sodium carbonate solution (100 ml) and dimethoxyethane (500 ml) was heated under reflux under an argon atmosphere for 5 hr. The insoluble material was removed by filtration, and the filtrate was concentrated, diluted with water and extracted with ethyl acetate. The extract was washed with water, dried over magnesium sulfate and concentrated. The obtained crude crystals were washed with diethyl ether to give the title compound (4.58 g, yield 46%) as yellow crystals. purity 80%. M+H: 216.

Reference Example 15

5-phenylpyridine-2,3-diamine

The title compound (yield 74%) was obtained as brown amorphous powder using 3-nitro-5-phenylpyridine-2-amine obtained in Reference Example 14 and according to the method of Reference Example 13. M+H: 186. $^1$H NMR (DMSO-$d_6$) δ: 4.81 (2H, s), 5.59 (2H, s), 7.02 (1H, d, J=1.3 Hz), 7.19-7.51 (5H, m), 7.61 (1H, d, J=1.7 Hz).

Reference Example 16

2-[5-(benzyloxy)-2-isopropoxyphenyl]-3H-imidazo[4,5-b]pyridine 4-oxide

A solution (10 ml) of 2-[5-(benzyloxy)-2-isopropoxyphenyl]-3H-imidazo[4,5-b]pyridine (0.2 g) and m-chloroperbenzoic acid (0.15 g) in chloroform was stirred at room temperature for 18 hr. The reaction mixture was washed with aqueous sodium hydrogencarbonate solution, dried over magnesium sulfate and concentrated to give the title compound as colorless crystals. purity 80%. M+H: 376.

Reference Example 17 methyl 5-(benzyloxy)-2-hydroxybenzoate

The title compound was prepared using a procedure analogous to that described in connection with Example 156a.

Reference Example 18 methyl 3-(benzyloxy)-5-hydroxybenzoate

The title compound was prepared using a procedure analogous to that described in connection with Example 156a.

Reference Example 19 methyl 5-hydroxy-2-isopropoxybenzoate

The title compound was prepared using a procedure analogous to that described in connection with Example 156a.

Reference Example 20 methyl 3-hydroxy-5-isopropoxybenzoate

The title compound was prepared using a procedure analogous to that described in connection with Example 156a.

Reference Example 21 methyl 4-hydroxy-2-isopropoxybenzoate

The title compound was prepared using a procedure analogous to that described in connection with Example 156a.

Reference Example 22 methyl 3-hydroxy-5-((1-methyl-1H-imidazol-2-yl)methoxy)benzoate

The title compound was prepared using a procedure analogous to that described in connection with Example 164.

The structural formulas of the compounds produced in the above-mentioned Reference Examples 1 to 22 are shown in Table 1.

TABLE 1

| Reference Example No. | Structural formula |
| --- | --- |
| 1 | |
| 2 | |

TABLE 1-continued

| Reference Example No. | Structural formula |
|---|---|
| 3 | 2,5-bis(benzyloxy)benzoic acid |
| 4 | 5-(cyclopropylmethoxy)-2-isopropoxybenzoic acid |
| 5 | 3-(benzyloxy)-5-isopropoxybenzoic acid |
| 6 | 3-(cyclohexylmethoxy)-5-isopropoxybenzoic acid |
| 7 | 3,5-diisopropoxybenzoic acid |
| 8 | 4-(benzyloxy)-2-isopropoxybenzoic acid |
| 9 | 3-isopropoxy-5-(3-(pyridin-3-yl)propoxy)benzoic acid |
| 10 | 3-isopropoxy-5-(2-(thiophen-3-yl)ethoxy)benzoic acid |
| 11 | 6-amino-5-nitronicotinic acid |
| 12 | ethyl 6-amino-5-nitronicotinate |
| 13 | ethyl 5,6-diaminonicotinate |
| 14 | 6-amino-5-nitro-3-phenylpyridine |
| 15 | 5-phenylpyridine-2,3-diamine |

TABLE 1-continued

| Reference Example No. | Structural formula |
|---|---|
| 16 | (2-isopropoxy-5-benzyloxyphenyl imidazo[4,5-b]pyridine N-oxide structure) |
| 17 | (methyl 5-benzyloxy-2-hydroxybenzoate structure) |
| 18 | (methyl 3-benzyloxy-5-hydroxybenzoate structure) |
| 19 | (methyl 5-hydroxy-2-isopropoxybenzoate structure) |
| 20 | (methyl 3-hydroxy-5-isopropoxybenzoate structure) |
| 21 | (methyl 4-hydroxy-2-isopropoxybenzoate structure) |
| 22 | (methyl 3-[(1-methylimidazol-2-yl)methoxy]-5-hydroxybenzoate structure) |

Example 1

2-[5-(benzyloxy)-2-isopropoxyphenyl]-3H-imidazo[4,5-b]pyridine

A solution (20 ml) of pyridine-2,3-diamine (0.6 g), 5-(benzyloxy)-2-isopropoxybenzoic acid (1.31 g), 1-hydroxybenztriazole hydrate (0.93 g) and 1-ethyl-3-(3-dimethylaminopropyl)carbodiimide hydrochloride (1.32 g) in N,N-dimethylformamide was stirred at room temperature for 18 hr. The reaction mixture was diluted with water and extracted with ethyl acetate. The extract was washed with water, dried over magnesium sulfate and concentrated to give as pale-brown crystals. The obtained crystals were added to acetic acid (2.5 ml)-ethanol (2.5 ml), and the mixture was subjected to microwave irradiation in a sealed reaction container at 180° C. for 40 min. The reaction mixture was concentrated, and the precipitated crystals were collected by filtration and washed with ethanol to give the title compound (0.53 g, yield 32%) as colorless crystals. melting point 160-162° C. purity 95%. M+H: 360. $^1$H NMR (CDCl$_3$) δ: 1.50 (6H, d, J=6.2 Hz), 4.64-4.85 (1H, m), 5.16 (2H, s), 6.95-7.56 (8H, m), 8.08 (1H, d, J=7.9 Hz), 8.21 (1H, d, J=2.8 Hz), 8.36 (1H, t, J=5.6 Hz), 11.06 (1H, s).

The following compounds of Examples 2 to 8 were obtained according to the method of Example 1.

Example 2

2-[3-(benzyloxy)-5-isopropoxyphenyl]-3H-imidazo[4,5-b]pyridine

As colorless crystals (yield 19%). melting point 136-137° C. purity 93%. M+H: 360. $^1$H NMR (CDCl$_3$) δ: 1.40 (6H, d, J=6.0 Hz), 4.51-4.81 (1H, m), 5.17 (2H, s), 6.72 (1H, t, J=2.2 Hz), 7.02-7.64 (8H, m), 8.17 (1H, d, J=7.9 Hz), 8.60 (1H, dd, J=5.0, 1.2 Hz).

Example 3

2-{3-isopropoxy-5-[2-(3-thienyl)ethoxy]phenyl}-3H-imidazo[4,5-b]pyridine

As colorless crystals (yield 20%). melting point 82-83° C. purity 99%. M+H: 380. $^1$H NMR (CDCl$_3$) δ: 1.40 (6H, d, J=6.2 Hz), 3.19 (2H, t, J=6.7 Hz), 4.30 (2H, t, J=6.7 Hz), 4.56-4.84 (1H, m), 6.64 (1H, t, J=2.2 Hz), 7.07 (1H, dd, J=4.9, 1.1 Hz), 7.13 (1H, d, J=1.9 Hz), 7.24-7.32 (2H, m), 7.43 (2H, dd, J=7.2, 1.9 Hz), 8.17 (1H, dd, J=8.0, 1.2 Hz), 8.54 (1H, dd, J=5.0, 1.2 Hz).

Example 4

2-[3-isopropoxy-5-(3-pyridin-3-ylpropoxy)phenyl]-3H-imidazo[4,5-b]pyridine

As colorless crystals (yield 19%). melting point 110-112° C. purity 99%. M+H: 389. $^1$H NMR (CDCl$_3$) δ: 1.41 (6H, d, J=6.2 Hz), 2.00-2.37 (2H, m), 2.88 (2H, t, J=7.6 Hz), 4.09 (2H, t, J=6.0 Hz), 4.54-4.91 (1H, m), 6.62 (1H, t, J=2.1 Hz), 7.12-7.37 (2H, m), 7.40-7.47 (2H, m), 7.56 (1H, d, J=7.9 Hz), 8.17 (1H, dd, J=8.0, 1.2 Hz), 8.48 (1H, dd, J=4.8, 1.4 Hz), 8.54 (1H, d, J=1.9 Hz), 8.58(1H, dd, J=4.9, 1.1 Hz).

Example 5

2-(5-(benzyloxy)-2-methoxyphenyl)-3H-imidazo[4,5-b]pyridine $^1$H NMR (DMSO-d$_6$) δ ppm 3.19 (3 H, s), 4.35 and 4.39 (2 H, each s), 7.32-7.43 (1 H, m), 7.44-7.54 (2 H, m), 7.58-7.68 (2 H, m), 7.72 (2 H, d, J=7.09 Hz), 7.90 (1 H, dd, J=8.07, 2.45 Hz), 8.06 and 8.19 (1 H, each d, J=1.96 Hz), 8.55 and 8.64 (1 H, each d, J=1.96 Hz), 12.76 and 13.10 (1 H, each s).

Example 6

6-bromo-2-(4-(benzyloxy)-2-isopropoxyphenyl)-3H-imidazo[4,5-b]pyridine $^1$H NMR (CDCl$_3$) δ ppm 1.47 (5 H, d, J=6.0 Hz), 2.10 (2 H, s), 4.77 (1 H, sept, J=6.0 Hz), 4.84 (1 H, s), 5.13 (2 H, s), 6.61 (1 H, d, J=2.1 Hz), 6.73 (1 H, dd, J=8.9, 2.2 Hz), 7.34-7.47 (4 H, m), 8.00 (1 H, dd, J=11.6, 2.2 Hz), 8.24 (1 H, d, J=8.9 Hz), 9.67 (1 H, s).

Example 7

6-bromo-2-(3-(benzyloxy)-5-isopropoxyphenyl)-3H-imidazo[4,5-b]pyridine $^1$H NMR (CDCl$_3$) δ ppm 1.43 (6 H, d, J=6.03 Hz), 4.62-4.74 (1 H, m), 5.17 (2 H, s), 6.73 (1 H, t, J=2.17 Hz), 7.35-7.46 (5 H, m), 7.48-7.52 (2 H, m), 8.28 (1 H, d, J=1.51 Hz), 8.65 (1 H, d, J=2.07 Hz), 13.66 (1 H, s).

Example 8

6-bromo-2-(2,5-dibenzyloxy)-3H-imidazo[4,5-b]pyridine $^1$H NMR (CDCl$_3$) δ ppm 5.14 (2 H, s), 5.36 (2 H, s), 6.92-7.15 (2 H, m), 7.28-7.56 (10 H, m), 8.17 (1 H, s), 8.23 (1 H, s), 8.34 (1 H, s), 11.64 (1 H, s).

Example 9 ethyl 2-(2,5-diisopropoxyphenyl)-3H-imidazo[4,5-b]pyridine-6-carboxylate trifluoroacetate A solution (2 ml) of ethyl 5,6-diaminonicotinate (50 mg), 2,5-diisopropoxybenzoic acid (80 mg), 1-hydroxybenztriazole hydrate (80 mg) and 1-ethyl-3-(3-dimethylaminopropyl)carbodiimide hydrochloride (55 mg) in N,N-dimethylformamide was stirred at room temperature for 18 hr. The reaction mixture was diluted with water, and dichloromethane was added, and the mixture was stirred. The organic layer was passed through a PTFE tube (polytetrafluoroethylene film processed tube), and the solvent was evaporated under a nitrogen atmosphere. The resultant product was added to acetic acid (1.5 ml)-ethanol (1.5 ml), and the mixture was subjected to microwave irradiation in a sealed reaction container at 180° C. for 40 min. The reaction mixture was concentrated, and the residue was purified by preparative HPLC to give the title compound (9.6 mg, yield 7%) as colorless crystals. purity 89%. M+H: 384. $^1$H NMR (DMSO-d$_6$) δ: 1.30 (6H, d, J=6.0 Hz), 1.35-1.42 (9H, m), 4.38 (2H, q, J=7.1 Hz), 4.56-4.64 (1H, m), 4.68-4.76 (1H, m), 7.12 (1H, dd, J=9.0, 3.2 Hz), 7.23 (1H, d, J=9.2 Hz), 7.76 (1H, d, J=3.2 Hz), 8.59 (1H, d, J=2.1 Hz),8.97 (1H, d, J=2.1 Hz).

The following compounds of Examples 10 to 18 and 29 to 37 were obtained according to the method of Example 9. In an Example where the object product was not trifluoroacetate, the precipitated crystals were collected by filtration after completion of the reaction to give the object product.

The following compounds of Examples 19 to 22 and 24 to 28 were obtained according to the method of Example 23. In an Example where the object product was trifluoroacetate, the residue was purified by preparative HPLC after neutralization with citric acid to give the object product.

Example 10 ethyl 2-[2,4-bis(benzyloxy)phenyl]-3H-imidazo[4,5-b]pyridine-6-carboxylate trifluoroacetate HPLC purity 87%. m/e(M$^+$+1):480.

Example 11 ethyl 2-[4-(benzyloxy)-2-isopropoxyphenyl]-3H-imidazo[4,5-b]pyridine-6-carboxylate trifluoroacetate HPLC purity 93%. m/e(M$^+$+1):432.

Example 12 ethyl 2-(2,4-diisopropoxyphenyl)-3H-imidazo[4,5-b]pyridine-6-carboxylate trifluoroacetate HPLC purity 89%. m/e(M$^+$+1):384.

Example 13 ethyl 2-[3-(benzyloxy)-5-isopropoxyphenyl]-3H-imidazo[4,5-b]pyridine-6-carboxylate HPLC purity 91%. m/e(M$^+$+1):432.

Example 14 ethyl 2-(3,5-diisopropoxyphenyl)-3H-imidazo[4,5-b]pyridine-6-carboxylate

HPLC purity 88%. m/e(M$^+$+1):384.

Example 15 ethyl 2-[3-(cyclohexylmethoxy)-5-isopropoxyphenyl]-3H-imidazo[4,5-b]pyridine-6-carboxylate HPLC purity 85%. m/e(M$^+$+1):438.

Example 16 ethyl 2-{3-isopropoxy-5-[2-(3-thienyl)ethoxy]phenyl}-3H-imidazo[4,5-b]pyridine-6-carboxylate HPLC purity 85%. m/e(M$^+$+1):452.

Example 17 ethyl 2-[3-isopropoxy-5-(3-pyridin-3-ylpropoxy)phenyl]-3H-imidazo[4,5-b]pyridine-6-carboxylate ditrifluoroacetate HPLC purity 91%. m/e(M$^+$+1):461.

Example 18 ethyl 2-[3,5-bis(benzyloxy)phenyl]-3H-imidazo[4,5-b]pyridine-6-carboxylate

HPLC purity 86%. m/e(M$^+$+1):480.

Example 19

2-(2,5-diisopropoxyphenyl)-3H-imidazo[4,5-b]pyridine-6-carboxylic acid

HPLC purity 96%. m/e(M$^+$+1):356.

Example 20

2-[2,4-bis(benzyloxy)phenyl]-3H-imidazo[4,5-b]pyridine-6-carboxylic acid trifluoroacetate HPLC purity 95%. m/e(M$^+$+1):452.

Example 21

2-[4-(benzyloxy)-2-isopropoxyphenyl]-3H-imidazo[4,5-b]pyridine-6-carboxylic acid HPLC purity 88%. m/e(M$^+$+1):404.

Example 22

2-(2,4-diisopropoxyphenyl)-3H-imidazo[4,5-b]pyridine-6-carboxylic acid

HPLC purity 86%. m/e(M$^+$+1):356.

Example 23

2-[3-(benzyloxy)-5-isopropoxyphenyl]-3H-imidazo[4,5-b]pyridine-6-carboxylic acid A solution of ethyl 2-(2,5-diisopropoxyphenyl)-3H-imidazo[4,5-b]pyridine-6-carboxylate (40 mg) and 1N aqueous sodium hydroxide solution (1 ml) in ethanol (2 ml) was stirred at room temperature for 48 hr. The reaction mixture was adjusted with 1N citric acid to pH 4, and the precipitated crystals were collected by filtration and washed with water and ethanol to give the title compound (27 mg) as colorless crystals. purity 94%. M+H: 404. $^1$H NMR (DMSO-d$_6$) δ: 1.32 (6H, d, J=6.0 Hz), 4.70-4.78 (1H,m), 5.21 (2H, s), 6.75 (1H, s), 7.32-7.53 (8H, m), 8.44 (1H, s), 8.92 (1H, s).

Example 24

2-(3,5-diisopropoxyphenyl)-3H-imidazo[4,5-b]pyridine-6-carboxylic acid

HPLC purity 96%. m/e(M$^+$+1):356.

Example 25

2-[3-(cyclohexylmethoxy)-5-isopropoxyphenyl]-3H-imidazo[4,5-b]pyridine-6-carboxylic acid HPLC purity 95%. m/e(M$^+$+1):410.

Example 26

2-{3-isopropoxy-5-[2-(3-thienyl)ethoxy]phenyl}-3H-imidazo[4,5-b]pyridine-6-carboxylic acid HPLC purity 95%. m/e(M$^+$+1):424.

Example 27

2-[3-isopropoxy-5-(3-pyridin-3-ylpropoxy)phenyl]-3H-imidazo[4,5-b]pyridine-6-carboxylic acid ditrifluoroacetate HPLC purity 99%. m/e(M$^+$+1):433.

Example 28

2-[3,5-bis(benzyloxy)phenyl]-3H-imidazo[4,5-b]pyridine-6-carboxylic acid

HPLC purity 97%. m/e(M$^+$+1):452.

Example 29

2-[5-(benzyloxy)-2-isopropoxyphenyl]-6-phenyl-3H-imidazo[4,5-b]pyridine trifluoroacetate HPLC purity 93%. m/e(M$^+$+1):436.

Example 30

2-(2,5-diisopropoxyphenyl)-6-phenyl-3H-imidazo[4,5-b]pyridine trifluoroacetate

HPLC purity 99%. m/e(M$^+$+1):388.

Example 31

2-[2,4-bis(benzyloxy)phenyl]-6-phenyl-3H-imidazo[4,5-b]pyridine trifluoroacetate HPLC purity 93%. m/e(M$^+$+1):484.

Example 32

2-[4-(benzyloxy)-2-isopropoxyphenyl]-6-phenyl-3H-imidazo[4,5-b]pyridine trifluoroacetate HPLC purity 91%. m/e(M$^+$+1):436.

Example 33

2-(2,4-diisopropoxyphenyl)-6-phenyl-3H-imidazo[4,5-b]pyridine trifluoroacetate

HPLC purity 90%. m/e(M$^+$+1):388.

Example 34

2-[3-(cyclohexylmethoxy)-5-isopropoxyphenyl]-6-phenyl-3H-imidazo[4,5-b]pyridine

HPLC purity 92%. m/e(M$^+$+1):442.

Example 35

2-{3-isopropoxy-5-[2-(3-thienyl)ethoxy]phenyl}-6-phenyl-3H-imidazo[4,5-b]pyridine HPLC purity 97%. m/e(M$^+$+1):456.

Example 36

2-[3-isopropoxy-5-(3-pyridin-3-ylpropoxy)phenyl]-6-phenyl-3H-imidazo[4,5-b]pyridine ditrifluoroacetate HPLC purity 96%. m/e(M$^+$+1):465.

Example 37

2-[3,5-bis(benzyloxy)phenyl]-6-phenyl-3H-imidazo[4,5-b]pyridine

HPLC purity 89%. m/e(M$^+$+1):484.

Example 38

2-(3-(benzyloxy)-5-isopropoxyphenyl)-6-phenyl-3H-imidazo[4,5-b]pyridine

To a mixture of 2-(3-(benzyloxy)-5-isopropoxyphenyl)-6-bromo-3H-imidazo[4,5-b]pyridine (0.11 g), phenylboronic acid (0.05 g) and tetrakis(triphenylphosphine)palladium(0) (0.01 g) in a mixed solvent of dimethoxyethane (3.0 ml) and ethanol (1 ml) was 0.5M aqueous sodium carbonate solution (1 ml), and the mixture was subjected to microwave irradiation in a sealed reaction container and stirred at 150° C. for 4 min. After completion of the reaction, water (2 ml) was added to the reaction mixture, and the mixture was extracted with ethyl acetate (10 ml). The extract was washed successively with water and saturated brine and dried over magnesium sulfate. The solvent was concentrated under reduced pressure, and the obtained crystals were collected by filtration, washed with isopropyl ether and dried to give the title compound (0.11 g). $^1$H NMR (CDCl$_3$) δ ppm 1.33 (6 H, d, J=6.03 Hz), 4.59-4.71 (1 H, m), 5.19 (2 H, s), 6.70 (1 H, t, J=1.88 Hz), 7.35-7.50 (9 H, m), 7.58 (1 H, s), 7.70 (2 H, d, J=6.97 Hz), 8.37 (1 H, d, J=1.70 Hz), 8.86 (1 H, d, J=1.70 Hz), 14.11 (1 H, s).

Example 39

2-[2,5-bis(benzyloxy)phenyl]-6-pyridin-3-yl-3H-imidazo[4,5-b]pyridine

The title compound (yield 40%) was obtained as a colorless powder according to the method of the below-mentioned Example 40. $^1$H NMR (CDCl$_3$) δ ppm 5.17 (2 H, s), 5.32 (2 H, s), 7.09 (2 H, s), 7.32-7.38 (1 H, m), 7.37-7.55 (10 H, m), 7.86-7.99 (1 H, m), 8.25 (2 H, s), 8.50-8.59 (1 H, m), 8.60-8.70 (1 H, m), 8.91 (1 H, s), 11.05 (1 H, s).

Example 40

2-[5-(benzyloxy)-2-isopropoxyphenyl]-6-pyridin-3-yl-3H-imidazo[4,5-b]pyridine

To a mixture of 2-(5-(benzyloxy)-2-isopropoxyphenyl)-6-bromo-3H-imidazo[4,5-b]pyridine (0.06 mmol), pyridine-3-boronic acid (0.09 mmol) and tetrakis(triphenylphosphine)palladium(0) (0.3 μmol) in a mixed solvent of dimethoxyethane (1.0 ml) and ethanol (0.3 ml) was added 0.5M aqueous sodium carbonate solution (0.12 ml), and the mixture was subjected to microwave irradiation in a sealed reaction container and stirred at 150° C. for 4 min. After completion of the reaction, water (2 ml) and ethyl acetate (2 ml) were added to the reaction mixture, and the mixture was stirred for a while. The organic layer was passed through a PTFE tube (polytetrafluoroethylene film processed tube) to give a solution containing the object compound. The solvent was evaporated under reduced pressure, and the residue was purified by preparative HPLC to give the title compound (9.5 mg, LC-MS purity 98%).

The following compounds of Examples 41-73 were obtained according to the method of Example 40.

Example 41

2-[5-(benzyloxy)-2-isopropoxyphenyl]-6-(4-fluorophenyl)-3H-imidazo[4,5-b]pyridine HPLC purity 99%. m/e(M++1):455.

Example 42

2-[5-(benzyloxy)-2-isopropoxyphenyl]-6-(4-methoxyphenyl)-3H-imidazo[4,5-b]pyridine HPLC purity 91%. m/e(M$^+$+1):467.

Example 43

2-[5-(benzyloxy)-2-isopropoxyphenyl]-6-(4-chlorophenyl)-3H-imidazo[4,5-b]pyridine HPLC purity 98%. m/e(M$^+$+1):471.

Example 44

2-[5-(benzyloxy)-2-isopropoxyphenyl]-6-(2-chlorophenyl)-3H-imidazo[4,5-b]pyridine HPLC purity 97%. m/e(M$^+$+1):471.

Example 45

2-[5-(benzyloxy)-2-isopropoxyphenyl]-6-(2,4-dimethoxyphenyl)-3H-imidazo[4,5-b]pyridine HPLC purity 99%. m/e(M$^+$+1):497.

Example 46

2-[5-(benzyloxy)-2-isopropoxyphenyl]-6-[3-(trifluoromethyl)phenyl]-3H-imidazo[4,5-b]pyridine HPLC purity 97%. m/e(M$^+$+1):505.

Example 47

2-[5-(benzyloxy)-2-isopropoxyphenyl]-6-(2-methylphenyl)-3H-imidazo[4,5-b]pyridine HPLC purity 97%. m/e(M$^+$+1):451.

Example 48

2-[5-(benzyloxy)-2-isopropoxyphenyl]-6-(2-methoxyphenyl)-3H-imidazo[4,5-b]pyridine HPLC purity 100%. m/e(M$^+$+1):467.

Example 49

2-[5-(benzyloxy)-2-isopropoxyphenyl]-6-[2-(trifluoromethyl)phenyl]-3H-imidazo[4,5-b]pyridine HPLC purity 99%. m/e(M$^+$+1):505.

Example 50

2-[4-(benzyloxy)-2-isopropoxyphenyl]-6-(4-fluorophenyl)-3H-imidazo[4,5-b]pyridine HPLC purity 97%. m/e(M$^+$+1):455.

Example 51

2-[4-(benzyloxy)-2-isopropoxyphenyl]-6-(4-methoxyphenyl)-3H-imidazo[4,5-b]pyridine HPLC purity 97%. m/e(M$^+$+1):467.

Example 52

2-[4-(benzyloxy)-2-isopropoxyphenyl]-6-(4-chlorophenyl)-3H-imidazo[4,5-b]pyridine HPLC purity 100%. m/e(M$^+$+1):471.

Example 53

2-[4-(benzyloxy)-2-isopropoxyphenyl]-6-(2-chlorophenyl)-3H-imidazo[4,5-b]pyridine HPLC purity 100%. m/e(M$^+$+1):471.

Example 54

2-[4-(benzyloxy)-2-isopropoxyphenyl]-6-(2,4-dimethoxyphenyl)-3H-imidazo[4,5-b]pyridine HPLC purity 99%. m/e(M$^+$+1):497.

Example 55

2-[4-(benzyloxy)-2-isopropoxyphenyl]-6-[3-(trifluoromethyl)phenyl]-3H-imidazo[4,5-b]pyridine HPLC purity 96%. m/e(M$^+$+1):505.

Example 56

2-[4-(benzyloxy)-2-isopropoxyphenyl]-6-(2-methylphenyl)-3H-imidazo[4,5-b]pyridine HPLC purity 99%. m/e(M$^+$+1):451.

Example 57

2-[4-(benzyloxy)-2-isopropoxyphenyl]-6-(2-methoxyphenyl)-3H-imidazo[4,5-b]pyridine HPLC purity 99%. m/e(M$^+$+1):467.

Example 58

2-[4-(benzyloxy)-2-isopropoxyphenyl]-6-[2-(trifluoromethyl)phenyl]-3H-imidazo[4,5-b]pyridine HPLC purity 96%. m/e(M$^+$+1):505.

Example 59

2-[4-(benzyloxy)-2-isopropoxyphenyl]-6-(2,6-dimethylphenyl)-3H-imidazo[4,5-b]pyridine HPLC purity 99%. m/e(M$^+$+1):465.

Example 60

2-{2-[4-(benzyloxy)-2-isopropoxyphenyl]-3H-imidazo[4,5-b]pyridin-6-yl}phenol

HPLC purity 99%. m/e(M$^+$+1):453.

Example 61

2-[3-(benzyloxy)-5-isopropoxyphenyl]-6-pyridin-3-yl-3H-imidazo[4,5-b]pyridine

HPLC purity 97%. m/e(M$^+$+1):437.

Example 62

2-[3-(benzyloxy)-5-isopropoxyphenyl]-6-(4-methoxyphenyl)-3H-imidazo[4,5-b]pyridine HPLC purity 94%. m/e(M$^+$+1):466.

Example 63

2-[3-(benzyloxy)-5-isopropoxyphenyl]-6-(2-chlorophenyl)-3H-imidazo[4,5-b]pyridine HPLC purity 92%. m/e($M^+$+1):470.

Example 64

2-[3-(benzyloxy)-5-isopropoxyphenyl]-6-(2,4-dimethoxyphenyl)-3H-imidazo[4,5-b]pyridine HPLC purity 88%. m/e($M^+$+1):496.

Example 65

2-[3-(benzyloxy)-5-isopropoxyphenyl]-6-[3-(trifluoromethyl)phenyl]-3H-imidazo[4,5-b]pyridine HPLC purity 93%. m/e($M^+$+1):504.

Example 66

2-[3-(benzyloxy)-5-isopropoxyphenyl]-6-(2-methylphenyl)-3H-imidazo[4,5-b]pyridine HPLC purity 97%. m/e($M^+$+1):450.

Example 67

2-[3-(benzyloxy)-5-isopropoxyphenyl]-6-(2-methoxyphenyl)-3H-imidazo[4,5-b]pyridine HPLC purity 100%. m/e($M^+$+1):466.

Example 68

2-[3-(benzyloxy)-5-isopropoxyphenyl]-6-[2-(trifluoromethyl)phenyl]-3H-imidazo[4,5-b]pyridine HPLC purity 86%. m/e($M^+$+1):504.

Example 69

2-{2-[3-(benzyloxy)-5-isopropoxyphenyl]-3H-imidazo[4,5-b]pyridin-6-yl}phenol

HPLC purity 95%. m/e($M^+$+1):452.

Example 70

2-[3-(benzyloxy)-5-isopropoxyphenyl]-6-(3-fluorophenyl)-3H-imidazo[4,5-b]pyridine HPLC purity 99%. m/e($M^+$+1):454.

Example 71

2-[5-(benzyloxy)-2-isopropoxyphenyl]-6-(3-fluorophenyl)-3H-imidazo[4,5-b]pyridine HPLC purity 98%. m/e($M^+$+1):454.

Example 72

2-[4-(benzyloxy)-2-isopropoxyphenyl]-6-(2-fluorophenyl)-3H-imidazo[4,5-b]pyridine HPLC purity 98%. m/e($M^+$+1):454.

Example 73

2-[4-(benzyloxy)-2-isopropoxyphenyl]-6-(3-fluorophenyl)-3H-imidazo[4,5-b]pyridine HPLC purity 91%. m/e($M^+$+1):454.

Example 74 ethyl 2-[5-(benzyloxy)-2-isopropoxyphenyl]-3H-imidazo[4,5-b]pyridine-6-carboxylate The title compound was obtained as colorless crystals (yield 25%) according to the method of Example 1. melting point 138-140° C. purity 90%. M+H: 432.

Example 75

2-[5-(benzyloxy)-2-isopropoxyphenyl]-3H-imidazo[4,5-b]pyridine-6-carboxylic acid A solution of ethyl 2-[5-(benzyloxy)-2-isopropoxyphenyl]-3H-imidazo[4,5-b]pyridine-6-carboxylate (0.14 g) and 1N aqueous sodium hydroxide solution (6.5 ml) in ethanol (10 ml) was stirred at room temperature for 18 hr. The reaction mixture was adjusted with 1N hydrochloric acid to pH 4, and the precipitated crystals were collected by filtration, and washed with water and ethanol to give the title compound (0.12 g, yield 93%) as colorless crystals. purity 96%. M+H: 404. $^1$H NMR (DMSO-$d_6$) (: 1.35 (6H, d, J=6.0 Hz), 4.70-4.78 (1H, m), 5.19 (2H, s), 7.35-7.53 (8H, m), 8.44 (1H, s), 8.92 (1H, s).

Example 76

{2-[5-(benzyloxy)-2-isopropoxyphenyl]-3H-imidazo[4,5-b]pyridin-6-yl}methanol

To a mixture of ethyl 2-[5-(benzyloxy)-2-isopropoxyphenyl]-3H-imidazo[4,5-b]pyridine-6-carboxylate (0.36 g) in tetrahydrofuran (5 ml) was added lithium aluminum hydride (48 mg) under ice-cooling, and the reaction mixture was stirred at room temperature for 3 hrs. Water was added to the reaction mixture, and the mixture was extracted with ethyl acetate. The extract was washed with water, dried over magnesium sulfate and concentrated. The obtained crude crystals were washed with diethyl ether to give the title compound (0.12 g, yield 37%) as colorless crystals. melting point 167-168(C. purity 98%. M+H: 390.

Example 77

2-[5-(benzyloxy)-2-isopropoxyphenyl]-3H-imidazo[4,5-b]pyridine-6-carbaldehyde

To a solution of {2-[5-(benzyloxy)-2-isopropoxyphenyl]-3H-imidazo[4,5-b]pyridin-6-yl}methanol (1.0 g) in dichloromethane (50 ml) was added manganese peroxide (2.3 g), and the mixture was stirred at room temperature for 8 hr. The insoluble material was removed by filtration, and the filtrate was concentrated. The obtained crude crystals were washed with diethyl ether to give the title compound (0.70 g, yield 69%) as colorless crystals. melting point 170-171° C. purity 87%. M+H: 388. ¹H NMR (CDCl₃) δ: 1.52 (6H, d, J=6.0 Hz), 4.76-4.85 (1H, m), 5.17 (2H, s), 7.03-7.07 (1H, m), 7.11-7.16 (1H, m), 7.31-7.52 (5H, m), 8.20 (1H, d, J=3.2 Hz), 8.53 (1H, s), 8.88 (1H, d, J=1.5 Hz), 10.19 (1H, s).

Example 78

N-({2-[5-(benzyloxy)-2-isopropoxyphenyl]-3H-imidazo[4,5-b]pyridin-6-yl}methyl)-2-methylpropan-1-amine A solution of 2-[5-(benzyloxy)-2-isopropoxyphenyl]-3H-imidazo[4,5-b]pyridine-6-carbaldehyde (50 mg) and 2-methylpropan-1-amine (14 mg) in 10% acetic acid-dichloromethane (2 ml) was stirred at room temperature for 20 min. Sodium triacetoxyborohydride (55 mg) was added, and the mixture was stirred at room temperature for 18 hr. Water was added to the reaction mixture, and the mixture was extracted with dichloromethane. The extract was washed with water and concentrated. The residue was purified by preparative HPLC. Saturated aqueous sodium hydrogencarbonate solution was added to the obtained fraction to neutralize the mixture, and the mixture was extracted with dichloromethane. The extract was concentrated to give the title compound (32 mg, yield 56%) as colorless crystals. melting point 101-103° C. purity 97%. M+H: 445. ¹H NMR (CDCl₃) δ: 0.92 (6H, dd, J=6.6, 1.7 Hz), 1.49 (6H, dd, J=5.9, 1.6 Hz), 1.70-1.85 (1H, m), 2.50 (2H, d, J=6.8 Hz), 3.97 (2H, s), 4.71-4.78 (1H, m), 5.15 (2H, s), 6.98-7.08 (2H, m), 7.31-7.50 (5H, m), 8.05 (1H, s), 8.18 (1H, s), 8.33 (1H, s).

The following compounds of Examples 79 to 82 were obtained according to the method of Example 78.

Example 79

N-benzyl-1-{2-[5-(benzyloxy)-2-isopropoxyphenyl]-3H-imidazo[4,5-b]pyridin-6-yl}methaneamine As colorless crystals (yield 52%). melting point 92-94° C. purity 99%. M+H: 479. ¹H NMR (CDCl₃) δ: 1.50 (6H, d, J=6.0 Hz), 3.85 (2H, s), 3.97 (2H, s), 4.72-4.80 (1H, m), 5.17 (2H, s), 7.00-7.11 (2H, m), 7.32-7.50 (10H,m), 8.08 (1H, s), 8.20 (1H, d, J=3.0 Hz), 8.35 (1H, d, J=1.7 Hz).

Example 80

N-({2-[5-(benzyloxy)-2-isopropoxyphenyl]-3H-imidazo[4,5-b]pyridin-6-yl}methyl)-2-phenoxyethaneamine As colorless crystals (yield 37%). melting point 67-68° C. purity 91%. M+H: 509. ¹H NMR (CDCl₃) δ: 1.50 (6H, d, J=6.0 Hz), 3.06 (2H, t, J=5.0 Hz), 4.04 (2H, s), 4.11 (2H, d, J=5.0 Hz), 4.72-4.80 (1H, m), 5.17 (2H, s), 6.89-7.11 (2H, m), 7.27-7.50 (7H, m), 8.07 (1H, s), 8.20 (1H, d, J=3.0 Hz), 8.36 (1H, s).

Example 81

N-({2-[5-(benzyloxy)-2-isopropoxyphenyl]-3H-imidazo[4,5-b]pyridin-6-yl}methyl)-2-methoxyethaneamine As colorless crystals (yield 30%). melting point 80-81° C. purity 99%. M+H: 447. ¹H NMR (CDCl₃) δ: 1.50 (6H, d, J=6.0 Hz), 2.83-2.86 (2H, m), 3.36 (3H, s), 3.51-3.55 (2H, m), 3.98 (2H, s), 4.74-4.79 (1H, m), 5.17 (2H, s), 7.00-7.10 (2H, m), 7.32-7.50 (5H, m), 8.05 (1H, s), 8.20 (1H, d, J=3.0 Hz), 8.34 (1H, s).

Example 82 methyl N-({2-[5-(benzyloxy)-2-isopropoxyphenyl]-3H-imidazo[4,5-b]pyridin-6-yl}methyl)glycinate As colorless crystals (yield 32%). melting point 69-71° C. purity 99%. M+H: 461. ¹H NMR (CDCl₃) δ: 1.50 (6H, d, J=6.0 Hz), 3.46 (2H, s), 3.75 (3H, m), 3.98 (2H, s), 4.72-4.80 (1H, m), 5.17 (2H, s), 6.99-7.12 (2H, m), 7.29-7.51 (5H, m), 8.05 (1H, s), 8.19 (1H, d, J=3.0 Hz), 8.34 (1H, s).

Example 83

N-({2-[5-(benzyloxy)-2-isopropoxyphenyl]-3H-imidazo[4,5-b]pyridin-6-yl}methyl)glycine A solution of methyl N-({2-[5-(benzyloxy)-2-isopropoxyphenyl]-3H-imidazo[4,5-b]pyridin-6-yl}methyl)glycinate (15 mg) and 1N aqueous sodium hydroxide solution (0.1 ml) in methanol (2 ml) was stirred at room temperature for 18 hr. The reaction mixture was adjusted with 1N aqueous citric acid solution to pH 4. The precipitated crystals were collected by filtration and washed with diethyl ether to give the title compound (9.7 mg, yield 66%) as colorless crystals. melting point 182-184° C. purity 86%. M+H: 447. ¹H NMR (DMSO-d₆) δ: 1.48 (6H, d, J=6.0 Hz), 3.46 (2H, s), 3.98 (2H, s), 4.72-4.80 (1H, m), 5.17 (2H, s), 6.99-7.12 (2H, m), 7.29-7.51 (5H, m), 8.05 (1H, s), 8.19 (1H, s), 8.34 (1H, s).

Example 84

2-[5-(benzyloxy)-2-isopropoxyphenyl]-3H-imidazo[4,5-b]pyridine-5-carbonitrile

A solution (10 ml) of 2-[5-(benzyloxy)-2-isopropoxyphenyl]-3H-imidazo[4,5-b]pyridine 4-oxide, triethylamine (0.11 g) and trimethylsilyl cyanide (0.22 g) in acetonitrile was heated under reflux for 5 hr. The reaction mixture was diluted with water and extracted with ethyl acetate. The extract was washed with water, dried over magnesium sulfate and concentrated. The obtained crude crystals were washed with diethyl ether to give the title compound (0.15 g, yield 69%) as colorless crystals. melting point 214-215° C. purity 93%. M+H: 385. ¹H NMR (CDCl₃) δ: 1.53 (6H, d, J=6.0 Hz), 4.77-4.85 (1H, m), 5.16 (2H, s), 7.06 (1H, d, J=9.0 Hz), 7.12-7.18 (1H, m), 7.32-7.50 (5H, m), 7.66 (1H, d, J=8.1 Hz), 8.12 (1H, d, J=8.1 Hz), 8.20 (1H, d, J=3.0 Hz).

Example 85 methyl 2-[5-(benzyloxy)-2-isopropoxyphenyl]-3H-imidazo[4,5-b]pyridine-5-carboxylate A solution of 2-[5-(benzyloxy)-2-isopropoxyphenyl]-3H-imidazo[4,5-b]pyridine-5-carbonitrile (60 mg) in hydrochloric acid-methanol (5 ml) was heated under reflux for 6 hr. The reaction mixture was adjusted with aqueous sodium hydrogencarbonate solution to pH 8, and extracted with ethyl acetate. The extract was washed with water; dried over magnesium sulfate and concentrated. The obtained crude crystals were washed with ethanol to give the title compound (40 mg, yield 61%) as colorless crystals. purity 95%. M+H: 418. ¹H NMR (CDCl$_3$) δ: 1.50 (6H, d, J=6.2 Hz), 4.06 (3H, s), 4.75-4.82 (1H, m), 5.17 (2H, s), 7.02-7.07 (1H, m), 7.10-7.15 (1H, m), 7.31-7.50 (5H, m), 8.12-8.22 (3H, m), 11.17 (1H, s).

Example 86

2-[5-(benzyloxy)-2-isopropoxyphenyl]-3H-imidazo[4,5-b]pyridine-5-carboxylic acid A solution (2 ml) of methyl 2-[5-(benzyloxy)-2-isopropoxyphenyl]-3H-imidazo[4,5-b]pyridine-5-carboxylate (35 mg) and 1N aqueous sodium hydroxide solution (0.2 ml) in methanol was stirred at room temperature for 18 hr. The reaction mixture was adjusted with 1N hydrochloric acid to pH 3, and the precipitated crystals were collected by filtration and washed with acetonitrile to give the title compound (22 mg, yield 64%) as colorless crystals. purity 98%. M+H: 404. $^1$H NMR (DMSO-d$_6$) δ: 1.37 (6H, d, J=5.0 Hz), 4.67-4.72 (1H, m), 5.17 (2H, s), 7.16-7.52 (7H, m), 7.73-8.13 (3H, m).

Example 87

{2-[5-(benzyloxy)-2-isopropoxyphenyl]-3H-imidazo[4,5-b]pyridin-5-yl}methanol

To a mixture of methyl 2-[5-(benzyloxy)-2-isopropoxyphenyl]-3H-imidazo[4,5-b]pyridine-5-carboxylate (0.45 g) in tetrahydrofuran (10 ml) was added lithium aluminum hydride (82 mg) under ice-cooling. The reaction mixture was stirred at room temperature for 1 hr, and water was added. The insoluble material was removed by filtration, and the filtrate was concentrated to give the title compound (0.26 g, yield 61%) as colorless crystals. melting point 167-168° C. purity 99%. M+H: 390. $^1$H NMR (CDCl$_3$) δ: 1.52 (6H, d, J=6.0 Hz), 4.74-4.82 (1H, m), 5.16 (2H, s), 7.00-7.50 (8H, m), 8.06 (1H, d, J=8.1 Hz), 8.19 (1H, d, J=3.0 Hz).

Example 88

2-[5-(benzyloxy)-2-isopropoxyphenyl]-5-(chloromethyl)-3H-imidazo[4,5-b]pyridine

A solution of {2-[5-(benzyloxy)-2-isopropoxyphenyl]-3H-imidazo[4,5-b]pyridin-5-yl}methanol (0.11 g) and thionyl chloride (0.1 g) in chloroform (10 ml) was heated under reflux for 3 hr. The reaction mixture was concentrated, and saturated aqueous sodium hydrogencarbonate solution was added, and the mixture was extracted with ethyl acetate. The extract was washed with water, dried over magnesium sulfate and concentrated to give the title compound (0.11 g, yield 96%) as colorless crystals. purity 85%. M+H: 408. $^1$H NMR (CDCl$_3$) δ: 1.51 (6H, d, J=6.0 Hz), 3.97-4.15 (2H, m), 4.72-4.81 (1H, m), 5.16 (2H, s), 7.00-7.06 (1H, m), 7.07-7.12 (1H, m), 7.31-7.51 (6H, m), 8.07 (1H, d, J=7.9 Hz), 8.20 (1H, s).

Example 89

{2-[5-(benzyloxy)-2-isopropoxyphenyl]-3H-imidazo[4,5-b]pyridin-5-yl}acetonitrile A solution of 2-[5-(benzyloxy)-2-isopropoxyphenyl]-5-(chloromethyl)-3H-imidazo[4,5-b]pyridine (0.11 g) and potassium cyanide (30 mg) in N,N-dimethylformamide (5 ml) was stirred at 60° C. for 16 hr. Water was added to the reaction mixture, and the mixture was extracted with ethyl acetate. The extract was washed with water, dried over magnesium sulfate and concentrated. The residue was purified by preparative HPLC, and saturated aqueous sodium hydrogencarbonate solution was added to the obtained fraction to neutralize the mixture. The mixture was extracted with dichloromethane, and the extract was concentrated to give the title compound (56 mg, yield 52%) as colorless crystals. purity 90%. M+H: 399.

Example 90 methyl {2-[5-(benzyloxy)-2-isopropoxyphenyl]-3H-imidazo[4,5-b]pyridin-5-yl}acetate A mixture of {2-[5-(benzyloxy)-2-isopropoxyphenyl]-3H-imidazo[4,5-b]pyridin-5-yl}acetonitrile (50 mg) and hydrochloric acid-methanol (5 ml) was heated under reflux for 16 hr. The reaction mixture was concentrated, and the saturated aqueous sodium hydrogencarbonate solution was added, and the mixture was extracted with ethyl acetate. The extract was washed with water, dried over magnesium sulfate and concentrated to give the title compound (28 mg, yield 50%) as colorless crystals. purity 80%. M+H: 432.

Example 91

{2-[5-(benzyloxy)-2-isopropoxyphenyl]-3H-imidazo[4,5-b]pyridin-5-yl}acetic acid

A mixture of methyl {2-[5-(benzyloxy)-2-isopropoxyphenyl]-3H-imidazo[4,5-b]pyridin-5-yl}acetate (25 mg) and 1N sodium hydroxide (0.5 ml) in methanol (5 ml) was stirred at room temperature for 18 hr. The reaction mixture was adjusted with 1N citric acid to pH 4, and the precipitated crystals were collected by filtration and washed with diethyl ether to give the title compound (14 mg, yield 51%) as colorless crystals. purity 96%. M+H: 418. $^1$H NMR (CD$_3$OD) δ: 1.45 (6H, d, J=6.0 Hz), 4.06 (2H, s), 4.78-4.83 (1H, m), 5.16 (2H, s), 7.28-7.58 (8H, m), 7.84 (1H, d, J=2.8 Hz), 8.28 (1H, d, J=8.3 Hz).

Example 92

2-(5-(benzyloxy)-2-isopropoxyphenyl)-6-bromo-3H-imidazo[4,5-b]pyridine

The title compound was obtained according to the method of Example 1. $^1$H NMR (CD$_3$OD) δ: 1.50 (6 H, d, J=6.11 Hz) 4.70-4.83 (1 H, m) 5.16 (2 H, s) 6.98-7.06 (1 H, m) 7.07-7.14 (1 H, m) 7.30-7.37 (1 H, m) 7.37-7.44 (2 H, m) 7.44-7.51 (2 H, m) 8.16 (1 H, d, J=2.93 Hz) 8.20 (1 H, d, J=1.71 Hz) 8.39 (1 H, d, J=1.96 Hz) 11.13 (1 H, s).

Example 93

2-[5-(benzyloxy)-2-(cyclopropylmethoxy)phenyl]-3H-imidazo[4,5-b]pyridine trifluoroacetate A mixture of methyl 5-(benzyloxy)-2-hydroxybenzoate (52 mg), cesium carbonate (98 mg) and (chloromethyl)cyclopropane (27 mg) was stirred at room temperature for 18 hr. The reaction mixture was diluted with water and extracted with ethyl acetate. After evaporation of the solvent, 1N aqueous sodium hydroxide (0.5 ml) was added to a solution of the obtained compound in methanol (1.5 ml). The mixture was stirred at 60° C. for 18 hr. The reaction mixture was diluted with 1N aqueous hydrochloride (0.7 ml) and extracted with ethyl acetate. After concentration of the extract, a mixture of the obtained product, 1-hydroxybenztriazole hydrate (41 mg), 1-ethyl-3-(3-dimethylaminopropyl)carbodiimide hydrochloride (58 mg) and pyridine-2,3-diamine (30 mg) in N,N-dimethylformamide (2 ml) was stirred at room temperature for 15 hr. The reaction mixture was diluted with water and extracted with ethyl acetate. The extract was concentrated. The obtained product was added to acetic acid (1.5 ml)-ethanol (1.5 ml), and the mixture was subjected to microwave irradiation in a sealed reaction container at 180° C. for 40 min. The reaction mixture was concentrated, and the residue was purified by preparative HPLC to give the title compound (4.9 mg, LC-MS purity 91%). M+H: 372.

The following compounds of Examples 94 to 155 were obtained according to the method of Example 93.

Example 94

2-[2,5-bis(benzyloxy)phenyl]-3H-imidazo[4,5-b]pyridine trifluoroacetate

HPLC purity 99%. m/e($M^+$+1):408.

Example 95

2-[5-(benzyloxy)-2-(pyridin-2-ylmethoxy)phenyl]-3H-imidazo[4,5-b]pyridine ditrifluoroacetate HPLC purity 92%. m/e($M^+$+1):409.

Example 96

2-[5-(benzyloxy)-2-(pyridin-3-ylmethoxy)phenyl]-3H-imidazo[4,5-b]pyridine ditrifluoroacetate HPLC purity 100%. m/e($M^+$+1):409.

Example 97

2-[5-(benzyloxy)-2-(tetrahydrofuran-2-ylmethoxy)phenyl]-3H-imidazo[4,5-b]pyridine trifluoroacetate HPLC purity 100%. m/e($M^+$+1):402.

Example 98

2-[5-(benzyloxy)-2-(tetrahydro-2H-pyran-2-ylmethoxy)phenyl]-3H-imidazo[4,5-b]pyridine trifluoroacetate HPLC purity 92%. m/e($M^+$+1):416.

Example 99

2-[5-(benzyloxy)-2-(2-piperidin-1-ylethoxy)phenyl]-3H-imidazo[4,5-b]pyridine ditrifluoroacetate HPLC purity 93%. m/e($M^+$+1):429.

Example 100

2-{5-(benzyloxy)-2-[(3-methylbut-2-en-1-yl)oxy]phenyl}-3H-imidazo[4,5-b]pyridine trifluoroacetate HPLC purity 100%. m/e($M^+$+1):386.

Example 101

2-{5-(benzyloxy)-2-[(4-methoxybenzyl)oxy]phenyl}-3H-imidazo[4,5-b]pyridine trifluoroacetate HPLC purity 100%. m/e($M^+$+1):438.

Example 102

2-{5-(benzyloxy)-2-[(2-fluorobenzyl)oxy]phenyl}-3H-imidazo[4,5-b]pyridine trifluoroacetate HPLC purity 100%. m/e($M^+$+1):426.

Example 103

2-[3-(benzyloxy)-5-(cyclopropylmethoxy)phenyl]-3H-imidazo[4,5-b]pyridine trifluoroacetate HPLC purity 91%. m/e($M^+$+1):372.

Example 104

2-[3,5-bis(benzyloxy)phenyl]-3H-imidazo[4,5-b]pyridine trifluoroacetate

HPLC purity 98%. m/e($M^+$+1):408.

Example 105

2-[3-(benzyloxy)-5-(pyridin-3-ylmethoxy)phenyl]-3H-imidazo[4,5-b]pyridine ditrifluoroacetate HPLC purity 100%. m/e($M^+$+1):409.

Example 106

2-[3-(benzyloxy)-5-(2-phenylethoxy)phenyl]-3H-imidazo[4,5-b]pyridine trifluoroacetate HPLC purity 93%. m/e($M^+$+1):422.

Example 107

2-[3-(benzyloxy)-5-(tetrahydrofuran-2-ylmethoxy)phenyl]-3H-imidazo[4,5-b]pyridine trifluoroacetate HPLC purity 100%. m/e($M^+$+1):402.

Example 108

2-[3-(benzyloxy)-5-(1-naphthylmethoxy)phenyl]-3H-imidazo[4,5-b]pyridine trifluoroacetate HPLC purity 99%. m/e($M^+$+1):458.

Example 109

2-{3-(benzyloxy)-5-[(3-methylbut-2-en-1-yl)oxy]phenyl}-3H-imidazo[4,5-b]pyridine trifluoroacetate HPLC purity 95%. m/e($M^+$+1):386.

Example 110

2-{3-(benzyloxy)-5-[(2-fluorobenzyl)oxy]phenyl}-3H-imidazo[4,5-b]pyridine trifluoroacetate HPLC purity 100%. m/e(M$^+$+1):426.

Example 111

2-[4-(benzyloxy)-2-(cyclopropylmethoxy)phenyl]-3H-imidazo[4,5-b]pyridine trifluoroacetate HPLC purity 100%. m/e(M$^+$+1):372.

Example 112

2-[2,4-bis(benzyloxy)phenyl]-3H-imidazo[4,5-b]pyridine trifluoroacetate

HPLC purity 100%. m/e(M$^+$+1):408.

Example 113

2-[4-(benzyloxy)-2-(pyridin-2-ylmethoxy)phenyl]-3H-imidazo[4,5-b]pyridine ditrifluoroacetate HPLC purity 100%. m/e(M$^+$+1):409.

Example 114

2-[4-(benzyloxy)-2-(tetrahydrofuran-2-ylmethoxy)phenyl]-3H-imidazo[4,5-b]pyridine trifluoroacetate HPLC purity 100%. m/e(M$^+$+1):402.

Example 115

2-[4-(benzyloxy)-2-(tetrahydro-2H-pyran-2-ylmethoxy)phenyl]-3H-imidazo[4,5-b]pyridine trifluoroacetate HPLC purity 93%. m/e(M$^+$+1):416.

Example 116

2-[4-(benzyloxy)-2-(1-naphthylmethoxy)phenyl]-3H-imidazo[4,5-b]pyridine trifluoroacetate HPLC purity 97%. m/e(M$^+$+1):458.

Example 117

2-{4-(benzyloxy)-2-[(2-fluorobenzyl)oxy]phenyl}-3H-imidazo[4,5-b]pyridine trifluoroacetate HPLC purity 100%. m/e(M$^+$+1):426.

Example 118

2-[5-(benzyloxy)-2-isopropoxyphenyl]-3H-imidazo[4,5-b]pyridine trifluoroacetate

HPLC purity 96%. m/e(M$^+$+1):360.

Example 119

2-[2-isopropoxy-5-(pyridin-4-ylmethoxy)phenyl]-3H-imidazo[4,5-b]pyridine ditrifluoroacetate HPLC purity 100%. m/e(M$^+$+1):361.

Example 120

2-[2-isopropoxy-5-(pyridin-3-ylmethoxy)phenyl]-3H-imidazo[4,5-b]pyridine ditrifluoroacetate HPLC purity 100%. m/e(M$^+$+1):361.

Example 121

2-[5-(2-cyclohexylethoxy)-2-isopropoxyphenyl]-3H-imidazo[4,5-b]pyridine trifluoroacetate HPLC purity 100%. m/e(M$^+$+1):380.

Example 122

2-[2-isopropoxy-5-(2-morpholin-4-ylethoxy)phenyl]-3H-imidazo[4,5-b]pyridine trifluoroacetate HPLC purity 93%. m/e(M$^+$+1):383.

Example 123

2-(2-isopropoxy-5-{[4-(methylsulfonyl)benzyl]oxy}phenyl)-3H-imidazo[4,5-b]pyridine trifluoroacetate HPLC purity 100%. m/e(M$^+$+1):438.

Example 124

2-{5-[(2-fluorobenzyl)oxy]-2-isopropoxyphenyl}-3H-imidazo[4,5-b]pyridine trifluoroacetate HPLC purity 99%. m/e(M$^+$+1):378.

Example 125

2-[3-(benzyloxy)-5-isopropoxyphenyl]-3H-imidazo[4,5-b]pyridine trifluoroacetate

HPLC purity 95%. m/e(M$^+$+1):360.

Example 126

2-[3-isopropoxy-5-(pyridin-4-ylmethoxy)phenyl]-3H-imidazo[4,5-b]pyridine ditrifluoroacetate HPLC purity 100%. m/e(M$^+$+1):361.

Example 127

2-[3-isopropoxy-5-(pyridin-3-ylmethoxy)phenyl]-3H-imidazo[4,5-b]pyridine ditrifluoroacetate HPLC purity 100%. m/e(M$^+$+1):361.

Example 128

2-[3-isopropoxy-5-(2-phenylethoxy)phenyl]-3H-imidazo[4,5-b]pyridine trifluoroacetate HPLC purity 93%. m/e(M$^+$+1):374.

Example 129

2-[3-(2-cyclohexylethoxy)-5-isopropoxyphenyl]-3H-imidazo[4,5-b]pyridine trifluoroacetate HPLC purity 100%. m/e(M$^+$+1):380.

Example 130

2-[3-isopropoxy-5-(2-morpholin-4-ylethoxy)phenyl]-3H-imidazo[4,5-b]pyridine ditrifluoroacetate HPLC purity 100%. m/e(M$^+$+1):383.

Example 131

2-{3-[2-(4-acetylpiperazin-1-yl)ethoxy]-5-isopropoxyphenyl}-3H-imidazo[4,5-b]pyridine ditrifluoroacetate HPLC purity 100%. m/e(M$^+$+1):424.

Example 132

2-[3-isopropoxy-5-(2-piperidin-1-ylethoxy)phenyl]-3H-imidazo[4,5-b]pyridine ditrifluoroacetate HPLC purity 100%. m/e(M$^+$+1):381.

Example 133

2-(3-isopropoxy-5-{[4-(methylsulfonyl)benzyl]oxy}phenyl)-3H-imidazo[4,5-b]pyridine trifluoroacetate HPLC purity 100%. m/e(M$^+$+1):438.

Example 134

2-{3-[(2-fluorobenzyl)oxy]-5-isopropoxyphenyl}-3H-imidazo[4,5-b]pyridine trifluoroacetate HPLC purity 100%. m/e(M$^+$+1):378.

Example 135

2-[4-(benzyloxy)-2-isopropoxyphenyl]-3H-imidazo[4,5-b]pyridine trifluoroacetate

HPLC purity 91%. m/e(M$^+$+1):360.

Example 136

2-[2-isopropoxy-4-(pyridin-4-ylmethoxy)phenyl]-3H-imidazo[4,5-b]pyridine ditrifluoroacetate HPLC purity 100%. m/e(M$^+$+1):361.

Example 137

2-[2-isopropoxy-4-(pyridin-2-ylmethoxy)phenyl]-3H-imidazo[4,5-b]pyridine ditrifluoroacetate HPLC purity 100%. m/e(M$^+$+1):361.

Example 138

2-[4-(2-cyclohexylethoxy)-2-isopropoxyphenyl]-3H-imidazo[4,5-b]pyridine trifluoroacetate HPLC purity 100%. m/e(M$^+$+1):380.

Example 139

2-(2-isopropoxy-4-{[4-(methylsulfonyl)benzyl]oxy}phenyl)-3H-imidazo[4,5-b]pyridine trifluoroacetate HPLC purity 100%. m/e(M$^+$+1):438.

Example 140

2-{4-[(2-fluorobenzyl)oxy]-2-isopropoxyphenyl}-3H-imidazo[4,5-b]pyridine trifluoroacetate HPLC purity 98%. m/e(M$^+$+1):378.

Example 141

2-{3-[(4-methylbenzyl)oxy]-5-[(1-methyl-1H-imidazol-2-yl)methoxy]phenyl}-3H-imidazo[4,5-b]pyridine ditrifluoroacetate HPLC purity 100%. m/e(M$^+$+1):426.

Example 142

2-{3-[(3-fluorobenzyl)oxy]-5-[(1-methyl-1H-imidazol-2-yl)methoxy]phenyl}-3H-imidazo[4,5-b]pyridine ditrifluoroacetate HPLC purity 100%. m/e(M$^+$+1):430.

Example 143

2-(3-[(1-methyl-1H-imidazol-2-yl)methoxy]-5-{[4-(methylsulfonyl)benzyl]oxy}phenyl)-3H-imidazo[4,5-b]pyridine ditrifluoroacetate HPLC purity 100%. m/e(M$^+$+1):490.

Example 144

2-{3-[(2,6-difluorobenzyl)oxy]-5-[(1-methyl-1H-imidazol-2-yl)methoxy]phenyl}-3H-imidazo[4,5-b]pyridine ditrifluoroacetate HPLC purity 100%. m/e(M$^+$+1):448.

Example 145

2-{3-[(3,5-difluorobenzyl)oxy]-5-[(1-methyl-1H-imidazol-2-yl)methoxy]phenyl}-3H-imidazo[4,5-b]pyridine ditrifluoroacetate HPLC purity 100%. m/e(M$^+$+1):448.

Example 146

2-{3-[3-(4-fluorophenoxy)propoxy]-5-[(1-methyl-1H-imidazol-2-yl)methoxy]phenyl}-3H-imidazo[4,5-b]pyridine ditrifluoroacetate HPLC purity 100%. m/e(M$^+$+1):474.

Example 147

2-[3-[(1-methyl-1H-imidazol-2-yl)methoxy]-5-(2-phenylethoxy)phenyl]-3H-imidazo[4,5-b]pyridine ditrifluoroacetate HPLC purity 100%. m/e(M$^+$+1):426.

Example 148

2-{3-[2-(4-fluorophenyl)ethoxy]-5-[(1-methyl-1H-imidazol-2-yl)methoxy]phenyl}-3H-imidazo[4,5-b]pyridine ditrifluoroacetate HPLC purity 100%. m/e(M$^+$+1):444.

Example 149

2-{3-[2-(4-methoxyphenyl)ethoxy]-5-[(1-methyl-1H-imidazol-2-yl)methoxy]phenyl}-3H-imidazo[4,5-b]pyridine ditrifluoroacetate HPLC purity 100%. m/e(M$^+$+1):456.

Example 150

2-{3-[(1-methyl-1H-imidazol-2-yl)methoxy]-5-[(3-phenoxybenzyl)oxy]phenyl}-3H-imidazo[4,5-b]pyridine ditrifluoroacetate HPLC purity 100%. m/e(M$^+$+1):504.

Example 151

2-[3-[(1-methyl-1H-imidazol-2-yl)methoxy]-5-(3-phenylpropoxy)phenyl]-3H-imidazo[4,5-b]pyridine ditrifluoroacetate HPLC purity 100%. m/e(M$^+$+1):440.

Example 152

2-(3-[(1-methyl-1H-imidazol-2-yl)methoxy]-5-{[4-(morpholin-4-ylcarbonyl)benzyl]oxy}phenyl)-3H-imidazo[4,5-b]pyridine ditrifluoroacetate HPLC purity 100%. m/e(M$^+$+1):525.

Example 153

4-(2-{3-(3H-imidazo[4,5-b]pyridin-2-yl)-5-[(1-methyl-1H-imidazol-2-yl)methoxy]phenoxy}ethoxy)benzonitrile ditrifluoroacetate HPLC purity 100%. m/e(M$^+$+1):467.

Example 154

2-[3-[(1-methyl-1H-imidazol-2-yl)methoxy]-5-({2-[(E)-2-(2,4,6-trifluorophenyl)vinyl]-1,3-oxazol-4-yl}methoxy)phenyl]-3H-imidazo[4,5-b]pyridine ditrifluoroacetate HPLC purity 100%. m/e(M$^+$+1):559.

Example 155

1-[4-(2-{3-(3H-imidazo[4,5-b]pyridin-2-yl)-5-[(1-methyl-1H-imidazol-2-yl)methoxy]phenoxy}cyclopropyl)phenyl]ethanone ditrifluoroacetate HPLC purity 100%. m/e(M$^+$+1):480.

The structural formulas of the compounds produced in the above-mentioned Examples 1 to 155 are shown in Table 2.

TABLE 2

| Example No. | Structural formula |
| --- | --- |
| 1 | |

TABLE 2-continued
| Example No. | Structural formula |
|---|---|
| 2 | 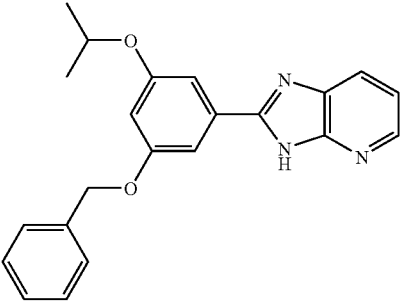 |
| 3 | 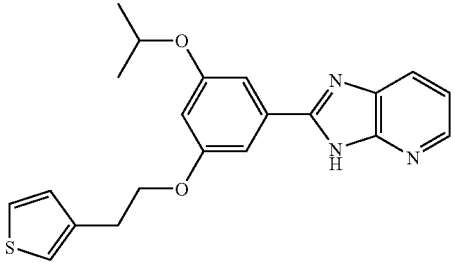 |
| 4 | 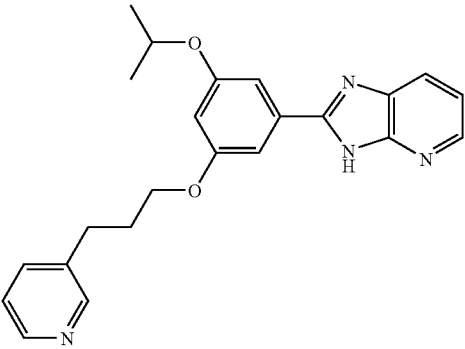 |
| 5 | 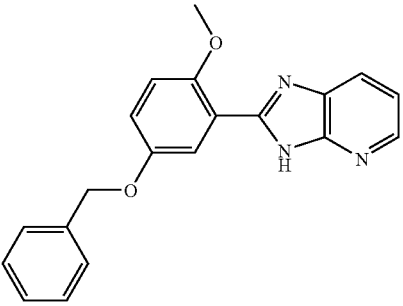 |
| 6 | 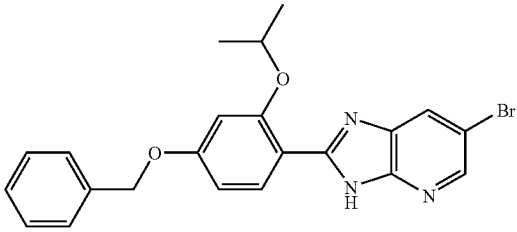 |

TABLE 2-continued
| Example No. | Structural formula |
|---|---|
| 7 | 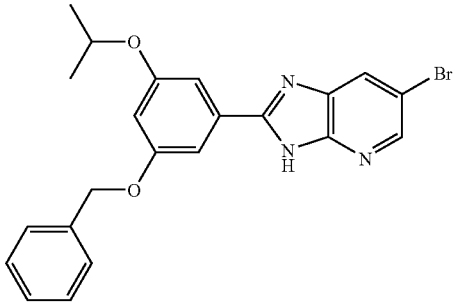 |
| 8 | 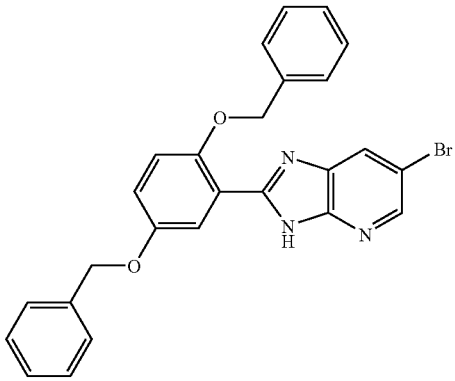 |
| 9 | 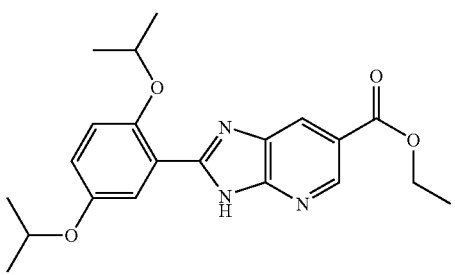 |
| 10 | 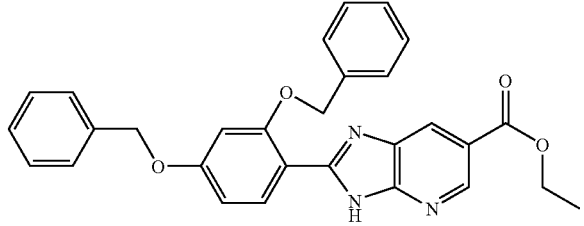 |
| 11 | 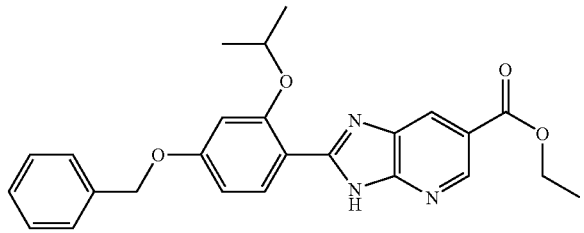 |

TABLE 2-continued
| Example No. | Structural formula |
|---|---|
| 12 | 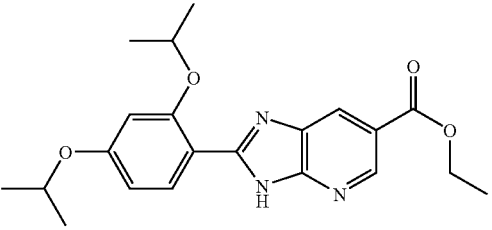 |
| 13 | 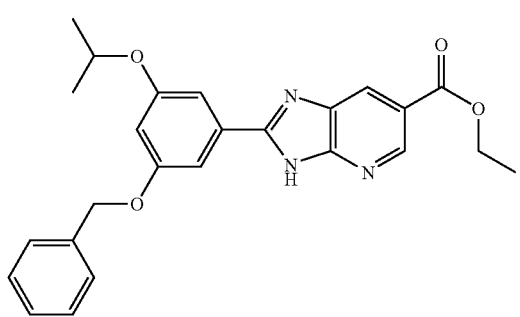 |
| 14 | 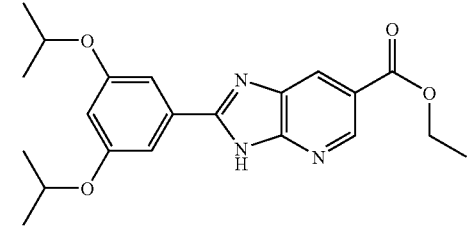 |
| 15 | 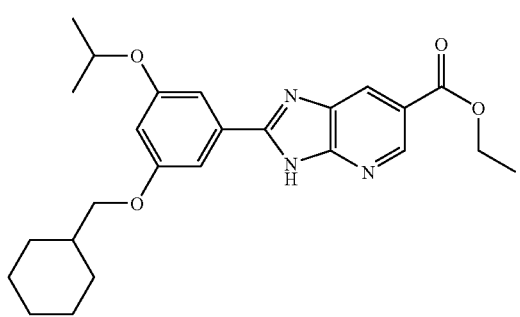 |
| 16 | 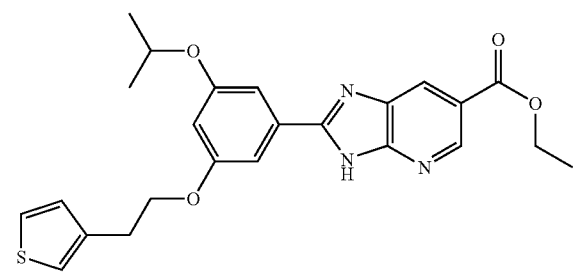 |

TABLE 2-continued

| Example No. | Structural formula |
| --- | --- |
| 17 | |
| 18 | |
| 19 | |
| 20 | |
| 21 | |

TABLE 2-continued

| Example No. | Structural formula |
|---|---|
| 22 | |
| 23 | |
| 24 | |
| 25 | |
| 26 | |

TABLE 2-continued

| Example No. | Structural formula |
|---|---|
| 27 | |
| 28 | |
| 29 | |
| 30 | |
| 31 | |

TABLE 2-continued

| Example No. | Structural formula |
|---|---|
| 32 | |
| 33 | |
| 34 | |
| 35 | |
| 36 | |

TABLE 2-continued

| Example No. | Structural formula |
|---|---|
| 37 | |
| 38 | |
| 39 | |
| 40 | |

TABLE 2-continued
| Example No. | Structural formula |
|---|---|
| 41 | 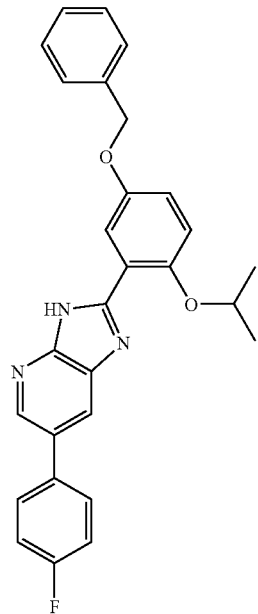 |
| 42 | 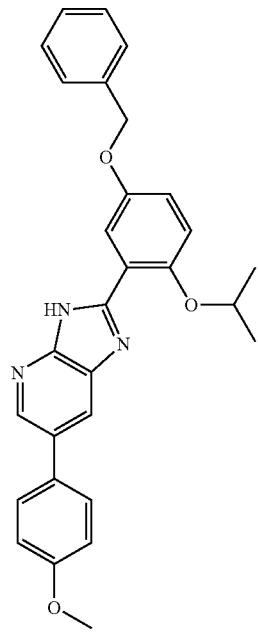 |

TABLE 2-continued
| Example No. | Structural formula |
| --- | --- |
| 43 | 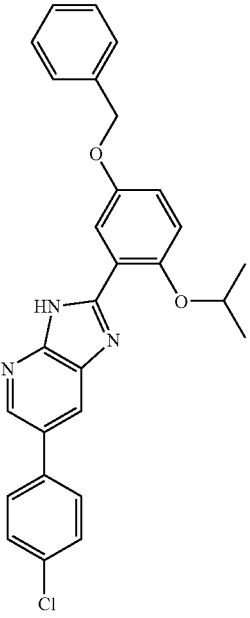 |
| 44 | 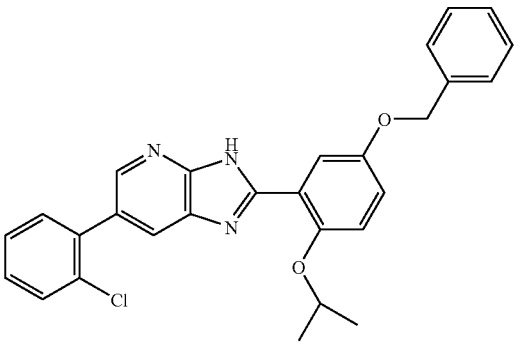 |
| 45 | 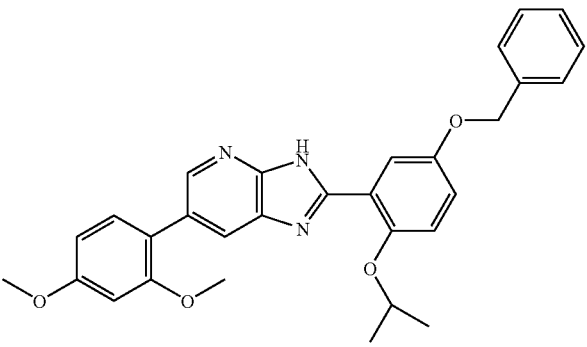 |

TABLE 2-continued
| Example No. | Structural formula |
|---|---|
| 46 | 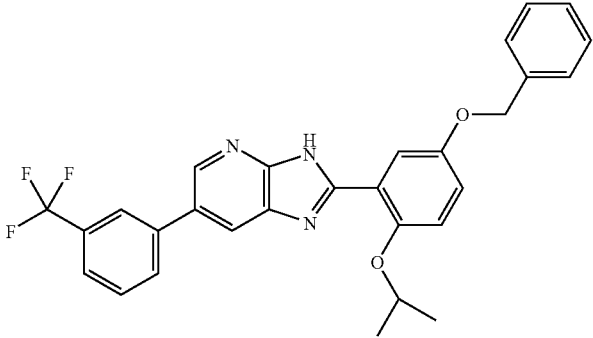 |
| 47 | 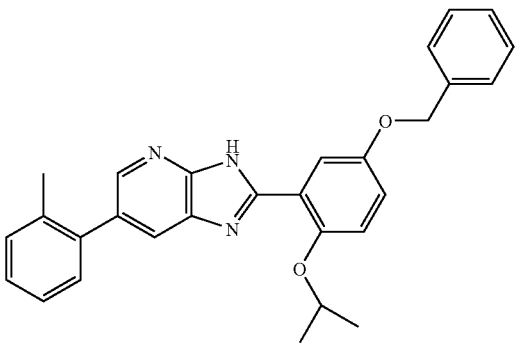 |
| 48 | 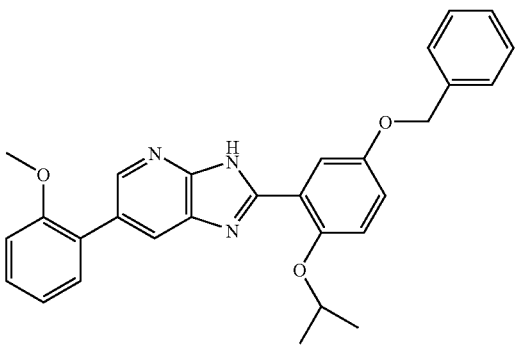 |
| 49 | 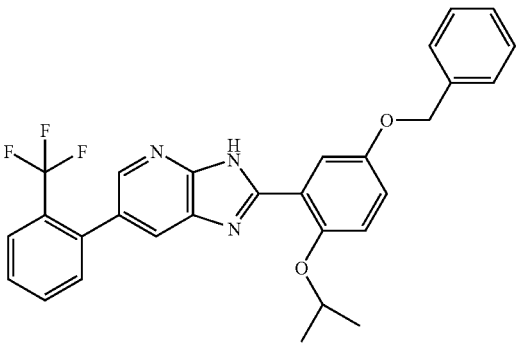 |

TABLE 2-continued
| Example No. | Structural formula |
| --- | --- |
| 50 | 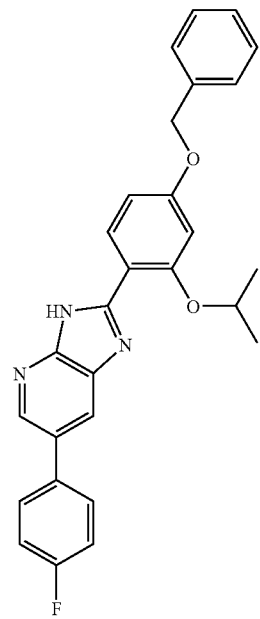 |
| 51 | 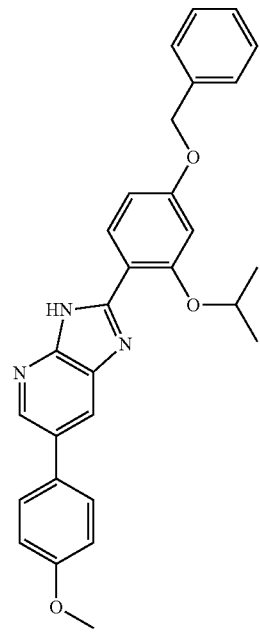 |

TABLE 2-continued

| Example No. | Structural formula |
| --- | --- |
| 52 | |
| 53 | |
| 54 | |
| 55 | |
| 56 | |

TABLE 2-continued

| Example No. | Structural formula |
|---|---|
| 57 | |
| 58 | |
| 59 | |
| 60 | |
| 61 | |

TABLE 2-continued
| Example No. | Structural formula |
|---|---|
| 62 | 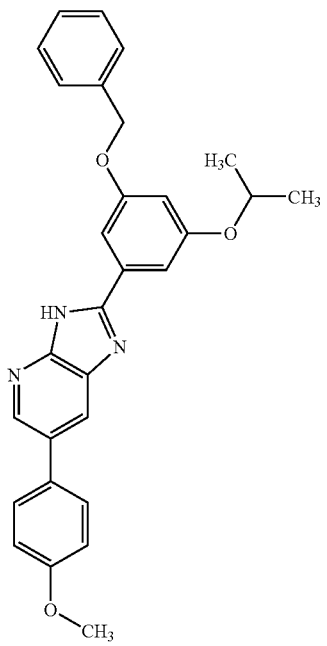 |
| 63 | 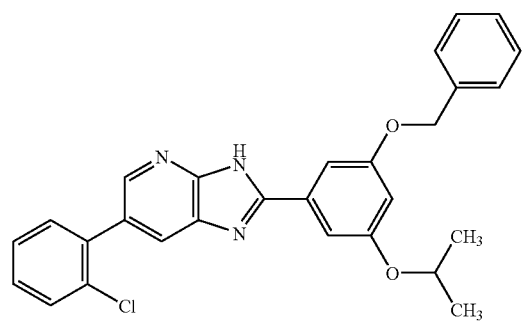 |
| 64 | 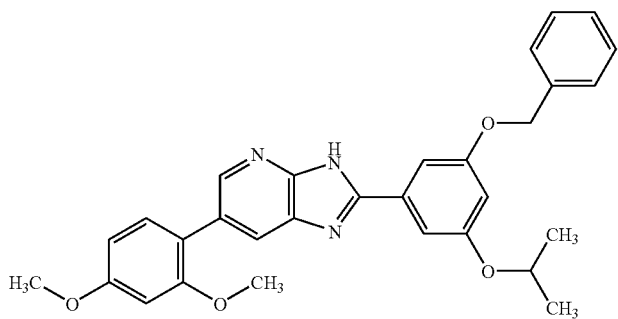 |

TABLE 2-continued
| Example No. | Structural formula |
| --- | --- |
| 65 | 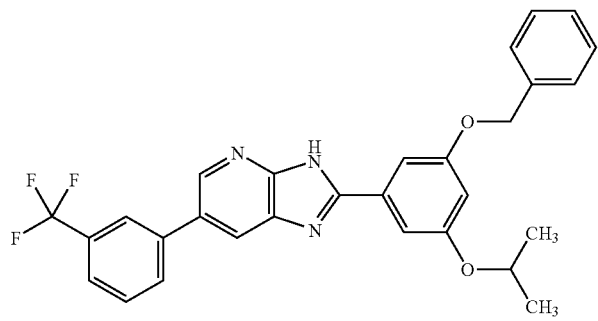 |
| 66 | 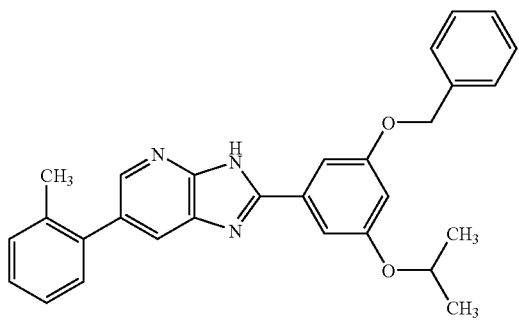 |
| 67 | 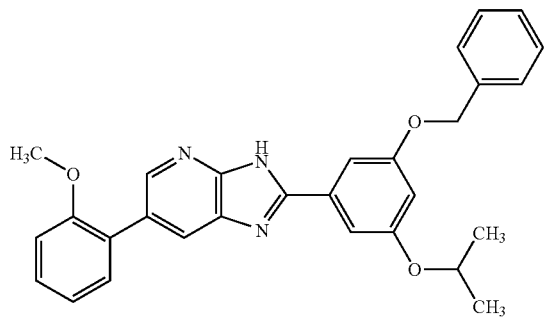 |
| 68 | 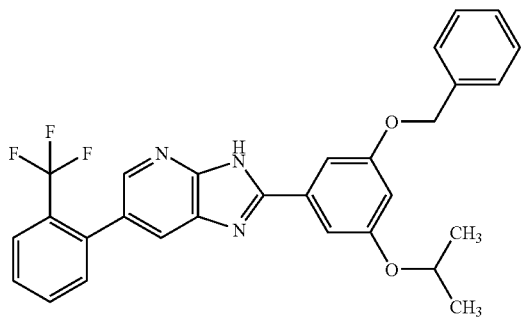 |

TABLE 2-continued
| Example No. | Structural formula |
|---|---|
| 69 | 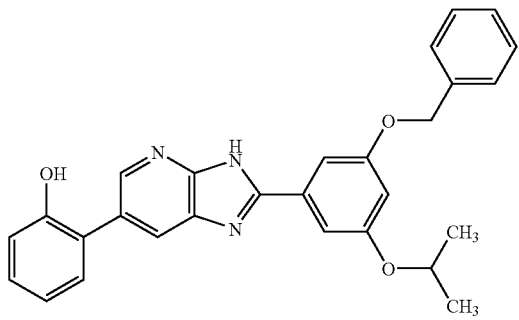 |
| 70 | 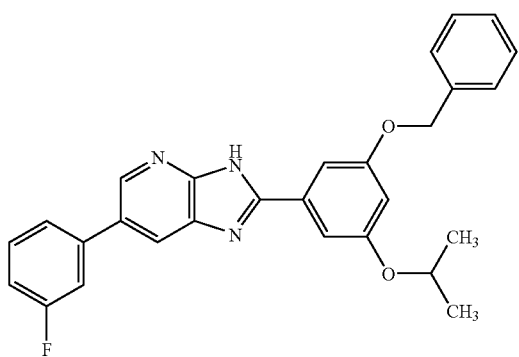 |
| 71 | 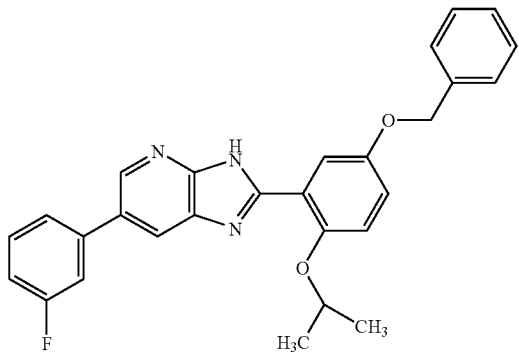 |
| 72 | 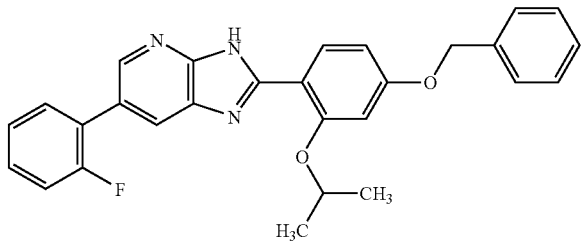 |
| 73 | 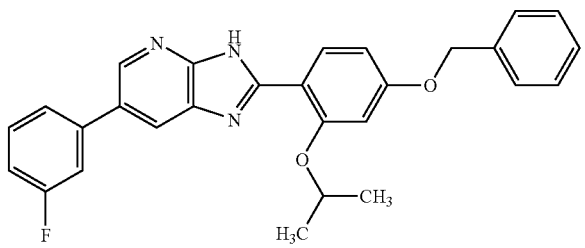 |

TABLE 2-continued

| Example No. | Structural formula |
|---|---|
| 74 | (2-isopropoxy-5-benzyloxyphenyl)-3H-imidazo[4,5-b]pyridine-6-carboxylic acid ethyl ester |
| 75 | (2-isopropoxy-5-benzyloxyphenyl)-3H-imidazo[4,5-b]pyridine-6-carboxylic acid |
| 76 | [2-(2-isopropoxy-5-benzyloxyphenyl)-3H-imidazo[4,5-b]pyridin-6-yl]methanol |
| 77 | 2-(2-isopropoxy-5-benzyloxyphenyl)-3H-imidazo[4,5-b]pyridine-6-carbaldehyde |

TABLE 2-continued
| Example No. | Structural formula |
|---|---|
| 78 | 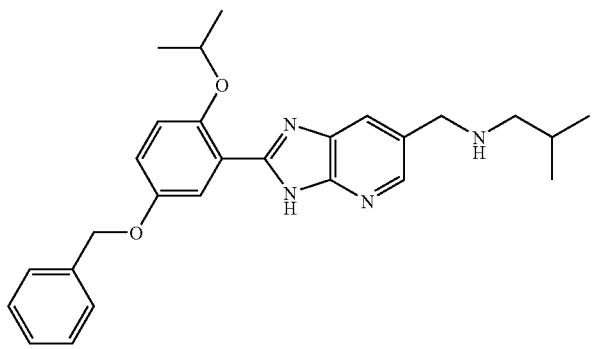 |
| 79 | 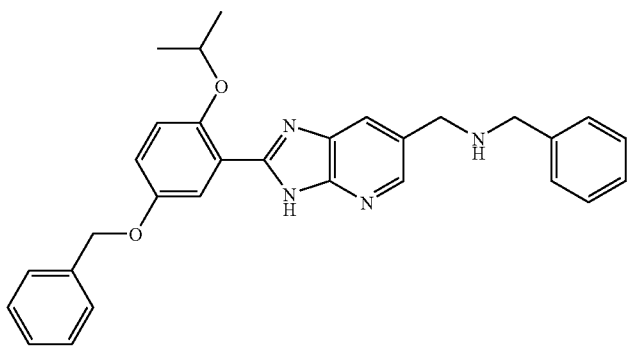 |
| 80 | 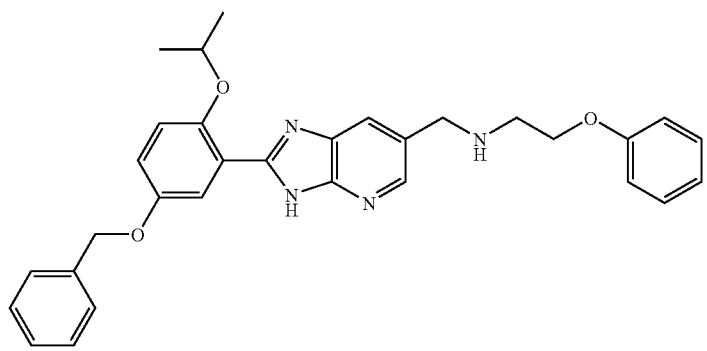 |
| 81 | 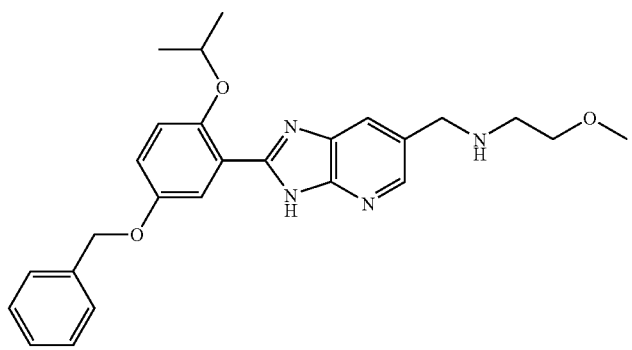 |

TABLE 2-continued
| Example No. | Structural formula |
|---|---|
| 82 | 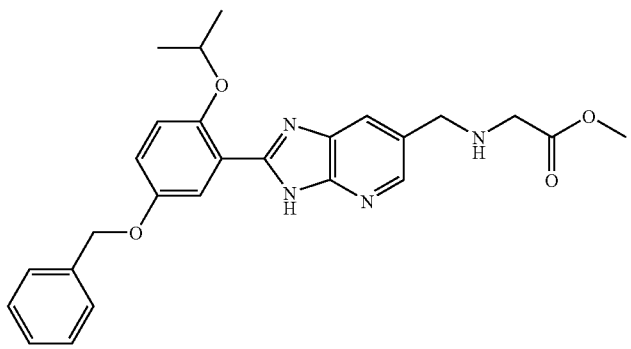 |
| 83 | 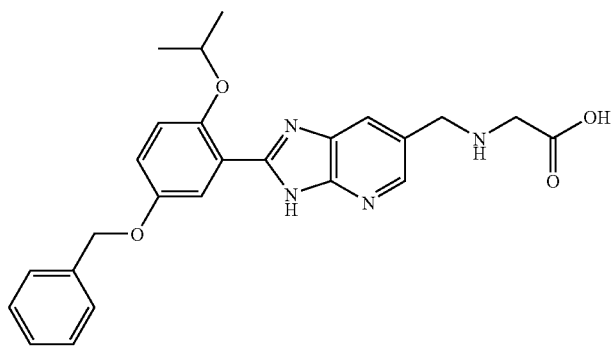 |
| 84 | 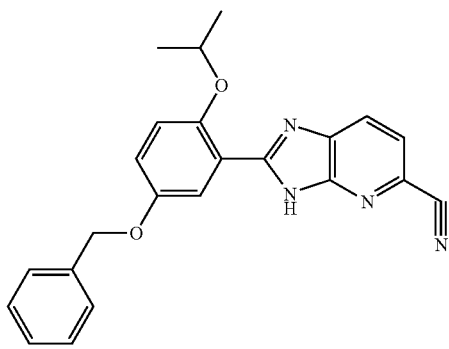 |
| 85 | 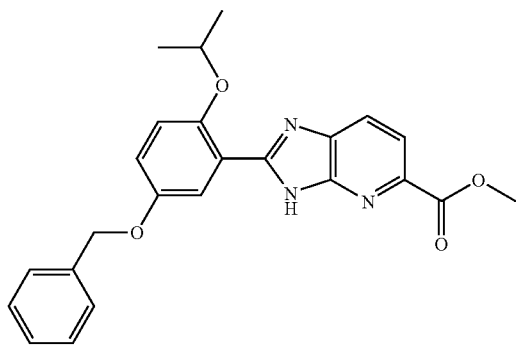 |

TABLE 2-continued

| Example No. | Structural formula |
|---|---|
| 86 | |
| 87 | |
| 88 | |
| 89 | |

TABLE 2-continued
| Example No. | Structural formula |
|---|---|
| 90 | 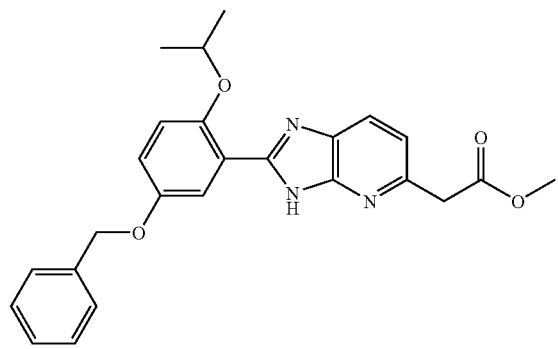 |
| 91 | 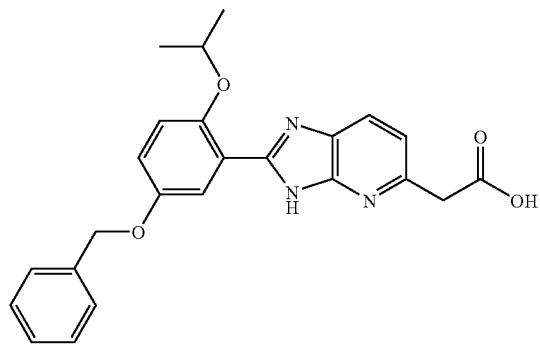 |
| 92 | 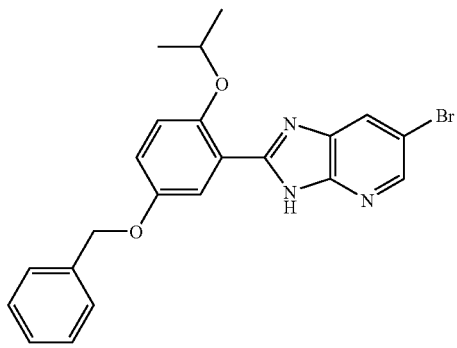 |
| 93 | 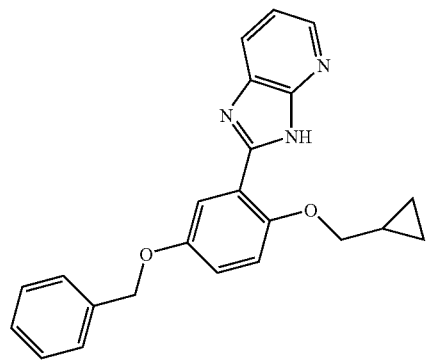 |

TABLE 2-continued
| Example No. | Structural formula |
|---|---|
| 94 | 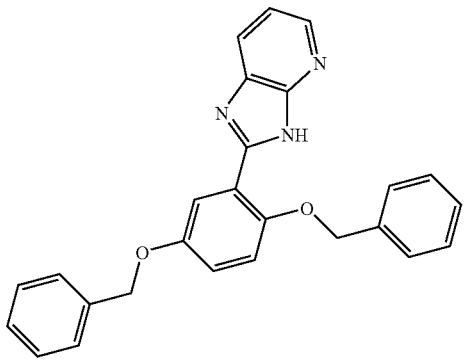 |
| 95 | 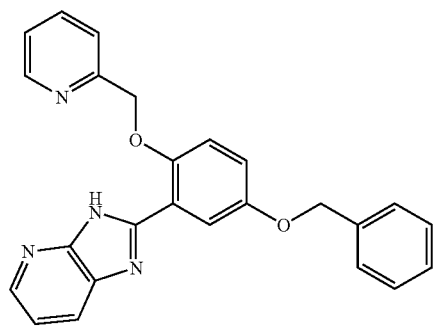 |
| 96 | 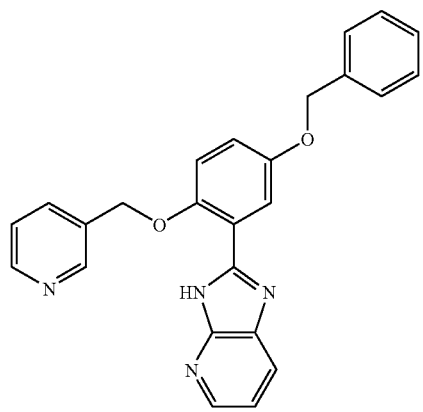 |
| 97 | 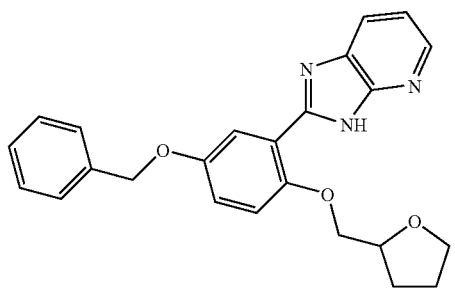 |

119 120
TABLE 2-continued
| Example No. | Structural formula |
|---|---|
| 98 | 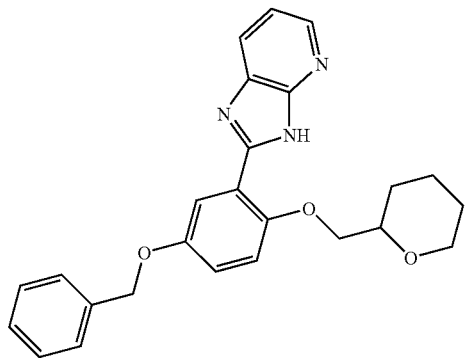 |
| 99 | 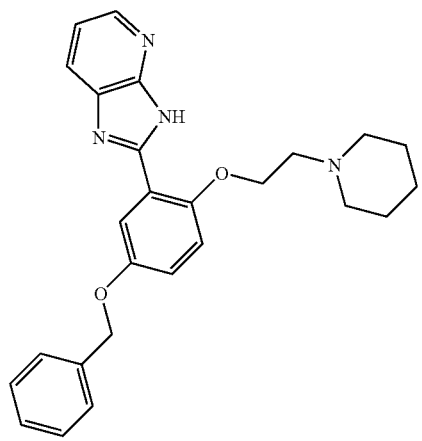 |
| 100 | 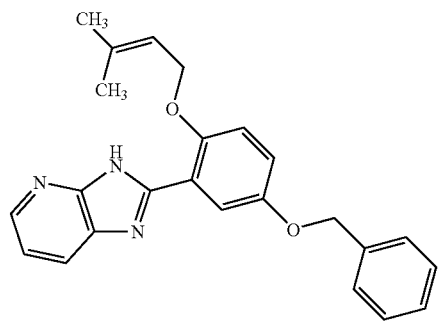 |
| 101 | 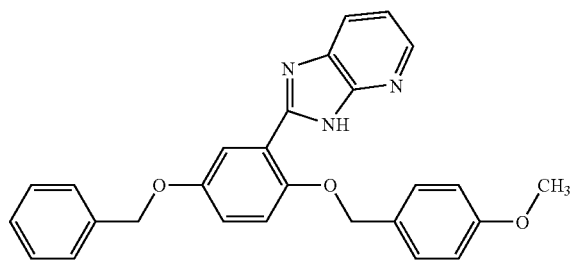 |

TABLE 2-continued

| Example No. | Structural formula |
|---|---|
| 102 | |
| 103 | |
| 104 | |
| 105 | |

TABLE 2-continued
| Example No. | Structural formula |
|---|---|
| 106 | 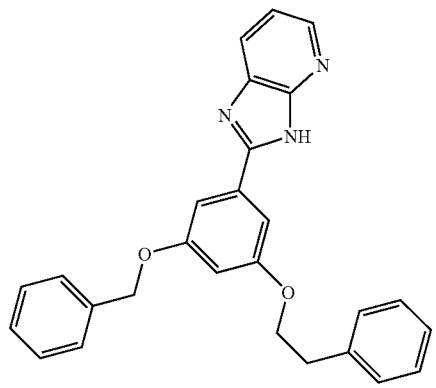 |
| 107 | 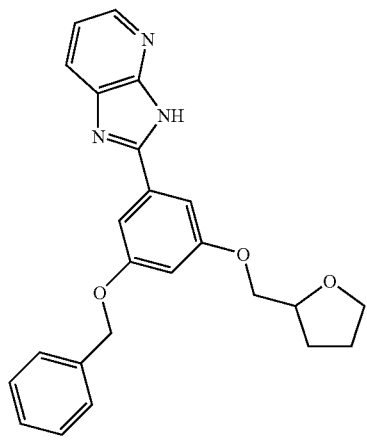 |
| 108 | 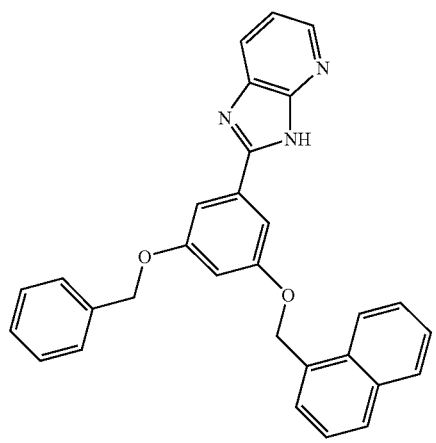 |

TABLE 2-continued
| Example No. | Structural formula |
|---|---|
| 109 | 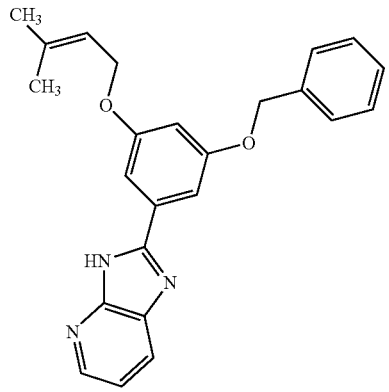 |
| 110 | 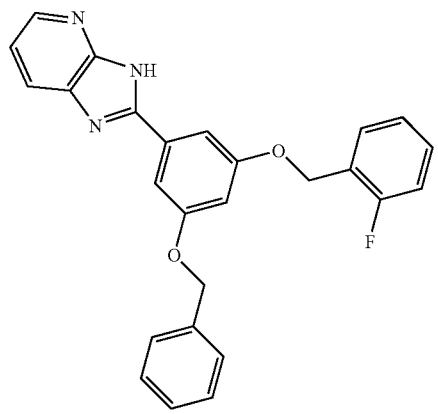 |
| 111 | 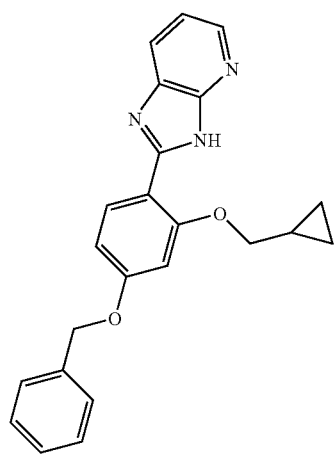 |

TABLE 2-continued
| Example No. | Structural formula |
|---|---|
| 112 | 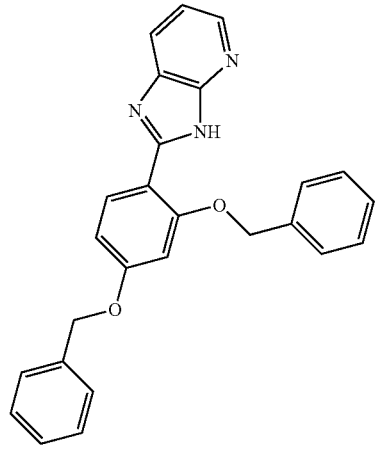 |
| 113 | 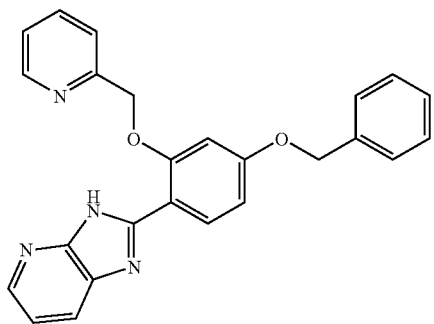 |
| 114 | 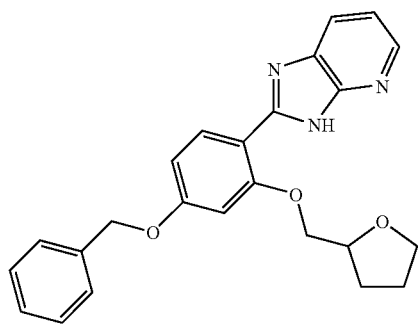 |
| 115 | 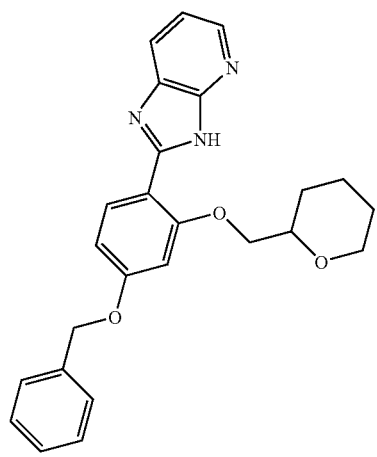 |

TABLE 2-continued
| Example No. | Structural formula |
|---|---|
| 116 | 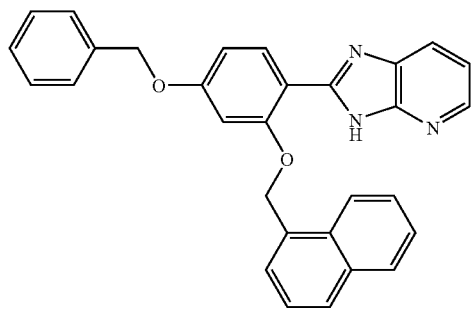 |
| 117 | 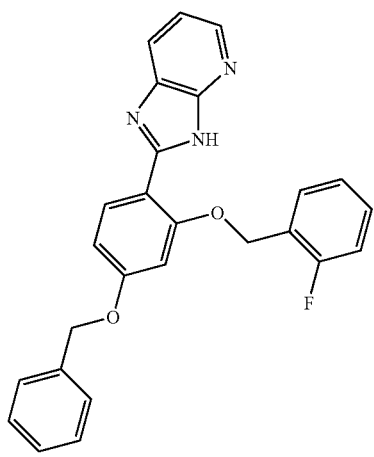 |
| 118 | 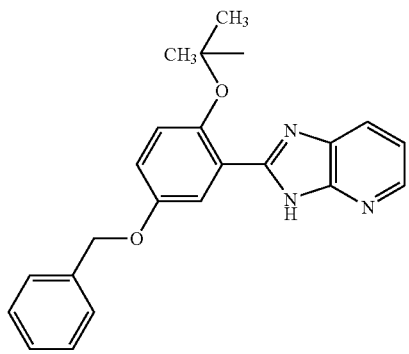 |
| 119 | 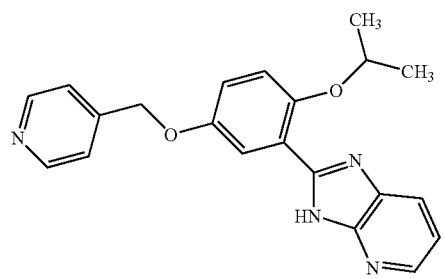 |

TABLE 2-continued
| Example No. | Structural formula |
|---|---|
| 120 | 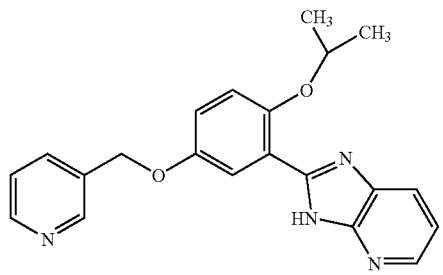 |
| 121 | 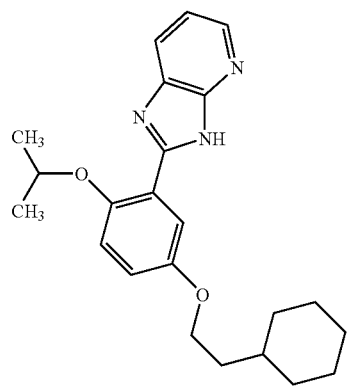 |
| 122 | 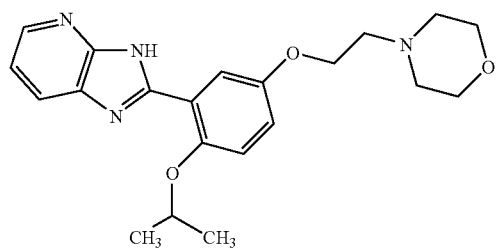 |
| 123 | 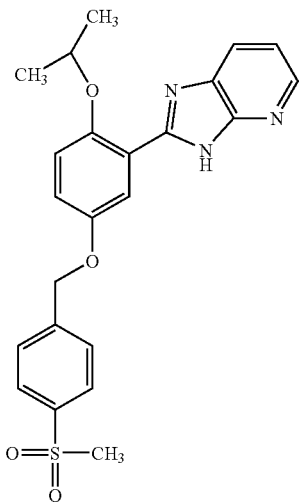 |

TABLE 2-continued
| Example No. | Structural formula |
|---|---|
| 124 | 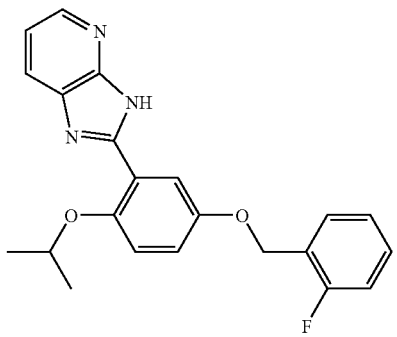 |
| 125 | 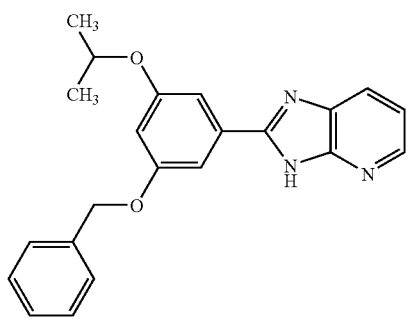 |
| 126 | 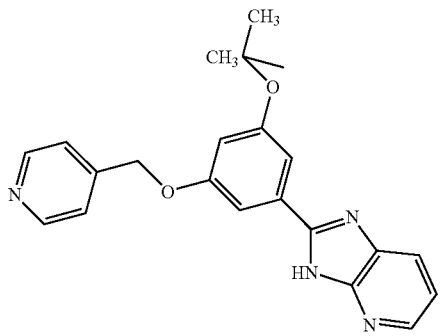 |
| 127 | 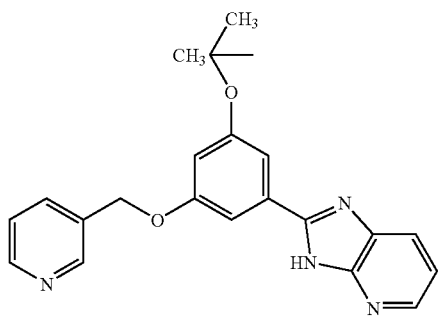 |

TABLE 2-continued
| Example No. | Structural formula |
|---|---|
| 128 | 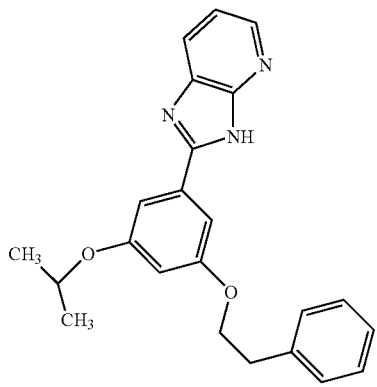 |
| 129 | 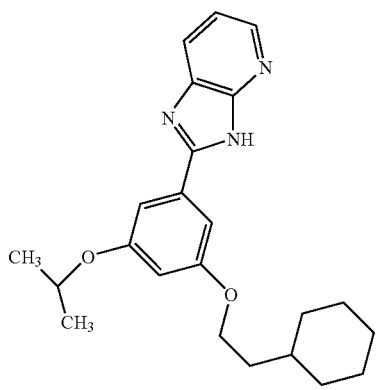 |
| 130 | 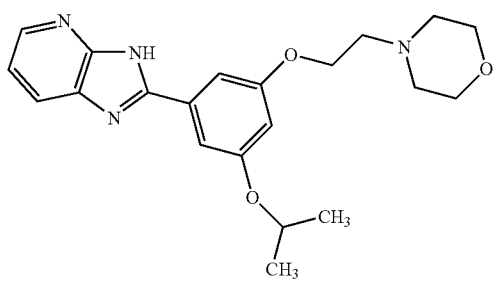 |
| 131 | 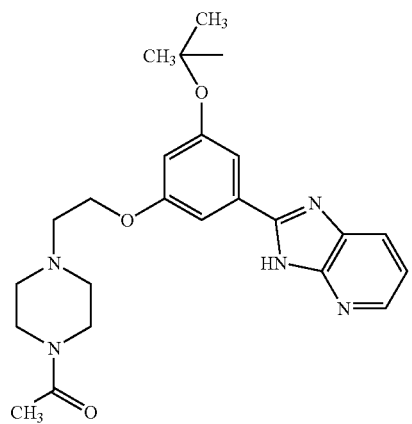 |

TABLE 2-continued
| Example No. | Structural formula |
|---|---|
| 132 | 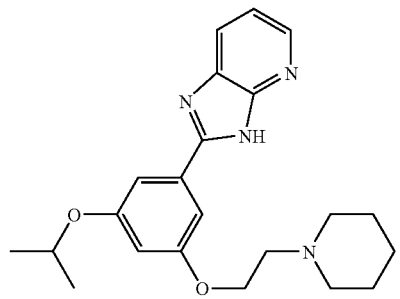 |
| 133 | 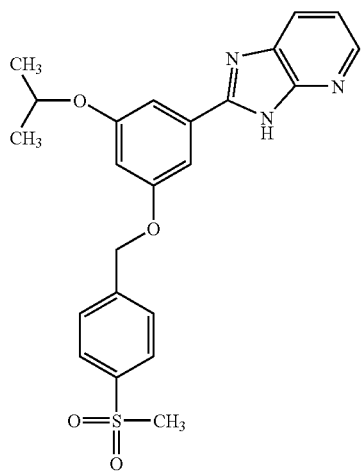 |
| 134 | 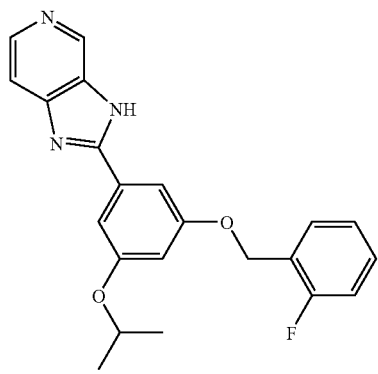 |
| 135 | 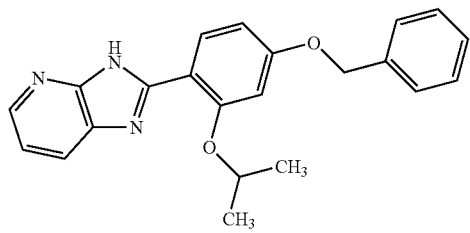 |

TABLE 2-continued

| Example No. | Structural formula |
| --- | --- |
| 136 | |
| 137 | |
| 138 | |
| 139 | |

TABLE 2-continued
| Example No. | Structural formula |
| --- | --- |
| 140 | 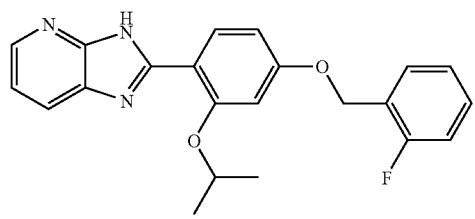 |
| 141 | 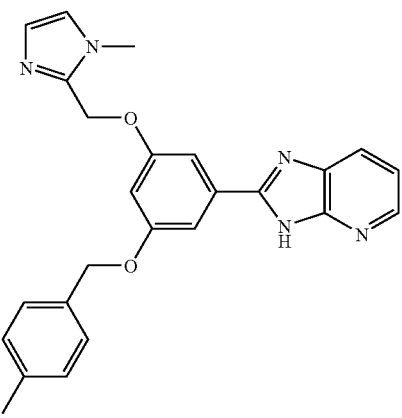 |
| 142 | 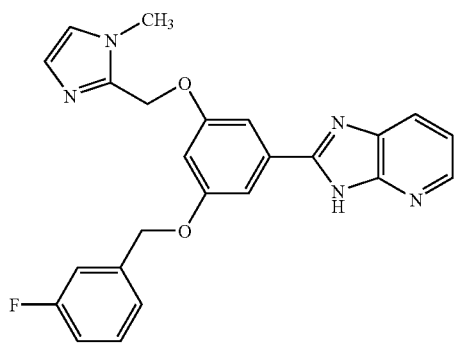 |
| 143 | 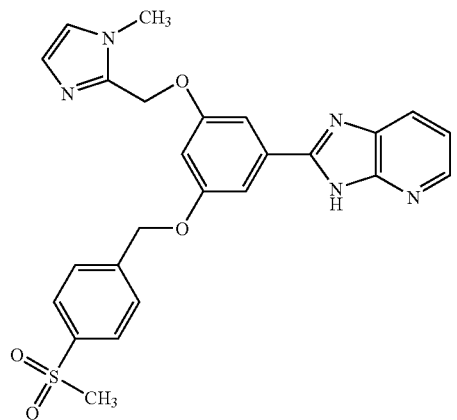 |

TABLE 2-continued
| Example No. | Structural formula |
| --- | --- |
| 144 | 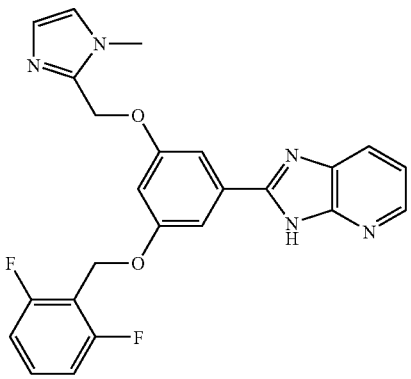 |
| 145 | 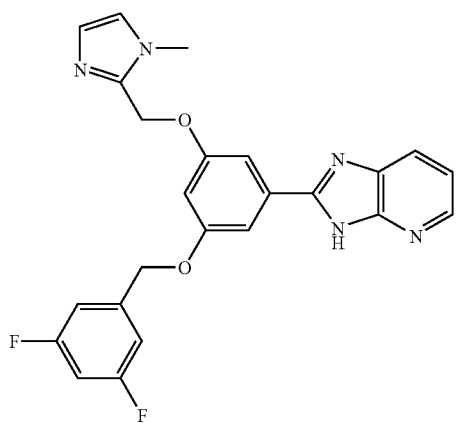 |
| 146 | 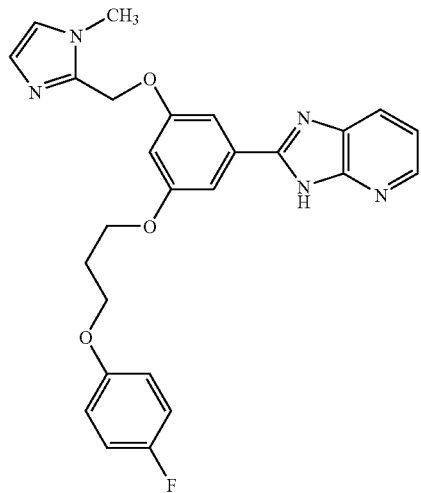 |

TABLE 2-continued
| Example No. | Structural formula |
|---|---|
| 147 | 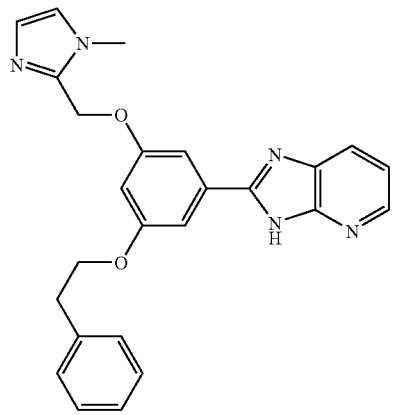 |
| 148 | 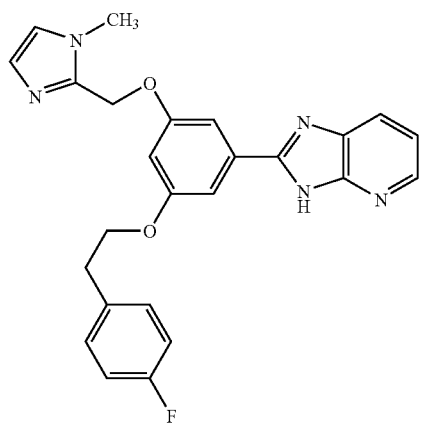 |
| 149 | 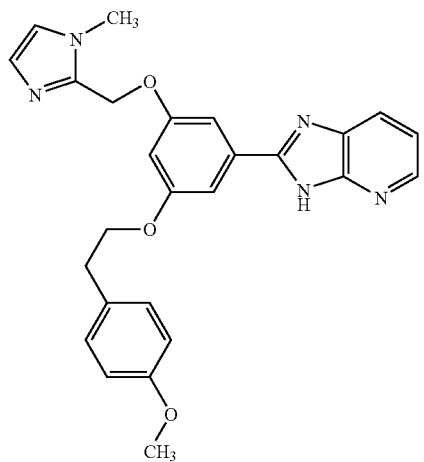 |

TABLE 2-continued
| Example No. | Structural formula |
|---|---|
| 150 | 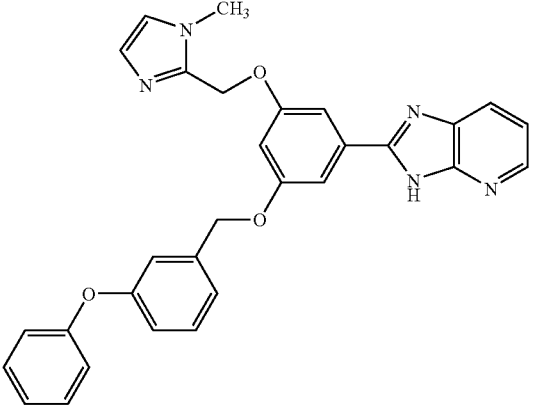 |
| 151 | 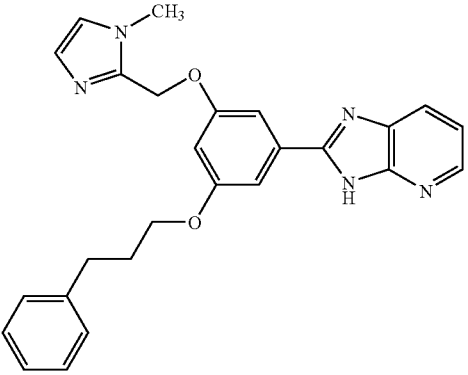 |
| 152 | 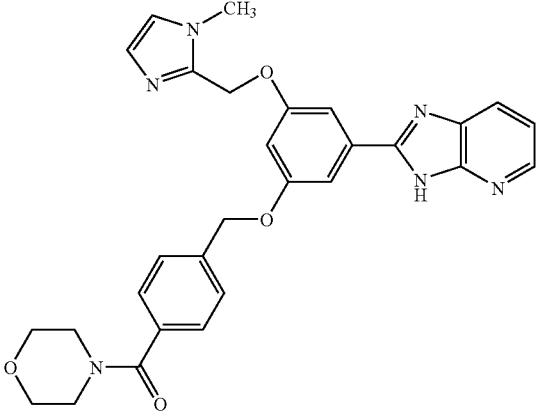 |

TABLE 2-continued
| Example No. | Structural formula |
|---|---|
| 153 | 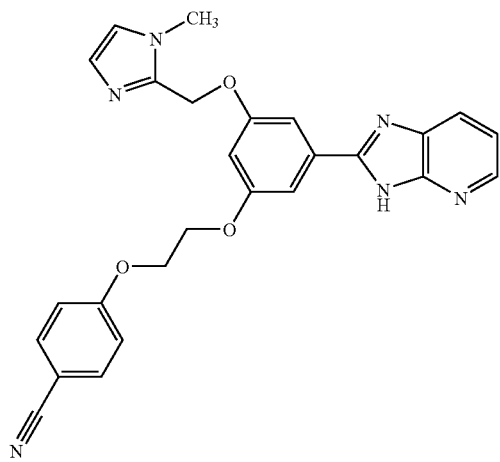 |
| 154 | 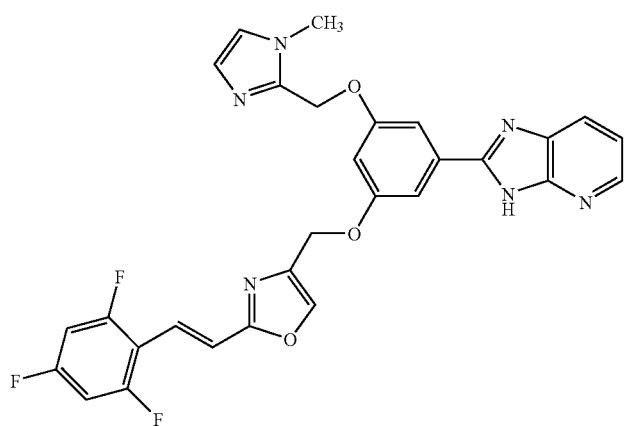 |
| 155 | 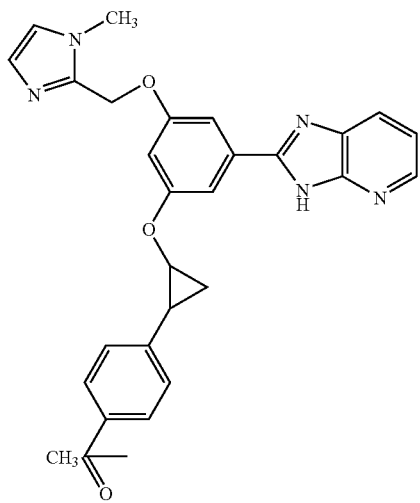 |

Example 156

2-(3-isopropoxy-5-(2-(thiophen-3-yl)ethoxy)phenyl)-3H-imidazo[4,5-b]pyridine

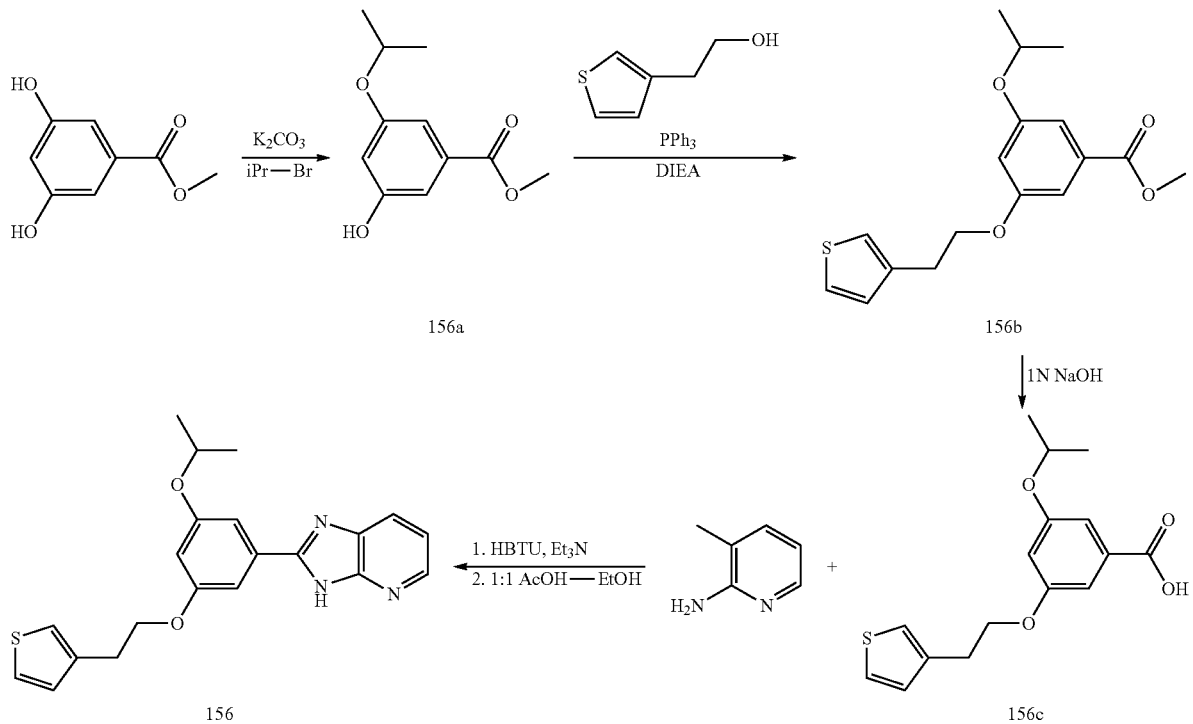

Potassium carbonate (10.35 g, 75.0 mmol) was added to a stirred solution of 3,5-dihydroxybenzoate (5.0 g, 30.0 mmol) in DMF (50 mL) followed by iso-propyl bromide (4.0 mL, 33 mmol) slowly over 30 min and stirred for 12 h. The reaction was quenched with ammonium chloride solution (100 mL) followed by water (200 mL). The aqueous suspension was extracted with dichloromethane (3×100 mL). The combined organic layers were washed with brine, dried (MgSO$_4$), filtered and concentrated in vacuo. The residue was purified by flash chromatography (30% to 50% EtOAc-Hexane) to afford example 93a (2.8 g, 34%) as a colorless oil. $^1$H NMR (400 MHz, chloroform-d) δ ppm 1.32 (d, J=6.12 Hz, 6 H) 3.89 (s, 3H) 4.48-4.52 (m, 1 H) 6.61 (t, J=6.32 Hz, 1 H) 7.13-7.14 (m, 1 H) 7.15-7.16 (m, 1H). MS (ES) [M+H] calculated for $C_{11}H_{15}O_4$, 211.09; found 211.30.

A solution of DIAD (0.5 mL, 2.5 mmol) was added dropwise to a stirred solution of example 156a (210 mg, 1.0 mmol), 2-(thiophen-3-yl)-ethanol (192 mg, 1.5 mmol) and triphenyl phosphine (655 mg, 2.5 mmol) in dichloromethane (5 mL) at 0° C. The reaction mixture was allowed to warm to rt and was stirred for 15 h. Water (25 mL) was added and the mixture was extracted with dichloromethane (3×50 mL). The combined organic layers were washed with brine, dried (MgSO$_4$), filtered and concentrated in vacuo. The residue was purified by flash chromatography (50% EtOAc-Hexane) to afford the title example 156b (285 mg, 67%) as a colorless oil. $^1$H NMR (400 MHz, chloroform-d) δ ppm 1.33 (d, J=6.12 Hz, 6 H) 3.13 (t, J=6.59 Hz, 2 H) 3.91 (s, 3H) 4.19 (t, J=6.62 Hz, 2 H) 4.56-4.59 (m, 1 H) 6.63 (t, J=6.32 Hz, 1 H) 7.04 (dd, J=5.94, 2.6 Hz, 1 H) 7.09-7.12 (m, 1 H) 7.15-7.18 (m, 2H) 7.26-7.29 (m, 1 H). MS (ES) [M+H] calculated for $C_{17}H_{21}O_4S$, 321.11; found 321.30.

1N Sodium hydroxide solution in water (10.0 mL, 10.0 mmol) was added to a solution of example 156b (1.2 g, 4.0 mmol) in MeOH (10 mL) and the reaction mixture was stirred for 8 h. MeOH was removed in vacuo and the pH of the resulting mixture was adjusted to 2 by the addition of 1N hydrochloric acid. The resulting white solid was filtered and dried to afford example 93c (924 mg, 75%) as a white solid. MS (ES) [M+H] calculated for $C_{16}H_{19}O_4S$, 307.09; found 307.14.

HBTU (2.3 mg, 6.0 mmol) was added to a solution of example 156c (918 mg, 3.0 mmol) and triethylamine (1.04 mL, 7.5 mmol) in DMF (5 mL). The resulting mixture was stirred for 15 min and pyridine-4,5-diamine (495 mg, 4.5 mmol) was added. The reaction was stirred for 10 h. Water (10 mL) was added and the mixture was extracted with ethylacetate (3×30 mL). The combined organic layers were washed with brine, dried (MgSO$_4$), filtered and concentrated in vacuo. The residue was dissolved in EtOH—AcOH (1:1, 2 mL) and subjected to microwave heating at 180° C. for 30 min. The resulting material was purified by LCMS (acetonitrile-water gradient) to give the title compound (840 mg, 74%) as a white solid. $^1$H NMR (400 MHz, chloroform-d) δ ppm 1.38 (d, J=6.12 Hz, 6 H) 3.15 (t, J=6.59 Hz, 2 H) 4.26 (t, J=6.62 Hz, 2 H) 4.65-4.68 (m, 1 H) 6.62 (s, 1 H) 7.04 (d, J=6.32 Hz, 1 H) 7.10 (s, 1H) 7.23-7.28 (m, 2 H) 7.46 (d, J=6.94 Hz, 2 H) 8.16 (d, J=6.04 Hz, 1 H) 8.50 (d, J=4.92 Hz, 1 H). MS (ES) [M+H] calculated for C$_{21}$H$_{22}$N$_3$O$_2$S, 380.14; found 380.30.

Example 157

5-(2-(3-(3H-imidazo[4,5-b]pyridin-2-yl)-5-isopropoxyphenoxy)ethyl)-4-methylthiazole

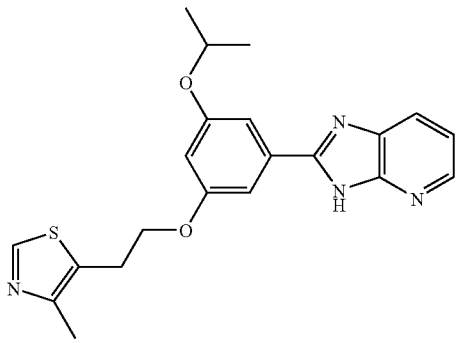

The title compound was synthesized using an analogous procedure described for Example 156 except that 2-(4-methylthiazol-5-yl)ethanol was used. $^1$H NMR (400 MHz, chloroform-d) δ ppm 1.35 (d, J=6.02 Hz, 6 H) 2.44 (s, 3H) 3.30 (t, J=6.29 Hz, 2 H) 3.97 (t, J=6.12 Hz, 2 H) 4.65-4.68 (m, 1 H) 6.32 (s, 1 H) 6.78 (d, J=6.32 Hz, 1 H) 7.34-7.42 (m, 5 H). MS (ES) [M+H] calculated for C$_{21}$H$_{23}$N$_4$O$_2$S, 395.15; found 395.08.

Example 158

2-(3-(benzyloxy)-5-isopropoxyphenyl)-3H-imidazo[4,5-b]pyridine

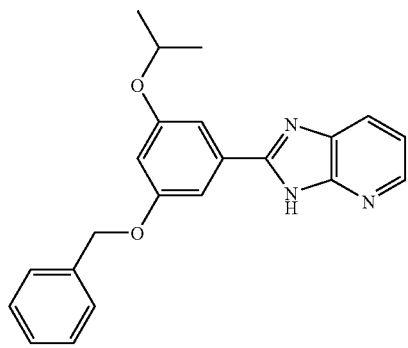

The title compound was synthesized using an analogous procedure described for Example 156 except that benzyl bromide and K$_2$CO$_3$ was used for alkylation of example 156b. $^1$H NMR (400 MHz, chloroform-d) δ ppm 1.37 (d, J=6.12 Hz, 6 H) 4.62-4.70 (m, 1 H) 5.17 (s, 2 H) 6.75 (s, 1H) 7.34-7.50 (m, 8H) 8.32-8.34 (m, 2H). MS (ES) [M+H] calculated for C$_{22}$H$_{22}$N$_3$O$_2$, 360.16; found 360.30.

Example 159

2-(3-isopropoxy-5-(3-phenylpropoxy)phenyl)-3H-imidazo[4,5-b]pyridine

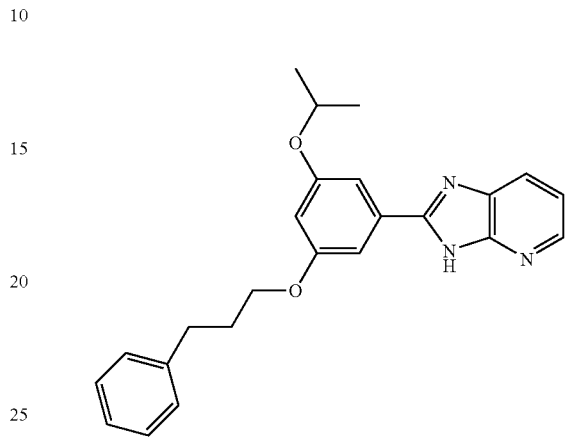

The title compound was synthesized using an analogous procedure described for Example 156 except that 3-phenylpropan-1-ol was used. $^1$H NMR (400 MHz, chloroform-d) δ ppm 1.38 (d, J=6.32 Hz, 6 H) 2.13 (t, J=6.09 Hz, 2 H) 2.82 (t, J=6.21 Hz, 2 H) 4.04 (t, J=5.92 Hz, 2 H) 4.66-4.69 (m, 1 H) 6.62 (s, 1H) 7.18-7.24 (m, 3 H) 7.27-7.31 (m, 2H) 7.37 (d, J=6.92 Hz, 2 H) 7.45 (t, J=6.32 Hz, 1 H) 8.37-8.42 (m, 2H). MS (ES) [M+H] calculated for C$_{24}$H$_{25}$N$_3$O$_2$, 388.19; found 388.29.

Example 160

2-(3-isopropoxy-5-(2-(pyridin-2-yl)ethoxy)phenyl)-3H-imidazo[4,5-b]pyridine

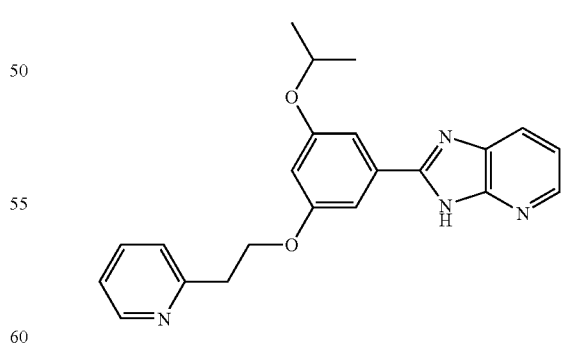

The title compound was synthesized using an analogous procedure described for Example 156 except that 2-(pyridin-2-yl)ethanol was used. $^1$H NMR (400 MHz, chloroform-d) δ ppm 1.38 (d, J=6.32 Hz, 6 H) 3.60 (t, J=5.92 Hz, 2 H) 5.22-5.27 (m, 1 H) 6.60 (s, 1H) 6.96 (d, J=6.92 Hz, 1 H) 7.14-7.24 (m, 1 H) 7.40-7.44 (m, 2H) 7.65 (t, J=6.92 Hz, 2 H) 8.21 (d,

Example 161

2-(3-isopropoxy-5-phenethoxyphenyl)-3H-imidazo[4,5-b]pyridine

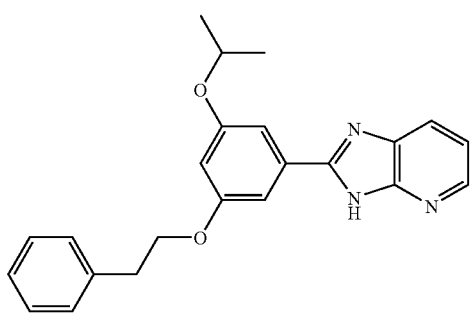

The title compound was synthesized using an analogous procedure described for Example 156 except that 2-phenylethanol was used. $^1$H NMR (400 MHz, chloroform-d) δ ppm 1.33 (d, J=6.32 Hz, 6 H) 3.08 (t, J=5.92 Hz, 2 H) 4.18 (t, J=6.12 Hz, 2 H) 4.56-4.58 (m, 1 H) 6.41 (s, 1H) 7.13-7.22 (m, 3 H) 7.26-7.31 (m, 5H) 7.98-8.17 (m, 2H). MS (ES) [M+H] calculated for $C_{23}H_{24}N_3O_2$, 374.18; found 374.23.

Example 162

2-(3-(benzyloxy)-5-((1-methyl-1H-imidazol-2-yl)methoxy)phenyl)-3H-imidazo[4,5-b]pyridine

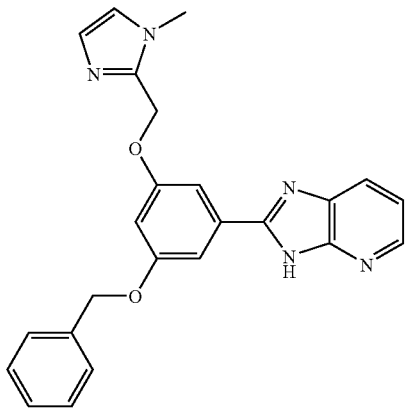

The title compound was synthesized using an analogous procedure described for Example 156 except that benzyl bromide and $K_2CO_3$ was used for alkylation of methyl-3,5 dihydroxy benzoate and (1-methyl-1H-imidazol-2-yl)methanol was used for Mitsunobu reaction. $^1$H NMR (400 MHz, chloroform-d) δ ppm 3.99 (s, 3H) 5.19 (s, 3H) 5.56 (s, 3H) 6.95 (t, J=5.12 Hz, 1 H) 7.30-7.41 (m, 3H) 7.48-7.51 (m, 2 H) 7.51 (d, J=5.12 Hz, 1 H) 7.56 (d, J=6.12 Hz, 1H) 7.59-7.68 (m, 3H) J=5.32 Hz, 1 H) 8.50-8.57 (m, 2H). MS (ES) [M+H] calculated for $C_{22}H_{23}N_4O_2$, 375.17; found 375.16.

Example 163

2-(3-(benzyloxy)-5-((1-methyl-1H-imidazol-2-yl)methoxy)phenyl)-6-bromo-3H-imidazo[4,5-b]pyridine

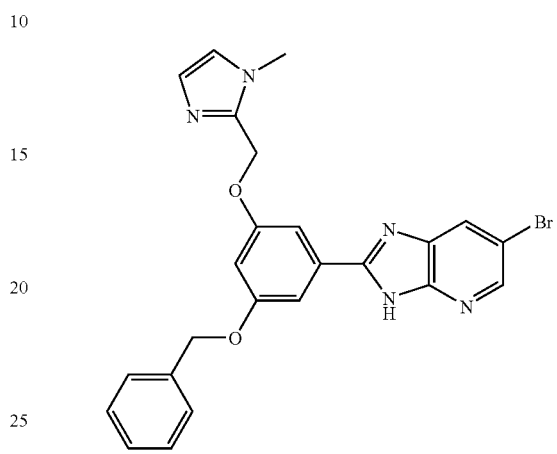

The title compound was synthesized using an analogous procedure described for Example 162 except that 5-bromopyridine-2,3-diamine was used. $^1$H NMR (400 MHz, chloroform-d) δ ppm 3.80 (s, 3H) 4.97 (s, 3H) 5.36 (s, 3H) 6.60 (s, 1H) 7.16-7.27 (m, 7H) 7.36-7.42 (m, 2 H) 7.96 (d, J=6.42 Hz, 1 H) 8.29 (d, J=6.12 Hz, 1 H). MS (ES) [M+H] calculated for $C_{24}H_{21}BrN_5O_2$, 490.08; found 490.20.

Example 164

6-bromo-2-(3-((1-methyl-1H-imidazol-2-yl)methoxy)-5-(2-(thiophen-3-yl)ethoxy)phenyl)-3H-imidazo[4,5-b]pyridine

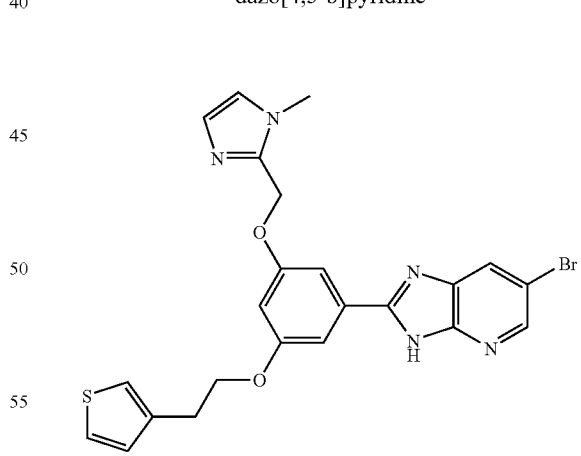

The title compound was synthesized using an analogous procedure described for Example 163 except that the benzyl group was removed and 2-(thiophen-3-yl)-ethanol was used for Mitsunobu reaction (see below). $^1$H NMR (400 MHz, chloroform-d) δ ppm 3.12 (t, J=6.42 Hz, 2H) 3.82 (s, 3H) 4.30 (t, J=6.12 Hz, 2H) 5.41 (s, 2H) 6.89 (t, J=4.42 Hz, 1H) 7.50 (d, J=6.42 Hz, 1H) 7.32-7.38 (m, 2H) 7.46-7.54 (m, 4H) 8.30 (d, J=6.12 Hz, 1 H) 8.44 (d, J=6.32 Hz, 1 H). MS (ES) [M+H] calculated for $C_{23}H_{21}BrN_5O_2S$, 510.05; found 510.21.

8.45 (d, J=6.42 Hz, 1H) 8.51 (d, J=6.12 Hz, 1 H). MS (ES) [M+H] calculated for $C_{24}H_{22}N_5O_2$, 412.17; found 412.11.

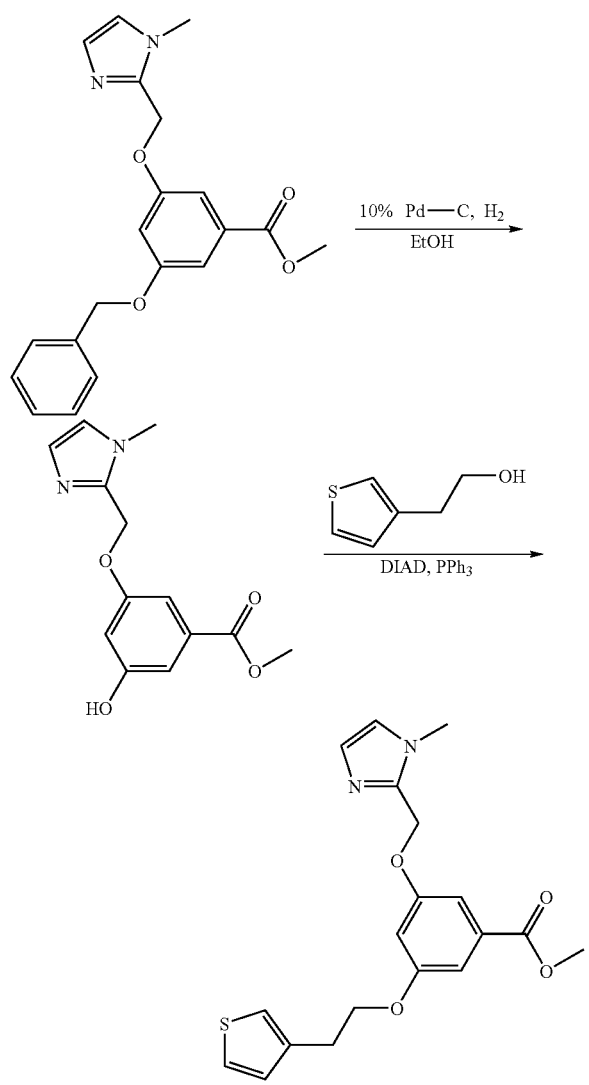

Example 165

2-(3-(2-fluorobenzyloxy)-5-((1-methyl-1H-imidazol-2yl)methoxy)phenyl)-3H-imidazo[4,5-b]pyridine

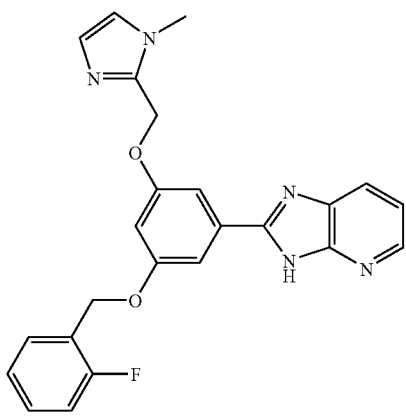

The title compound was synthesized using an analogous procedure described for Example 162 except that 2-fluorobenzyl bromide was used. $^1$H NMR (400 MHz, chloroform-d) δ ppm 3.30 (s, 3H) 4.62 (s, 3H) 4.93 (s, 3H) 6.38 (t, J=6.42 Hz, 1 H) 6.48-6.58 (m, 2H) 6.71-6.78 (m, 1 H) 6.91 (t, J=6.42 Hz, 1 H) 6.95-7.20 (m, 5H) 7.78 (d, J=6.12 Hz, 1 H) 7.88 (d, J=6.32 Hz, 1 H). MS (ES) [M+H] calculated for $C_{24}H_{21}FN_5O_2$, 430.16; found 430.30.

Example 166

6-chloro-2-(3-(2-fluorobenzyloxy)-5-((1-methyl-1H-imidazol-2-yl)methoxy)phenyl)-3H-imidazo[4,5-b]pyridine

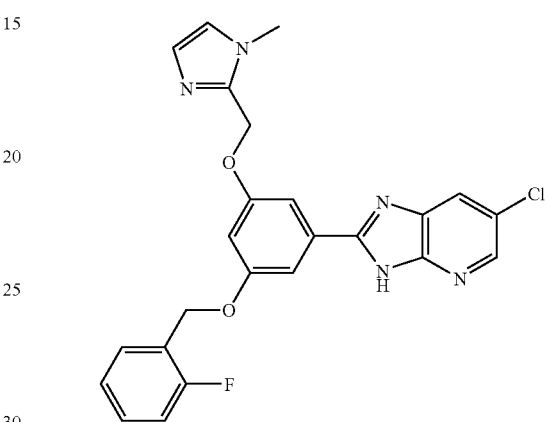

The title compound was synthesized using an analogous procedure described for Example 164 except that 5-chloropyridine-2,3-diamine was used. $^1$H NMR (400 MHz, chloroform-d) δ ppm 3.80 (s, 3H) 5.21 (s, 3H) 5.51 (s, 3H) 6.98 (t, J=6.42 Hz, 1H) 7.21-7.32 (m, 2H) 7.46-7.54 (m, 2H) 7.61-7.68 (m, 4 H) 8.19 (d, J=6.12 Hz, 1 H) 8.40 (d, J=6.32 Hz, 1H). MS (ES) [M+H] calculated for $C_{24}H_{30}ClFN_5O_2$, 464.12; found 464.59.

Example 167

6-bromo-2-(3-(2-fluorobenzyloxy)-5-((1-methyl-1H-imidazol-2-yl)methoxy)phenyl)-3H-imidazo[4,5-b]pyridine

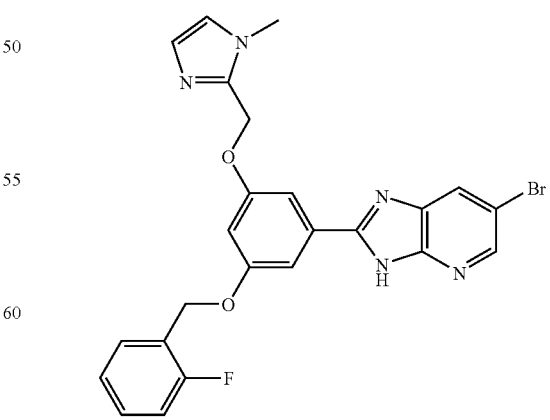

The title compound was synthesized using an analogous procedure described for Example 164 except that 5-bromopyridine-2,3-diamine was used. $^1$H NMR (400 MHz, chloroform-d) δ ppm 3.74 (s, 3H) 5.25 (s, 3H) 5.30 (s, 3H) 6.98 (t, J=6.42 Hz, 1 H) 7.02 (s, 1H) 7.28-7.34 (m, 3H) 7.41-7.48 (m, 1 H) 7.60-7.68 (m, 3H) 8.30 (d, J=6.12 Hz, 1H) 8.46 (d, J=6.32 Hz, 1H). MS (ES) [M+H] calculated for $C_{24}H_{30}BrFN_5O_2$, 508.07; found 508.09.

Example 168

3-(2-(3-(2-fluorobenzyloxy)-5-((1-methyl-1H-imidazol-2-yl)methoxy)phenyl)-3H-imidazo[4,5-]pyridin-6-yl)propan-1-ol

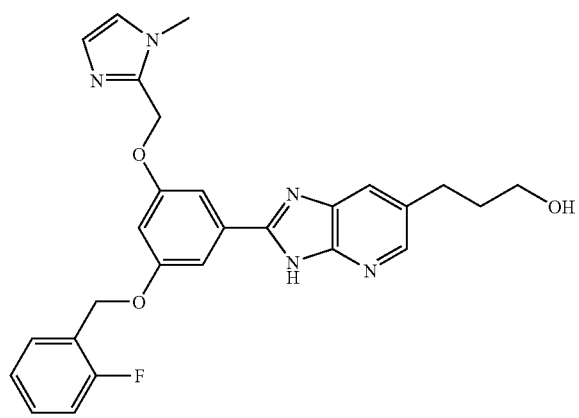

The title compound was synthesized using an analogous procedure described for Example 162 except that 3-(5,6-diaminopyridin-3-yl)propan-1-ol (prepared by shinagoshira coupling reaction of 5-iodo-2-nitropyridin-3-amine with propargyl alcohol, followed by palladium catalyzed hydrogenation) was used (see below). $^1$H NMR (400 MHz, chloroform-d) δ ppm 1.98-2.02(m, 2H) 3.04 (t, J=6.42 Hz, 2H) 3.68 (t, J=6.42 Hz, 2H) 4.04 (s, 3H) 5.33 (s, 2H) 5.64 (s, 3H) 7.10 (t, J=6.42 Hz, 1 H) 7.21-7.29 (m, 2H) 7.41-7.44 (m, 1 H) 7.56-7.64 (m, 1H) 7.66 (d, J=6.32 Hz, 1 H) 7.68-7.70 (m, 3H) 8.41 (d, J=6.12 Hz, 1 H) 8.51 (d, J=6.32 Hz, 1 H). MS (ES) [M+H] calculated for $C_{27}H_{27}FN_5O_3$, 488.20; found 488.21.

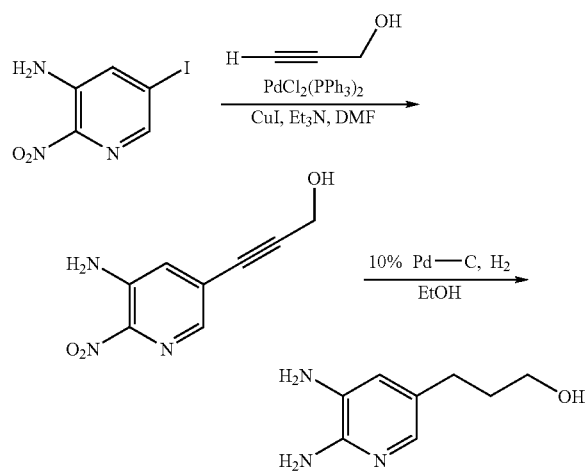

Example 169

2-(3,5-bis(2-fluorobenzyloxy)phenyl)-3H-imidazo[4,5-b]pyridine

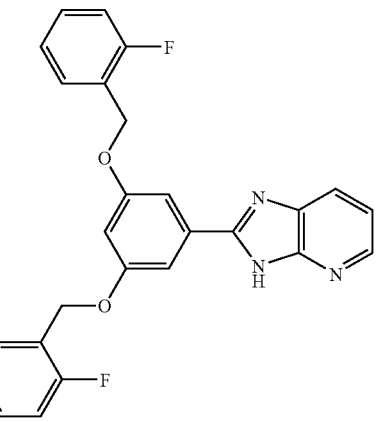

The title compound was synthesized using an analogous procedure described for Example 156 except that 2-fluorobenzyl bromide was used for the dialkylation of methyl-3,5-dihydroxy benzoate. $^1$H NMR (400 MHz, chloroform-d) δ ppm 4.29 (s, 4H) 5.95 (s, 1H) 6.28-6.38 (m, 5H) 6.48-6.51 (m, 2H) 6.62-6.70 (m, 4H) 7.08 (d, J=6.42 Hz, 1H) 7.40 (d, J=6.32 Hz, 1 H). MS (ES) [M+H] calculated for $C_{26}H_{20}F_2N_2O_3$, 444.14; found 444.18.

Example 170

2-(3-(2-fluorobenzyloxy)-5-(pyridin-2-ylmethoxy)phenyl)-3H-imidazo[4,5-b]pyridine

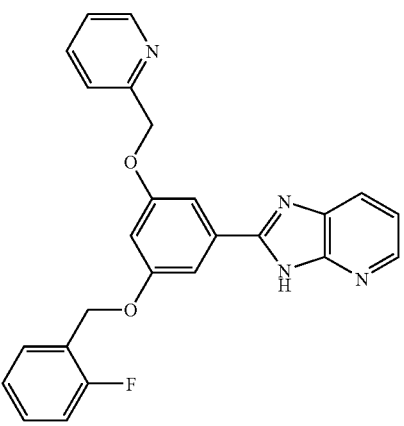

The title compound was synthesized using an analogous procedure described for Example 162 except that pyridin-2-ylmethanol was used. $^1$H NMR (400 MHz, chloroform-d) δ ppm 3.86 (s, 2H) 4.19 (s, 2H) 5.64 (s, 1H) 5.75-5.86 (m, 2H) 5.90-5.98 (m, 1H) 6.00-6.26 (m, 5H) 6.48 (m, 1H) 6.98 (m, 2H) 7.14 (m, 2 H). MS (ES) [M+H] calculated for C25H20FN4O2, 427.15; found 427.18.

Example 171

2-(3-(2-fluorobenzyloxy)-5-(3H-imidazo[4,5-b]pyridin-2-yl)phenoxy)methyl)thiazole

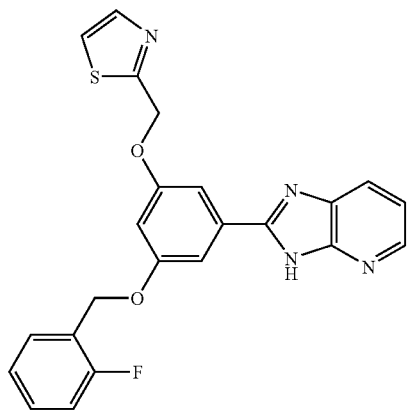

The title compound was synthesized using an analogous procedure described for Example 162 except that thiazol-2-ylmethanol was used. ¹H NMR (400 MHz, chloroform-d) δ ppm 3.82 (s, 2H) 4.09 (s, 2H) 5.49 (s, 1H) 5.65-5.80 (m, 2H) 5.92-5.98 (m, 1H) 6.02-6.20 (m, 5H) 6.40 (s, 1H) 6.84 (d, J=6.42 Hz, 1H) 7.04 (d, J=6.32 Hz, 1 H). MS (ES) [M+H] calculated for C23H18FN4O2S, 433.11; found 433.25.

Example 172

(R)-2-(3-(2-fluorobenzyloxy)-5-(1-methoxypropan-2-yloxy)phenyl)-3H-imidazo[4,5-b]pyridine

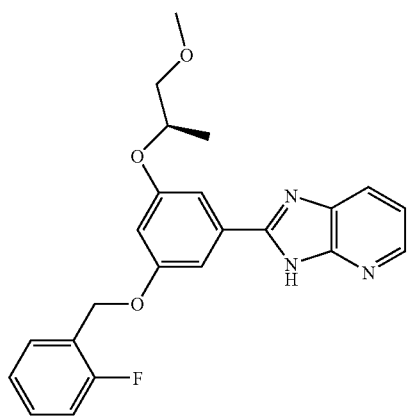

The title compound was synthesized using an analogous procedure described for Example 162 except that (S)-1-methoxypropan-2-ol was used. ¹H NMR (400 MHz, chloroform-d) δ ppm 1.28 (d, J=6.78 Hz, 3 H) 3.42 (s, 3 H) 3.52-3.61 (m, 2 H) 4.61-4.65 (m, 1 H) 5.03 (s, 2 H) 6.54 (s, 1 H) 7.04 (t, J=12.21 Hz, 1 H) 7.12 (t, J=12.42 Hz, 1 H) 7.26-7.32 (m, 4 H)

7.44 (t, J=12.11 Hz, 1 H) 8.26-8.29 (m, 2 H). MS (ES) [M+H] calculated for C23H23FN3O3, 408.16; found 408.21.

Example 173

(R)-6-chloro-2-(3-(2-fluorobenzyloxy)-5-(1-methoxypropan-2-yloxy)phenyl)-3H-imidazo[4,5-b]pyridine

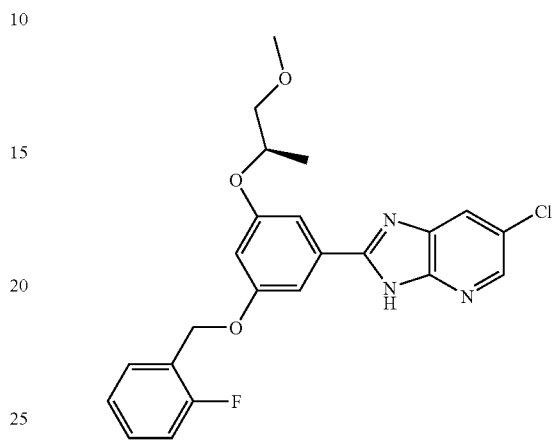

The title compound was synthesized using an analogous procedure described for Example 172 except that 5-choloro-pyridine-2,3-diamine was used. ¹H NMR (400 MHz, chloroform-d) δ ppm 1.34 (d, J=6.78 Hz, 3 H) 3.42 (s, 3 H) 3.52-3.65 (m, 2 H) 4.62-4.66 (m, 1 H) 5.03 (s, 2 H) 6.70 (s, 1 H) 7.09 (t, J=12.21 Hz, 1 H) 7.17 (t, J=12.42 Hz, 1 H) 7.30-7.38 (m, 3 H) 7.53 (t, J=12.11 Hz, 1 H) 8.07 (s, 1 H) 8.45 (s, 1H). MS (ES) [M+H] calculated for C23H22ClFN3O3, 442.13; found 442.15.

Example 174

(R)-6-bromo-2-(3-(2-fluorobenzyloxy)-5-(1-methoxypropan-2-yloxy)phenyl)-3H-imidazo[4,5-b]pyridine

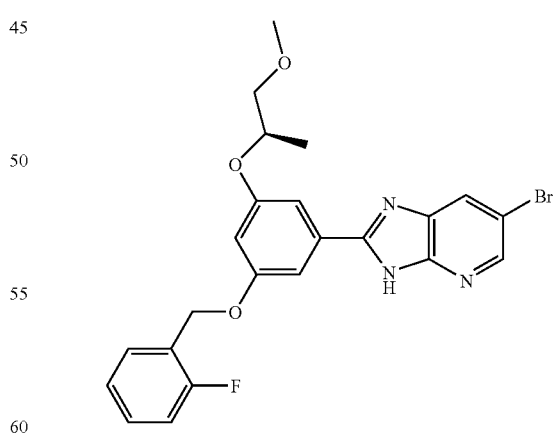

The title compound was synthesized using an analogous procedure described for Example 172 except that 5-bromopyridine-2,3-diamine was used. ¹H NMR (400 MHz, chloroform-d) δ ppm 1.36 (d, J=6.78 Hz, 3 H) 3.44 (s, 3 H) 3.54-3.66 (m, 2 H) 4.64-4.68 (m, 1 H) 5.16 (s, 2 H) 6.70 (s, 1 H) 7.11 (t, J=12.21 Hz, 1 H) 7.19 (t, J=12.42 Hz, 1 H) 7.32-7.38 (m, 3 H)

7.55 (t, J=12.11 Hz, 1 H) 8.24 (s, 1 H) 8.55 (s, 1H). MS (ES) [M+H] calculated for C₂₃H₂₂BrFN₃O₃, 486.08; found 486.11.

Example 175

(S)-6-bromo-2-(3-(2-fluorobenzyloxy)-5-(1-methoxypropan-2-yloxy)phenyl)-3H-imidazo[4,5-b]pyridine

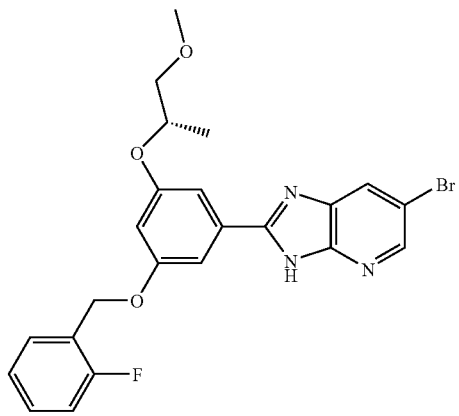

The title compound was synthesized using an analogous procedure described for Example 174 except that (R)-1-methoxypropan-2-ol was used. ¹H NMR (400 MHz, chloroform-d) δ ppm 1.34 (d, J=6.78 Hz, 3 H) 3.54 (s, 3 H) 3.55-3.63 (m, 2 H) 4.61-4.65 (m, 1 H) 5.09 (s, 2 H) 6.70 (s, 1 H) 7.11 (t, J=12.21 Hz, 1 H) 7.19 (t, J=12.42 Hz, 1 H) 7.32-7.38 (m, 3 H) 7.55 (t, J=12.11 Hz, 1 H) 8.24 (s, 1 H) 8.55 (s, 1H). MS (ES) [M+H] calculated for C₂₃H₂₂BrFN₃O₃, 486.08; found 486.13.

Example 176

(S)-2-(3-(2-fluorobenzyloxy)-5-(1-methoxypropan-2-yloxy)phenyl)-6-(pyridin-3-yl)-3H-imidazo[4,5-b]pyridine

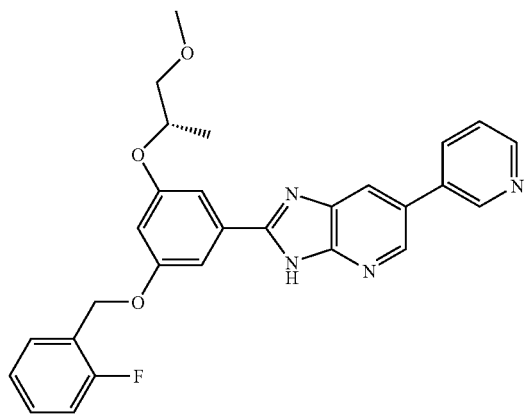

The title compound was synthesized using an analogous procedure described for Example 175 except that 3,3'-bipyridine-5,6-diamine (prepared by Suzuki coupling reaction of 5-iodopyridine-2,3-diamine with pyridin-3-ylboronic acid) was used. ¹H NMR (400 MHz, chloroform-d) δ ppm 1.32 (d, J=6.78 Hz, 3 H) 3.34 (s, 3 H) 3.45-3.66 (m, 2 H) 4.51-4.55 (m, 1 H) 5.10 (s, 2 H) 6.57 (s, 1 H) 7.08 (t, J=12.21 Hz, 1 H) 7.18 (t, J=12.42 Hz, 1 H) 7.32-7.48 (m, 4 H) 7.61 (t, J=11.11 Hz, 1 H) 8.20 (d, J=6.78 Hz, 1 H) 8.31 (s, 1 H) 8.63 (s, 1H) 8.71 (s, 1H) 9.07 (s, 1H). MS (ES) [M+H] calculated for C₂₈H₂₅FN₄O₃, 485.19; found 485.25.

Example 177

(S)-3-(2-(3-(2-fluorobenzyloxy)-5-(1-methoxypropan-2-yloxy)phenyl)-3H-imidazo[4,5-b]pyridin-6-yl)propan-1-ol

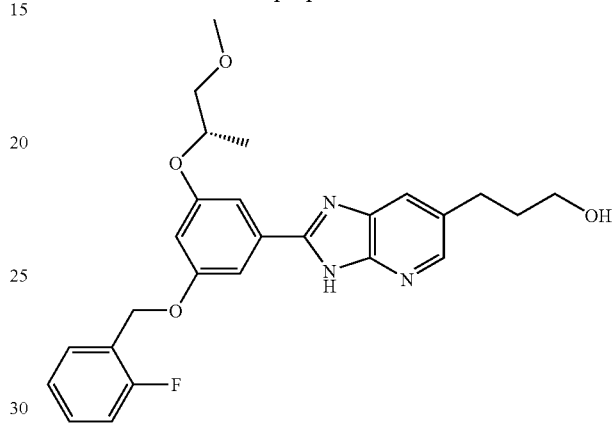

The title compound was synthesized using an analogous procedure described for Example 168. ¹H NMR (400 MHz, chloroform-d) δ ppm 1.34 (d, J=6.78 Hz, 3 H) 1.88-2.00 (m, 2H) 2.94 (t, J=6.42 Hz, 2H) 3. 43 (s, 3 H) 3.55-3.76 (m, 4 H) 4.61-4.65 (m, 1 H) 5.20 (s, 2 H) 6.79 (s, 1 H) 7.10 (t, J=12.21 Hz, 1 H) 7.21 (t, J=12.42 Hz, 1 H) 7.32-7.41 (m, 1 H) 7.45 (s, 1 H) 7.50-7.58 (m, 2 H) 8.17 (s, 1 H) 8.27 (s, 1H). MS (ES) [M+H] calculated for C₂₆H₂₉FN₃O₄, 466.21; found 466.31.

Example 178

(S)-2-(3-(2-fluorobenzyloxy)-5-(1-methoxypropan-2-yloxy)phenyl)-3H-imidazo[4,5-b]pyridine-6-carbonitrile

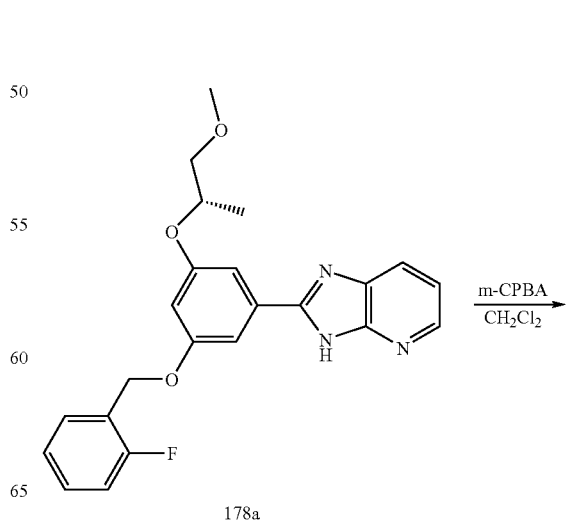

178a

-continued

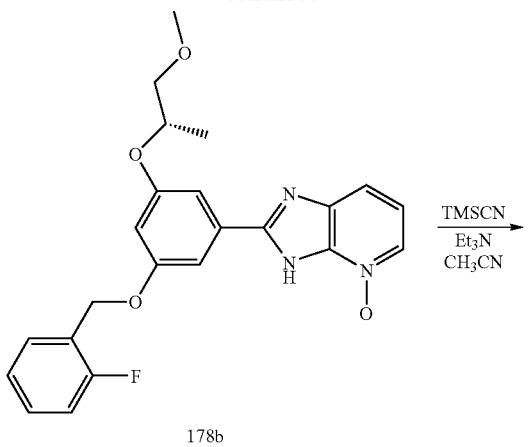

178b

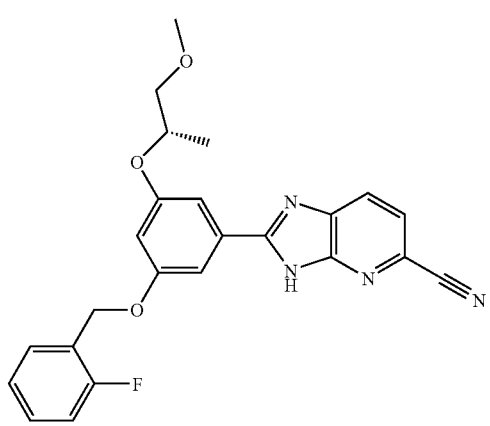

178 m-CPBA (70%, 500 mg, 2.25 mmol) was slowly added portion-wise to a stirred solution of example 178a (610 mg, 1.5 mmol) in CH$_2$Cl$_2$ at 0° C. and the reaction mixture was stirred for 3 h, diluted with CH$_2$Cl$_2$ and washed with sodium thiosulfate solution and brine. The mixture was dried (MgSO$_4$) and concentrated in vacuo to afford example 178b. TMSCN (0.8 ml, 6.0 mmol) was added to a solution of example 178b in CH$_3$CN (5 mL), followed by Et$_3$N (0.42 mL, 3.0 mmol). The resulting mixture was refluxed for 24 h, cooled to rt and concentrated. The residue was purified by flash chromatography (30% to 50% EtOAc-Hexane) to afford the title compound (216 mg, 54%) as colorless oil. $^1$H NMR (400 MHz, chloroform-d) δ ppm 0.92 (d, J=6.78 Hz, 3 H) 3.03 (s, 3 H) 3.15-3.26 (m, 2 H) 4.21-4.25 (m, 1 H) 4.81 (s, 2 H) 6.37 (s, 1 H) 6.64 (t, J=12.21 Hz, 1 H) 6.77 (t, J=12.42 Hz, 1 H) 6.92-6.98 (m, 1 H) 7.00 (s, 1 H) 7.05 (s, 1H) 7.12 (t, J=9.21 Hz, 1 H) 7.66 (d, J=6.21 Hz, 1 H) 7.69 (t, J=5.91 Hz, 1 H). MS (ES) [M+H] calculated for C$_{24}$H$_{22}$FN$_4$O$_3$, 433.16; found 433.09.

Example 179

(S)-methyl 2-(3-(2-fluorobenzyloxy)-5-(1-methoxypropan-2-yloxy)phenyl)-3H-imidazo[4,5-b]pyridine-6-carboxylate

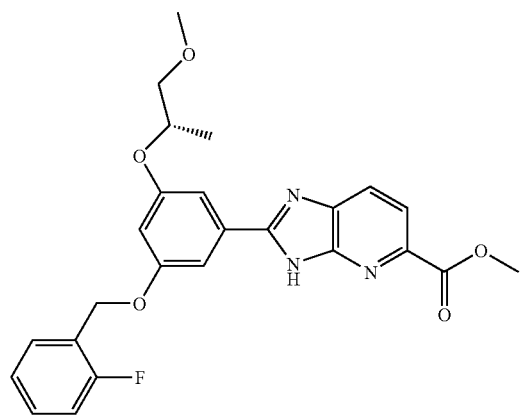

The title compound was prepared by the hydrolysis (HCl-MeOH) of Example 178. $^1$H NMR (400 MHz, chloroform-d) δ ppm 0.90 (d, J=6.78 Hz, 3 H) 3.00 (s, 3 H) 3.15-3.18 (m, 2 H) 3.60 (s, 3 H) 4.01-4.05 (m, 1 H) 4.61 (s, 2 H) 6.17 (s, 1 H) 6.58 (t, J=11.81 Hz, 1 H) 6.62 (t, J=11.94 Hz, 1 H) 6.79-6.82 (m, 1 H) 6.98 (s, 1 H) 7.05 (s, 1H) 7.14 (t, J=9.21 Hz, 1 H) 7.68 (d, J=6.21 Hz, 1 H) 7.72 (t, J=5.91 Hz, 1 H). MS (ES) [M+H] calculated for C$_{25}$H$_{25}$FN$_3$O$_5$, 466.17; found 466.09.

Example 180

(S)-2-(3-(2-fluorobenzyloxy)-5-(1-methoxypropan-2-yloxy)phenyl)-3H-imidazo[4,5-b]pyridine-6-carboxylic acid

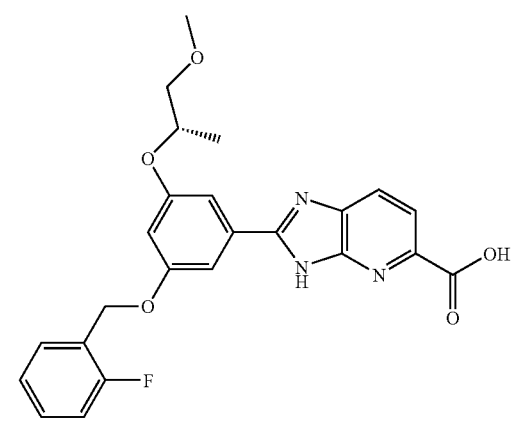

The title compound was prepared by the hydrolysis (1N NaOH-MeOH) of Example 179. $^1$H NMR (400 MHz, chloroform-d) δ ppm 0.98 (d, J=6.78 Hz, 3 H) 2.98 (s, 3 H) 3.18-3.20 (m, 2 H) 4.01-4.05 (m, 1 H) 4.81 (s, 2 H) 6.27 (s, 1 H) 6.68 (t, J=11.81 Hz, 1 H) 6.72 (t, J=11.94 Hz, 1 H) 6.84-6.89 (m, 1 H) 7.02 (s, 1 H) 7.25 (s, 1H) 7.34 (t, J=9.21 Hz, 1 H) 7.68 (d, J=6.21 Hz, 1 H) 7.74 (t, J=5.91 Hz, 1 H). MS (ES) [M+H] calculated for C$_{24}$H$_{23}$FN$_3$O$_5$, 452.15; found 452.05.

Example 181

(S)-2-(3-(1-methoxypropan-2-yloxy)-5-(4-(methyl-sulfonyl)phenoxy)phenyl)-3H-imidazo[4,5-b]pyridine

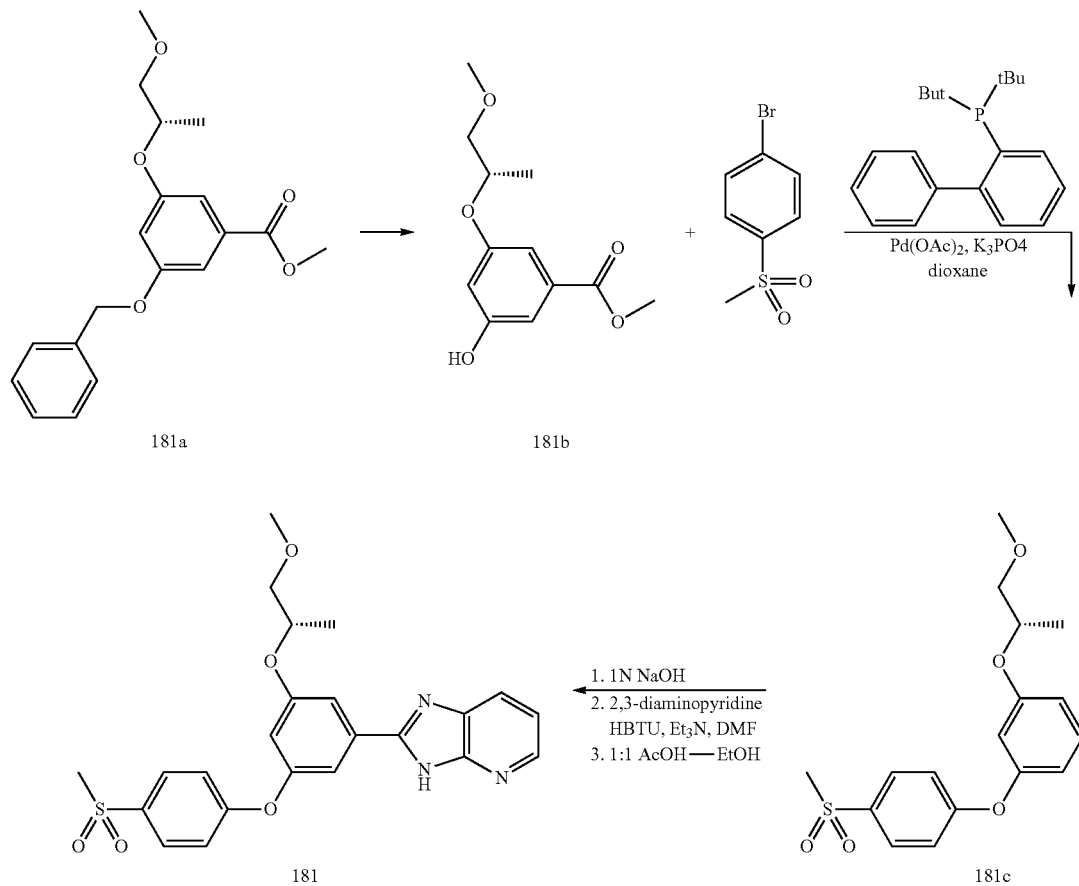

10% Pd—C (100 mg) was added to a solution of 181a (1.0 g, 3.0 mmol) in EtOH (10 mL). The resulting mixture was hydrogenated at 40 psi in a Parr shaker for 12 h. The resulting suspension was filtered through a celite bed and washed several times with 1:1 EtOH—AcOH mixture. The filtrate was concentrated and crystallized from EtOH to afford example 181b (687mg, 95%). MS (ES) [M+H] calculated for $C_{13}H_{21}O_5$, 257.13; found 257.21.

An oven dried round bottom flask was charged with 181b (960 mg, 4.0 mmol), 1-bromo-4-(methylsulfonyl)benzene (1.13 g, 4.8 mmol), potassium phosphate (1.7 g, 8.0 mmol), palladium acetate (18 mg, 0.08 mmol) and 2-(di-tert-buytl-phosphino)biphenyl (36 mg, 0.12 mmol). The flask was purged 3 times with nitrogen; toluene (10 mL) was added through the septum and the mixture was heated at 100° C. for 24 h. The reaction mixture was cooled to rt and diluted with ethyl acetate. The suspension was washed with brine solution (3×50 mL), dried (MgSO₄) and concentrated. The residue was purified by flash chromatography (30%-50% EtOAc-hexane) to afford example 181c (982 mg, 62%) as a white solid. MS (ES) [M+H] calculated for $C_{29}H_{22}O_7S$, 394.11; found 395.30.

The title compound was synthesized using an analogous procedure described for Example 156 using example 181c.

$^1$H NMR (400 MHz, chloroform-d) δ ppm 1.34 (d, J=6.18 Hz, 3 H) 3.11 (s, 3 H) 3.43 (s, 3 H) 3.65-3.70 (m, 2 H) 4.13-4.18 (m, 1 H) 6.86 (s, 1 H) 7.20 (d, J=6.21 Hz, 2 H) 7.50 (t, J=6.01 Hz, 1 H) 7.57 (s, 1 H) 7.73 (s, 1 H) 7.91 (d, J=6.11 Hz, 2 H) 8.41-8.43 (m, 2H). MS (ES) [M+H] calculated for $C_{23}H_{24}N_3O_5S$, 454.14; found 454.12.

Example 182

2-(3-(3-chloropyridin-2-yl)-5-nitrophenyl)-3H-imidazo[4,5-b]pyridine

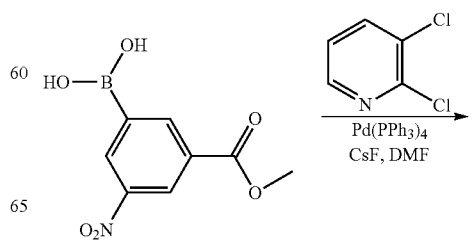

-continued

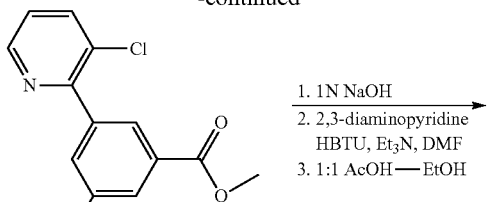

182a 1. 1N NaOH
2. 2,3-diaminopyridine HBTU, Et₃N, DMF
3. 1:1 AcOH—EtOH

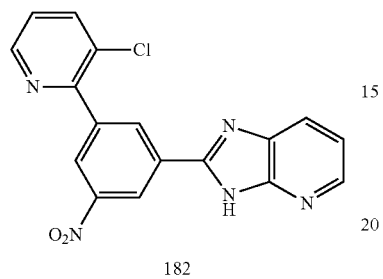

182

Example 182a was prepared from 3-(methoxycarbonyl)-5-nitrophenyl boronicacid (1.0 g, 4.8 mmol), 2,3-dichloropyridine (592 mg, 4.0 mmol), palladium acetate (45 mg, 0.2 mmol), 2-dicyclohexylphosphino-2-(N,N-dimethylamino) biphenyl (118 mg, 0.3 mmol), CsF (1.8 g, 12.0 mmol) and dioxane (10 mL) by using similar procedure described for example 181c. MS (ES) [M+H] calculated for $C_{13}H_{10}ClN_2O_4$, 293.03; found 293.03.

The title compound was synthesized using an analogous procedure described for Example 156 using example 182a. MS (ES) [M+H] calculated for $C_{17}H_1ClN_5O_2$, 352.05; found 352.03.

Example 183

3-(3-chloropyridin-2-yl)-5-(3H-imidazo[4,5-b]pyridin-2-yl)aniline

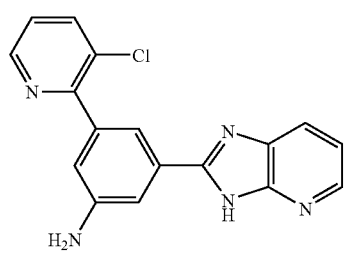

SnCl₂ (450 mg, 2.0 mmol) was added to a solution of Example 182 (140 mg, 0.4 mmol) in EtOH (5 mL) and the resulting suspension was heated at 100° C. for 3 h. The mixture was cooled to rt and saturated NaHCO₃ solution (500 mL) was slowly added. The resulting milky white suspension was extracted with ethylacetate (3×100 mL). The combined organic layers were washed with brine, dried (MgSO₄), filtered and concentrated in vacuo. The resulting material was purified by LCMS (acetonitrile-water gradient) to give the title compound (90 mg, 70%) as a white solid. ¹H NMR (400 MHz, chloroform-d) δ ppm 7.31 (t, J=5.21 Hz, 1 H) 7.43 (dd, J=7.21, 4.42, Hz, 1 H) 7.55 (dd, J=5.27, 3.48 Hz, 1 H) 7.69 (t, J=5.11 Hz, 1 H) 7.86 (t, J=5.11 Hz, 1 H) 7.98 (dd, J=9.21, 5.42, Hz, 1 H) 8.56 (d, J=5.91 Hz, 1 H) 8.62 (d, J=5.91 Hz, 1 H). MS (ES) [M+H] calculated for $C_{17}H_{13}ClN_5$, 322.01; found 321.98.

Example 184

3-(3-chloropyridin-2-yl)-5-(3H-imidazo[4,5-b]pyridin-2-yl)-N-(4-methylbenzyl)aniline

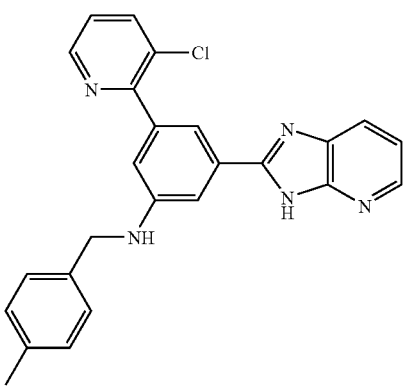

NaCNBH₄ (15.5 mg, 0.25 mmol) was added to a solution of Example 183 (32.1 mg, 0.1 mmol) in CH₂Cl₂-MeOH (2 mL) containing sodium acetate (12.3 mg, 0.15 mmol) and p-methyl benzaldehyde (14.4 mg, 0.12 mmol) at 0° C. The resulting suspension was stirred overnight and water (50 mL) was slowly added and the mixture extracted with CH₂Cl₂ (3×50 mL). The combined organic layers were washed with brine, dried (MgSO₄), filtered and concentrated in vacuo. The resulting material was purified by LCMS (acetonitrile-water gradient) to give the title compound (20 mg, 45%) as a white solid. ¹H NMR (400 MHz, chloroform-d) δ ppm 2.27 (s, 3H) 4.3 (s, 2H) 7.01 (t, J=5.21 Hz, 1 H) 7.08 (d, J=5.11 Hz, 2 H) 7.13 (dd, J=7.21, 4.42, Hz, 1 H) 7.25 (dd, J=5.27, 3.48 Hz, 1 H) 7.39 (t, J=5.11 Hz, 1 H) 7.46 (t, J=5.11 Hz, 1 H) 7.58 (d, J=5.11 Hz, 2 H) 7.68 (dd, J=9.21, 5.42, Hz, 1 H) 8.76 (d, J=5.91 Hz, 1 H) 8.82 (d, J=5.91 Hz, 1 H). MS (ES) [M+H] calculated for $C_{25}H_{21}ClN_5$, 426.14; found 426.09.

Example 185

N-(3-(3-chloropyridin-2-yl)-5-(3H-imidazo[4,5-b]pyridin-2-yl)phenyl)methanesulfonamide

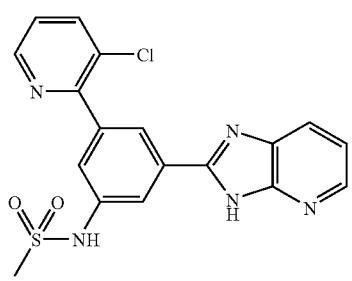

Methanesulfonyl chloride (10.0 μL, 0.12 mmol) was added to a solution of Example 183 (32.1 mg, 0.1 mmol) in CH₂Cl₂ (2 mL) followed by Et₃N (20.0 μL, 0.15 mmol) at 0° C. The resulting mixture was stirred overnight and saturated NH₄Cl solution (50 mL) was added and the mixture extracted with CH$_2$Cl$_2$ (3×50 mL). The combined organic layers were washed with brine, dried (MgSO$_4$), filtered and concentrated in vacuo. The resulting material was purified by LCMS (acetonitrile-water gradient) to give the title compound (15 mg, 38%) as a white solid. $^1$H NMR (400 MHz, CHLOROFORM-d) δ ppm 2.99 (s, 3H) 7.33 (dd, J=7.21, 4.42, Hz, 1 H) 7.52 (dd, J=5.27, 3.48 Hz, 1 H) 7.83 (t, J=5.21 Hz, 1 H) 7.87 (d, J=5.11 Hz, 2 H) 8.03 (t, J=5.11 Hz, 1 H) 8.21 (t, J=5.11 Hz, 1 H) 8.34 (d, J=5.11 Hz, 2 H) 8.51 (d, J=5.42, Hz, 1 H) 8.56 (d, J=5.91 Hz, 1 H). MS (ES) [M+H] calculated for C$_{18}$H$_{15}$ClN$_5$O$_2$S, 400.06; found 400.02.

Example 186

N-(3-(3H-imidazo[4,5-b]pyridin-2-yl)-5-(1-methoxypropan-2-ylamino)phenyl)methane sulfonamide

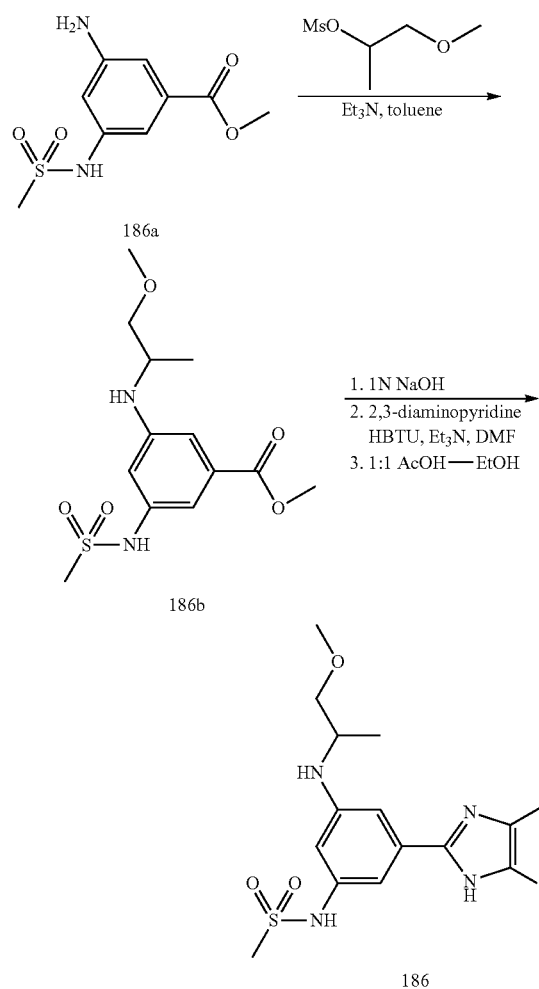

1-Methoxypropan-2-yl methanesulfonate (244 mg, 1.0 mmol) was added to a solution of example 186a (32.1 mg, 0.1 mmol) in toluene (5 mL) followed by Et$_3$N (0.3 mL, 2.0 mmol). The resulting mixture was heated at 100° C. overnight and then cooled to rt. Water (100 mL) was added and the mixture extracted with ethyl acetate (3×100 mL). The combined organic layers were washed with brine, dried (MgSO$_4$), filtered and concentrated in vacuo. The residue was purified by flash chromatography (30%-50% EtOAc-hexane) to afford example 186b (176 mg, 56%) as colorless oil. MS (ES) [M+H] calculated for C$_{13}$H$_{21}$N$_2$O$_5$S, 317.11; found 317.36.

The title compound was synthesized using an analogous procedure described for Example 156 using example 186b. $^1$H NMR (400 MHz, CHLOROFORM-d) δ ppm 1.28 (d, J=5.11 Hz, 3 H) 3.07 (s, 3 H) 3.42 (s, 3 H) 3.46-3.49 (m, 2 H) 3.68-3.72 (m, 1H) 7.99 (t, J=5.27 Hz, 1 H) 7.23 (t, J=5.21 Hz, 1 H) 7.87 (t, J=5.11 Hz, 1 H) 7.58 (t, J=5.11 Hz, 1 H) 8.31 (d, J=5.11 Hz, 1 H) 8.54 (d, J=5.11 Hz, 2 H). MS (ES) [M+H] calculated for C$_{17}$H$_{22}$N$_5$O$_3$S, 376.14; found 376.25.

Example 187

2-(2,5-dimethoxyphenyl)-3H-imidazo[4,5-b]pyridine

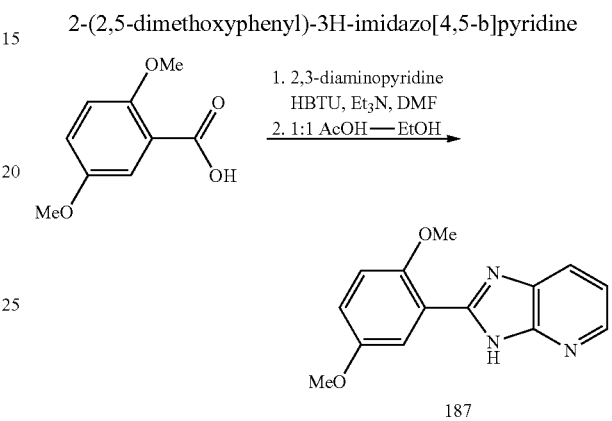

The title compound was synthesized using an analogous procedure from 156c to 156 described for Example 156. $^1$H NMR (400 MHz, DMSO-d) δ ppm 3.8-4.02 (dd, 6H) 7.06-8.42 (m, 6H) 12.2 (d, 1H). MS (ES) [M+H] calculated for C$_{14}$H$_{14}$N$_3$O$_2$, 256.11; found 256.25.

Example 188

6-bromo-2-(2-phenoxyphenyl)-3H-imidazo[4,5-b]pyridine

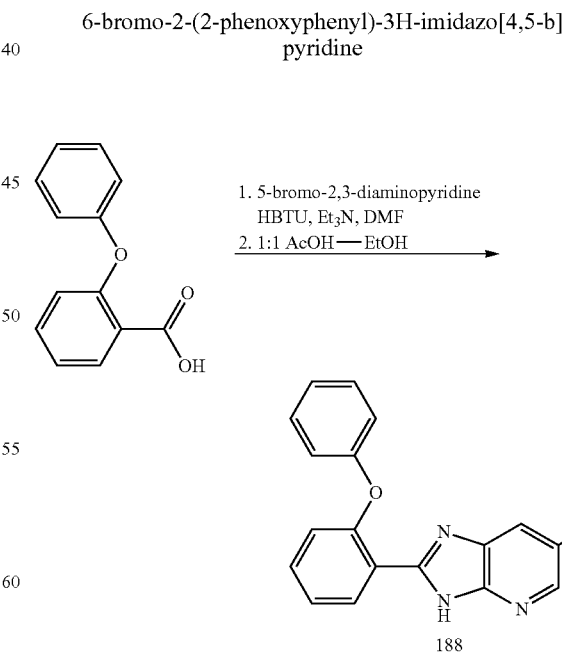

The title compound was synthesized using an analogous procedure from 156c to 156 described for Example 156. $^1$H NMR (400 MHz, DMSO-d) δ ppm 6.52-7.56 (m, 6H) 8.22 (d, 1H) 8.28-8.32 (d, br., 1H) 8.46 (d, 1H)>11 (br, 1H). MS (ES) [M+H] calculated for $C_{18}H_{13}BrN_3O$, 367.21; found 367.27.

Example 189

6-bromo-2-(3-phenoxyphenyl)-3H-imidazo[4,5-b]pyridine

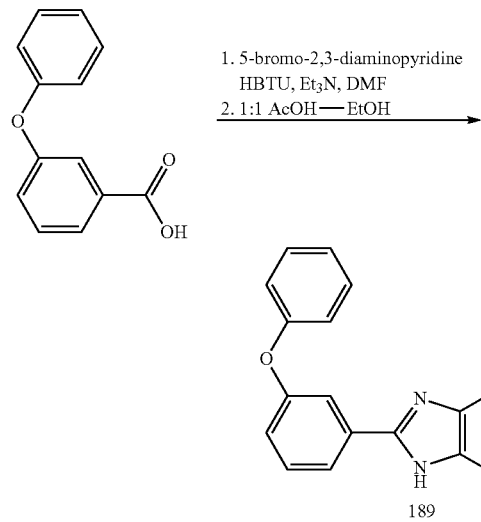

The title compound was synthesized using an analogous procedure from 156c to 156 described for Example 156. $^1$H NMR (400 MHz, DMSO-d) δ ppm 6.84-7.58 (m, 5H) 7.82 (t, 1H) 8.02 (d, 1H) 8.28 (d, 1H) 8.46 (d, 1H)>11 (br, 1H). MS (ES) [M+H] calculated for $C_{18}H_{13}BrN_3O$, 367.21; found 367.27.

Example 190

6-bromo-2-(3-(pyrimidin-2-yloxy)phenyl)-3H-imidazo[4,5-b]pyridine

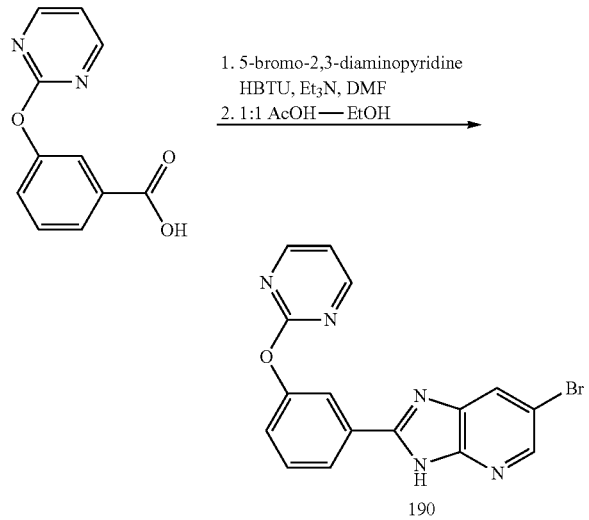

The title compound was synthesized using an analogous procedure from 156c to 156 described for Example 156. $^1$H NMR (400 MHz, DMSO-d$_6$) δ ppm 8.01 (none, 18 H) 7.33 (t, J=4.80 Hz, 13 H) 7.42 (dd, J=7.58, 2.02 Hz, 10 H) 7.41 (s, 2 H) 7.66 (t, J=8.08 Hz, 12 H) 8.03 (d, J=2.02 Hz, 8 H) 8.03 (s, 3 H) 8.13 (d, J=7.83 Hz, 11 H) 8.30 (s, 10 H) 8.44 (d, J=2.27 Hz, 11 H) 8.70 (d, J=4.80 Hz, 21 H). MS (ES) [M+H] calculated for $C_{16}H_{11}BrN_5O$, 369.21; found 369.27.

Example 191

2-(5-(benzyloxy)-2-((1-methyl-1H-imidazol-2-yl)methoxy)phenyl)-3H-imidazo[4,5-b]pyridine

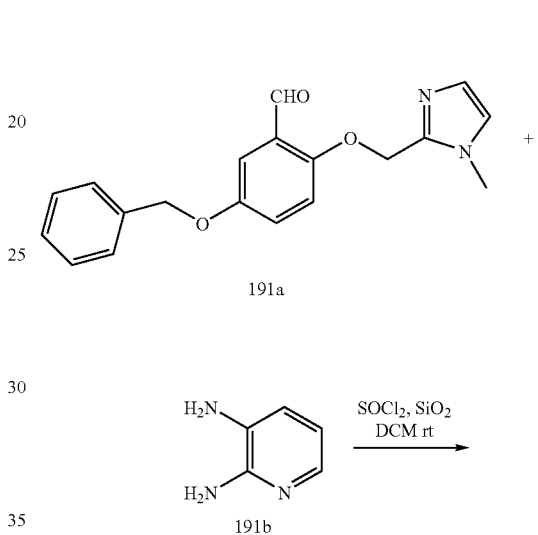

Starting material 191a (60 mg, 0.186 mmol) was dissolved in dichloromethane (10 ml). To this solution was added 2,3-diaminopyridine 191b (24 mg, 0.22 mmol) and thionyl chloride on silica gel (70 mg, 50%). The resulting suspension was stirred at 50° C. for 12 h. The reaction mixture was filtered, and the filtrate was purified by prep HPLC to afford the title compound 191. $^1$H NMR (400 MHz, DMSO-d6) δ ppm 3.83 (s, 3 H) 5.19 (s, 2 H) 5.66 (s, 2 H) 7.26 (dd, J=9.09, 3.28 Hz, 1 H) 7.32-7.43 (m, 4 H) 7.46-7.51 (m, 2 H) 7.70 (s, 2 H) 7.83

(d, J=3.28 Hz, 1 H) 8.12 (dd, J=8.08, 1.52 Hz, 1 H) 8.43 (dd, J=4.80, 1.52 Hz, 1 H). ESI-MS: m/z 412 (m+H)+

Example 192

2-(5-(benzyloxy)-2-((1-methyl-1H-imidazol-2-yl)methoxy)phenyl)-6-(pyridin-3-yl)-3H-imidazo[4,5-b]pyridine

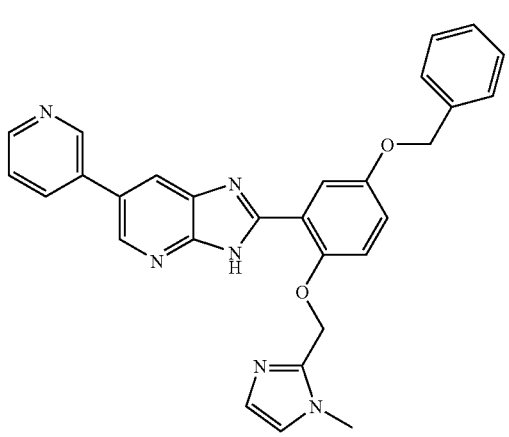

The title compound was synthesized using the procedure described for example 191. ¹H NMR (400 MHz, DMSO-d6) δ ppm 3.86 (s, 3 H) 5.21 (s, 2 H) 5.69 (s, 2 H) 7.26-7.31 (m, 1 H) 7.32-7.45 (m, 4 H) 7.47-7.53 (m, 2 H) 7.74-7.78 (m, 2 H) 7.85-7.91 (m, 2 H) 8.49 (d, J=2.02 Hz, 1 H) 8.59-8.65 (m, 1 H) 8.80 (dd, J=5.30, 1.26 Hz, 1 H) 8.86 (d, J=2.02 Hz, 1 H) 9.21 (d, J=2.02 Hz, 1 H). ESI-MS: m/z 489 (m+H)+

Example 193

2-(5-(benzyloxy)-2-((1-methyl-1H-imidazol-2-yl)methoxy)phenyl)-6-bromo-3H-imidazo[4,5-b]pyridine

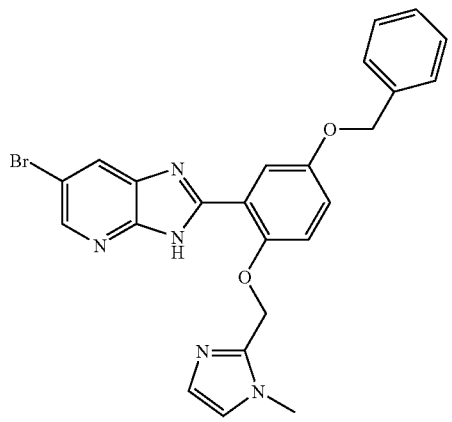

The title compound was synthesized using the procedure described for example 191. ¹H NMR (400 MHz, DMSO-d6) δ ppm 3.81 (s, 3 H) 5.19 (s, 2 H) 5.62 (s, 2 H) 7.25 (dd, J=9.09, 3.28 Hz, 1 H) 7.32-7.43 (m, 4 H) 7.46-7.51 (m, 2 H) 7.61-7.66 (m, 2 H) 7.83 (d, J=3.03 Hz, 1 H) 8.30 (d, J=2.02 Hz, 1 H) 8.47 (d, J=2.02 Hz, 1 H). ESI-MS: m/z 491 (m+H)+.

Example 194

N-(3-(3H-imidazo[4,5-b]pyridin-2-yl)-4-isopropoxyphenyl)-2-phenylacetamide

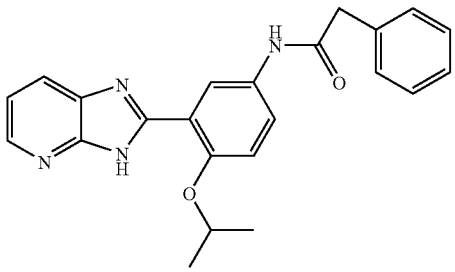

The title compound was synthesized using the procedure described for example 191. ¹H NMR (400 MHz, CHLOROFORM-d) δ ppm 1.44 (d, J=6.06 Hz, 6 H) 3.81 (s, 2 H) 4.69-4.79 (m, 1 H) 6.93 (d, J=9.09 Hz, 1 H) 7.25-7.38 (m, 5 H) 7.48 (t, J=6.82 Hz, 1 H) 7.90 (d, J=9.09 Hz, 1 H) 8.26 (s, 1 H) 8.35 (d, J=7.83 Hz, 1 H) 8.42 (d, J=5.31 Hz, 1 H) 8.76 (s, 1 H) 13.50 (br s, 1 H). ESI-MS: m/z 387 (m+H)+.

Example 195

2-(5-(benzyloxy)-2-(2-(pyridin-2-yl)ethoxy)phenyl)-3H-imidazo[4,5-b]pyridine

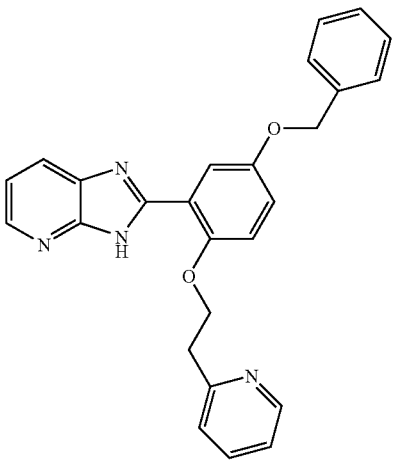

The title compound was synthesized using the procedure described for example 191. ¹H NMR (400 MHz, MeOD) δ ppm 3.53 (t, J=5.68 Hz, 2 H) 4.57 (t, J=5.56 Hz, 2 H) 5.15 (s, 2 H) 7.21-7.38 (m, 5 H) 7.44 (d, J=7.33 Hz, 2 H) 7.58 (t, J=6.69 Hz, 1 H) 7.61-7.67 (m, 1 H) 7.78 (d, J=8.08 Hz, 1 H) 7.83 (d, J=2.78 Hz, 1 H) 8.18 (td, J=7.83, 1.77 Hz, 1 H) 8.32 (dd, J=8.08, 1.26 Hz, 1 H) 8.55 (dd, J=5.31, 1.26 Hz, 1 H) 8.81-8.85 (m, 1 H). ESI-MS: m/z 423 (m+H)+

Example 196

(E)-2-(2-isopropoxy-5-styrylphenyl)-3H-imidazo[4,5-b]pyridine

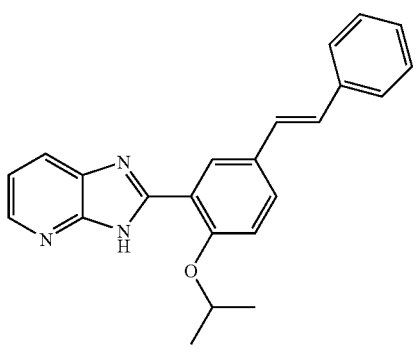

The title compound was synthesized using the procedure described for example 191. $^1$H NMR (400 MHz, CHLOROFORM-d) δ ppm 1.50 (d, J=6.06 Hz, 6 H) 4.72-4.81 (m, 1 H) 6.82-7.00 (m, 3 H) 7.19-7.24 (m, 1 H) 7.26-7.31 (m, 2 H) 7.35-7.40 (m, 3 H) 7.51 (dd, J=8.84, 2.27 Hz, 1 H) 8.30-8.36 (m, 2 H) 8.42 (dd, J=8.08, 1.26 Hz, 1 H). ESI-MS: m/z 356 (m+H)$^+$

Example 197

2-(2-isopropoxy-5-phenethylphenyl)-3H-imidazo[4,5-b]pyridine

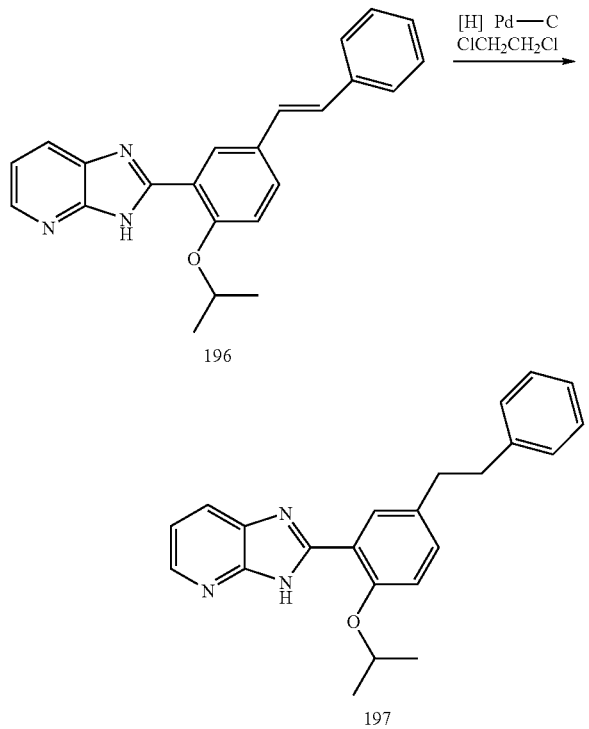

196 (125 mg, 0.47 mmol) was dissolved in isopropanol (5 ml), and then Pd—C (10%) was added. The hydrogenation was completed in 10 h at 25° C. The mixture was filtered and the filtrate was purified by HPLC to afford the title example 197. $^1$H NMR (400 MHz, CHLOROFORM-d) δ ppm 1.55 (d, J=6.06 Hz, 6 H) 2.94-2.99 (m, 4 H) 4.81-4.91 (m, 1 H) 7.02 (d, J=8.84 Hz, 1 H) 7.18-7.23 (m, 3 H) 7.27-7.33 (m, 3 H) 7.47 (t, J=6.69 Hz, 1 H) 8.32 (d, J=2.27 Hz, 1 H) 8.39 (d, J=5.30 Hz, 1 H) 8.49 (d, J=7.33 Hz, 1 H) 12.54 (br s, 1 H). ESI-MS: m/z 358 (m+H)$^+$

Example 198

N-(3-(3H-imidazo[4,5-b]pyridin-2-yl)-4-isopropoxyphenyl)-4-chlorobenzamide

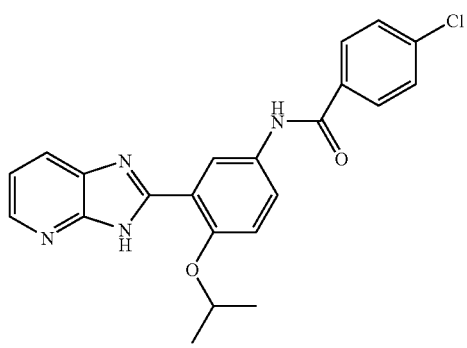

The title compound was synthesized using the procedure described for example 191. $^1$H NMR (400 MHz, CHLOROFORM-d) δ ppm 1.59 (d, J=6.06 Hz, 6 H) 4.88-4.98 (m, 1 H) 7.14 (d, J=9.09 Hz, 1 H) 7.46-7.53 (m, 3 H) 8.09 (d, J=8.59 Hz, 2 H) 8.29 (d, J=7.58 Hz, 1 H) 8.54 (d, J=5.05 Hz, 1 H) 8.63 (d, J=9.09 Hz, 1 H) 8.93 (d, J=1.52 Hz, 1 H) 9.36 (s,1 H). ESI-MS: m/z 407 (m+H)$^+$

Example 199

N-(3-(3H-imidazo[4,5-b]pyridin-2-yl)-4-isopropoxyphenyl)-5-methylfuran-2-carboxamide

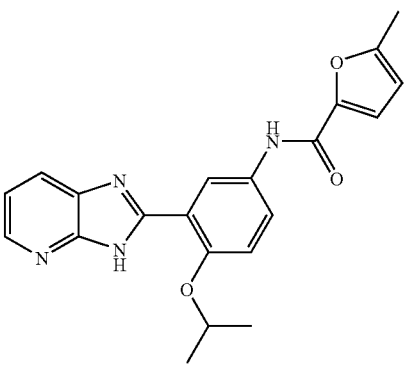

The title compound was synthesized using the procedure described for example 191. $^1$H NMR (400 MHz, CHLOROFORM-d) δ ppm 1.53 (d, J=6.06 Hz, 6 H) 2.44 (s, 3 H) 4.78-4.89 (m, 1 H) 6.17-6.22 (m, 1 H) 7.04 (d, J=9.09 Hz, 1 H) 7.22 (d, J=3.54 Hz, 1 H) 7.47 (m, 1 H) 8.32-8.38 (m, 2 H) 8.44 (dd, J=5.05, 1.26 Hz, 1 H) 8.50 (d, J=2.53 Hz, 1 H) 8.75 (s, 1 H). ESI-MS: m/z 377(m+H)$^+$

Example 200

3-(6-bromo-3H-imidazo[4,5-b]pyridin-2-yl)-5-nitro-N-phenylbenzamide

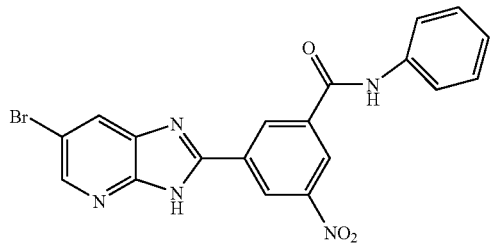

The title compound was synthesized using the procedure described for Example 156. ¹H NMR (400 MHz, DMSO-$d_6$) δ ppm 7.17 (t, J=7.33 Hz, 1 H) 7.41 (t, J=7.96 Hz, 2 H) 7.82 (d, J=7.58 Hz, 2 H) 8.41 (s, 1 H) 8.51 (s, 1 H) 8.93 (s, 1 H) 9.23 (d, J=1.77 Hz, 2 H) 10.80 (s, 1 H) 14.04 (s, 1 H). ESI-MS: m/z 439 (m+H)$^+$

Example 201

N-benzyl-3-(6-bromo-3H-imidazo[4,5-b]pyridin-2-yl)-5-nitrobenzamide

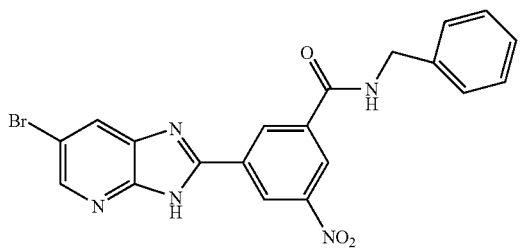

The title compound was synthesized using the procedure described for Example 156. ¹H NMR (400 MHz, DMSO-$d_6$) δ ppm 4.57 (d, J=5.81 Hz, 2 H) 7.25-7.30 (m, 1 H) 7.34-7.41 (m, 4 H) 8.33-8.48 (m, 1 H) 8.48-8.57 (m, 1 H) 8.87 (s, 1 H) 9.16-9.25 (m, 2 H) 9.65 (s, 1 H). m/z 453 (m+H)$^+$

Example 202

3-amino-N-benzyl-5-(6-bromo-3H-imidazo[4,5-b]pyridin-2-yl)benzamide

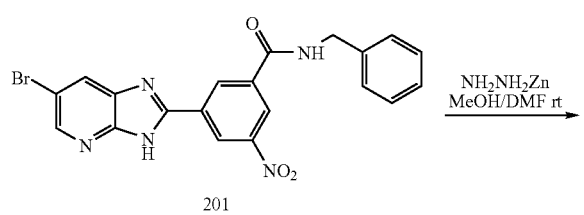

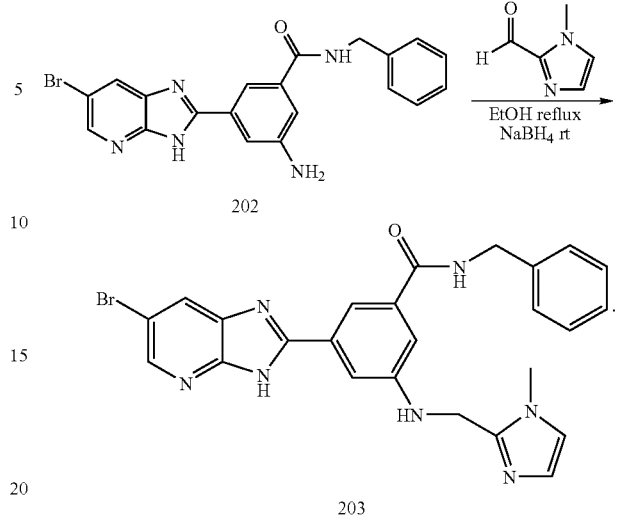

201 (280 mg, 0.619 mmol) was dissolved in DMF/MeOH=1:1(4.0 ml). The solution was treated with Zn dust (2.0 mmol) and hydrazine monohydrate (2.0 mmol) for 40 min at 25° C. The reaction mixture was filtered and the filtrate was concentrated. The residue was diluted with AcOEt and water, and the organic layer was dried over MgSO$_4$ then purified by flash chromatography (AcOEt/Hexane) to afford title example 202. ¹H NMR (400 MHz, DMSO-$d_6$) δ ppm 4.47 (d, J=5.81 Hz, 2 H) 7.23 (d, J=9.85 Hz, 2 H) 7.34 (d, J=4.55 Hz, 4 H) 7.57 (s, 1 H) 7.85 (s, 1 H) 8.23 (s, 1 H) 8.41 (d, J=2.02 Hz, 1 H) 8.94-9.03 (m, 1 H). ESI-MS: m/z 423 (m+H)$^+$

Example 203

N-benzyl-3-(6-bromo-3H-imidazo[4,5-b]pyridin-2-yl)-5-((1-methyl-1H-imidazol-2-yl)methylamino) benzamide

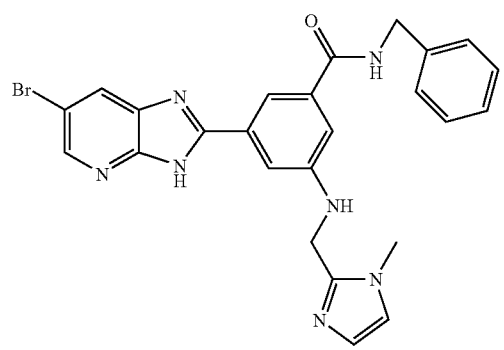

202 (25 mg, 0.06 mmol) was dissolved in EtOH (2.0 ml), then aldehyde (0.12 mmol) was added, the mixture was heated to reflux for 8 h. The mixture was cooled to 25° C., followed by addition of NaBH$_4$. The resulting mixture was stirred for 2 h at 25° C., and then filtered. The filtrate was purified by HPLC to afford the title compound. ¹H NMR (400 MHz, DMSO) δ ppm 3.88 (s, 3 H) 4.50 (d, J=6.06 Hz, 2 H) 4.79 (d, J=4.55 Hz, 2 H) 6.83-6.93 (m, 1 H) 7.24-7.38 (m, 6 H) 7.54-7.64 (m, 2 H) 7.71 (d, J=2.02 Hz, 1 H) 8.03 (s, 1 H) 8.21-8.31 (m, 1 H) 8.44 (d, J=2.02 Hz, 1 H) 9.07 (t, J=6.06 Hz, 1 H). ESI-MS: m/z 517 (m+H)$^+$

Example 204

3-amino-5-(6-bromo-3H-imidazo[4,5-b]pyridin-2-yl)-N-phenylbenzamide

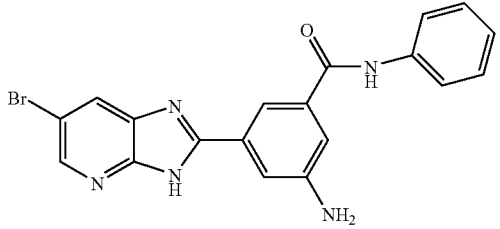

The title compound was synthesized using the procedure described for 202. $^1$H NMR (400 MHz, DMSO-d$_6$) δ ppm 7.08-7.14 (m, 1 H) 7.24 (s, 1 H) 7.36 (t, J=7.71 Hz, 2 H) 7.64 (s, 1 H) 7.79 (d, J=8.59 Hz, 2 H) 7.89 (s, 1 H) 8.26 (s, 1 H) 8.43 (d, J=2.02 Hz, 1 H) 10.32 (s, 1 H). ESI-MS: m/z 409 (m+H)$^+$

Example 205

N-benzyl-3-(6-bromo-3H-imidazo[4,5-b]pyridin-2-yl)-5-((6-methoxypyridin-2-yl)methylamino)benzamide

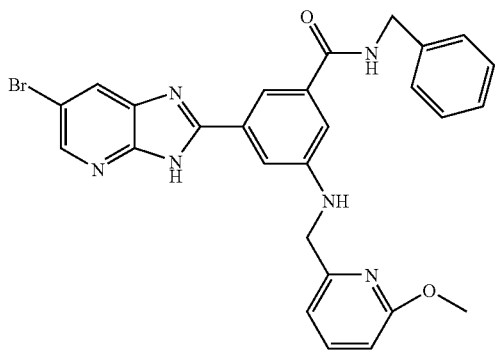

The title compound was synthesized using the procedure described for 203. $^1$H NMR (400 MHz, DMSO-d$_6$) δ ppm 3.88 (s, 3 H) 4.35-4.54 (m, 4 H) 6.67 (d, J=8.34 Hz, 1 H) 6.95 (d, J=7.33 Hz, 1 H) 7.21-7.43 (m, 6 H) 7.59-7.68 (m, 2 H) 7.90 (s, 1 H) 8.24 (s, 1 H) 8.41 (d, J=1.77 Hz, 1 H) 9.03 (s, 1 H). ESI-MS: m/z 544 (m+H)$^+$

Example 206

N-benzyl-3-(6-bromo-3H-imidazo[4,5-b]pyridin-2-yl)-5-(2-fluoro-6-methoxybenzylamino)benzamide

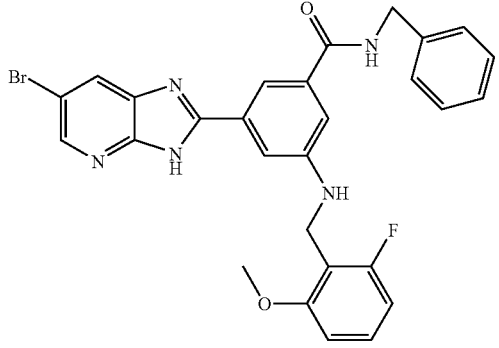

The title compound was synthesized using the procedure described for 203. $^1$H NMR (400 MHz, MeOD) δ ppm 3.87 (s, 3 H) 4.46 (s, 2 H) 4.58 (s, 2 H) 6.70 (t, J=8.72 Hz, 1 H) 6.81 (d, J=8.59 Hz, 1 H) 7.21-7.29 (m, 2 H) 7.31-7.40 (m, 5 H) 7.62 (t, J=1.89 Hz, 1 H) 7.71-7.76 (m, 1 H) 8.18 (d, J=2.02 Hz, 1 H) 8.46 (d, J=1.77 Hz, 1 H). ESI-MS: m/z 561 (m+H)$^+$

Example 207

3-(3H-imidazo[4,5-b]pyridin-2-yl)-5-((1-methyl-1H-imidazol-2-yl)methylamino)-N-phenylbenzamide

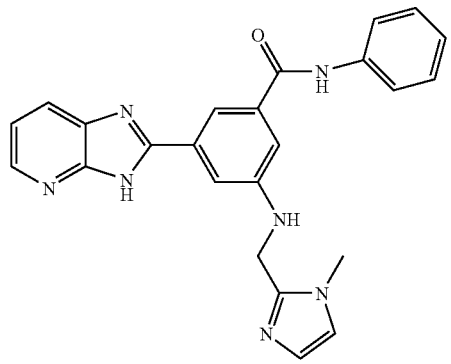

The title compound was synthesized using the procedure described for 203. $^1$H NMR (400 MHz, MeOD) δ ppm 2.64 (s, 3 H) 3.97 (s, 2H) 7.16 (t, J=7.45 Hz, 1 H) 7.34-7.40 (m, 3 H) 7.44 (d, J=2.02 Hz, 1 H) 7.50 (m, 1 H) 7.56 (d, J=2.02 Hz, 1 H) 7.68-7.72 (m, 3 H) 7.96 (s, 2 H) 8.05-8.10 (m, 1 H) 8.25 (dd, J=7.96, 1.14 Hz, 1 H) 8.45-8.51 (m, 1 H). ESI-MS: m/z 424 (m+H)$^+$

Example 208

3-(3H-imidazo[4,5-b]pyridin-2-yl)-5-(4-methyl-1H-pyrazol-5-yl)methylamino)-N-phenylbenzamide

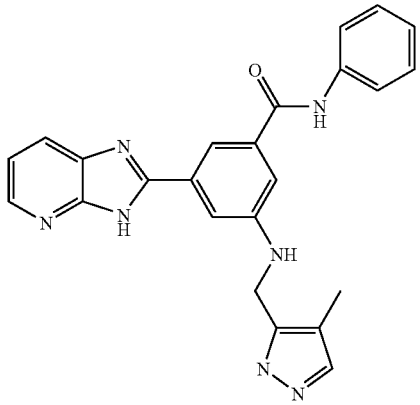

The title compound was synthesized using the procedure described for 203. $^1$H NMR (400 MHz, MeOD) δ ppm 4.48 (s, 2 H) 7.15 (t, J=7.45 Hz, 1 H) 7.33-7.43 (m, 3 H) 7.51 (m, 1 H) 7.65-7.73 (m, 4 H) 7.94 (s, 1 H) 8.26 (d, J=7.83 Hz, 1 H) 8.47 (d, J=5.05 Hz, 1 H). ESI-MS: m/z 489 (m+H)+

Example 209

5-fluoro-2-(3H-imidazo[4,5-b]pyridin-2-yl)-4-(1-methyl-1H-imidazol-2-ylthio)aniline

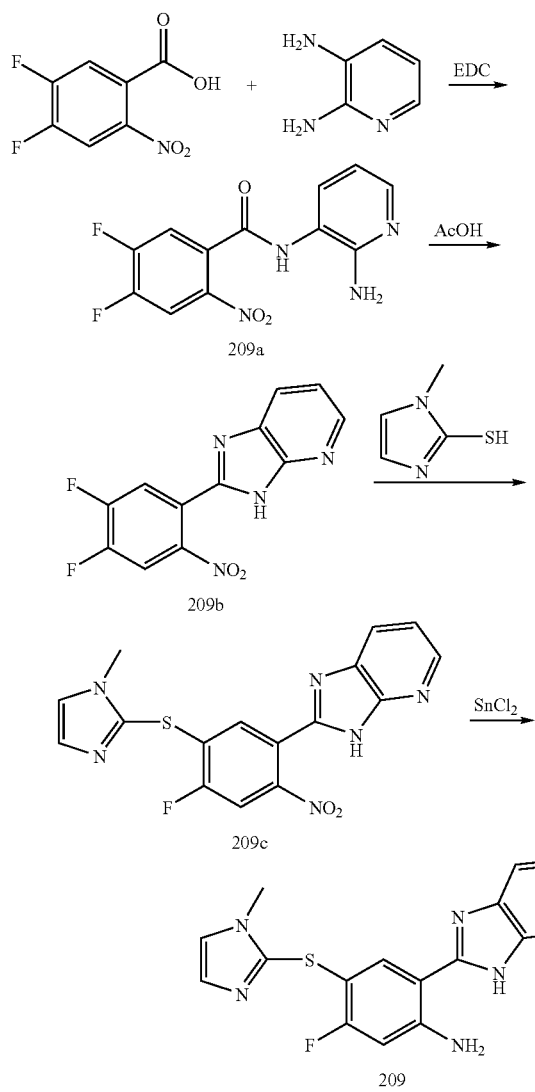

4,5-Difluoro, 2-nitrobenzoic acid (1.16 g, 5.7 mmol) was stirred with 2,3-diaminopyridine (0.62 g, 5.7 mmol) and EDC (1.3 g, 6.8 mmol) in DMF (10 ml) for 15 hours at room temperature. The reaction mixture was diluted with brine and extracted with ethyl acetate. The organics were further washed once with brine, dried and concentrated. Chromatography (SiO$_2$; 70 to 100% ethyl acetate in hexanes) gave 209a which was not characterized or further manipulated, but carried forward in the next step.

Example 209a (158 mg, 0.54 mmol) was dissolved in ethanol (4.5 mL) and acetic acid (1.5 mL) and heated in a microwave at 150° C. for 1 hour. The reaction mixture was cooled and concentrated in vacuo. The residue was partitioned between ethyl acetate and 1 M K$_2$CO$_3$. The aqueous layer was further extracted with ethyl acetate. The combined organics were dried and concentrated. Chromatography (SiO$_2$; 40 to 60% ethyl acetate in hexanes) gave 209b (33 mg pale yellow solid, 22%). $^1$H NMR (400 MHz, DMSO) δ 7.25 (m, 1 H) 8.1 (m, 2 H) 8.4 (m, 2H) 13.6 (br s, 1H).

209b (25 mg, 0.091 mmol) was stirred with 1-methyl-2-thioimidazole (11 mg, 0.095 mmol) in DMA (1 mL) and Et$_3$N (30 uL) at 80° C. for 4 days. The mixture was cooled, diluted with ethyl acetate and washed with brine. The organics were dried and concentrated. This residue was taken up in ethanol (5 mL) and was treated with SnCl$_2$ (95 mg, 0.5 mmol) at 80° C. for 2 hours. The mixture was cooled and concentrated. Prep HPLC (1 to 30% acetonitrile in 0.05% TFA buffered water) gave 209 (5 mg yellow solid, 15% for 2 steps). $^1$H NMR (400 MHz, MeOD) δ 3.97 (s, 3 H) 6.77 (d, J=11.6 Hz, 1 H) 7.55 (d, J=1.76 Hz, 1 H) 7.60-7.56 (dd, J=5.63, 7.64 Hz, 1 H) 7.64 (d, J=1.85 Hz, 1 H) 8.35 (d, J=7.73 Hz, 2 H) 8.48 (m, 1 H). [M+H] calc'd for C$_{16}$H$_{13}$FN$_6$S, 341; found, 341.

Example 210a methyl 5-(benzyloxy)-2-(thiophene-2-sulfonamido)benzoate

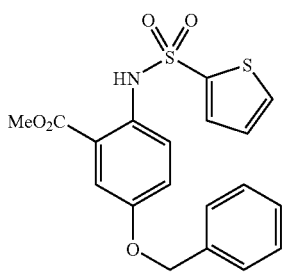

Methyl 5-(benzyloxy)-2-(amino)benzoate ([116027-17-9], 1.3 g, 5.06 mmol) was stirred in DCM (20 mL) and pyridine (1.2 mL) at 0° C. Thiophene-2-sulfonyl chloride (1.02 g, 5.56 mmol) was added. After one hour, the cooling bath was removed and the reaction was stirred overnight. The mixture was washed once with 10% aqueous HCl. The organics were dried and concentrated. Chromatography (20 to 40% ethyl acetate in hexanes) gave the title compound. [M+H] calc'd for C$_{19}$H$_{17}$NO$_5$S$_2$, 404; found, 404.

Example 210b 5-(benzyloxy)-2-(thiophene-2-sulfonamido)benzoic acid

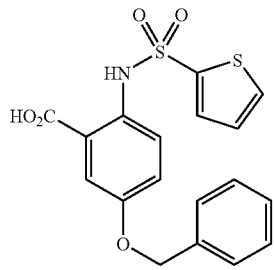

210a (1.14 g, 2.83 mmol) was stirred in THF (20 mL). LiOH (1 M) was added and the mixture heated at 50° C. overnight. After cooling, the reaction mixture was partitioned between ethyl acetate and 10% HCl. The organic layer was further washed once with brine, dried and concentrated to afford the crude title compound. [M+H] calc'd for $C_{18}H_{15}NO_5S_2$, 390; found, 390.

Example 210

N-(4-(benzyloxy)-2-(3H-imidazo[4,5-b]pyridin-2-yl) phenyl)thiophene-2-sulfonamide

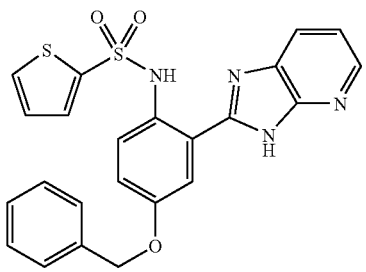

The title compound was synthesized using an analogous procedure to that described in connection with Example 156. $^1$H NMR (400 MHz, DMSO) δ 5.15 (s, 2 H), 6.9 (dd, 1 H), 7.2-7.25 (dd, 1 H), 7.3-7.4 (m, 5 H), 7.65 (d, 1 H), 7.75 (d, 1 H), 7.8 (s, 1 H), 8.1 (br s, 1 H), 8.4 (s, 1 H), 12.8 (br s, 1 H), 13.8 (br s, 1 H). [M+H] calc'd for $C_{23}H_{18}N_4O_3S_2$, 463; found, 463.

Example 211a methyl 3-(methylsulfonamido)-5-nitrobenzoate

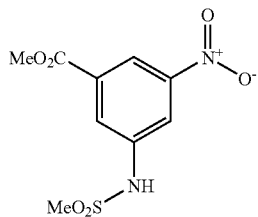

The title compound was synthesized using an analogous procedure to that described in connection with 210a starting from 3-amino-5-nitrobenzoic acid [23218-93-1]. $^1$H NMR (400 MHz, DMSO) δ 3.15 (s, 3 H), 3.9 (s, 3 H), 8.15 (s, 1 H), 8.25 (s, 1 H), 8.3 (s, 1 H), 10.6 (s, 1 H).

Example 211b methyl 3-amino-5-(methylsulfonamido)benzoate

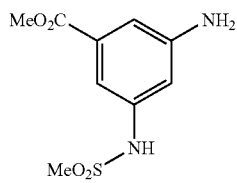

211a (2.68 g, 9.78 mmol) was suspended in MeOH (50 mL) and DCE (25 mL). Tin (II) chloride (9.3 g, 49 mmol) was added and the mixture was heated to 70° C. After 2.5 hours, the mixture was cooled and most of the solvent was removed in vacuo. The residue was partitioned between ethyl acetate and saturated aqueous sodium bicarbonate. The organic layer was further washed once with brine, dried and concentrated to give the title compound. [M+H] calc'd for $C_9H_{12}N_2O_4S$, 245; found, 245.

Example 211c 3-(methylsulfonamido)-5-(phenylsulfonamido)benzoic acid

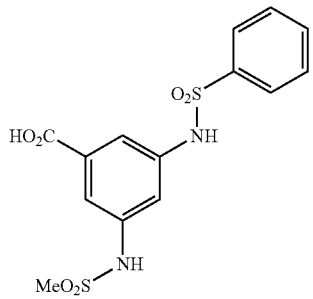

The title compound was synthesized using procedures analogous to that described for Examples 210a and 210b. [M+H] calc'd for $C_{14}H_{14}N_2O_6S_2$, 371; found, 371.

Example 211

N-(3-(6-bromo-3H-imidazo[4,5-b]pyridin-2-yl)-5-(methylsulfonamido)phenyl)benzenesulfonamide

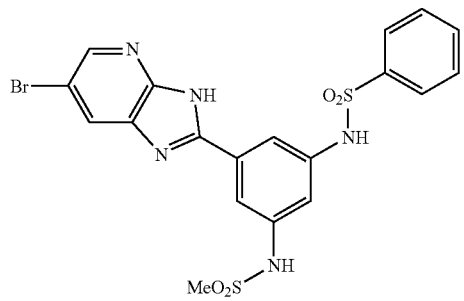

The title compound was synthesized using procedures analogous to those described for Example 156. $^1$H NMR (400 MHz, DMSO) δ 2.91 (s, 3 H) 7.11 (s, 1 H) 7.478 (m, 3 H) 7.60 (m, 2 H) 7.75 (m, 2 H) 8.21 (br s, 1 H) 8.35 (d, J=1.42 Hz, 1 H) 9.98 (s, 1 H) 10.55 (s, 1H) 13.9 (br s, 1H). [M+H] calc'd for $C_{19}H_{16}BrN_5O_4S_2$, 522; found, 522.

Example 212a 3-(methylsulfonamido)-5-(phenylmethylsulfonamido)benzoic acid

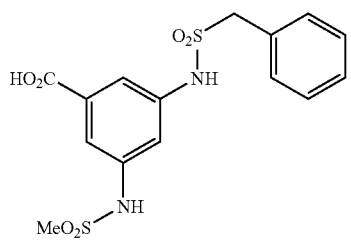

The title compound was synthesized using procedures analogous to that described for Examples 210a and 210b.

Example 212

N-(3-(6-bromo-3H-imidazo[4,5-b]pyridin-2-yl)-5-(methylsulfonamido)phenyl)-1-phenylmethanesulfonamide

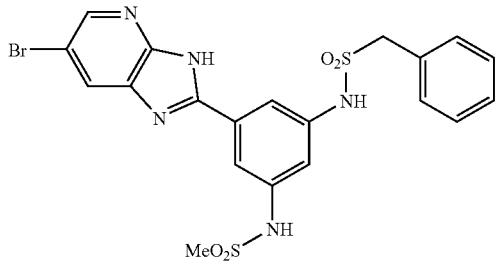

The title compound was synthesized using procedures analogous to those described for Example 156. $^1$H NMR (400 MHz, DMSO) δ 3.02 (s, 3 H) 4.48 (s, 2 H) 7.14 (s, 1 H) 7.24 (m, 4 H) 7.67 (m, 2 H) 8.34 (d, J=1.88 Hz, 1 H) 10.01 (s, 1 H) 10.09 (s, 1 H). [M+H] calc'd for $C_{20}H_{18}BrN_5O_4S_2$, 536; found, 536.

Example 213a 3-nitro-5-(phenylsulfonamido)benzoic acid

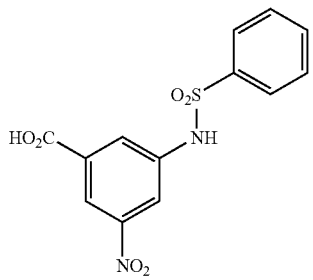

The title compound was synthesized using a procedure analogous to that described in connection with Example 210b. This material was used without purification in the next step.

Example 213b

N-(3-(6-bromo-3H-imidazo[4,5-b]pyridin-2-yl)-5-nitrophenyl)benzenesulfonamide

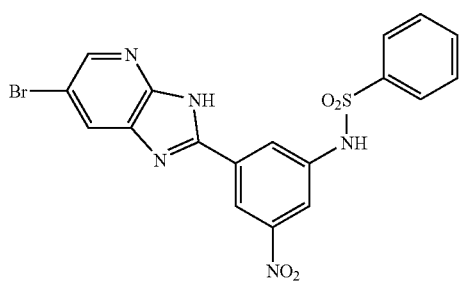

Starting with example 213a, the title compound was synthesized using a procedure analogous to that described in connection with Example 156. [M+H] calc'd for $C_{18}H_{12}BrN_5O_4S$, 474; found, 474.

Example 213c

N-(3-amino-5-(6-bromo-3H-imidazo[4,5-b]pyridin-2-yl)phenyl)benzenesulfonamide

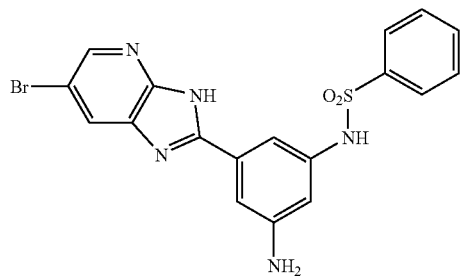

The title compound was synthesized using an analogous procedure to that described in connection with Example 211b. [M+H] calc'd for $C_{18}H_{14}BrN_5O_2S$ 444; found, 444.

Example 213

N-(3-(6-bromo-3H-imidazo[4,5-b]pyridin-2-yl)-5-((1-methyl-1H-imidazol-2-yl)methylamino)phenyl)benzenesulfonamide

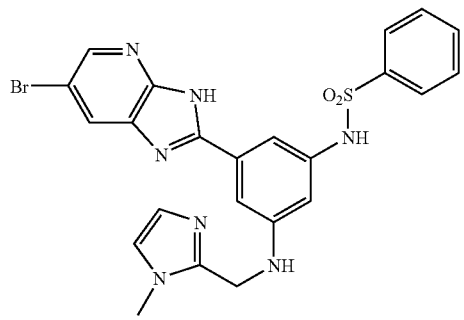

The title compound was synthesized using an analogous procedure to that described in connection with Example 184 except that 1-methyl imidazole-2-carboxaldehyde was used. $^1$H NMR (400 MHz, DMSO) δ 3.86 (s, 3 H) 4.66 (s, 2 H) 6.60 (m, 1 H) 6.83 (br s, 1 H) 7.12 (s, 1 H) 7.35 (s, 1 H) 7.52-7.68 (m, 4 H) 7.72 (d, J=1.94 Hz, 1 H) 7.77 (m, 2H) 8.25 (d, J=2.06 Hz, 1H) 8.41 (d, J=2.11 Hz, 1H) 10.42 (s, 1H) 14.25 (br s, 1H). [M+H] calc'd for $C_{23}H_{20}BrN_7O_2S$ 538; found, 538.

Example 214a 3-(methylsulfonamido)-5-nitrobenzoic acid

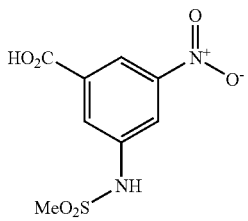

Starting from Example 2111a, the title compound was synthesized using an analogous procedure to that described in connection with Example 210b. [M+H] calc'd for $C_8H_8N_2O_6S$ 261; found, 261.

Example 214b

N-(3-amino-5-(6-bromo-3H-imidazo[4,5-b]pyridin-2-yl)phenyl)methanesulfonamide

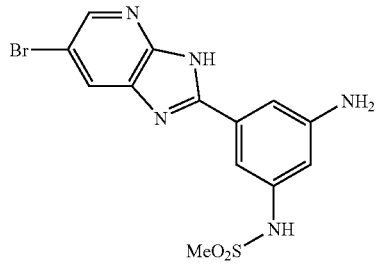

The title compound was synthesized using an analogous procedure to that described in connection with Example 211b. [M+H] calc'd for $C_{13}H_{12}BrN_5O_2S$ 382; found, 382.

Example 214

N-(3-(6-bromo-3H-imidazo[4,5-b]pyridin-2-yl)-5-((1-methyl-1H-imidazol-2-yl)methylamino)phenyl)methanesulfonamide

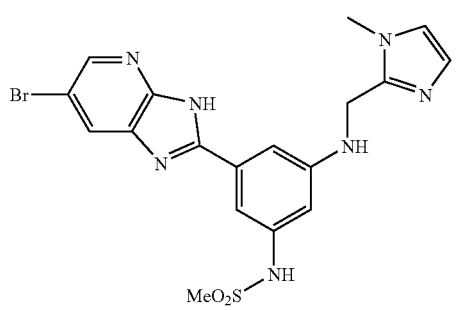

The title compound was synthesized using an analogous procedure to that described in connection with Example 213. [M+H] calc'd for $C_{18}H_{18}BrN_7O_2S$ 476; found, 476.

Example 215a methyl 3-acetamido-5-nitrobenzoate

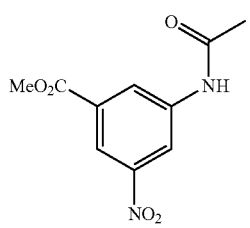

3-Amino-5-nitrobenzoic acid ([23218-93-1], 0.99 g, 5.05 mmol) was stirred in DCM (20 mL) and pyridine (2 mL) at 0° C. Acetic anhydride (1 mL, 10 mmol) was added. The reaction was stirred overnight. Water (30 mL) was added. A precipitate formed and was collected by filtration. [M+H] calc'd for $C_{10}H_{10}N_2O_5$ 239; found, 239.

Example 215b 3-acetamido-5-nitrobenzoic acid

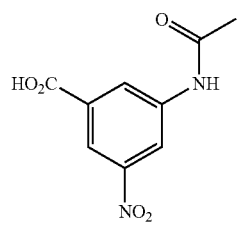

Starting from Example 215a, the title compound was synthesized using an analogous procedure to that described in connection with Example 210b. [M+H] calc'd for $C_9H_8N_2O_5$ 225; found, 225.

Example 215c

N-(3-(3H-imidazo[4,5-b]pyridin-2-yl)-5-nitrophenyl)acetamide

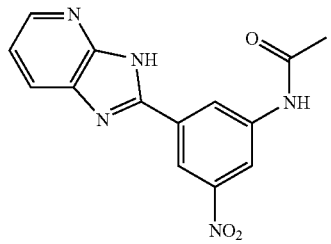

Starting from Example 215b, the title compound was synthesized using an analogous procedure to that described in connection with Example 156. [M+H] calc'd for $C_{14}H_{11}N_5O_3$ 298; found, 298.

Example 215

N-(3-(3H-imidazo[4,5-b]pyridin-2-yl)-5-((1-methyl-1H-imidazol-2-yl)methylamino)phenyl)acetamide

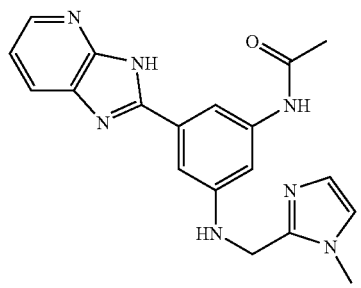

The title compound was synthesized using procedures analogous to those described in connection with Example 213. [M+H] calc'd for $C_{19}H_{19}N_7O$ 362; found, 362.

Example 216

N-(3-(3H-imidazo[4,5-b]pyridin-2-yl)-5-((1-methyl-1H-imidazol-2-yl)methylamino)phenyl)methanesulfonamide

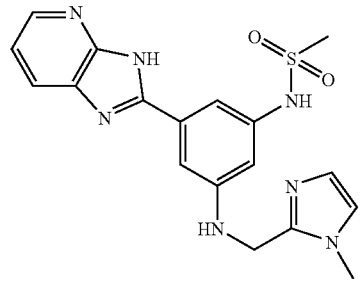

The title compound was synthesized using an analogous procedure to that described in connection with Example 214 except that 2,3-diaminopyridine was used. $^1$H NMR (400 MHz, MeOD) δ 3.04 (s, 3 H) 3.99 (s, 3H) 4.83 (s, 2 H) 6.81 (m, 1 H) 7.30 (s, 1 H) 7.38 (s, 1 H) 7.46 (d, J=2.0 Hz, 1H) 7.53 (m, 1 H) 7.59 (d, J=2.0 Hz, 1 H) 8.26 (m, 1H) 8.49 (m, 1H). [M+H] calc'd for $C_{18}H_{19}N_7O_2S$ 398; found, 398.

Example 217a 3-(2-fluorobenzyloxy)-5-hydroxybenzaldehyde

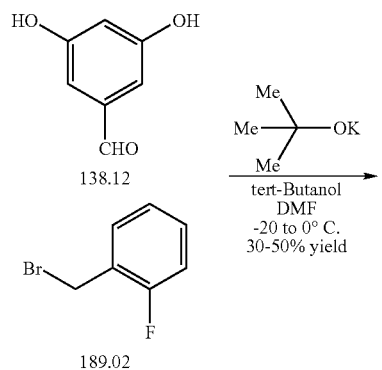

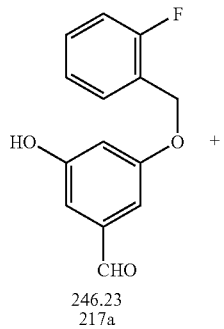

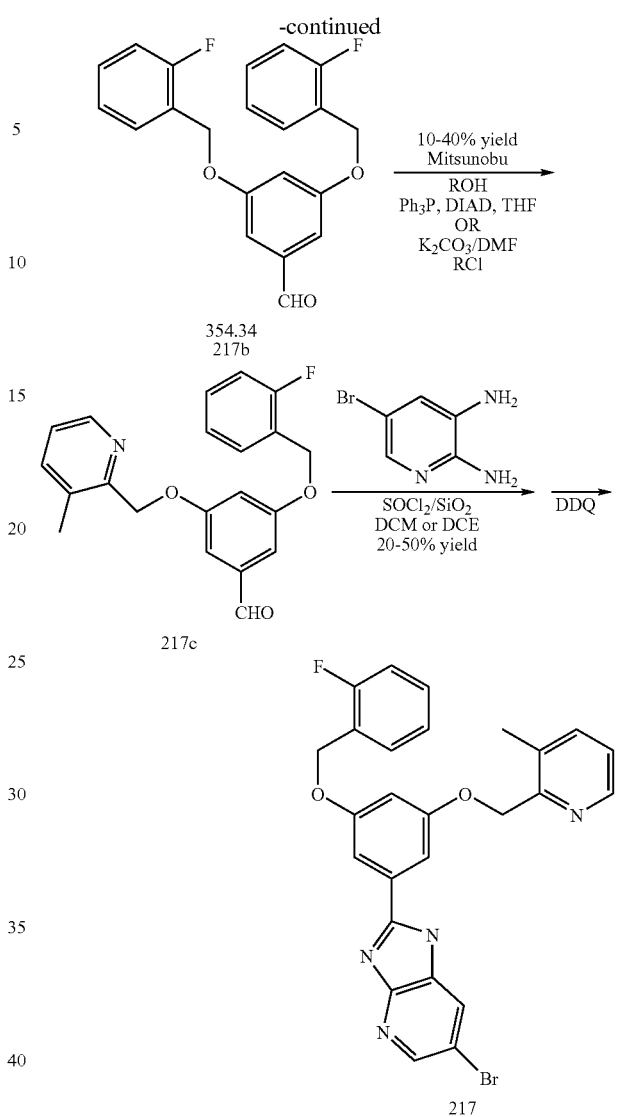

To a clean, dry 1L flask were added 3,5-dihydroxy benzaldehyde (10 g, 70.9 mmole, 1 eq) and anhydrous DMF (70.9 mL). The mixture was cooled to −70° C. in dry ice/acetone bath while stirring under nitrogen gas. A solution of 1 M tert-butoxide in tert-butanol (70.9 mL) was slowly added drop-wise over 30 min. to the solution while the mixture was allowed to warm to −30° C. The mixture was stirred for ten minutes, then 2-fluorobenzylbromide (13.7 g, 70.9 mmole, 1 eq) was added over 10 min at −30° C. The mixture was stirred at −10° C. for one hour prior to warming to room temperature. The mixture was quenched with 200 mL of saturated ammonium chloride solution. This is an exothermic reaction and the mixture warmed to 45° C. The mixture was filtered by suction onto a 150 mL coarse fritted buchner funnel. The filtrate was added to the material on the funnel. The solid is dried and is a tan to off-white solid (13.0 g, 74.4% yield) of a 1:1 mixture of desired mono-adduct (217a) to undesired bis-adduct (217b). Recrystallization of this material from 1-butanol yields clean product (217a) in the filtrate. Alternatively, flash chromatography can be used to obtain pure product. A white solid (5.2 g, 30% overall yield), was obtained of the desired product (217a). $^1$H NMR (400 MHz, CDCl$_3$) δ ppm 10.04 (s, 1H), 9.87 (s, 1H), 7.56 (dt, 1H, J=2, 8 Hz), 7.41 (m, 1H), 7.25

(dq, 2H, J=2,8 Hz), 7.04 (dd, 1H, J=1.1, 2.4 Hz), 6.92 (dd, 1H, J=1.1, 2.4 Hz), 6.72 (t, 1H, J=2.3 Hz), 5.17 (s, 2H); Calc'd for $C_{14}H_{11}FO_3$(M+H$^+$)=247; Found 247.

Example 217c 3-(2-fluorobenzyloxy)-5-((3-methylpyridin-2-yl)methoxy)benzaldehyde To a clean, dry 100 mL flask were added 3-(2-fluorobenzyloxy)-5-hydroxybenzaldehyde (217a, 0.3 g, 1.2 mmole, 1.0 eq), 2-hydroxymethyl-3-methylpyridine (0.18 g, 1.46 mmole, 1.2 eq), triphenylphosphine (0.64 g, 2.4 mmole, 2.0 eq.), DIAD (0.47 mL, 2.4 mmole, 2.0 eq.) and THF (2 mL). The mixture was rapidly stirred at room temperature under nitrogen gas for 18 hrs. The mixture was partitioned between water and ethyl acetate (5 mL each) and extracted into the organic layer. The combined organic layers were dried over magnesium sulfate, filtered and evaporated. The product was taken up in 5% ethyl acetate in hexane and filtered through a small pad of silica gel 60. 64.8 mg of compound 217c were isolated of a yellow to white solid (15% yield); Calc'd for $C_{21}H_{18}FNO_3$(M+H$^+$)=352; Found 352.

Example 217

6-bromo-2-(3-(2-fluorobenzyloxy)-5-((3-methylpyridin-2-yl)methoxy)phenyl)-1H-imidazo[4,5-b]pyridine The final product (217) was obtained using the procedure described for Example 191 except that 3-(2-fluorobenzyloxy)-5-((3-methylpyridin-2-yl)methoxy)benzaldehyde (217c) and 2,3-diamino-5-bromopyridine were used. $^1$H NMR (400 MHz, 90% DMSO-d6; 10% CDCl$_3$) δ ppm 8.46 (br s, 1H), 8.39 (s, 1H), 8.11 (s, 1H), 7.78 (m, 1H), 7.52 (s, 1H), 7.48 (m, 1H), 7.45 (m, 2H), 7.40 (m, 2H), 7.16 (t, 1H, J=8.2 Hz), 7.08 (t, 1H, J=8.2 Hz), 6.79 (s, 1H), 5.32 (s, 2H), 5.19 (s, 2H), 2.31 (s, 3H). Calc'd for $C_{26}H_{20}BrFN_4O_2$; m/z (M+2H$^+$)=521; found 521.

Example 218

6-bromo-2-(3-(2-fluorobenzyloxy)-5-((6-methylpyridin-2-yl)methoxy)phenyl)-1H-imidazo[4,5-b]pyridine

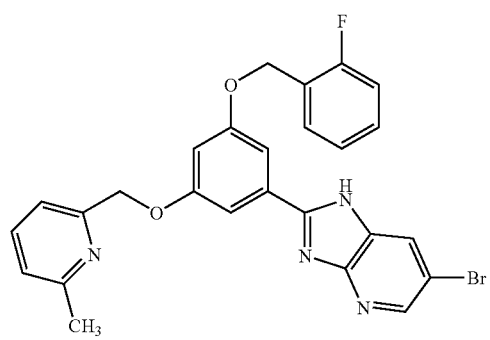

$^1$H NMR (400 MHz, CDCl$_3$) δ ppm 9.90 (s, 1H), 8.36 (s, 1H), 8.12 (d, 1H, J=8.5 Hz), 7.84 (d, 1H, J=8.5 Hz), 7.6 (m, 1H), 7.53 (m, 1H), 7.39 (m, 1H), 7.09 (m, 1H), 7.08 (m, 1H), 7.07 (m, 2H), 6.75 (s, 1H), 5.34 (s, 2H), 5.16 (s, 2H), 4.90 (br s, 1H), 2.57 (s, 3H). Calc'd for $C_{26}H_{20}BrFN_4O_2$; m/z (M+2H$^+$)=521; found 521.

Example 219

2-((3-(6-bromo-1H-imidazo[4,5-b]pyridin-2-yl)-5-(2-fluorobenzyloxy)phenoxy)-methyl)thiazole

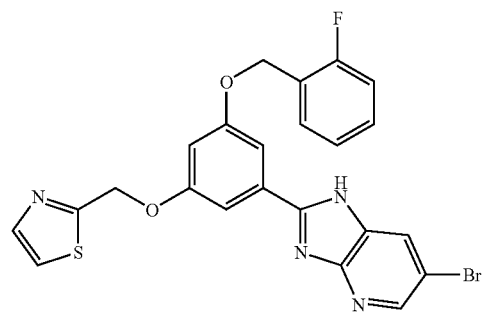

$^1$H NMR (400 MHz, CDCl$_3$) δ ppm 9.94 (s, 1H), 8.47 (s, 1H), 8.22 (s, 1H,), 7.84 (d, 1H, J=8.5 Hz), 7.52 (m, 1H), 7.42 (m, 2H), 7.32 (m, 2H), 7.20 (m, 1H), 7.10 (m, 1H), 6.79 (s, 1H), 5.50 (s, 2H), 5.19 (s, 2H). Calc'd for $C_{23}H_{16}BrFN_4O_2S$; m/z (M+2H$^+$)=513; found 513.

Example 220a 3-(2-fluorobenzyloxy)-5-(thiazol-4-ylmethoxy)benzaldehyde

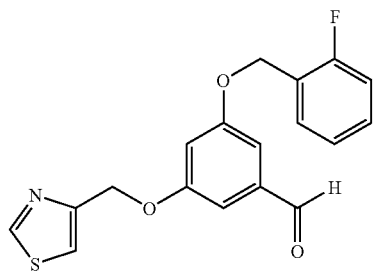

$^1$H NMR (400 MHz, DMSO-d6) δ ppm 9.93 (s, 1H), 9.14 (s, 1H), 8.03 (s, 1H,), 7.58 (dt, 1H, J=1.5, 8.0 Hz), 7.44 (m, 1H), 7.42 (m, 2H), 7.26 (q, 1H, J=8.0 Hz), 7.22-7.20 (m, 3H), 7.07 (t, 1H, J=2.3 Hz), 5.50 (s, 2H), 5.20 (s, 2H); Calc'd for $C_{18}H_{14}FNO_3S$; m/z (M+H$^+$)=344; found 344.

Example 220

4-(3-(6-bromo-1H-imidazo[4,5-b]pyridin-2-yl)-5-(2-fluorobenzyloxy)phenoxy)-methyl)thiazole

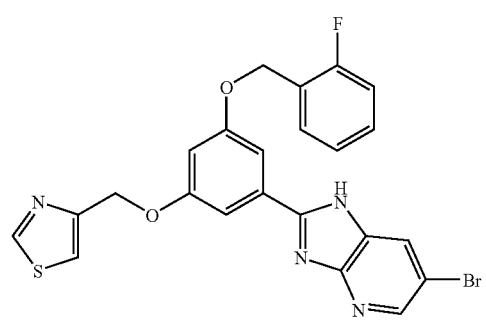

¹H NMR (400 MHz, CDCl₃) δ ppm 9.94 (s, 1H), 8.47 (s, 1H), 8.22 (s, 1H,), 7.84 (d, 1H, J=8.5 Hz), 7.52 (m, 1H), 7.42 (m, 2H), 7.32 (m, 2H), 7.20 (m, 1H), 7.10 (m, 1H), 6.79 (s, 1H), 5.50 (s, 2H), 5.19 (s, 2H); Calc'd for $C_{23}H_{16}BrFN_4O_2S$; m/z (M+2H⁺)=513; found 513.

Example 221

5-((3-(6-bromo-1H-imidazo[4,5-b]pyridin-2-yl)-5-(2-fluorobenzyloxy)phenoxy)-methyl)thiazole

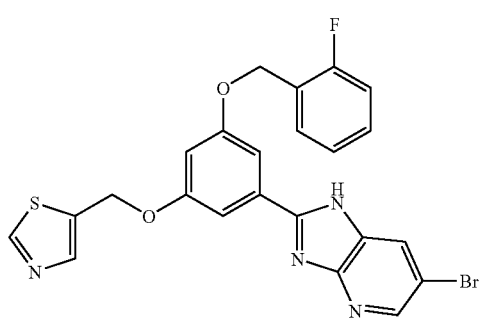

¹H NMR (400 MHz, CD₃OD) δ ppm 8.85 (m, 1H), 8.68 (br s, 1H), 8.58 (m, 1H), 8.15 (s, 1H,), 7.35 (m, 3H), 7.23 (m, 1H), 7.21 (m, 1H), 7.15 (m, 1H), 6.87 (s, 1H), 5.37 (s, 2H), 5.25 (s, 2H), 2.68 (br s, 1H). Calc'd for $C_{23}H_{16}BrFN_4O_2S$; m/z (M+2H⁺)=513; found 513.

Example 222a 3-(2-fluorobenzyloxy)-5-(pyrazin-2-ylmethoxy)benzaldehyde

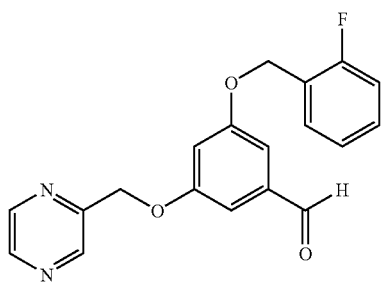

¹H NMR (400 MHz, DMSO-d6) δ ppm 9.93 (s, 1H), 8.84 (d, 1H, J=1.5 Hz), 8.69 (dd, 1H, J=1.5, 2.5 Hz), 8.65 (d, 1H, J=2.5 Hz), 7.60 (dt, 1H, J=1.5, 8.0 Hz), 7.57 (m, 1H), 7.30-7.23 (m, 4H), 7.11 (t, 1H, J=2.3 Hz), 5.36 (s, 2H), 5.23 (s, 2H); Calc'd for $C_{19}H_{15}FN_2O_3$; m/z (M+H⁺)=339; found 339.

Example 222

6-bromo-2-(3-(2-fluorobenzyloxy)-5-(pyrazin-2-ylmethoxy)phenyl)-1H-imidazo[4,5-b]pyridine

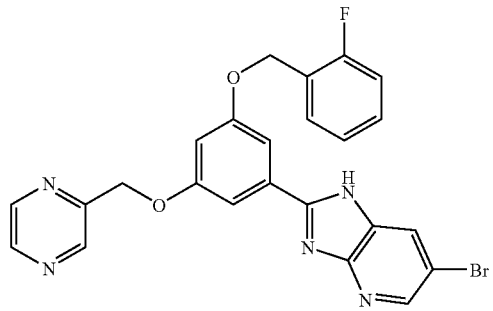

¹H NMR (400 MHz, DMSO-d6) δ ppm 8.85 (m, 1H), 8.68 (br s, 1H), 8.58 (br s, 1H), 8.15 (s, 1H,), 7.35 (m, 5H), 7.23 (m, 1H), 7.21 (m, 1H), 7.15 (m, 1H), 6.87 (m, 1H), 5.37 (s, 2H), 5.25 (s, 2H). Calc'd for $C_{24}H_{17}BrFN_5O_2$; m/z (M+2H⁺)=508; found 508.

Example 223

3-(3-(6-bromo-1H-imidazo[4,5-b]pyridin-2-yl)-5-(2-fluorobenzyloxy)phenoxy)methyl)-5-methylisoxazole

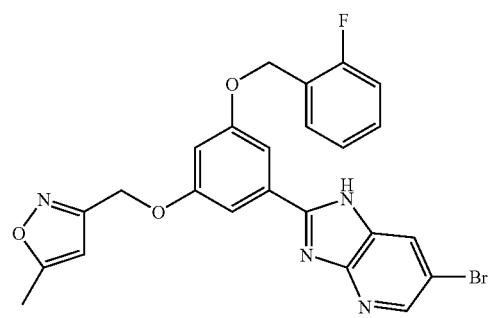

¹H NMR (400 MHz, CDCl₃) δ ppm 8.50 (s, 1H), 8.36 (s, 1H), 7.73 (s, 1H,), 7.54 (s, 1H), 7.48 (m, 1H), 7.32 (m, 1H), 7.27 (s, 1H), 7.15 (m, 1H), 7.02 (m, 1H), 6.68 (br s, 1H), 6.15 (s, 1H), 5.25 (s, 2H), 5.18 (s, 2H), 2.42 (s, 3H). Calc'd for $C_{24}H_{18}BrFN_4O_3$; m/z (M+2H⁺)=511; found 511.

Example 224a

Methyl 3-(2-fluorobenzyloxy)-5-hydroxybenzoate

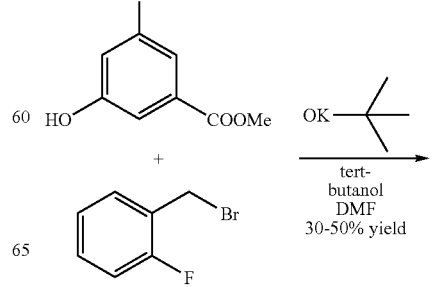

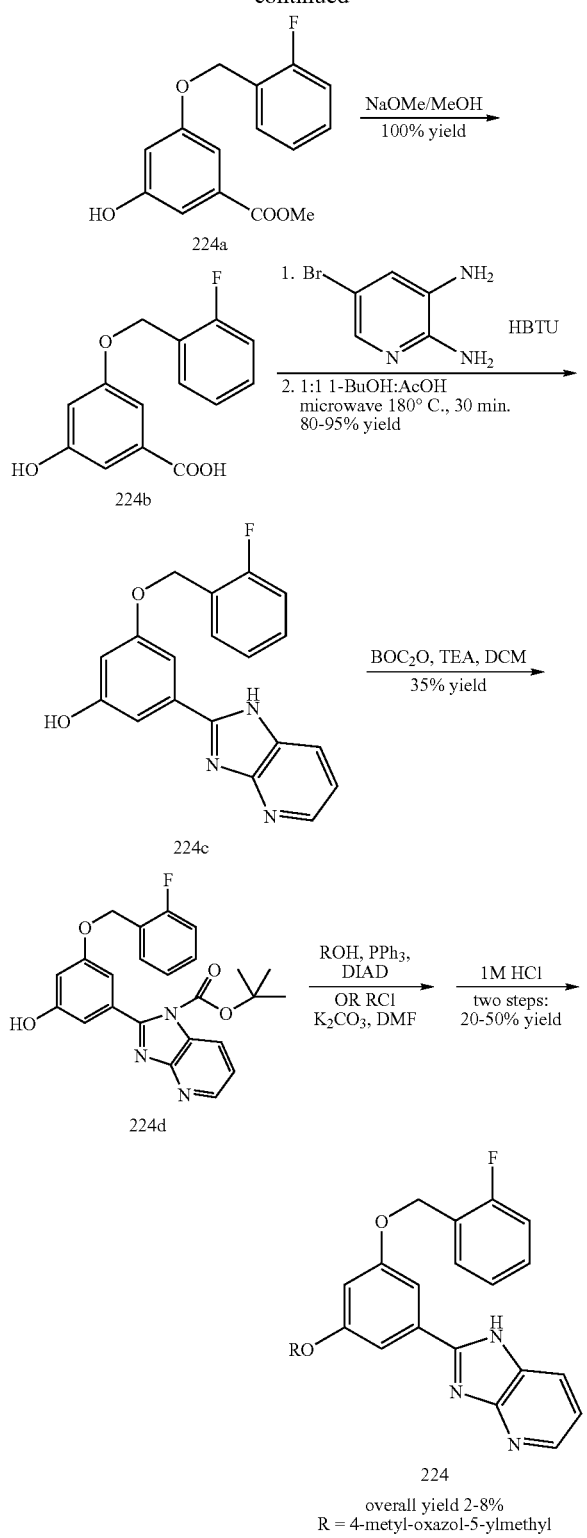

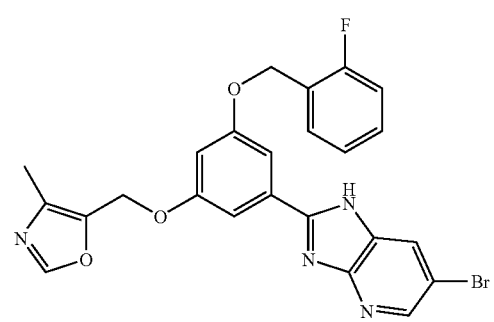

224
overall yield 2-8%
R = 4-metyl-oxazol-5-ylmethyl

The same experimental conditions were used as described previously for the synthesis of 3-(2-fluorobenzyloxy)-5-hydroxybenzaldehyde (217a) except that the reaction began with 3,5-dihydroxy benzoic acid. The LC/MS gave a calculated and found (M+H$^+$)=277.

Example 224b 3-(2-fluorobenzyloxy)-5-hydroxybenzoic acid

Methyl 3-(2-fluorobenzyloxy)-5-hydroxybenzoate (224a), 10 mL of Methyl alcohol and 10 mL of 1N NaOH were stirred at ambient temperature for 4 h, acidified with 1N HCl until neutral and extracted into ethyl acetate. The combined organic extracts were dried over magnesium sulfate, filtered and evaporated. The LC/MS gave a calculated and found (M+H$^+$)=263.

Example 224c 3-(2-fluorobenzyloxy)-5-(1H-imidazo[4,5-b]pyridin-2-yl)phenol

Reaction of 3-(2-fluorobenzyloxy)-5-hydroxybenzoic acid (3.9 g, 15 mmole, 1.0 eq.) with 5-bromo-2,3-diaminopyridine (5.6 g, 30 mmole, 2 eq.), HBTU (11.3 g, 30 mmole, 2 eq.) and TEA (5.2 mL) in DMF (40 mL) over 18 h gave the amide intermediate (LC/MS calculated and found (M+2H$^+$)=434 and 416 final product). This intermediate was isolated by pouring the reaction mixture into 400 g of ice water and filtering the subsequent white solid which formed. After the solid was thoroughly dried to 6.2 g, the material was brought through to the next step. The solid (2 g) was dissolved in 10 mL of ethyl alcohol and 10 mL of glacial acetic acid and put in the microwave at 180° C. for 30 min. This was repeated two more times to bring all 6.2 g through to the final product. This product crashed out of solution and was isolated as a brown solid after cooling the mixture to 0° C. for 10 h. The light tan solid (5.6 g) had an LC/MS with a calculated and found (M+H$^+$)=416.

Example 224d tert-butyl 2-(3-(2-fluorobenzyloxy)-5-hydroxyphenyl)-1H-imidazo[4,5-b]pyridine-1-carboxylate 3-(2-fluorobenzyloxy)-5-(1H-imidazo[4,5-b]pyridin-2-yl)phenol (224c, 1.67 g, 4 mmole, 1 eq) was added to a solution of di-tert-butyl carbonate (boc anhydride) (0.97 g., 4.4 mmole, 1.1 eq), TEA (o.62 mL, 4.4 mmole, 1.1 eq) and dichloromethane (10 mL) and stirred rapidly for 5 h. The resulting product was evaporated and crystallized from ethyl acetate-methanol 1:1 mixture to give 0.28 g tan solid (14% yield). LC/MS with a calculated and found (M+2H$^+$)=516. Examination of LC/MS showed a 1:1:1 mixture of starting material, desired product and bis adduct.

Example 224

5-((3-(6-bromo-1H-imidazo[4,5-b]pyridin-2-yl)-5-(2-fluorobenzyloxy)phenoxy)methyl)-4-methyloxazole This product was made by reaction of tert-butyl 2-(3-(2-fluorobenzyloxy)-5-hydroxyphenyl)-1H-imidazo[4,5-b]pyridine-1-carboxylate (224d) (0.03 g., 0.06 mmole, 1 eq) with 4-methyloxazole-5-methanol (0.067 g, 0.064 mmole, 1.1 eq.), triphenyl phosphine (0.1 g., 0.12 mmole, 2 eq) and DIAD (0.2 mL, 0.12 mmole, 2 eq) in anhydrous tetrahydrofuran (0.05 mL) at ambient temperature. The product was stirred in 4 N HCl in dioxane for 4 h prior to work up including preparative HPLC. $^1$H NMR (400 MHz, CDCl$_3$) δ ppm 9.56 (s, 1H), 7.66 (m, 2H), 7.50 (m, 2H), 7.45 (m, 1H), 7.27 (m, 2H), 7.18 (m, 2H), 6.25 (m, 1H), 5.40 (s, 2H), 5.20 (s, 2H), 3.48 (s, 3H); Calc'd for C$_{24}$H$_{18}$BrFN$_4$O$_3$; m/z (M+H$^+$)=511; found 511.

Example 225

6-bromo-2-(3-(2-fluorobenzyloxy)-5-((1-methyl-1H-imidazol-5-yl)methoxy)phenyl)-1H-imidazo[4,5-b]pyridine

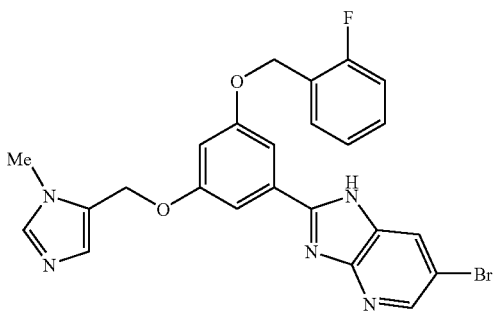

This compound was synthesized as described for 224. The second ether forming reaction was carried out using 5-chloromethyl-N-methyl-(1H)-imidazole synthesized by reaction of thionyl chloride in dichloromethane with the corresponding alcohol. $^1$H NMR (400 MHz, DMSO-d6) δ ppm 8.50 (s, 1H), 8.24 (s, 1H), 7.89 (s, 1H,), 7.64 (s, 1H), 7.55 (m, 4H), 7.45 (m, 1H), 7.29 (m, 1H), 7.18 (m, 1H), 6.89 (m, 1H), 5.40 (s, 2H), 5.29 (s, 2H), 2.29 (s, 3H). Calc'd for C$_{24}$H$_{19}$BrFN$_5$O$_2$; m/z (M+H$^+$)=510; found 510.

Example 226

6-bromo-2-(3-(2-fluorobenzyloxy)-5-((4-methyl-M-imidazol-5-yl)methoxy)phenyl)-1H-imidazo[4,5-b]pyridine

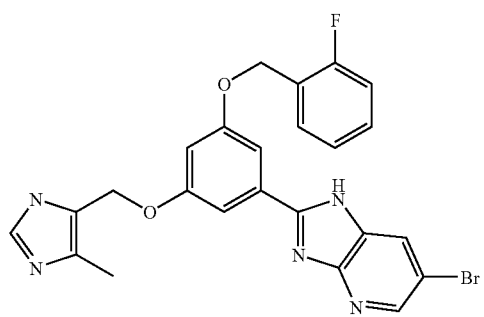

This compound was synthesized as described previously. The Mitsunobu reaction was carried out using boc-protected 4-hydroxymethyl-5-methyl imidazole. The boc protecting group was removed with 4N HCl in dioxane at room temperature in the last step. $^1$H NMR (400 MHz, CDCl$_3$) δ ppm 8.47 (s, 1H), 8.24 (s, 1H), 7.52 (s, 1H,), 7.42 (s, 1H), 7.33 (m, 4H), 7.20 (m, 1H), 7.10 (m, 1H), 6.89 (m, 1H), 5.30 (s, 2H), 5.09 (s, 2H), 2.34 (s, 3H). Calc'd for C$_{24}$H$_{19}$BrFN$_5$O$_2$; m/z (M+H$^+$)=510; found 510.

Example 227

2-(3-(2-(1H-imidazol-1-yl)ethoxy)-5-(2-fluorobenzyloxy)phenyl)-6-bromo-4H-imidazo[4,5-b]pyridine

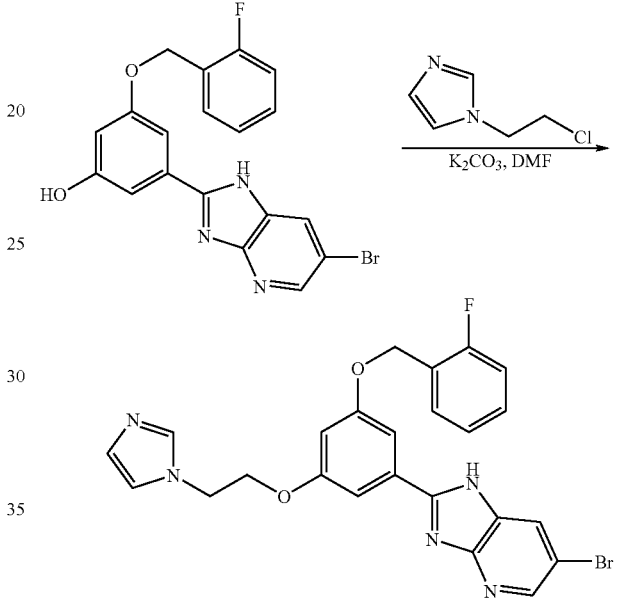

Intermediate (224c) was reacted with N-2-chloroethylimidazole hydrochloride in the presence of potassium carbonate and dimethylformamide to produce 227. $^1$H NMR (400 MHz, DMSO-d6) δ ppm 8.73 (s, 1H), 8.50 (s, 1H), 8.27 (s, 1H), 8.20 (s, 1H,), 7.64 (s, 1H), 7.55 (m, 4H), 7.45 (m, 1H), 7.20 (m, 1H), 7.15 (m, 1H), 6.89 (m, 1H), 5.32 (s, 2H), 3.89 (t, 2H, J=7.0 Hz), 3.57 (t, 2H, J=7.0 Hz); Calc'd for C$_{24}$H$_{19}$BrFN$_5$O$_2$; m/z (M+H$^+$)=510 calc'd; found 510.

Example 228

6-bromo-2-(3-((1-methyl-1H-imidazol-2-yl)methoxy)phenyl)-1H-imidazo[4,5-b]pyridine

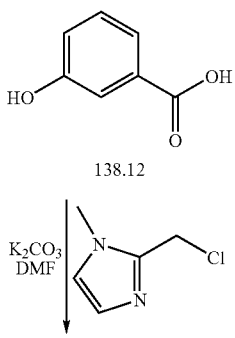

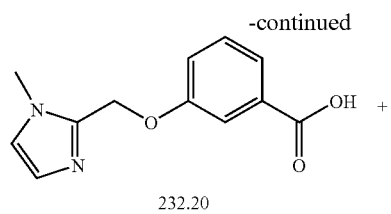

232.20

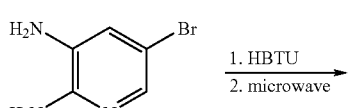

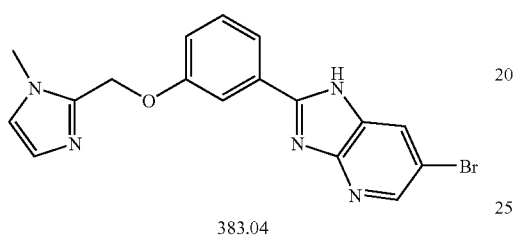

383.04

3-Hydroxybenzoic acid was reacted with N-methyl-2-imidazoylchloride in the presence of potassium carbonate in dimethylformamide to produce the ether adduct as shown. Subsequent reactions as described previously with 5-bromo-2,3-diaminopyridine followed by microwave reaction gave the final product. $^1$H NMR (400 MHz, CDCl$_3$) δ ppm 8.37 (s, 1H), 8.09 (s, 1H), 7.84 (s, 1H), 7.35 (m, 3H), 6.95 (m, 1H), 6.87 (m, 1H), 6.73 (m, 1H), 5.30 (s, 2H), 2.25 (s, 3H); Calc'd for C$_{17}$H$_{14}$BrN$_5$O; m/z (M+2H$^+$)=385; found 385.

Example 229

2-(3-ethoxy-5-(pyridin-3-ylmethoxy)phenyl)-1H-imidazo[4,5-b]pyridine

Reaction of Methyl 3,5-dihydroxybenzoate with ethyl bromide in the presence of potassium carbonate and dimethylformamide for 18 h at room temperature gave a 1:1 mixture of the mono and bis ether adducts. These compounds were separated by chromatography column. The mono adduct was reacted with 3-pyridylmethylbromide in the presence of potassium carbonate and dimethylformamide to give the desired bis ether. The ether was hydrolyzed with sodium hydroxide in methanol, acidified and the subsequent acid was reacted with 2,3-diaminopyridine in HBTU, TEA and DMF. The amide was cyclized to the imidazopyridine by reaction in the microwave at 180° C. for 30 min in 1:1 n-butanol:glacial acetic acid. $^1$H NMR (400 MHz, CDCl$_3$) δ ppm 8.54 (s, 1H), 8.41 (m, 2H), 7.50 (m, 1H), 7.28 (m, 1H), 7.25 (m, 1H), 6.99 (m, 1H), 6.81 (m, 1H), 6.69 (m, 1H), 6.68 (m, 1H), 5.16 (s, 2H), 4.30 (br s, 1H), 4.09 (q, 2H, J=7 Hz), 1.43 (t, 3H, J=7 Hz); Calc'd for C$_{20}$H$_{18}$N$_4$O$_2$; m/z (M+H$^+$)=347; found 347.

Example 230

2-(3-ethoxy-5-(pyridin-4-ylmethoxy)phenyl)-1H-imidazo[4,5-b]pyridine

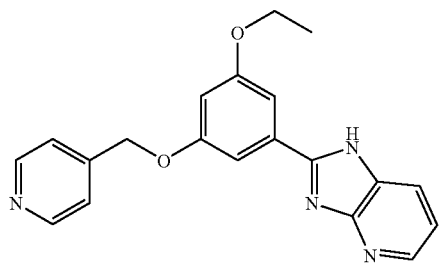

In an analogous reaction to that described in example 229, reaction of methyl 3-ethoxy-5-hydroxybenzoate with 4-pyridylmethyl bromide in the presence of potassium carbonate and dimethylformamide gave the bis ether. Subsequent reactions as described previously gave the title compound. $^1$H NMR (400 MHz, DMSO-d6) δ ppm 8.61 (m, 2H), 8.43 (m,

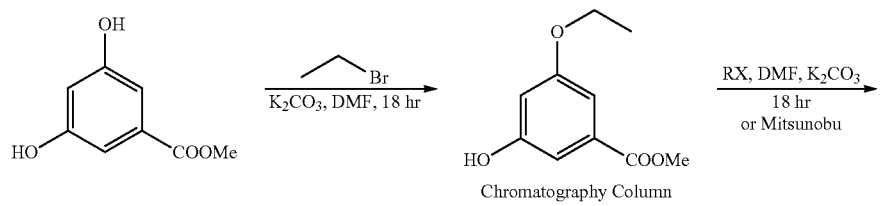

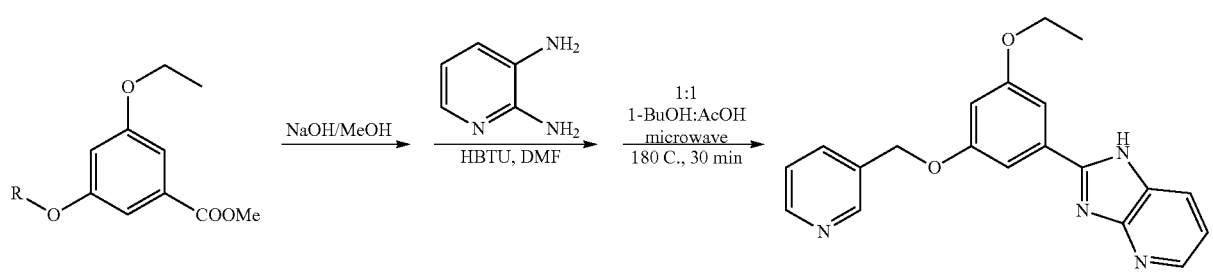

1H), 7.84 (m, 1H), 7.46 (m, 2H), 7.22 (m, 1H), 6.92 (m, 2H), 6.33 (m, 1H), 5.16 (s, 2H), 4.15 (q, 2H, J=7.0 Hz), 1.09 (t, 3H, J=7.0 Hz); Calc'd for $C_{20}H_{18}N_4O_2$; m/z (M+H$^+$)=347; found 347.

Example 231

2-(3-ethoxy-5-(pyridin-4-yl)phenyl)-1H-imidazo[4,5-b]pyridine

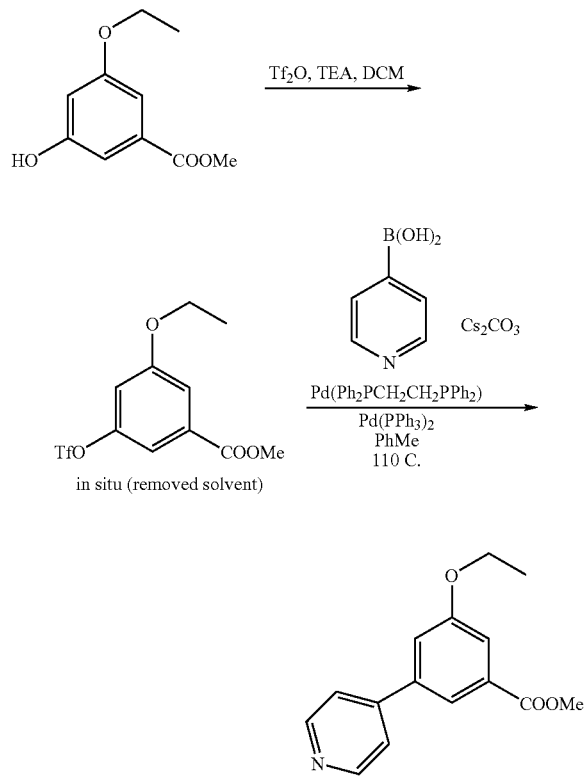

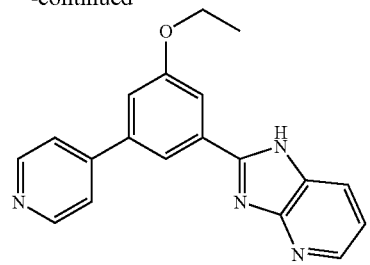

$^1$H NMR (400 MHz, DMSO-d6) δ ppm 8.74 (m, 2H), 8.40 (m, 1H), 8.28 (m, 1H), 8.07 (d, 1H, J=8 Hz), 7.96 (m, 2H), 7.93 (m, 1H), 7.53 (br s, 1H), 7.33 (dd, 1H, J=4.8, 8.0 Hz), 4.26 (q, 2H, J=7.0 Hz), 1.47 (t, 3H, J=7.0 Hz); Calc'd for $C_{19}H_{16}N_4O$; m/z (M+H$^+$)=317; found 317.

Example 232

2-(3-ethoxy-5-(4-(methylsulfonyl)benzyloxy)phenyl)-1H-imidazo[4,5-b]pyridine

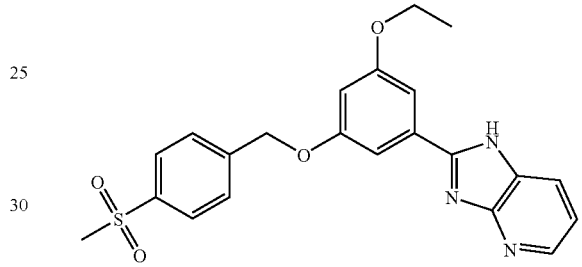

Reaction of methyl 3-ethoxy-5-hydroxybenzoate with 4-methylsulphonylbenzylbromide in the presence of potassium carbonate and dimethylformamide gave the bis ether. Subsequent reactions as described previously gave the title compound. $^1$H NMR (400 MHz, CDCl$_3$) δ ppm 8.40 (br s, 1H), 8.16 (m, 1H), 7.89 (m, 2H), 7.59 (m, 2H), 7.47 (s, 1H), 7.37 (s, 1H), 7.27 (m, 1H), 6.60 (s, 1H), 5.18 (s, 2H), 4.03 (q, 2H, J=7.0 Hz), 3.20 (br s, 1H), 3.00 (s, 3H), 1.36 (t, 3H, J=7.0 Hz); Calc'd for $C_{22}H_{21}N_3O_4S$; m/z (M+H$^+$)=424; found 424.

Example 233a methyl 3-(2-tert-butoxy-2-oxoethoxy)-5-(2-fluorobenzyloxy)benzoate

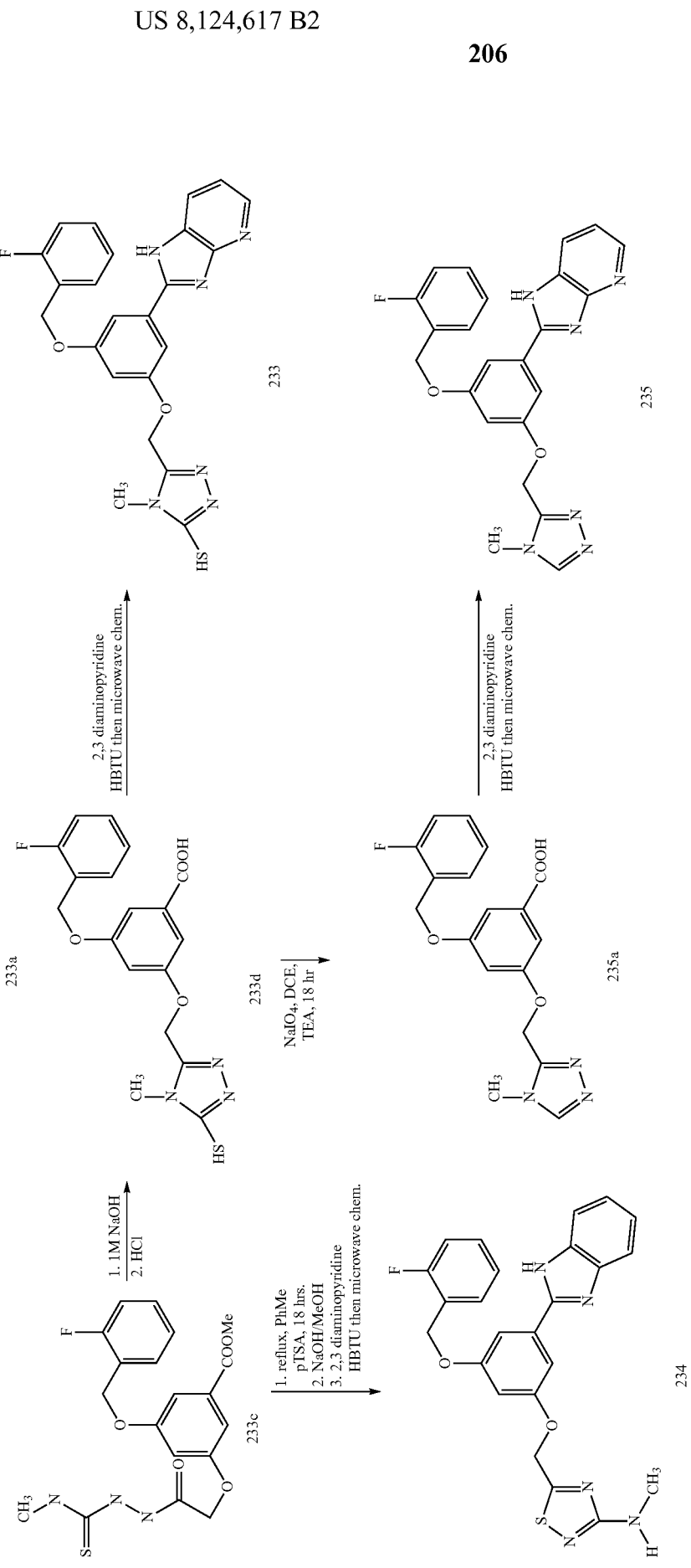

Methyl 3-(2-fluorobenzyloxy)-5-hydroxybenzoate (1.9 g, 1.0 eq., 6.9 mmole) was reacted with tert-butyl bromoacetate (1.6 g, 1.2 eq., 8.3 mmole) in the presence of potassium carbonate (2.4 g., 2.5 eq., 17.3 mmole) in dimethylformamide (5 mL) over 18 h. The product was partitioned between ethyl acetate and aqueous media. The combined organic extracts were dried over magnesium sulfate, filtered and evaporated to give 2.4 g (89% yield) of a yellow oil. The LC/MS was as expected with an (M+H$^+$) of 391 calculated and found.

Example 233b 2-(3-(2-fluorobenzyloxy)-5-(methoxycarbonyl)phenoxy)acetic acid 2-(3-(2-fluorobenzyloxy)-5-(methoxycarbonyl)phenoxy) acetic acid (233a, 2.4 g., 6.2 mmole, 1 eq) and 20 mL of 40% TFA in dichloromethane were stirred for 18 h at ambient temperature. Neutralization with sodium bicarbonate followed by extraction into ethyl acetate, drying over magnesium sulfate, filtering and evaporation provided a white solid with LC/MS calculated and found=335 (>99% pure).

Example 233c

Methyl 3-(2-fluorobenzyloxy)-5-hydroxybenzoate with N-methyl-2-propionylhydrazinecarbothioamide (1:1)

2-(3-(2-fluorobenzyloxy)-5-(methoxycarbonyl)phenoxy) acetic acid (233b, 3.1 g., 9.5 mmole, 1 eq), 4-methyl-3-thiosemicarbazide (1.2 g., 11.4 mmole, 1.2 eq), EDC (2.9 g., 19 mmole, 2 eq) in DMF (10 mL) were combined and stirred at ambient temperature for 18 h. The mixture was added to ice water and was extracted with ethyl acetate. The combined organic layers were dried over magnesium sulfate, filtered through celite and silica gel and evaporated. This compound was recrystallized from dichloroethane to give 1.5 g (37% yield) of a tan solid. $^1$H NMR (400 MHz, MeOD-d$_3$) δ ppm 7.48 (dt, 1H, J=1.7, 8.0 Hz), 7.37 (dd, 1H, J=1.1, 2.4 Hz), 7.33 (m, 1H), 7.31 (dd, 1H, J=1.3, 2.3 Hz), 7.18 (dd, 1H, J=1.3, 2.3 Hz), 7.16 (br s, 1H), 7.11 (dd, 1H, J=1.3, 2.3 Hz), 7.09 (br s, 1H), 7.07 (dd, 1H, J=1.8, 3.5 Hz), 5.15 (s, 2H), 5.12 (s, 2H), 3.73 (s, 3H); Calc'd for C$_{17}$H$_{16}$FN$_3$O$_4$S; m/z (M+H$^+$)=422; found 422.

Example 233d 3-(2-fluorobenzyloxy)-5-(5-mercapto-4-methyl-4H-1,2,4-triazol-3-yl)methoxy)benzoic acid Methyl 3-(2-fluorobenzyloxy)-5-hydroxybenzoate with N-methyl-2-propionylhydrazinecarbothioamide (233c, 1.0 g., 2.3 mmole, 1 eq) and 10 mL of 1M NaOH were heated to reflux and stirred for 3 h. After cooling to ambient temperature, 1M HCl was added to neutralize. The product was extracted into ethyl acetate, dried over magnesium sulfate, filtered and evaporated to a white solid (0.3 g, 33% yield) with LC/MS calculated and found=390.

Example 233

5-(3-(2-fluorobenzyloxy)-5-(1H-imidazo[4,5-b]pyridin-2-yl)phenoxy)methyl)-4-methyl-4H-1,2,4-triazole-3-thiol 3-(2-fluorobenzyloxy)-5-(5-mercapto-4-methyl-4H-1,2,4-triazol-3-yl)methoxy)benzoic acid (233d, 0.03 g., 0.08 mmole, 1 eq.), 2,3 diaminopyridine (0.017 g., 0.16 mmole, 2 eq), HBTU (0.06 g., 0.16 mmole, 2 eq.), TEA (0.02 mL, 2 eq), and DMF (4 mL) were stirred at room temperature for 18 h as described previously. Addition to 50 g of ice water followed by extraction into ethyl acetate and subsequent work up led to a brown oil which was dissolved in 0.8 mL each of 1-butanol and glacial acetic acid. This solution was subject to microwave at 180° C. for 30 min and then isolated after work up by preparative HPLC. $^1$H NMR (400 MHz, DMSO-d$_6$) δ ppm 8.54 (br s, 2H), 8.44 (m, 1H), 8.11 (m, 1H), 8.00 (m, 1H), 7.5-7.3 (m, 3H), 7.28 (m, 1H), 7.24 (m, 1H), 7.14 (m, 1H), 7.01 (s, 1H), 5.31 (s, 2H), 5.29 (s, 2H), 3.70 (s, 3H); Calc'd for C$_{23}$H$_{19}$FN$_6$O$_2$S; m/z (M+H$^+$)=463; found 463.

Example 235a 3-(2-fluorobenzyloxy)-5-(4-methyl-4H-1,2,4-triazol-3-yl)methoxy)benzoic acid 3-(2-fluorobenzyloxy)-5-((mercapto-4-methyl-4H-1,2,4-triazol-3-yl)methoxy)benzoic acid (233d) (0.2 g., 0.5 mmole, 1 eq.), sodium periodate (0.4 g., 1.77 mmole, 3.6 eq) and TEA (0.2 mL) in dichloroethane (2 mL) were combined and stirred at room temperature for 18 h. LC/MS calculated and found=358. The mixture was neutralized by addition of 1M HCl and extracted into ethyl acetate. The combined organic layers were dried over magnesium sulfate, filtered and evaporated to give a quantitative amount of white solid.

Example 233

5-((3-(2-fluorobenzyloxy)-5-(1H-imidazo[4,5-b]pyridin-2-yl)phenoxy)methyl)-4-methyl-4H-1,2,4-triazole-3-thiol

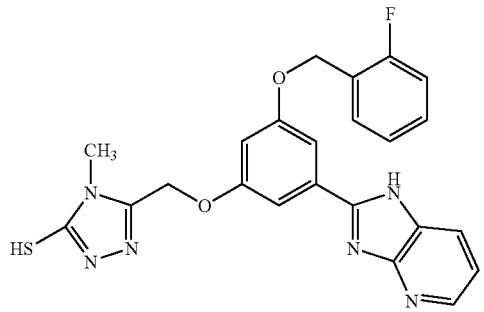

$^1$H NMR (400 MHz, DMSO-d$_6$) δ ppm 8.54 (br s, 2H), 8.44 (m, 1H), 8.11 (m, 1H), 8.00 (m, 1H), 7.5-7.3 (m, 3H), 7.28 (m, 1H), 7.24 (m, 1H), 7.14 (m, 1H), 7.01 (s, 1H), 5.31 (s, 2H), 5.29 (s, 2H), 3.70 (s, 3H); Calc'd for $C_{23}H_{19}FN_6O_2S$; m/z (M+H$^+$)=463; found 463.

Example 234

5-(3-(2-fluorobenzyloxy)-5-(1H-imidazo[4,5-b]pyridin-2-yl)phenoxy)methyl)-N-methyl-1,2,4-thiadiazol-3-amine

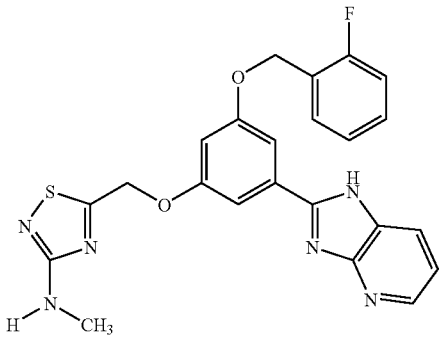

Methyl 3-(2-fluorobenzyloxy)-5-hydroxybenzoate with N-methyl-2-propionylhydrazinecarbothioamide (233c, 0.84 g, 2 mmole, 1 eq), para-toluene sulfonic acid (0.31 g., 2 mmole, 1 eq) and toluene (3 mL) were combined and stirred at reflux for 18 h. 1M NaOH was added to neutralize pH. The product was partitioned between aqueous and ethyl acetate organic layer. The combined organic layers were dried over magnesium sulfate, filtered and evaporated. The white solid product (0.06 g) was isolated by preparative HPLC. LC/MS calculated and found=404. The methyl ester was hydrolyzed to the acid using the procedure described previously. The acid was subsequently reacted with 2,3-diaminopyridine to form the amide which was cyclized to the imidazopyridine in the microwave with conditions described previously. $^1$H NMR (400 MHz, CDCl$_3$) δ ppm 8.49 (m, 1H), 8.29 (s, 1H), 7.89 (m, 2H), 7.59 (m, 2H), 7.5-7.2 (m, 5H), 7.06 (m, 3H), 6.99 (m, 1H), 6.71 (m, 1H), 5.45 (s, 2H), 5.24 (s, 2H), 2.92 (s, 3H); Calc'd for $C_{23}H_{19}FN_6O_2S$; m/z (M+H$^+$)=463; found 463.

Example 235

2-(3-(2-fluorobenzyloxy)-5-(4-methyl-4H-1,2,4-triazol-3-yl)methoxy)phenyl)-1H-imidazo[4,5-b]pyridine

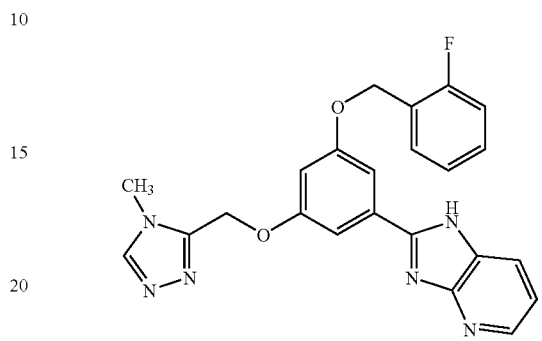

3-(2-fluorobenzyloxy)-5-((4-methyl-4H-1,2,4-triazol-3-yl)methoxy)benzoic acid (235a) (0.18 g., 0.5 mmole, 1 eq) was converted to the imidazopyridine in the procedure described previously reacting for 18 h with 2,3-diaminopyridine (0.11 g. 1 mmole, 2 eq), HBTU (0.4 g, 1 mmole, 2 eq) and TEA (0.14 mL, 1 mmole, 2 eq) in DMF to form the amide and cyclization at 180° C. for 30 min in the microwave after dissolving in 0.8 mL each of 1-BuOH and glacial acetic acid. The final product was isolated by preparative HPLC. $^1$H NMR (400 MHz, DMSO-d$_6$) δ ppm 8.54 (br s, 1H), 8.44 (m, 1H), 8.29 (s, 1H), 7.88 (m, 1H), 7.5-7.3 (m, 4H), 7.06 (m, 2H), 7.01 (s, 1H), 5.31 (s, 2H), 5.20 (s, 2H), 3.70 (s, 3H); Calc'd for $C_{23}H_{19}FN_6O_2$; m/z (M+H$^+$)=431; found 431.

Example 236a

Methyl 3-hydroxy-5-phenoxybenzoate

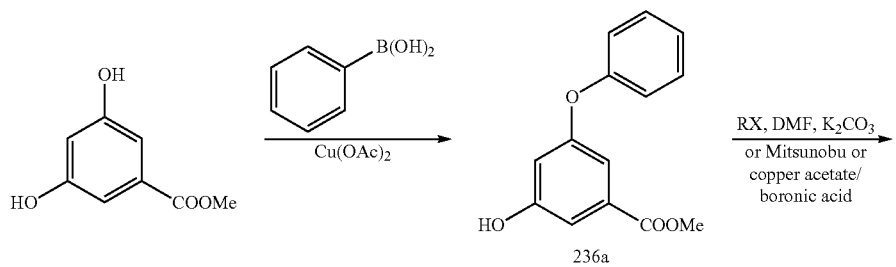

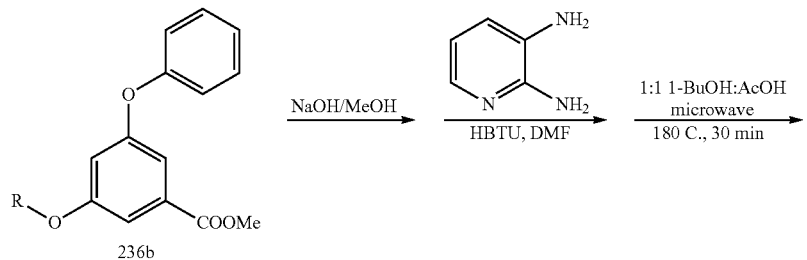

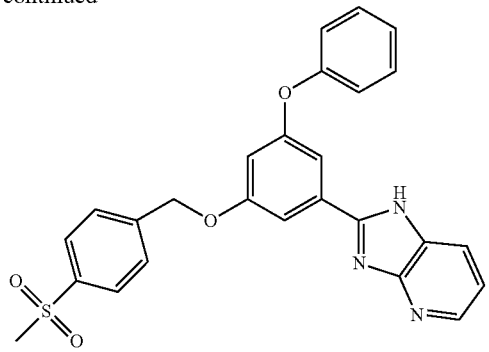

236

Methyl 3,5-dihydroxybenzoate (20 g., 0.12 mole, 1 eq), phenylboronic acid (30 g., 0.25 mole, 2.1 eq.), Copper II acetate (45 g., 0.25 mmole, 2.1 eq.), TEA (90 mL, 0.65 mmole, 5.4 eq.) in dichloromethane (200 mL) and 4 Angstrom molecular sieves (35 g) were stirred at ambient temperature for 24 h under nitrogen gas. The reaction mixture was filtered through silica gel 60 to remove copper acetate to give 8.8 g (30% yield) of crude product. Flash chromatography gave product at 40% ethyl acetate in an ethyl acetate/hexane system. The product is an off-white solid (2.0 g, 7% yield). $^1$H NMR (400 MHz, chloroform-d$_3$) δ ppm 9.64 (s, 1H), 7.43 (m, 2H), 7.28 (s, 1H), 7.31 (s, 1H), 7.11-7.06 (m, 3H), 6.81 (s, 1H), 3.79s (s, 3H); Calc'd for C$_{14}$H$_{12}$O$_4$; m/z (M+H$^+$)=245; found 245.

Example 236b

Methyl 3-(4-methyldsulfonyl)benzyloxy-5-phenoxybenzoate

Methyl 3-hydroxy-5-phenoxybenzoate (236a, 0.32 g., 1.31 mmole, 1 eq.), 4-methylsulfonylbenzyl bromide (0.65 g, 2.6 mmole, 2 eq.), potassium carbonate (1.1 g., 7.8 mmole, 6 eq) and DMF (5 mL) were stirred for 18 h at ambient temperature. The reaction mixture was quenched with water, extracted with ethyl acetate and the combined organic layers were dried over magnesium sulfate, filtered and evaporated. Calc'd for C$_{20}$H$_{12}$O$_6$S; m/z (M+H$^+$)=413; found 413.

Example 236

2-(3-(4-(methylsulfonyl)benzyloxy)-5-phenoxyphenyl)-1H-imidazo[4,5-b]pyridine

Hydrolysis of Methyl 3-(4-methyldsulfonyl)benzyloxy-5-phenoxybenzoate (236b) to the acid followed by imidazopyridine formation with 2,3-diaminopyridine and microwave was conducted using the same procedure described previously. $^1$H NMR (400 MHz, DMSO-d$_6$) δ ppm 8.45 (s, 1H), 8.00 (m, 1H), 7.80 (m, 1H), 7.64 (m, 2H), 7.55 (dd, 1H, J=3.0, 7.0 Hz), 7.21 (m, 2H), 7.12 (m, 2H), 7.07 (m, 2H), 7.01 (m, 2H), 6.96 (s, 1H), 6.86 (s, 1H), 5.16 (s, 2H), 3.27 (s, 3H); Calc'd for C$_{26}$H$_{21}$N$_3$O$_4$S; m/z (M+H$^+$)=472; found 472.

Example 237

2-(3-(4-(methylsulfonyl)phenoxy)-5-phenoxyphenyl)-1H-imidazo[4,5-b]pyridine

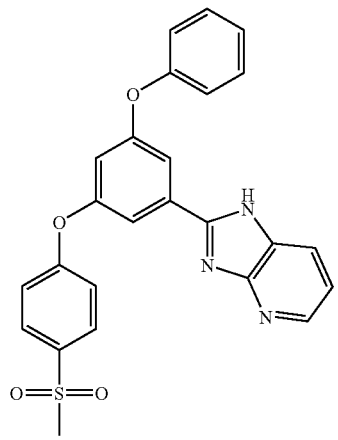

The key coupling step for this compound was carried out as described in the formation of methyl 3-hydroxy-5-phenoxybenzoate (236a) above using the phenylboronic acid and 4-methylsulfonyphenylboronic acid. The remaining steps are the same as described for example 236. $^1$H NMR (400 MHz, DMSO-d$_6$) δ ppm 8.46 (s, 1H), 7.80 (m, 1H), 7.64 (m, 3H), 7.55 (dd, 1H, J=3.0, 7.0 Hz), 7.21 (m, 2H), 7.12 (m, 2H), 7.07 (m, 2H), 7.01 (m, 2H), 6.96 (s, 1H), 6.86 (s, 1H), 3.27 (s, 3H); Calc'd for C$_{25}$H$_{19}$N$_3$O$_4$S; m/z (M+H$^+$)=458; found 458.

Example 238

2-(4'-(methylsulfonyl)-5-phenoxybiphenyl-3-yl)-1H-imidazo[4,5-b]pyridine

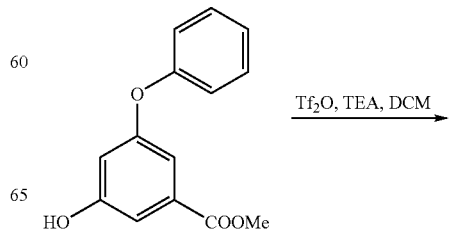

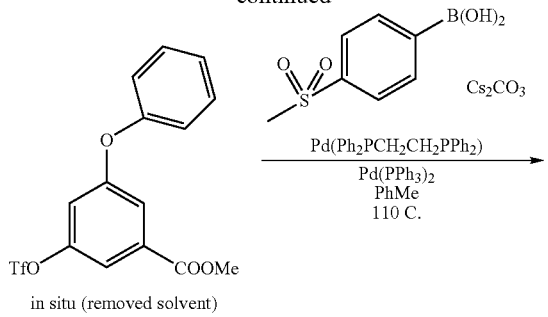

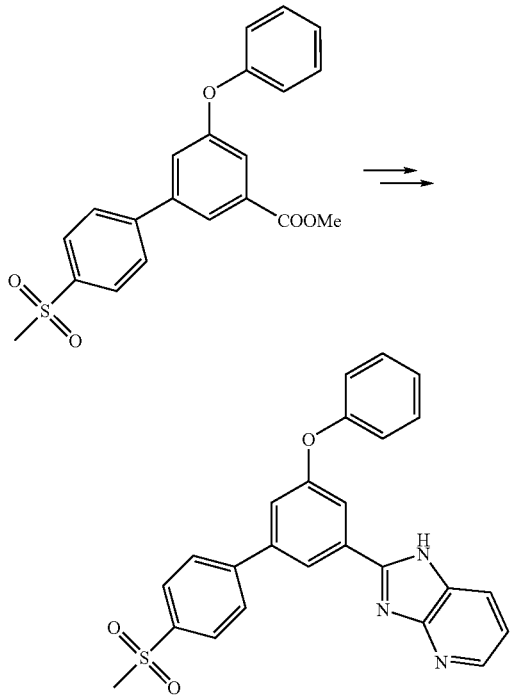

¹H NMR (400 MHz, DMSO-d₆) δ ppm 8.45 (s, 1H), 8.00 (m, 2H), 7.80 (m, 3H), 7.64 (m, 3H), 7.47 (m, 3H), 7.07 (m, 2H), 7.01 (m, 2H), 3.27 (s, 3H); Calc'd for $C_{25}H_{19}N_3O_3S$; m/z (M+H⁺)=442; found 442.

Example 239

2-(3-phenoxy-5-(pyridin-4-ylmethoxy)phenyl)-1H-imidazo[4,5-b]pyridine

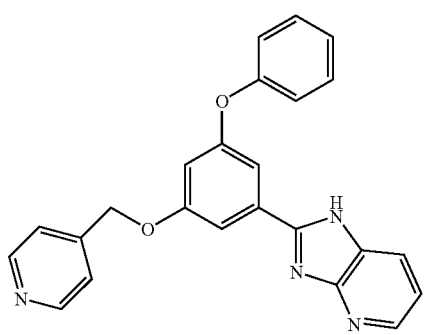

The chemistry is the same as described for example 236 except that 4-pyridylmethyl bromide was used. ¹H NMR (400 MHz, DMSO-d₆) δ ppm 8.61 (m, 2H), 8.43 (m, 1H), 8.29 (s, 1H), 7.89 (m, 2H), 7.59 (m, 2H), 7.5-7.2 (m, 3H), 7.06 (m, 1H), 6.99 (m, 1H), 6.71 (m, 1H), 5.24 (s, 2H); Calc'd for $C_{19}H^{16}N_4O$; m/z (M+H⁺)=395; found 395.

Example 240a

Methyl 3-hydroxy-5-nitrobenzoate

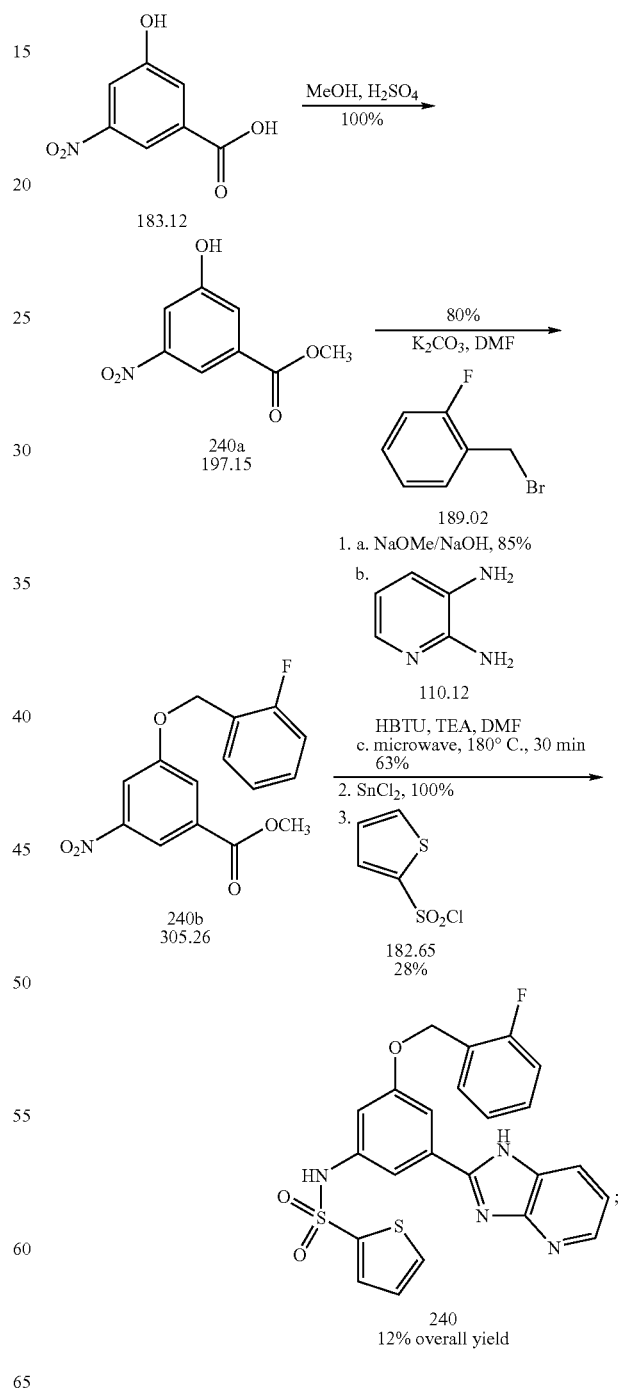

To a clean, dry 100 mL round bottom flask is added 3-hydroxy-5-nitrobenzoic acid (1 g, 5.5 mmole, 1 eq) followed by 10 mL methanol and 2 mL of concentrated sulfuric acid. The exothermic reaction mixture reached 60° C. prior to cooling to room temperature. The reaction mixture was stirred for 18 h prior to partitioning between ethyl acetate and water. After extraction, the organic layer was dried over magnesium sulfate, filtered and evaporated. A white solid product was obtained (1 g, 100%). Calc'd for $C_8H_7NO_5$; m/z (M+H$^+$)=198; found 198.

Example 240b

Methyl 3-(2-fluorobenzyloxy)-5-nitrobenzoate

To a clean, dry 100 mL round bottom flask is added methyl 3-hydroxy-5-nitrobenzoate (240a, 0.4 g, 2 mmole, 1 eq), orthofluorobenzyl bromide (0.57 g, 3 mmole, 1.5 eq), potassium carbonate (0.56 g, 4 mmole, 2 eq), and DMF (3 mL). The reaction mixture was stirred at room temperature for 18 h and quenched with water and ethyl acetate. The product was extracted into the organic layer, dried over magnesium sulfate, filtered and evaporated. A white solid was obtained (0.49 g, 80% yield). 1H NMR (400 MHz, DMSO-d6) δ ppm 8.41 (s, 1H), 8.09 (s, 1H), 8.00 (s, 1H), 7.59 (dt, 1H, J=1.8, 8.0 Hz), 7.42 (m, 1H), 7.24 (dt, 1H, J=1.0, 8.0 Hz), 7.22 (dt, 1H, J=1.3, 8.0 Hz), 5.33 (s, 2H), 3.98 (s, 3H). Calc'd for $C_{15}H_{12}FNO_5$; m/z (M+H$^+$)=306; found 306.

3-(2-fluorobenzyloxy)-5-nitrobenzoic acid: To a clean, dry 100 mL round bottom flask is added methyl 3-(2-fluorobenzyloxy)-5-nitrobenzoate (0.49 g, 1.6 mmole, 1 eq), methanol (5 mL) and 1M sodium hydroxide in water (20 mL). The reaction mixture was stirred at room temperature for 18 h and then quenched with 1M HCl and ethyl acetate. The product was extracted into the organic layer, dried over magnesium sulfate, filtered and evaporated. A white solid was obtained (0.4 g, 85% yield). Calc'd for $C_{14}H_{10}NFO_5$; m/z (M+H$^+$)=292; found 292.

Example 240

N-(3-(2-fluorobenzyloxy)-5-(1H-imidazo[4,5-b]pyridin-2-yl)phenyl)thiophene-2-sulfonamide

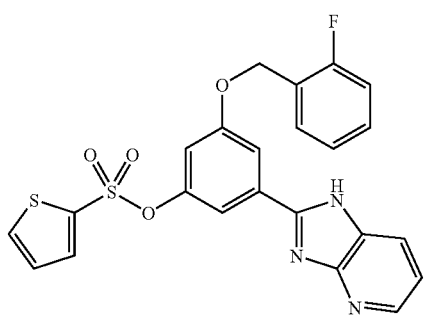

The subsequent steps have been described previously and include formation of the amide (LC/MS calculated and found 383) from the 3-(2-fluorobenzyloxy)-5-nitrobenzoic acid and 2,3-diaminopyridine with HBTU, TEA, and DMF followed by cyclization to the imidazopyridine (LC/MS calculated and found 365) in the microwave at 180° C. in 1:1 BuOH-glacial acetic acid for 30 min. Finally, the nitro group was reduced to the amine using tin (II) chloride in refluxing ethyl alcohol (LC/MS calculated and found 335) and the resulting amine was reacted with 2-thiophene sulfonyl chloride to form the sulfonamide final product (LC/MS calculated and found 481). $^1$H NMR (400 MHz, DMSO-d$_6$) δ ppm 8.45 (m, 1H), 7.84 (m, 1H), 7.70 (m, 2H), 7.59 (m, 3H), 7.5-7.2 (m, 5H), 7.06 (m, 1H), 6.99 (m, 1H), 6.71 (m, 1H), 5.16 (s, 2H); Calc'd for $C_{23}H_{17}FN_4O_3S_2$; m/z (M+H$^+$)=481; found 481.

Example 241

N-(3-(1H-imidazo[4,5-b]pyridin-2-yl)-5-(4-methylbenzyloxy)phenyl)thiophene-2-sulfonamide

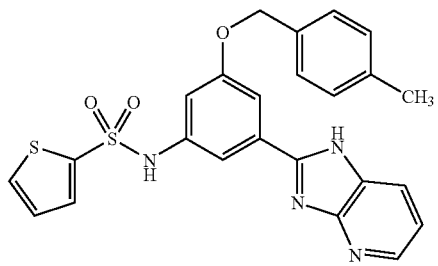

The experimental as described for example 177 was followed except that 4-toluenylbenzyl bromide was used to make the ether by reaction with methyl 3-hydroxy-5-nitrobenzoate (240a). $^1$H NMR (400 MHz, DMSO-d$_6$) δ ppm 8.43 (m, 1H), 7.89 (m, 2H), 7.59 (m, 2H), 7.5-7.2 (m, 4H), 7.06-7.2 (m, 4H), 6.99 (m, 1H), 6.71 (m, 1H), 5.16 (s, 2H), 2.35 (s, 3H); Calc'd for $C_{24}H_{20}N_4O_4S_2$; m/z (M+H$^+$)=477; found 477.

Example 242a

Methyl 3-(thiophene-2-sulfonamido)benzoate

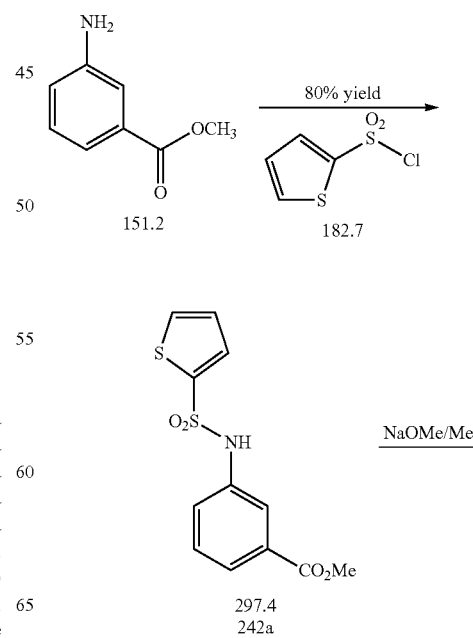

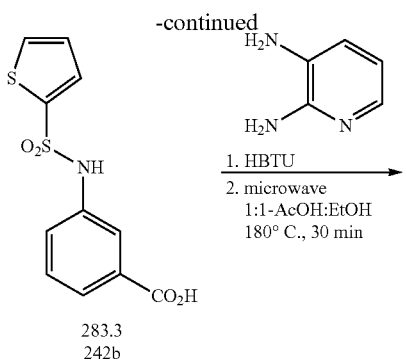

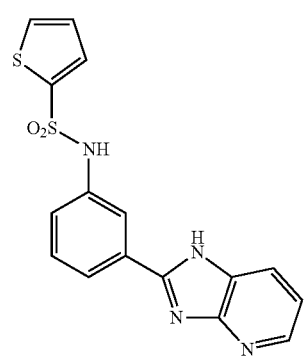

242

2-Thiophenylthionyl chloride was added to methyl 3-aminobenzoate in pyridine and stirred for 18 h. The product was partitioned between ethyl acetate and water and the combined organic extracts were dried over magnesium sulfate, filtered and evaporated to give an 80% yield of (242a) with calculated and found LC/MS of 298.

Example 242b 3-(thiophene-2-sulfonamido)benzoic acid

Methyl 3-(thiophene-2-sulfonamido)benzoate (242a) was hydrolyzed to the acid in an analogous matter to that described in for the formation of 3-(2-fluorobenzyloxy)-5-nitrobenzoic acid.

Example 242

N-(3-(1H-imidazo[4,5-b]pyridin-2-yl)phenyl)thiophene-2-sulfonamide 3-(thiophene-2-sulfonamido)benzoic acid (242b) was reacted with 2,3-diaminopyridine, HBTU and TEA in DMF followed by microwave as described previously for example 235. $^1$H NMR (400 MHz, DMSO-$d_6$) δ ppm 10.74 (s, 1H), 8.45 (d, 1H, J=4.6 Hz), 8.20 (d, 1H, J=7.3 Hz), 8.11 (m, 1H), 7.92 (m, 2H), 7.61 (dd, 1H, J=1.4, 3.7 Hz), 7.52 (t, 2H, J=8.0 Hz), 7.40 (dd, 1H, J=5.0, 7.8 Hz), 7.33 (dd, 1H, J=1.3, 8.0 Hz), 7.12 (dd, 1H, J=3.8, 5.0 Hz); Calc'd for $C_{16}H_{12}N_4O_2S_2$; (M+H)=357; found 357.

Example 243

2-(5-(benzyloxy)-2-methoxyphenyl)-6-bromo-3H-imidazo[4,5-b]pyridine

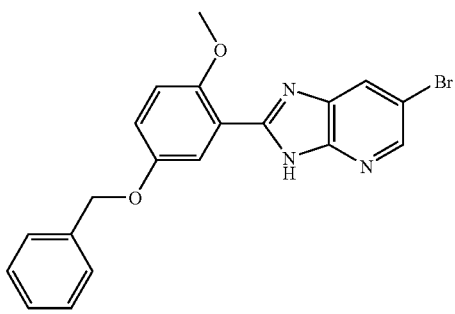

The title compound was synthesized using an analogous procedure described for Example 1 using methyl 5-(benzyloxy)-2-methoxybenzoate. $^1$H NMR (400 MHz, chloroform-d) δ ppm 4.05 (s, 3 H) 5.16 (s, 2 H) 7.03 (t, J=11.29 Hz, 1 H) 7.14 (dd, J=4.12, 10.91 Hz, 1 H) 7.38 (d, J=6.32 Hz, 1 H) 7.42 (t, J=8.32 Hz, 2 H) 7.46 (d, J=6.72 Hz, 2 H) 8.20 (d, J=11.32 Hz, 2 H) 8.42 (s, 1 H). MS (ES) [M+H] calculated for $C_{20}H_{17}BrN_3O_2$, 410.04; found 410.06.

Example 244

6-bromo-2-(2-(pyridin-3-yloxy)phenyl)-3H-imidazo[4,5-b]pyridine

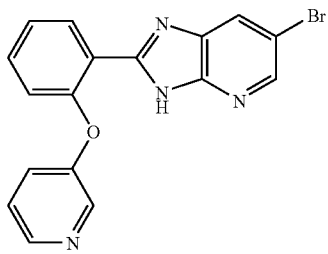

Example 245

6-bromo-2-(3-(2-fluorobenzyloxy)-5-(pyrimidin-2-yloxy)phenyl)-3H-imidazo[4,5-b]pyridine

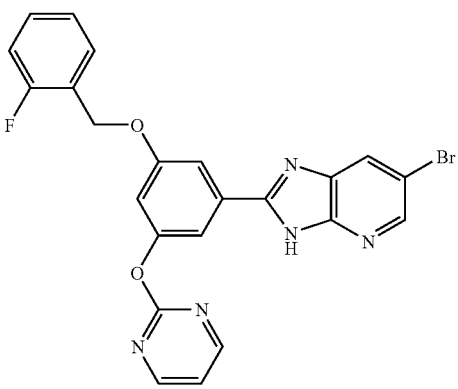

Example 246

(E)-2-(2-methoxy-5-(2-(pyridin-4-yl)vinyl)phenyl)-3H-imidazo[4,5-b]pyridine

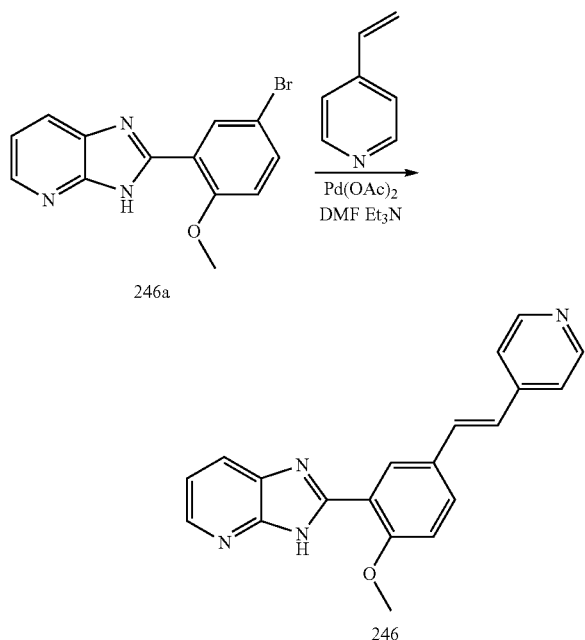

Starting material 246a was synthesized using the procedure described for Example 191.

Example 246 (250 mg, 0.82 mmol) was dissolved in DMF (6.0 ml). To this solution was added Et$_3$N (0.16 ml, 1.15 mmol) and 4-vinylpyridine (104 mg, 0.97 mmol). The solution was filled with nitrogen, then treated with palladium acetate (25 mg). The resulting mixture was heated to 180° C. for 2 h in a microwave oven. The reaction mixture was filtered, and the filtrate was purified by prep HPLC to afford the title Example 246. $^1$H NMR (400 MHz, DMSO-d6) ppm 4.10 (s, 3 H) 7.30-7.35 (m, 1 H) 7.39-7.47 (m, 2 H) 7.91-8.09 (m, 5 H) 8.42-8.43 (dd, J=4.67, 1.39 Hz, 1 H) 8.70-8.76 (m, 3 H). ESI-MS: m/z 329 (m+H)$^+$.

Reference Example 1A

Construction of Glucokinase (GK) Expression Vector

A plasmid DNA for expression of protein (GST-hLGK1) containing GST (Glutathione S-transferase) added to human hepatic GK amino terminal in *Escherichia coli* was prepared as follows.

First, PCR was performed using a human liver cDNA (Marathon Ready cDNA, Clontech) as a template and two kinds of synthetic DNAs (5'-CAGCTCTCCATCCAAG-CAGCCGTTGCT-3' [SEQ ID No. 1] and 5'-GGCGGC-CTGGGTCCTGACAAG-3' [SEQ ID No.2]), and the obtained DNA fragment was cloned using TOPO TA Cloning Kit (Invitrogen). PCR was performed using the obtained plasmid DNA as a template and a synthetic DNA (5'-GGATC-CATGCCCAGACCAAGATCCCAACTCCCA-CAACCCAACTCCCAGGTAG AGCAGATCCTGGCAGAG-3' [SEQ ID No.3]) having a BamHI site added to immediately before the initiation codon and a synthetic DNA (5'-GAATTCCTGGCCCAGCATA-CAGGC-3' [SEQ ID No.4]) having an EcoRI site added to immediately after the stop codon. The obtained DNA fragment was subcloned to pGEX6P-2 (Amersham Biosciences) digested with BamHI and EcoRI to give a human hepatic GK expression plasmid (pGEX6P-2/hLGK1).

Reference Example 2A

Expression and Purification of GST-hLGK1

BL21 strain (Stratagene) transformed with pGEX6P-2/hLGK1 obtained in Reference Example 1A was cultured with shaking in a 200 ml Erlenmeyer flask containing a 100 μg/ml ampicillin-containing LB medium (50 ml) at 37° C. for 14 hr. The culture medium (25 ml) was diluted with 100 μg/ml ampicillin-containing LB medium (225 ml), and further cultured with shaking in a 1 L Erlenmeyer flask at 37° C. for 1 hr. After cooling on ice the Erlenmeyer flask after culture, 100 mM Isopropyl-Thio-β-D-Galactopyranoside (IPTG) (125 μL) was added (final concentration 50 μM), and the mixture was cultured at 17° C. for 20 hr. After centrifugation of the culture medium, the obtained cells were ultrasonicated, and the object protein (GST-hLGK1) was purified from the supernatant using Glutathione Sepharose 4B (Amersham Biosciences).

Experimental Example 1

Measurement of GK Activation Value

A 50% solution (5 μL) of the test compound in dimethyl sulfoxide was added to each well of a 384 well black plate (Nalge Nunc). Then, 35 μL of a liquid obtained by diluting GST-hLGK1 obtained in Reference Example 2A with a measurement buffer (50 mM HEPES (pH 7.4), containing 200 mM KCl, 5 mM MgCl$_2$, 2.5 mM DTT and 50 μM 2'-(or-3')-O—(N-methylanthraniloyl)adenosine 5'-triphosphate (Mant-ATP) (Jena Bioscience)) was added to each well to 6 μg/mL.

Each well was stood at 37° C. for 10 min, and a 25 mM D-glucose solution (10 μL) was added to start the reaction.

Each well after the start of the reaction was stood at 37° C. for 60 min, and the reaction was quenched by adding 25 μL of a reaction quenching solution (200 mM HEPES (pH 7.4), containing 20 mM MgCl$_2$, 200 mM EDTA, 0.03% Triton-X 100, 0.3% Coating 3 reagent (Caliper Life Sciences)).

Mant-ATP (substrate) and Mant-ADP (reaction resultant product) were separated from each well after quenching the reaction, with a microchip type capillary electrophoresis apparatus 250HTS (Caliper Life Sciences). The reaction rate [(peak height of reaction resultant product)/(peak height of reaction resultant product+peak height of substrate)×100 (%)] was calculated from the ratio of the substrate peak height and the reaction resultant product peak height, which were obtained by fluorescence detection (excitation wavelength 355 nm, measurement wavelength 460 nm), and used as an index of the GK activity.

For the control, the reaction rate was calculated in the same manner as in the above except that "50% dimethyl sulfoxide solution" was used instead of the "50% solution of the test compound in dimethyl sulfoxide".

A percentage obtained by dividing the reaction rate of the well added with the test compound (test compound addition group) by the reaction rate of the well added with a 50% dimethyl sulfoxide solution alone (control group) was taken as the GK activation value by the test compound, and the concentration of the test compound necessary for the activation of 50% of the maximum activity value is shown as an $EC_{50}$ value. The results are shown in Table 3.

TABLE 3

| test compound (Example No.) | $EC_{50}$ value (μM) |
|---|---|
| 2 | 0.13 |
| 3 | 0.15 |
| 4 | 1.6 |
| 5 | 2.1 |
| 40 | 0.44 |
| 45 | 0.28 |
| 47 | 0.40 |
| 48 | 0.24 |
| 50 | 0.29 |
| 51 | 0.25 |
| 61 | 1.1 |
| 72 | 0.20 |
| 73 | 0.15 |
| 76 | 0.73 |
| 80 | 0.82 |
| 82 | 3.7 |

Experimental Example 2

Measurement of GK Activation Value

Purified glucokinase may be obtained as follows. DNA encoding residues 12-465 of the full-length sequence of the human enzyme may be amplified by PCR and cloned into the HindIII and EcoRI sites of pFLAG-CTC (Sigma). SEQ ID No. 5 corresponds to residues 12-465 of glucokinase.

The expression of recombinant glucokinase protein may be carried out by transformation and growth of DH10b-T1r E. coli cells incorporating the (pFLAG-CTC) plasmid in LB media. Protein expression can be induced in this system by the addition of IPTG to the culture medium.

Recombinant protein may be isolated from cellular extracts by passage over Sepharose Q Fast Flow resin (Pharmacia). This partially purified GK extract may then be further purified by a second passage over Poros HQ10 (Applied Biosystems). The purity of GK may be determined on denaturing SDS-PAGE gel. Purified GK may then be concentrated to a final concentration of 20.0 mg/ml. After flash freezing in liquid nitrogen, the proteins can be stored at −78° C. in a buffer containing 25 mM TRIS-HCl pH 7.6, 50 mM NaCl, and 0.5 mM TCEP.

It should be noted that a variety of other expression systems and hosts are also suitable for the expression of glucokinase, as would be readily appreciated by one of skill in the art.

The assay reaction may be initiated as follows: 4 μl of substrate mixture (12.5 μM ATP and 12.5 mM Glucose) was added to each well of the plate, followed by the addition of 2 μl of activator (2 fold serial dilutions for 11 data points for each activator) containing 10% DMSO. 4 μL of 1.25 nM GK solution may be added to initiate the reaction. The reaction mixture may then be incubated at room temperature for 60 min, and quenched and developed by addition of 10 μL of luciferase reagent. Luminescence intensities of the resulting reaction mixtures may be measured after a 10 min incubation at room temperature. The luminescence intensity may be measured by using the Analyst HT from LJL Biosystems.

$pK_{act}$ and % $ACT_{max}$ values may be calculated by non-linear curve fitting of the compound concentrations and luminescence intensities to a standard inhibition/activation equation. $K_{act}$ is the concentration that displays 50% of the maximal increase in GK activity observed using a saturating activator concentration. % $Act_{max}$ represents the calculated maximal gain in GK enzyme activity at a saturating concentration of the compound. $pK_{act}$ and % $ACT_{max}$ values for select compounds of the present invention are given in Table 4.

TABLE 4

| Example | $pK_{act}$ | % $ACT_{maxc}$ |
|---|---|---|
| 71 | 6.0-6.4 | 20.0-29.9 |
| 158 | 6.5-6.9 | 20.0-29.9 |
| 159 | 6.0-6.4 | 20.0-29.9 |
| 161 | >7.0 | 30.0-49.9 |
| 162 | 6.5-6.9 | >70.0 |
| 163 | >7.0 | 50.0-69.9 |
| 164 | 6.5-6.9 | 50.0-69.9 |
| 165 | >7.0 | >70.0 |
| 166 | >7.0 | >70.0 |
| 167 | >7.0 | >70.0 |
| 168 | 6.5-6.9 | >70.0 |
| 172 | 6.0-6.4 | 50.0-69.9 |
| 173 | 6.5-6.9 | 50.0-69.9 |
| 174 | 6.5-6.9 | 30.0-49.9 |
| 177 | 6.0-6.4 | 20.0-29.9 |
| 179 | 6.5-6.9 | >70.0 |
| 180 | 6.0-6.4 | 30.0-49.9 |
| 181 | 6.0-6.4 | >70.0 |
| 188 | 6.0-6.4 | 30.0-49.9 |
| 196 | 6.0-6.4 | >70.0 |
| 213 | 6.5-6.9 | 30.0-49.9 |
| 214 | 6.0-6.4 | 30.0-49.9 |
| 243 | 6.5-6.9 | 30.0-49.9 |
| 244 | 6.0-6.4 | 20.0-29.9 |
| 245 | 6.0-6.4 | >70.0 |
| 246 | 6.0-6.4 | 30.0-49.9 |

Formulation Example 1

Production of Capsule

| | |
|---|---|
| 1) compound of Example 1 | 30 mg |
| 2) microcrystalline cellulose | 10 mg |
| 3) lactose | 19 mg |
| 4) magnesium stearate | 1 mg |
| Total | 60 mg |

The above-mentioned 1), 2), 3) and 4) are mixed and filled in a gelatin capsule.

Formulation Example 2

Production of Tablet

| | |
|---|---|
| 1) compound of Example 1 | 30 g |
| 2) lactose | 50 g |
| 3) cornstarch | 15 g |
| 4) carboxymethylcellulose calcium | 44 g |
| 5) magnesium stearate | 1 g |
| 1000 tablets Total | 140 g |

The total amount of the above-mentioned 1), 2) and 3) and 30 g of 4) are kneaded with water, vacuum dried and granulated. The granulated powder is mixed with 14 g of 4) and 1 g of 5) and tableted with a tableting machine. In this way, 1000 tablets containing 30 mg of the compound of Example 1 per tablet are obtained.

The glucokinase activator of the present invention has a superior activity and is useful as a pharmaceutical agent for the prophylaxis or treatment of diabetes, obesity and the like.

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A compound represented by the formula (II):

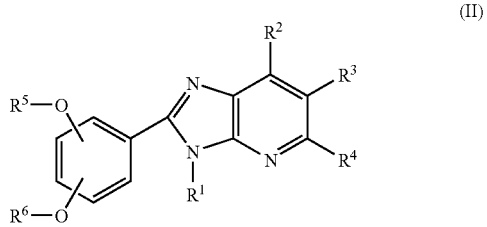

(II)

wherein
$R^1$ is a hydrogen atom;
$R^2$ is a hydrogen atom;
$R^3$ is
  (1) a hydrogen atom;
  (2) a $C_{6-14}$ aryl group optionally substituted by 1 to 3 substituents selected from
    (a) a halogen atom,
    (b) a $C_{1-6}$ alkyl group optionally substituted by 1 to 3 halogen atoms,
    (c) a $C_{1-6}$ alkoxy group, and
    (d) a hydroxy group;
  (3) a $C_{1-6}$ alkyl group optionally substituted by 1 to 3 substituents selected from
    (a) an amino group optionally substituted by 1 or 2 substituents selected from
      (i) a $C_{1-6}$ alkyl group optionally substituted by 1 to 3 substituents selected from a $C_{1-6}$ alkoxy group, a $C_{6-14}$ aryloxy group, a carboxyl group and a $C_{1-6}$ alkoxy-carbonyl group, and
      (ii) a $C_{7-13}$ aralkyl group, and
    (b) a hydroxy group;
  (4) an optionally substituted aromatic heterocyclic group;
  (5) a formyl group;
  (6) a carboxyl group;
  (7) a $C_{1-6}$ alkoxy-carbonyl group; or
  (8) a halogen atom;
$R^4$ is
  (1) a hydrogen atom;
  (2) a $C_{1-6}$ alkyl group optionally substituted by 1 to 3 substituents selected from
    (a) a hydroxy group,
    (b) a carboxyl group,
    (c) a $C_{1-6}$ alkoxy-carbonyl group,
    (d) a halogen atom, and
    (e) a cyano group;
  (3) a cyano group;
  (4) a carboxyl group; or
  (5) a $C_{1-6}$ alkoxy-carbonyl group;
$R^5$ is a $C_{1-6}$ alkyl group substituted by 1 to 3 substituents selected from
  (a) (2-fluoro)phenyl,
  (b) a 5- or 6-membered aromatic heterocyclic group, and
  (c) a 5- or 6-membered non-aromatic heterocyclic group,
  wherein each of (b) and (c) is optionally substituted by 1 to 3 substituents selected from a halogen atom, a $C_{1-6}$ alkyl group, a $C_{1-6}$ alkoxy group, a thiol group, a $C_{1-6}$ alkyl-carbonyl group, a $C_{1-6}$ alkylsulfonyl group, a $C_{6-14}$ aryloxy group, a mono-or di-$C_{1-6}$ alkyl-amino group); and
$R^6$ is
  (1) a $C_{1-6}$ alkyl group substituted by 1 to 3 substituents selected from
    (a) a $C_{6-14}$ aryl group,
    (b) a $C_{3-10}$ cycloalkyl group,
    (c) a 5- or 6-membered aromatic heterocyclic group, and
    (d) a 5- or 6-membered non-aromatic heterocyclic group,
    wherein each of (a) to (d) is optionally substituted by 1 to 3 substituents selected from a halogen atom, a $C_{1-6}$ alkyl group, a $C_{1-6}$ alkoxy group, a thiol group, a $C_{1-6}$ alkyl-carbonyl group, a $C_{1-6}$ alkylsulfonyl group, a $C_{6-14}$ aryloxy group, a mono-or di-$C_{1-6}$ alkyl-amino group); or
  (2) a $C_{3-6}$ alkyl group optionally substituted by 1 to 3 substituents selected from a $C_{1-6}$ alkoxy group and a $C_{6-14}$ aryloxy group optionally substituted by 1 to 3 substituents selected from a cyano group and a halogen atom, or a salt thereof.

2. A compound selected from the group consisting of:
2-(3-(benzyloxy)-5-((1-methyl-1H-imidazol-2-yl)methoxy)phenyl)-3H-imidazo[4,5-b]pyridine;
2-(3-(benzyloxy)-5-((1-methyl-1H-imidazol-2-yl)methoxy)phenyl)-6-bromo-3H-imidazo[4,5-b]pyridine;
6-bromo-2-(3-((1-methyl-1H-imidazol-2-yl)methoxy)-5-(2-(thiophen-3-yl) ethoxy)phenyl)-3H-imidazo[4,5-b]pyridine;
2-(3-(2-fluorobenzyloxy)-5-((1-methyl-1H-imidazol-2y1)methoxy) phenyl)-3H-imidazo[4,5-b]pyridine;
6-chloro-2-(3-(2-fluorobenzyloxy)-5-((1-methyl-1H-imidazol-2-yl)methoxy)phenyl)-3H-imidazo[4,5-b]pyridine;
6-bromo-2-(3-(2-fluorobenzyloxy)-5-((1-methyl-1H-imidazol-2-yl)methoxy)phenyl)-3H-imidazo[4,5-b]pyridine;
3-(2-(3-(2-fluorobenzyloxy)-5-((1-methyl-1H-imidazol-2-yl)methoxy)phenyl)-3H-imidazo[4,5-b]pyridin-6-yl)propan-1-ol;
(R)-2-(3-(2-fluorobenzyloxy)-5-(1-methoxypropan-2-yloxy)phenyl)-3H-imidazo [4,5-b]pyridine;
(R)-6-chloro-2-(3-(2-fluorobenzyloxy)-5-(1-methoxypropan-2-yloxy) phenyl)-3H-imidazo[4,5-b]pyridine;
(R)-6-bromo-2-(3-(2-fluorobenzyloxy)-5-(1-methoxypropan-2-yloxy) phenyl)-3H-imidazo[4,5-b]pyridine;
(S)-3-(2-(3-(2-fluorobenzyloxy)-5-(1-methoxypropan-2-yloxy)phenyl)-3H-imidazo [4,5-b]pyridin-6-yl)propan-1 -ol;
(S)-methyl 2-(3-(2-fluorobenzyloxy)-5-(1-methoxypropan-2-yloxy) phenyl)-3H-imidazo[4,5-b] pyridine-6-carboxylate; and
(S)-2-(3 -(2-fluorobenzyloxy)-5 -(1-methoxypropan-2-yloxy)phenyl)-3H-imidazo [4,5-b]pyridine-6-carboxylic acid.

3. A pharmaceutical agent comprising a compound according to claim 1 and one or more pharmacologically acceptable carriers.

* * * * *